US012600794B2

(12) United States Patent
Mandel et al.

(10) Patent No.: US 12,600,794 B2
(45) Date of Patent: Apr. 14, 2026

(54) 5T4 BINDING POLYPEPTIDES AND USES THEREOF

(71) Applicant: ABDERA THERAPEUTICS INC., South San Francisco, CA (US)

(72) Inventors: Alexander Laurence Mandel, Vancouver (CA); Raja Solomon Viswas, Richmond (CA); Adam Daniel Judge, Bainbridge Island, WA (US); Michael J. Abrams, Custer, WA (US); Emma Jane Cummins, Vancouver (CA); Brandon Robert McLeod, Vancouver (CA); Iva Kulic, Vancouver (CA); Douglas Bruce MacKay, Ottawa (CA)

(73) Assignee: ABDERA THERAPEUTICS INC., South San Francisco, CA (US)

( * ) Notice: Subject to any disclaimer, the term of this patent is extended or adjusted under 35 U.S.C. 154(b) by 0 days.

(21) Appl. No.: 19/275,203

(22) Filed: Jul. 21, 2025

(65) Prior Publication Data

US 2026/0028414 A1 Jan. 29, 2026

Related U.S. Application Data

(60) Provisional application No. 63/793,071, filed on Apr. 23, 2025, provisional application No. 63/776,761, (Continued)

(51) Int. Cl.

| | |
|---|---|
| ***C07K 16/30*** | (2006.01) |
| ***A61K 51/10*** | (2006.01) |
| ***A61P 35/00*** | (2006.01) |

(52) U.S. Cl.
CPC .......... *C07K 16/30* (2013.01); *A61K 51/1045* (2013.01); *A61K 51/1096* (2013.01); (Continued)

(58) Field of Classification Search
CPC ................ C07K 16/30; C07K 2317/53; C07K 2317/565; C07K 2317/569; (Continued)

(56) References Cited

U.S. PATENT DOCUMENTS

| | | | |
|---|---|---|---|
| 5,965,131 | A | 10/1999 | Griffiths et al. |
| 6,165,745 | A | 12/2000 | Ward et al. |

(Continued)

FOREIGN PATENT DOCUMENTS

| | | | |
|---|---|---|---|
| CA | 2431600 | A1 | 8/2002 |
| CA | 2768658 | A1 | 1/2011 |

(Continued)

OTHER PUBLICATIONS

Alfthan, Kaija et al. Properties of a single-chain antibody containing different linker peptides. Protein Eng. 8:725-731 (1995).

(Continued)

*Primary Examiner* — Joanne Hama
*Assistant Examiner* — Jami Michelle Gurley
(74) *Attorney, Agent, or Firm* — WILSON SONSINI GOODRICH & ROSATI

(57) ABSTRACT

Described herein are polypeptides that bind to 5T4 useful for cancer therapy. Further disclosed herein are polypeptides that bind to 5T4 that are conjugated to a chelating agent or a radionuclide complex thereof.

36 Claims, 42 Drawing Sheets

Specification includes a Sequence Listing.

Related U.S. Application Data filed on Mar. 24, 2025, provisional application No. 63/744,661, filed on Jan. 13, 2025, provisional application No. 63/674,465, filed on Jul. 23, 2024.

(52) U.S. Cl.
CPC .......... *A61P 35/00* (2018.01); *A61K 2121/00* (2013.01); *A61K 2123/00* (2013.01); *C07K 2317/53* (2013.01); *C07K 2317/565* (2013.01); *C07K 2317/569* (2013.01); *C07K 2317/71* (2013.01); *C07K 2317/94* (2013.01)

(58) Field of Classification Search
CPC ............ C07K 2317/71; C07K 2317/94; A61K 51/1045; A61K 51/1096; A61K 2121/00; A61K 2123/00; A61P 35/00
See application file for complete search history.

(56) References Cited

U.S. PATENT DOCUMENTS

| | | | |
|---|---|---|---|
| 6,277,375 | B1 | 8/2001 | Ward |
| 6,403,771 | B1 | 6/2002 | Geerlings |
| 7,083,784 | B2 | 8/2006 | Dall'Acqua et al. |
| 7,374,936 | B2 | 5/2008 | Geerlings |
| 8,044,178 | B2 | 10/2011 | Boghaert et al. |
| 8,088,376 | B2 | 1/2012 | Chamberlain et al. |
| 8,318,907 | B2 | 11/2012 | Chamberlain et al. |
| 8,324,351 | B2 | 12/2012 | Chamberlain et al. |
| 8,338,574 | B2 | 12/2012 | Chamberlain et al. |
| 8,367,805 | B2 | 2/2013 | Chamberlain et al. |
| 8,394,925 | B2 | 3/2013 | Chamberlain et al. |
| 8,759,495 | B2 | 6/2014 | Boghaert et al. |
| 8,852,586 | B2 | 10/2014 | Chamberlain et al. |
| 8,883,973 | B2 | 11/2014 | Chamberlain et al. |
| 9,603,954 | B2 | 3/2017 | Simon et al. |
| 9,855,348 | B2 | 1/2018 | Devoogdt et al. |
| 9,902,771 | B2 | 2/2018 | Boghaert et al. |
| 10,336,818 | B2 | 7/2019 | Chamberlain et al. |
| 11,419,821 | B2 | 8/2022 | Fallon et al. |
| 2012/0046872 | A1 | 2/2012 | Kühn et al. |
| 2021/0340273 | A1 | 11/2021 | Timmer et al. |
| 2022/0105194 | A1 | 4/2022 | Akaiwa et al. |
| 2023/0181770 | A1 | 6/2023 | Gonzales et al. |
| 2024/0207462 | A1 | 6/2024 | Judge et al. |

FOREIGN PATENT DOCUMENTS

| | | | | |
|---|---|---|---|---|
| CA | 2954359 | A1 | 2/2016 | |
| CA | 2991398 | A1 | 1/2017 | |
| DE | 266710 | A3 | 4/1989 | |
| EP | 2203180 | A1 | 7/2010 | |
| EP | 2341060 | A1 | 7/2011 | |
| EP | 2354149 | A1 | 8/2011 | |
| JP | 5985392 | B2 | 9/2016 | |
| JP | 6268127 | B2 | 1/2018 | |
| JP | 6289733 | B2 | 3/2018 | |
| WO | WO-9015625 | A1 | 12/1990 | |
| WO | WO-9938884 | A2 | 8/1999 | |
| WO | WO-02060919 | A2 | 8/2002 | |
| WO | WO-03038098 | A2 | 5/2003 | |
| WO | WO-2006031653 | A2 | 3/2006 | |
| WO | WO-2011011592 | A1 | 1/2011 | |
| WO | WO-2013050617 | A1 | 4/2013 | |
| WO | WO-2019169289 | A1 | 9/2019 | |
| WO | WO-2020065045 | A1 | 4/2020 | |
| WO | WO-2020076977 | A2 | 4/2020 | |
| WO | WO-2020076992 | A1 | 4/2020 | |
| WO | WO-2020186328 | A1 | 9/2020 | |
| WO | WO-2020219715 | A1 | 10/2020 | |
| WO | WO-2021000017 | A1 | 1/2021 | |
| WO | WO-2021000018 | A1 | 1/2021 | |
| WO | WO-2021142258 | A1 | 7/2021 | |
| WO | WO-2022084915 | A1 | 4/2022 | |
| WO | WO-2022175750 | A1 | 8/2022 | |
| WO | WO-2022266499 | A1 | 12/2022 | |
| WO | WO-2024044549 | A1 | 2/2024 | |
| WO | WO-2024044552 | A1 | 2/2024 | |
| WO | WO-2024106394 | A1 * | 5/2024 | ............. A61P 35/00 |
| WO | WO-2025179031 | A1 | 8/2025 | |

OTHER PUBLICATIONS

Altunay et al.: HER2-directed antibodies, affibodies and nanobodies as drug-delivery vehicles in breast cancer with a specific focus on radioimmunotherapy and radioimmunoimaging. Eur J Nucl Med Mol Imaging. 48(5):1371-1389 (2021).

Andersen et al.: Anti-carcinoembryonic antigen single-chain variable fragment antibody variants bind mouse and human neonatal Fc receptor with different affinities that reveal distinct cross-species differences in serum half-life. J Biol Chem. 287(27):22927-22937 (2012).

Aweda, Tolulope A. et al. New covalent capture probes for imaging and therapy, based on a combination of binding affinity and disulfide bond formation. Bioconjugate Chemistry 22(8): 1479-1483 (2011).

Blom, Elisabeth et al. Synthesis and characterization of scVEGF-PEG-[68Ga] NOTA and SCVEGF-PEG-[68Ga] DOTA PET tracers. Journal of Labelled Compounds and Radiopharmaceuticals 54(11):685-692 (2011).

Borrok et al.: pH-dependent binding engineering reveals an FcRn affinity threshold that governs IgG recycling. J Biol Chem. 290(7):4282-4290 (2015).

Burvenich et al.: Engineering anti-Lewis-Y hu3S193 antibodies with improved therapeutic ratio for radioimmunotherapy of epithelial cancers. EJNMMI Res. 6(1):26:1-13 (2016).

CAS RN 1174123-05-7, STN Entry Date Aug. 12, 2009, Yttrate(3-)-90Y, [L-γ-glutamyl-S-[2,5-dioxo-1-[4-[[4-[[1,4,7,10-tetrakis[(carboxy-κO)methyl]-1,4,7,10-tetraazacyclododec-2-yl-κN1,κN4,κN7,κN10]methyl]phenyl]amino]-4-oxobutyl]-3-pyrrolidinyl]-L-cysteinylglycinato(6-)]—(2009).

CAS RN 1195873-66-5, STN Entry Date Dec. 3, 2009, Lutetate(4-), [L-arginyl-L-α-aspartyl-S-[2,5-dioxo-1-[3-oxo-3-[[4-[[1,4,7,10-tetrakis[(carboxy-κO)methyl]-1,4,7,10-tetraazacyclododec-2-yl-κN1, κN4,κN7,κN10]methyl]phenyl]amino]propyl]-3-pyrrolidinyl]-L-cysteinyl-L-lysyl-L-seryl-L-threonyl-L-tyrosyl-L-arginyl-L-lysyl-L-α-aspartyl-L-arginyl-L-lysyl-L-phenylalanyl-L-tryptophyl-L-leucyl-L-leucyl-L-methionyl-L-prolyl-L-alanyl-L-valinato(7-)]—(2009).

CAS RN 2376050-85-8, STN Entry Date Sep. 27, 2019.

CAS RN 2453242-83-4, STN Entry Date Aug. 5, 2020.

CAS RN 2453242-91-4, STN Entry Date Aug. 5, 2020.

CAS RN 2453242-93-6, STN Entry Date Aug. 5, 2020.

CAS RN 2527701-33-1, STN Entry Date Nov. 23, 2020.

CAS RN 687619-41-6, STN Entry Date May 31, 2004, Gadolinate(1-), [2-[[4-[3-(2,5-dihydro-2,5-dioxo-1H-pyrrol-1-yl)propoxy]phenyl]methyl]-1,4,7,10-tetraazacyclododecane-1,4,7,10-tetraacetato(4-)-N1,N4,N7,N10,O1,O4,O7,O10]—(2004).

Co-pending U.S. Appl. No. 19/104,937, inventors Abrams; Michael J. et al., filed Feb. 19, 2025.

D'Huyvetter et al.: Targeted radionuclide therapy with A 177Lu-labeled anti-HER2 nanobody. Theranostics. 4(7):708-720 (2014).

D'Huyvetter, Matthias, et al. Radiolabeled nanobodies as theranostic tools in targeted radionuclide therapy of cancer. Expert Opin. Drug Deliv. 11(12):1939-1954 (2014).

Dumet et al.: Insights into the IgG heavy chain engineering patent landscape as applied to IgG4 antibody development. MAbs 11(8):1341-1350 (2019).

Günaydin, Gökçe, et al. Fusion of the mouse IgG1 Fc domain to the VHH fragment (ARP1) enhances protection in a mouse model of rotavirus. Scientific Reports 6:30171 (2016). DOI: 10.1038/srep30171.

Hamblett. et al. Altering Antibody-Drug Conjugate Binding to the Neonatal Fc Receptor Impacts Efficacy and Tolerability. Molecular Pharmaceutics 13(7):2387-2396 (2016).

He, Yingfang, et al. Preclinical evaluation and pilot clinical study of [68Ga]Ga-NOTA-H006 for non-invasive PET imaging of 5T4 oncofetal antigen. European Journal of Nuclear Medicine and Molecular Imaging 52(2):611-622 (2024).

(56) References Cited

OTHER PUBLICATIONS

Hornick et al.: Single amino acid substitution in the Fc region of chimeric TNT-3 antibody accelerates clearance and improves immunoscintigraphy of solid tumors. J Nucl Med. 41(2):355-362 (2000).
Kenanova et al.: Radioiodinated versus radiometal-labeled anti-carcinoembryonic antigen single-chain Fv-Fc antibody fragments: optimal pharmacokinetics for therapy. Cancer Res. 67(2):718-726 (2007).
Kenanova et al.: Tailoring the pharmacokinetics and positron emission tomography imaging properties of anti-carcinoembryonic antigen single-chain Fv-Fc antibody fragments. Cancer Res. 65(2):622-631 (2005).
Kim et al.: Mapping the site on human IgG for binding of the MHC class I-related receptor, FcRn. Eur J Immunol. 29(9):2819-2825 (1999).
Miranda, Ana Claudia Camargo et al. Anti-hER2 Monoclonal Antibody Based-radioimmunoconjugates: Assessment of the Chelating Agent Influence. Bioorganic & Medicinal Chemistry 33:115996, 1-9 (2021).
Miranda, Ana Claudia Camargo. et al. Radioimmunotheranostic Pair Based on the Anti-HER2 Monoclonal Antibody: Influence of Chelating Agents and Radionuclides on Biological Properties. Pharmaceutics 13(7):971, 1-16 (2021).
Olafsen et al.: Optimizing radiolabeled engineered anti-p185HER2 antibody fragments for in vivo imaging. Cancer Res. 65(13):5907-5916 (2005).
Olafsen et al.: Recombinant anti-CD20 antibody fragments for small-animal PET imaging of B-cell lymphomas. Recombinant anti-CD20 antibody fragments for small-animal PET imaging of B-cell lymphomas. J Nucl Med. 50(9): 1500-1508 (2009).
PCT/IB2022/000077 International Search Report and Written Opinion dated Jun. 29, 2022.
PCT/US2023/072585 International Search Report and Written Opinion dated Nov. 1, 2023.
PCT/US2025/038525 International Search Report and Written Opinion dated Sep. 24, 2025.
Pothin, Elodie, et al. Brain Delivery of Single-Domain Antibodies: A Focus on VHH and VNAR. Pharmaceutics 12, 937 (2020). doi: 10.3390/pharmaceutics12100937.
Puttemans, Janik, et al. Preclinical Targeted alpha- and beta-Radionuclide Therapy in HER2-Positive Brain Metastasis Using Camelid Single-Domain Antibodies. Cancers 12, 1017 (2020). doi:10.3390/cancers12041017.
Quadri, S. M, and H. M. Vriesendorp. Effects of linker chemistry on the pharmacokinetics of radioimmunoconjugates. The Quarterly Journal of Nuclear Medicine and Molecular Imaging 42(4):250-261 (1998).
Rotman et al.: Fusion of hIgG1-Fc to 111In-anti-amyloid single domain antibody fragment VHH-pa2H prolongs blood residential time in APP/PS1 mice but does not increase brain uptake. Nucl Med Biol. 42(8):695-702 (2015).
Sathekge et al.: 225Ac-PSMA-617 in chemotherapy-naive patients with advanced prostate cancer: a pilot study. Eur J Nucl Med Mol Imaging. 46(1):129-138 (2019).
Sharma, Rohit et al. Dose-dependent cell cycle arrest and apoptosis in HER2 breast cancer cells by177Lu-CHX-A''-DTPA-Trastuzumab. Journal of Cancer Research and Therapeutics 16(6):1426-1434 (2020).
Wu, Yanling, et al. A highly stable human single-domain antibody-drug conjugate exhibits superior penetration and treatment of solid tumors. Molecular Therapy 30(8):2785-2799 (2022).
Wu, Yanling, et al. Single-domain antibodies as therapeutics against human viral diseases. Frontiers in Immunology 8(1802):1-13 (2017).
Yu et al.: Humanized CD7 nanobody-based immunotoxins exhibit promising anti-T-cell acute lymphoblastic leukemia potential. Int J Nanomedicine. 12:1969-1983 (2017).
Alizadeh, Elahe, et al. 89Zr-Labeled Domain II-Specific scFv-Fc ImmunoPET Probe for Imaging Epidermal Growth Factor Receptor In Vivo. Cancers (Basel). 13(3):560 (2021). doi: 10.3390/cancers13030560.
Bannas, Peter, et al. Nanobodies and Nanobody-Based Human Heavy Chain Antibodies As Antitumor Therapeutics. Front Immunol. 8:1603, 13 pages (2017). doi: 10.3389/fimmu.2017.01603.
EP22755635.4 Extended European Search Report dated Dec. 8, 2025.
Kitson, Sean L.. Antibody-Drug Conjugates and Radionuclides to Target Cancer. Cancer Studies and Molecular Medicine—Open Journal 1(1):8-15 (2014). DOI:10.17140/CSMMOJ-1-102.
Wei, Weijun, et al. ImmunoPET: Concept, Design, and Applications. Chem Rev. 120(8):3787-3851 (2020). doi:10.1021/acs.chemrev.9b00738.
White, Jordan M., et al. Perspectives on metals-based radioimmunotherapy (RIT): moving forward. Theranostics. 11(13):6293-6314 (2021). doi: 10.7150/thno.57177.

* cited by examiner

111In-Ab-5-Linker Chelator 1

Non-radiolabeled Ab-5-linker chelator 2

H&E Staining

Anti-5T4 Staining $^{225}$Ac-Ab-5-linker-chelator-2 (20 kBq)

H&E Staining

Anti-5T4 Staining

Bars left to right: 1 hour, 24 hours, 72 hours, 144 hours, 240 hours

5T4 BINDING POLYPEPTIDES AND USES THEREOF

CROSS REFERENCE

This application claims the benefit of priority to U.S. Provisional App. No. 63/674,465 filed Jul. 23, 2024, U.S. Provisional App. No. 63/744,661 filed Jan. 13, 2025, U.S. Provisional App. No. 63/776,761 filed Mar. 24, 2025, and U.S. Provisional App. No. 63/793,071 filed Apr. 23, 2025, all of which are incorporated by reference herein in their entirety.

SEQUENCE LISTING

The instant application contains a Sequence Listing in XML format with a file name 60924-735_601_SL.xml, created on Jun. 12, 2025, and with a file size of 47 kB which is hereby incorporated by reference in its entirety.

BACKGROUND

5T4, also known as trophoblast glycoprotein (TPBG), is an oncofetal tumor-associated antigen that is highly expressed on the surface of various tumor cells. 5T4 is an attractive target due to its selective expression on the surface of cancer cells and cancer stem cells and its involvement in tumor progression.

SUMMARY

There is a need for molecules with highly selective binding affinity for 5T4 for the development of effective cancer therapeutics. For use with radiotherapies, including alpha or beta emitting therapies, and delivery of other types of cytotoxic molecules there is a need for antibodies that are internalized. There is also a need for immunoconjugates that are cleared rapidly from the body to reduce radiation exposure to patients receiving radiation therapy.

Disclosed herein, in some embodiments, are polypeptides that bind 5T4, wherein the polypeptides comprise an immunoglobulin variable domain comprising: (i) a complementarity determining region 1 (CDR1) comprising the amino acid sequence of SEQ ID NO: 1; a complementarity determining region 2 (CDR2) comprising the amino acid sequence of SEQ ID NO: 2; and a complementarity determining region 3 (CDR3) comprising the amino acid sequence of SEQ ID NO: 3; (ii) a complementarity determining region 1 (CDR1) comprising the amino acid sequence of SEQ ID NO: 4; a complementarity determining region 2 (CDR2) comprising the amino acid sequence of SEQ ID NO: 5; and a complementarity determining region 3 (CDR3) comprising the amino acid sequence of SEQ ID NO: 6; (iii) a complementarity determining region 1 (CDR1) comprising the amino acid sequence of SEQ ID NO: 7; a complementarity determining region 2 (CDR2) comprising the amino acid sequence of SEQ ID NO: 8; and a complementarity determining region 3 (CDR3) comprising the amino acid sequence of SEQ ID NO: 9; or (iv) a complementarity determining region 1 (CDR1) comprising the amino acid sequence of SEQ ID NO: 10; a complementarity determining region 2 (CDR2) comprising the amino acid sequence of SEQ ID NO: 11; and a complementarity determining region 3 (CDR3) comprising the amino acid sequence of SEQ ID NO: 12. In some embodiments, the immunoglobulin variable domain comprises at least 80%, 85%, 90%, 95%, 97%, 98%, 99%, or 100% sequence identity to SEQ ID NO: 25. In some embodiments, the immunoglobulin variable domain comprises at least 80%, 85%, 90%, 95%, 97%, 98%, 99%, or 100% sequence identity to SEQ ID NO: 26.

Further disclosed herein, in some embodiments, are polypeptide that bind 5T4, wherein the polypeptides comprise an immunoglobulin variable domain comprising: (i) a complementarity determining region 1 (CDR1) comprising the amino acid sequence of SEQ ID NO: 13; a complementarity determining region 2 (CDR2) comprising the amino acid sequence of SEQ ID NO: 14; and a complementarity determining region 3 (CDR3) comprising the amino acid sequence of SEQ ID NO: 15; (ii) a complementarity determining region 1 (CDR1) comprising the amino acid sequence of SEQ ID NO: 16; a complementarity determining region 2 (CDR2) comprising the amino acid sequence of SEQ ID NO: 17; and a complementarity determining region 3 (CDR3) comprising the amino acid sequence of SEQ ID NO: 18; (iii) a complementarity determining region 1 (CDR1) comprising the amino acid sequence of SEQ ID NO: 19; a complementarity determining region 2 (CDR2) comprising the amino acid sequence of SEQ ID NO: 20; and a complementarity determining region 3 (CDR3) comprising the amino acid sequence of SEQ ID NO: 21; or (iv) a complementarity determining region 1 (CDR1) comprising the amino acid sequence of SEQ ID NO: 22; a complementarity determining region 2 (CDR2) comprising the amino acid sequence of SEQ ID NO: 23; and a complementarity determining region 3 (CDR3) comprising the amino acid sequence of SEQ ID NO: 24. In some embodiments, the immunoglobulin variable domain comprises at least 80%, 85%, 90%, 95%, 97%, 98%, 99%, or 100% sequence identity to SEQ ID NO: 27. In some embodiments, the immunoglobulin variable domain comprises at least 80%, 85%, 90%, 95%, 97%, 98%, 99%, or 100% sequence identity to SEQ ID NO: 28. In some embodiments, the immunoglobulin variable domain comprises at least 80%, 85%, 90%, 95%, 97%, 98%, 99%, or 100% sequence identity to SEQ ID NO: 29.

In some embodiments, the polypeptide comprises an Fc domain and/or an immunoglobulin hinge region. In some embodiments, the Fc domain and/or the immunoglobulin hinge region comprises an amino acid sequence having at least about 80%, 85%, 90%, 95%, 97%, 98%, 99%, or 100% sequence identity to SEQ ID NO: 47. In some embodiments, the Fc domain is a human Fc domain. In some embodiments, the human Fc domain is an IgG1 Fc domain. In some embodiments, the human Fc domain is an IgG4 Fc domain. In some embodiments, the Fc domain comprises one or more amino acid residue alterations that reduce effector function of the polypeptide. In some embodiments, the one or more amino acid residue alterations that reduce effector function comprises L234A, L235E, G237A, A330S, and P331S. In some embodiments, the Fc domain comprises one or more amino acid residues that alter binding of the polypeptide to a neonatal Fc receptor (FcRn), thereby reducing the serum half-life of the polypeptide. In some embodiments, the one or more amino acid residues that alter binding of the polypeptide to the neonatal Fc receptor (FcRn) comprise H310A, H310D, H310E, H310Q, H435A, H435Q, and combinations thereof, per EU numbering.

Further disclosed herein, in some embodiments, are polypeptides comprising an immunoglobulin variable domain having at least 80%, 85%, 90%, 95%, 97%, 98%, 99%, or 100% sequence identity to any one of SEQ ID NOs: 25-29.

Further disclosed herein, in some embodiments, are polypeptides comprising an amino acid sequence having at least 80%, 85% 90%, 95%, 97%, 98%, 99%, or 100% sequence identity to any one of SEQ ID NOs: 30-34. Further disclosed herein, in some embodiments, are polypeptides comprising an amino acid sequence having at least 80%, 85%, 90%, 95%, 97%, 98%, 99%, or 100% sequence identity to SEQ ID NO: 42 or SEQ ID NO: 43.

In some embodiments, the polypeptide of any one of the embodiments disclosed herein binds to a 5T4 protein with an equilibrium dissociation constant (KY) equal to or less than $100\times10^{-9}$ M, $50\times10^{-9}$M, $25\times10^{-9}$ M, $15\times10^{-9}$ M, $10\times10^{-9}$ M, or $5\times10^{-9}$ M. In some embodiments, the 5T4 protein comprises the amino acid sequence of SEQ ID NO: 37.

In some embodiments, the polypeptide of any one of the embodiments disclosed herein is internalized by a cell expressing 5T4. In some embodiments, the internalization is increased relative to an H8 antibody control. In some embodiments, the cell is a NCI-H1975 cell or a MDA-MB-231 cell. In some embodiments, the internalization of the polypeptide by the cell expressing 5T4 is at least 2-fold greater than an internalization of an H8 antibody by the cell expressing 5T4, wherein the H8 antibody comprises: a heavy chain variable domain comprising SEQ ID NO: 39 and a light chain variable domain comprising SEQ ID NO: 40.

In some embodiments, the immunoglobulin variable domain of any one of the embodiments disclosed herein is an immunoglobulin heavy chain variable domain, optionally wherein the immunoglobulin heavy chain variable domain is a variable heavy domain of heavy chain (VHH).

Disclosed herein, in some embodiments, are dimers comprising two of the polypeptides disclosed herein.

Disclosed herein, in some embodiments, are immunoconjugates comprising the polypeptide of any one of the embodiments disclosed herein conjugated to a chelating agent or a radionuclide complex thereof.

In some embodiments, the chelating agent or the radionuclide complex thereof comprises:

1,4,7,10-tetraazacyclododecane-1,4,7,10-tetraacetic acid (DOTA);

1,4,7,10-tetraazacyclododecane-1,4,7-triacetic acid (DO3A);

1,4,7,10-tetraazacyclododecane-1,7-diacetic acid (DO2A);

α,α',α",α'"-tetramethyl-1,4,7,10-tetraazacyclododecane-1,4,7,10-tetraacetic acid (DOTMA);

1,4,7,10-tetrakis(carbamoylmethyl)-1,4,7,10-tetraazacyclododecane (DOTAM);

1,4,7,10-tetraazacyclododecane-1,4,7,10-tetrapropionic acid (DOTPA);

2,2',2"-(10-(2-amino-2-oxoethyl)-1,4,7,10-tetraazacyclododecane-1,4,7-triyl)triacetic acid;

6,6'-(((pyridine-2,6-diylbis(methylene))bis((carboxymethyl)azanediyl))-bis(methylene))dipicolinic acid (H4pypa);

6,6',6" 6'"-(((pyridine-2,6-diylbis(methylene))bis(azanetriyl))tetrakis(methylene))-tetrapicolinic acid (H4py4pa);

10-((6-carboxypyridin-2-yl)methyl)-1,4,7,10-tetra-azacyclododecane-1,4,7-triacetic acid (DO3Apic); or 3,6,9,12-tetrakis(carboxymethyl)-3,6,9,12-tetraazatetradecanedioic acid (TTHA).

In some embodiments, the immunoconjugate comprises a linker covalently linking the chelating agent or the radionuclide complex thereof to the polypeptide.

In some embodiments, the immunoconjugate is represented by Formula (I) or a pharmaceutically acceptable salt thereof:

Formula (I)

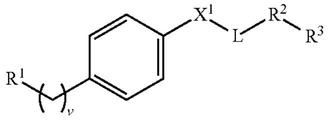

wherein:

$R^1$ is a chelating agent or a radionuclide complex thereof;

$X^1$ is absent, —O—, —S—, —S(═O)—, —S(═O)$_2$—, —NRa—, —C(═O)—, —NRaC(═O)—, —C(═O)NR$^a$—, —($C_1$-$C_6$ alkylene)-$X^2$—, or —($C_4$-$C_{20}$polyethylene glycol)-$X^2$—;

$X^2$ is absent, —C(═O)—, —NR$^a$C(═O)—, —C(═O)NR$^a$—, or —C(═O)$X^4$—;

each $R^a$ is independently selected from hydrogen and $C_1$-$C_4$ alkyl;

$X^4$ is —NR$^a$— or —NR$^a$S(═O)$_2$—; L is an optional linker;

$R^2$ is a moiety that is capable of reacting with an amine (—$NH_2$) or thiol (—SH) of the polypeptide;

$R^3$ is the polypeptide; and v is 1, 2, 3, or 4.

In some embodiments, $R^2$ is a moiety that is capable of reacting with an amine (—$NH_2$) of the polypeptide and comprises a tetrafluorophenyl ester, pentafluorophenyl ester, dinitrophenyl ester, succinimide ester, sulfosuccinimide ester, or isothiocyanate.

In some embodiments, $R^2$ is a moiety that is capable of reacting with an amine (—$NH_2$) of the polypeptide and —$R^2$-$R^3$ comprises:

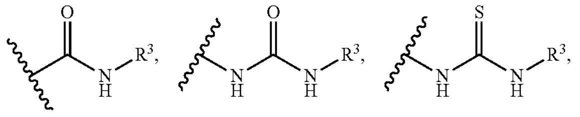

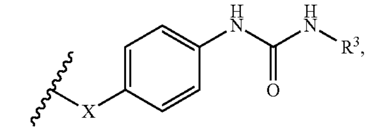

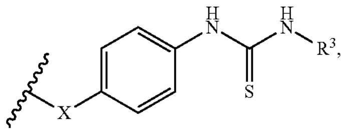

or

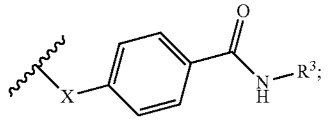

X is absent —O—, —S—, —S(═O)—, —S(═O)$_2$, —NR$^a$—, —C(═O)—, —NR$^a$C(═O)—, —C(═O)NR$^a$—, —C(═O)O—, —OC(═O)—, —OC(═O)NR$^a$—, —NR$^a$C(═O)NR$^a$—, —NR$^a$C(═S)NR$^a$—, or —NR$^a$C(═O)O—;

each $R^a$ is independently selected from hydrogen, and $C_1$-$C_4$ alkyl; and

—NH—$R^3$ is the polypeptide.

In some embodiments, the immunoconjugate is represented by any one of Formulas (II)-(V) or a pharmaceutically acceptable salt thereof:

Formula (II)

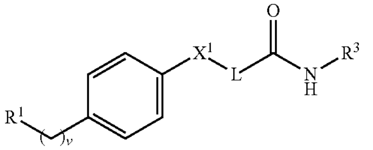

Formula (III)

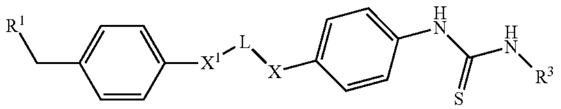

Formula (IV)

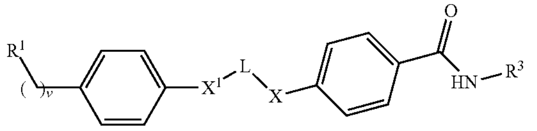

Formula (V)

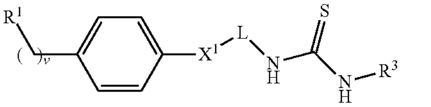

wherein:

$R^1$ is a chelating agent or a radionuclide complex thereof;

$X^1$ is absent, —O—, —S—, —S(═O)—, —$S(═O)_2$—, —$NR^a$—, —C(═O)—, —$NR^a$C(═O)—, —C(═O)$NR^a$—, —($C_1$-$C_6$alkylene)-$X^2$—, or —($C_4$-$C_{20}$polyethylene glycol)-$X^2$—;

$X^2$ is absent, —C(═O)—, —$NR^a$C(═O)—, —C(═O)$NR^a$—, or —C(═O)$X^4$—;

each $R^a$ is independently selected from hydrogen and $C_1$-$C_4$ alkyl;

$X^4$ is —$NR^a$— or —$NR^aS(═O)_2$—;

L is an optional linker;

—NH—$R^3$ is the polypeptide; and v is 1, 2, 3, or 4.

In some embodiments, $R^2$ is a moiety that is capable of reacting with a thiol (—SH) of a polypeptide $R^3$ and comprises a maleimide group, a haloacetamide group, a haloacetyl group, a haloacetate group, a pyrdinylthio group, a vinylcarbonyl group, an aziridinyl group, a disulfide group, an acetylene group, a hydroxsuccinimide group or a thiol group.

In some embodiments, $R^2$ is a moiety that is capable of reacting with a thiol (—SH) of the polypeptide $R^3$ and —$R^2$-$R^3$ comprises:

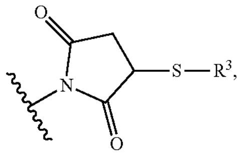
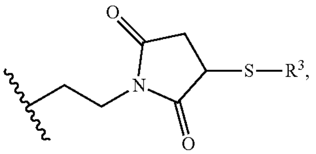
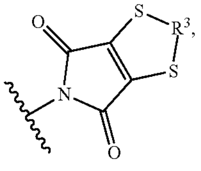
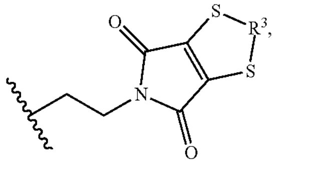

-continued

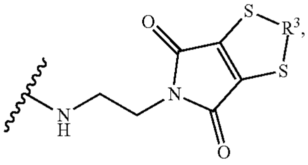

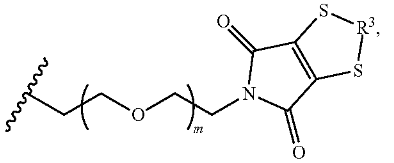

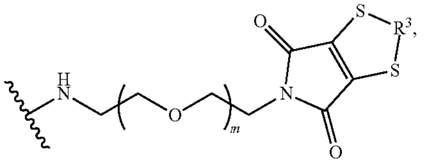

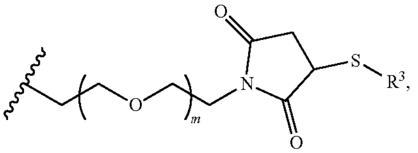

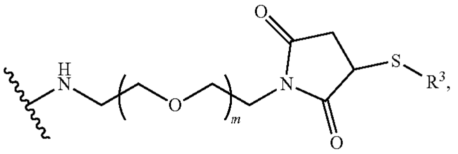

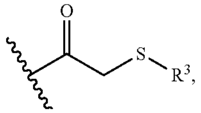 or 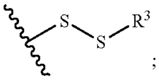 ;

wherein m is 0, 1, 2, 3, 4, or 5.

In some embodiments, the immunoconjugate by Formula (IIa) or Formula (IIb), or a pharmaceutically acceptable salt thereof:

Formula (IIa)

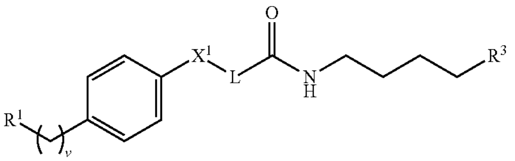

Formula (IIb)

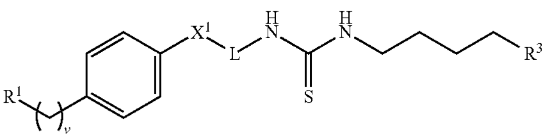

wherein:

—$NHCH_2CH_2CH_2CH_2$— is the side chain of a lysine residue of the polypeptide $R^3$.

In some embodiments, the immunoconjugate is represented by any one of Formulas (VI)-(IX) or a pharmaceutically acceptable salt thereof:

Formula (VI)

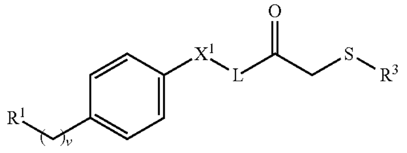

Formula (VII)

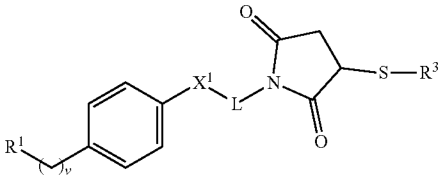

Formula (VIII)

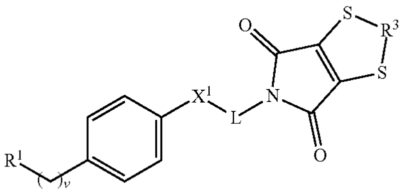

Formula (IX)

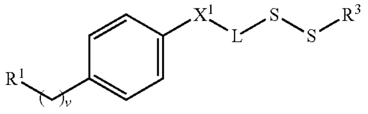

wherein:

$R^1$ is a chelating agent or a radionuclide complex thereof;

$X^1$ is absent, —O—, —S—, —S(═O)—, —S(═O)$_2$—, —NR$^a$—, —C(═O)—, —NR$^a$C(═O)—, —C(═O)NR$^a$—, —($C_1$-$C_6$alkylene)-$X^2$—, or —($C_4$-$C_2$polyethylene glycol)-$X^2$—;

$X^2$ is absent, —C(═O)—, —NR$^a$C(═O)—, —C(═O)NR$^a$—, or —C(═O)$X^4$—;

each $R^a$ is independently selected from hydrogen and $C_1$-$C_4$alkyl;

$X^4$ is —NR$^a$— or —NR$^a$S(═O)$_2$—;

L is an optional linker;

—S—$R^3$ is the polypeptide; and v is 1, 2, 3, or 4.

In some embodiments, $R^1$ is:

1,4,7,10-tetraazacyclododecane-1,4,7,10-tetraacetic acid (DOTA);

1,4,7,10-tetraazacyclododecane-1,4,7-triacetic acid (DO3A);

1,4,7,10-tetraazacyclododecane-1,7-diacetic acid (DO2A);

α,α',α",α'"-tetramethyl-1,4,7,10-tetraazacyclododecane-1,4,7,10-tetraacetic acid (DOTMA);

1,4,7,10-tetrakis(carbamoylmethyl)-1,4,7,10-tetraazacyclododecane (DOTAM);

1,4,7,10-tetraazacyclododecane-1,4,7,10-tetrapropionic acid (DOTPA);

2,2',2"-(10-(2-amino-2-oxoethyl)-1,4,7,10-tetraazacyclododecane-1,4,7-triyl)triacetic acid;

6,6'-(((pyridine-2,6-diylbis(methylene))bis((carboxymethyl)azanediyl))-bis(methylene))dipicolinic acid ($H_4$pypa);

6,6',6",6'"-(((pyridine-2,6-diylbis(methylene))bis(azanetriyl))tetrakis(methvlene))-tetrapicolinic acid ($H_4$py4pa);

10-((6-carboxypyridin-2-yl)methyl)-1,4,7,10-tetra-azacyclododecane-1,4,7-triacetic acid (DO3Apic); or 3,6,9,12-tetrakis(carboxymethyl)-3,6,9,12-tetraazatetradecanedioic acid (TTHA).

In some embodiments, $R^1$ is a chelating moiety or a radionuclide complex thereof, wherein the chelating moiety is:

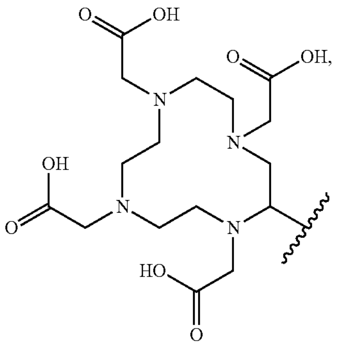

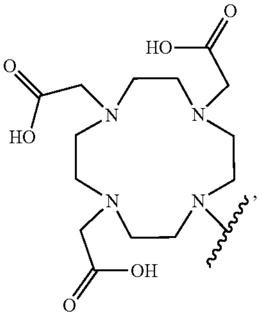

, or

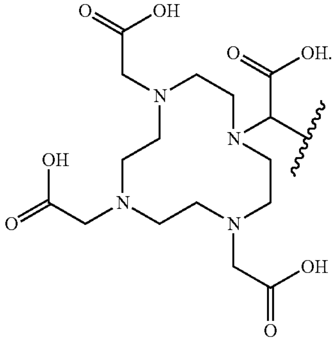

In some embodiments, $X^1$ is absent, —O—, —S—, —NR$^a$—, —C(═O)—, —NR$^a$C(═O)—, or —C(═O)NR$^a$—; or $X^1$ is —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2$—$X^2$—, —$CH_2CH_2$—$X^2$—, —$CH_2CH_2CH_2$—$X^2$—, —$CH_2CH_2CH_2CH_2$-$X^2$-, —$CH_2CH_2CH_2CH_2CH_2$—$X^2$—, or —$CH_2CH_2CH_2CH_2CH_2CH_2$—$X^2$—.

In some embodiments, $X^1$ is —$CH_2CH_2$— or —$CH_2CH_2$—$X^2$—;

$X^2$ is —C(═O)$X^4$—; and $X^4$ is —NH—, —N($CH_3$)—, or —N($CH_2CH_3$)—.

In some embodiments, $X^1$ is —$CH_2CH_2$—C(═O)N($CH_3$)— or —$CH_2CH_2$—C(═O)N($CH_2CH_3$)—.

In some embodiments,

L is absent, -$L^2$-$L^4$-, or -$L^1$-$L^2$-$L^3$-$L^4$-$L^5$;

$L^1$ is absent, unsubstituted or substituted $C_1$-$C_{20}$ alkylene, unsubstituted or substituted $C_1$-$C_{20}$ heteroalkylene, $C_4$-$C_{20}$ polyethylene glycol, unsubstituted or substituted $C_3$-$C_8$ cycloalkylene, unsubstituted or substituted monocyclic $C_3$-$C_8$heterocycloalkylene, unsubstituted or substituted phenylene, or unsubstituted or substituted monocyclic heteroarylene;

$L^2$ is absent, unsubstituted or substituted $C_1$-$C_{10}$alkylene, —C(═O)NR$^4$-(unsubstituted or substituted $C_1$-$C_{10}$(alkylene)-, unsubstituted or substituted $C_1$-$C_{10}$alkylene, —NR$^4$C(═O)-(unsubstituted or substituted $C_1$-$C_{10}$alkylene)-, —C(═O)—$(CH_2CH_2O)_m$—$(CH_2)_p$—, —C(O)NR$^4$—$(CH_2CH_2O)_m$—$(CH_2)_p$—, —NR$^4$C(═O)—$(CH_2CH_2O)_m$—$(CH_2)_p$—, or —$(CH_2CH_2O)_m$—$(CH_2)_p$—;

each $R^4$ is independently selected from hydrogen and $C_1$-$C_6$alkyl;

each m is independently 1, 2, 3, 4, 5, 6, 7, 8, 9, 10, 11, or 12;

each p is independently 1, or 2;

$L^3$ is absent, —C(═O)-(unsubstituted or substituted $C_1$-$C_{10}$alkylene)-, —C(═O)NR$^4$-(unsubstituted or substituted $C_1$-$C_{10}$alkylene)-, —NR$^4$C(═O)-(unsubstituted or substituted $C_1$-$C_{10}$alkylene)-, —C(═O)—$(CH_2CH_2O)$—$(CH_2)_u$—, —C(═O)NR$^4$—$(CH_2CH_2O)_r$—$(CH_2)_u$—, —NR$^4$C(═O)—$(CH_2CH_2O)_t$—$(CH_2)_u$—, or —$(CH_2CH_2O)_t$—$(CH_2)_u$—;

each t is independently 1, 2, 3, 4, 5, 6, 7, 8, 9, 10, 11, or 12;

each u is independently 1 or 2;

$L^4$ is absent, —C(═O)-(unsubstituted or substituted $C_1$-$C_6$alkylene)-, —C(═O)NR$^4$-(unsubstituted or substituted $C_1$-$C_6$alkylene)-, —NR$^4$C(═O)-(unsubstituted or substituted $C_1$-$C_6$alkylene)-, —C(═O)—$(CH_2CH_2O)_n$—$(CH_2)_q$—, —C(═O)NR$^4$—$(CH_2CH_2O)_n$—$(CH_2)_q$—, —NR$^4$C(═O)—$(CH_2CH_2O)_n$—$CH_2)_q$—, or —$(CH_2CH_2O_n$—$(CH_2)_q$;

$L^5$ is absent, —C(═O)—$(CH_2)_n$—, —C(═O)NR$^4$—$(CH_2)_n$—, —NR$^4$C(═O)—$(CH_2)_n$—, —C(═O)—$(CH_2CH_2O)_n$—$(CH_2)_q$—, —C(═O)NR$^4$—$(CH_2CH_2O)_n$—$(CH_2)_q$—, —NR$^4$C(═O)—$(CH_2CH_2O)_n$—$(CH_2)_q$—, —$(CH_2CH_2O)_n$—$(CH_2)_q$—, —C(═O)—$(OCH_2CH_2)_n$—, or —$(OCH_2CH_2)_n$—;

each n is independently 1, 2, 3, 4, 5, 6, 7, 8, 9, 10, 11, or 12;

each q is independently 0, 1, or 2;

wherein heteroalkylene is an alkylene where one carbon atom is replaced with —S(═O)(═NH)—, —S(═O)(═NR$^5$)—, —P(═O)OH—, —NHC(═N—CN)NH—, or —NHC(═N—R$^5$)NH—;

wherein when any one of -$L^1$-, -$L^2$-, -$L^3$-, -$L^4$-, and -$L^5$- is substituted then -$L^1$-, -$L^2$-, -$L^3$--$L^4$-, and -$L^5$- is substituted with 1, 2, 3, or 4 groups selected from halogen, —OH, —OR$^5$, —$CO_2$H, —NHR$^5$, —C(═O)NHR$^5$, —NHC(═O)R$^5$ and substituted $C_1$-$C_6$alkyl, wherein the substituted $C_1$-$C_6$alkyl is substituted with —OH, —$CO_2$H, —NHR$^5$, —C(═O)NHR$^5$, or —NHC(═O)R$^5$; and each $R^5$ is independently selected from $C_1$-$C_{10}$alkyl, $C_4$-$C_{30}$polyethylene glycol, unsubstituted or substituted arylene, and unsubstituted or substituted heteroarylene.

In some embodiments, $L^1$ is unsubstituted or substituted $C_1$-$C_6$ alkylene, unsubstituted or substituted $C_1$-$C_{10}$ heteroalkylene, $C_4$-$C_{20}$ polyethylene glycol, unsubstituted or substituted cyclohexylene, or unsubstituted or substituted phenylene.

In some embodiments, $L^5$ is absent, —NR$^4$C(═O)—$(CH_2)_n$—, —C(═O)—$(CH_2CH_2O)_n$—$(CH_2)_q$—, —C(═O)NR$^4$—$(CH_2CH_2O)_n$—$(CH_2)_q$—, or —NR$^4$C(═O)—$(CH_2CH_2O)_n$—$(CH_2)_q$—; and each q is independently 1, or 2.

In some embodiments, $L^1$ is absent, unsubstituted or substituted $C_1$-$C_6$alkylene, unsubstituted or substituted $C_1$-$C_{10}$heteroalkylene, $C_4$-$C_{20}$polyethylene glycol, unsubstituted or substituted cyclohexylene, or unsubstituted or substituted phenylene;

$L^2$ is absent, —C(═O)NR$^4$-(unsubstituted or substituted $C_1$-$C_{10}$alkylene)-, —NR$^4$C(═O)-(unsubstituted or substituted $C_1$-$C_{10}$alkylene)-, —C(═O)—$(CH_2CH_2O)_m$—$(CH_2)_p$—, —C(═O)NR$^4$—$(CH_2CH_2O)_m$—$(CH_2)_p$—, —NR$^4$C(═O)—$(CH_2CH_2O)_m$—$(CH_2)_p$—, or —$(CH_2CH_2O)_m$—$(CH_2)_p$—;

each m is independently 1, 2, 3, 4, 5, 6, 7, 8, 9, 10, 11, or 12;

each p is independently 1 or 2;

$L^4$ is absent;

$L^5$ is —NR$^4$C(═O)—$(CH_2)_n$—, —C(═O)—$(CH_4CH_2O)_n$—$(CH_2)_q$—, —C(═O)NR$^4$—$(CH_2CH_2O)_n$—$(CH_2)_q$—, or —NR$^4$C(═O)—$(CH_2CH_2O)_n$—$(CH_2)_q$—;

each n is independently 1, 2, 3, 4, 5, 6, 7, 8, 9, 10, 11, or 12; and each q is independently 1 or 2.

In some embodiments, $L^1$ is unsubstituted or substituted $C_1$-$C_6$ alkylene, unsubstituted or substituted $C_1$-$C_{10}$heteroalkylene, $C_4$-$C_{20}$polyethylene glycol, unsubstituted or substituted cyclohexylene, or unsubstituted or substituted phenylene;

$L^2$ is absent, —C(═O)NR$^4$-(unsubstituted or substituted $C_1$-$C_{10}$alkylene)-, —NR$^a$C(═O)-(unsubstituted or substituted $C_1$-$C_{10}$alkylene)-, —C(═O)—$(CH_2CH_2O)_m$—$(CH_2)_p$—, —C(═O)NR$^4$—$(CH_2CH_2O)_m$—$(CH_2)_p$—, NR$^4$C(═O)—$(CH_2CH_2O)_m$—$(CH_2)_p$—, or —$(CH_2CH_2O)_m$—$(CH_2)_p$—;

each m is independently 1, 2, 3, 4, 5, or 6;

each p is independently 1 or 2;

$L^4$ is absent;

$L^5$ is absent, —NR$^4$C(═O)—$(CH_2)_n$—, —C(═O)—$(CH_2CH_2O)_n$—$(CH_2)_q$, —C(═O)NR$^4$—$(CH_2CH_2O)_n$—$(CH_2)_q$—, or —NR$^4$C(═O)—$(CH_2CH_2O)_n$—$(CH_2)_q$—;

each n is independently 1, 2, 3, 4, 5, or 6; and each q is independently 1 or 2.

In some embodiments, $L^1$ is unsubstituted or substituted $C_1$-$C_6$ alkylene, unsubstituted or substituted $C_1$-$C_{10}$ heteroalkylene, $C_4$-$C_{20}$ polyethylene glycol, unsubstituted or substituted cyclohexylene, or unsubstituted or substituted phenylene;

$L^2$ is absent;

$L^4$ is absent;

$L^5$ is absent, —NR$^4$C(═O)—$(CH_2)_n$—, —C(═O)—$(CH_2CH_2O)_n$—$(CH_2)_q$—, —C(O)NR$^4$—$(CH_2CH_2O)_n$—$(CH_2)_q$—, or —NR$^4$C(═O)—$(CH_2CH_2O)_n$—$(CH_2)_q$—;

each n is independently 1, 2, 3, 4, 5, or 6; and each q is independently 1 or 2.

In some embodiments, the immunoconjugate is represented by Formula (II) or a pharmaceutically acceptable salt thereof:

Formula (II)

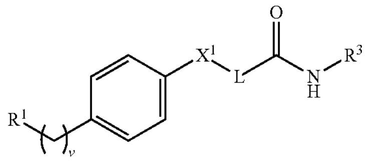

wherein:

$X^1$ is absent, —C(=O)NH—, —C(=O)N($CH_3$)—, —C(=O)N($CH_2CH_3$)—, —$CH_2$—C(=O)NH—, —$CH_2$—C(=O)N($CH_3$)—, —$CH_2$—C(=O)N($CH_2CH_3$)—, $CH_2CH_2$—C(=O)NH—, —$CH_2CH_2$—C(=O)N($CH_3$)— or —$CH_2CH_2$—C(=O)N($CH_2CH_3$)—;

L is -$L^2$-$L^4$-;

$L^2$ is unsubstituted or substituted $C_1$-$C_{10}$alkylene, —C(=O)$NR^4$-(unsubstituted or substituted $C_1$-$C_{10}$alkylene)-, unsubstituted or substituted $C_1$-$C_{10}$alkylene, —$NR^4$C(=O)-(unsubstituted or substituted $C_1$-$C_{10}$alkylene)-, —C(=O)—($CH_2CH_2O$)$_m$—($CH_2$)$_p$—, —C(=O)$NR^4$—($CH_2CH_2O$)$_m$—($CH_2$)$_p$—, —$NR^4$C(=O)—($CH_2CH_2O$)$_m$—($CH_2$)$_p$—, or —($CH_2CH_2O$)$_m$—($CH_2$)$_p$—;

each m is independently 1, 2, 3, 4, 5, 6, 7, 8, 9, 10, 11, or 12;

each p is independently 0, 1, or 2

$L^4$ is —C(=O)—($CH_2$)$_n$—, —C(=O)$NR^4$—($CH_2$)$_n$—, —$NR^4$C(=O)—($CH_2$)$_n$—, —C(=O)—($CH_2CH_2O$)$_n$—($CH_2$)$_q$—, —C(=O)$NR^4$—($CH_2CH_2O$)$_n$—($CH_2$)$_q$—, —$NR^4$C(=O)—($CH_2CH_2O$)$_n$—($CH_2$)$_p$—, —($CH_2CH_2O$)$_n$—($CH_2$)$_q$—, —C(=O)—($OCH_2CH_2$)$_n$—, or —($OCH_2CH_2$)$_2$—;

each n is independently 1, 2, 3, 4, 5, 6, 7, 8, 9, 10, 11, or 12; and each q is independently 0, 1, or 2.

$L^4$ is —C(=O)$NR^4$—($CH_2$)$_n$—, —$NR^4$C(=O)—($CH_2$)$_n$—, —C(=O)$NR^4$—($CH_2CH_2O$)$_n$—($CH_2$)$_q$—, or —$NR^4$C(=O)—($CH_2CH_2O$)$_n$—($CH_2$)$_q$—;

each n is independently 1, 2, 3, 4, 5, or 6; and each q is 2.

In some embodiments, $L^2$ is unsubstituted $C_1$-$C_{10}$alkylene or —($CH_2CH_2O$)$_m$—($CH_2$)$_p$—; and $L^4$ is —$NR^4$C(=O)—($CH_2$)$_n$— or —$NR^4$C(=O)—($CH_2CH_2O$)$_n$—($CH_2$)$_q$—.

In some embodiments, $X^1$ is absent, —$CH_2$—, or —$CH_2CH_2$—;

L is -$L^2$-$L^4$-;

$L^2$ is —C(=O)$NR^4$-(unsubstituted or substituted $C_1$-$C_{10}$alkylene)-, —$NR^4$C(=O)-(unsubstituted or substituted $C_1$-$C_{10}$alkylene)-, —C(=O)—($CH_2CH_2O$)$_m$—($CH_2$)$_p$—, —C(=O)$NR^4$—($CH_2CH_2O$)$_m$—($CH_2$)$_p$—, or —$NR^4$C(=O)—($CH_2CH_2O$)$_m$—($CH_2$)$_p$—; and $L^4$ is —C(=O)—($CH_2$)$_n$—, —C(=O)$NR^4$—($CH_2$)$_n$—, —$NR^4$C(=O)—($CH_2$)$_n$—, —C(=O)—($CH_2CH_2O$)$_n$—($CH_2$)$_q$—, —C(=O)$NR^4$—($CH_2CH_2O$)$_n$—($CH_2$)$_q$—, —$NR^4$C(=O)—($CH_2CH_2O$)$_n$—($CH_2$)$_q$, —($CH_2CH_2O$)$_n$—($CH_2$)$_q$—, —C(=O)—($OCH_2CH_2$)$_n$—, or —($OCH_2CH_2$)$_n$.

In some embodiments,

L2 is —C(=O)$NR^4$-(unsubstituted or substituted $C_1$-$C_{10}$alkylene)-, or —C(=O)$NR^4$—($CH_2CH_2O$)$_m$—($CH_2$)$_p$— and $L^4$ is —$NR^4$C(=O)—($CH_2$)$_n$—, or —$NR^4$C(=O)—($CH_2CH_2O$)$_n$—($CH_2$)$_q$.

In some embodiments, each $R^a$ is independently selected from $C_1$-$C_6$ alkyl; and each $R^4$ is independently selected from $C_1$-$C_6$ alkyl.

In some embodiments, $X^1$-L is:

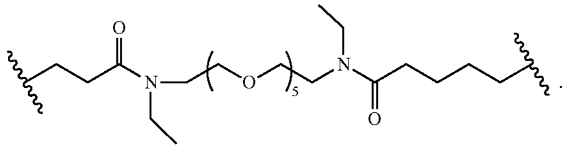

In some embodiments, v is 1; and

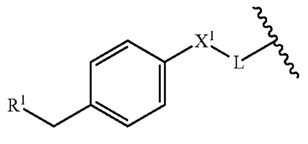

is:

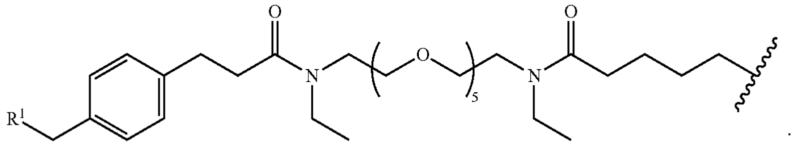

In some embodiments, $X^1$ is —C(=O)NH—, —C(=O)N($CH_3$)—, —C(=O)N($CH_2CH_3$)—, —$CH_2$—C(=O)NH—, —$CH_2$—C(=O)N($CH_3$)—, —$CH_2$—C(=O)N($CH_2CH_3$)—, —$CH_2CH_2$—C(=O)NH—, —$CH_2CH_2$—C(=O)N($CH_3$)— or —$CH_2CH_2$—C(=O)N($CH_2CH_3$)—;

L is -$L^2$-$L^4$-;

$L^2$ is unsubstituted or substituted $C_1$-$C_{10}$alkylene, unsubstituted or substituted $C_1$-$C_{10}$alkylene, or —($CH_2CH_2O$)$_m$—($CH_2$)$_p$—;

each m is independently 1, 2, 3, 4, 5, or 6;

each p is 2;

In some embodiments, the immunoconjugate is represented by Formula (V) or a pharmaceutically acceptable salt thereof:

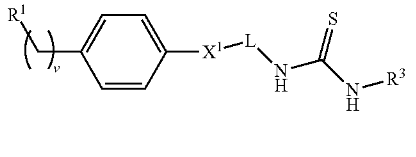

Formula (V) wherein, $R^1$ is a chelating agent or a radionuclide complex thereof; $X^1$ is absent, —O—, —S—, —S(=O)—, —S(=O)$_2$, —NR$^a$—, —C(=O)—, —NR$^a$C(=O)—, —C(=O)NR$^a$—, —($C_1$-$C_6$alkylene)-X$^2$—, or —($C_4$-$C_{20}$polyethylene glycol)-X$^2$—; X$^2$ is absent, —C(=O)—, —NR$^a$C(=O)—, —C(=O)NR$^a$—, or —C(=O)X$^4$—; each R$^a$ is independently selected from hydrogen and $C_1$-$C_4$ alkyl; X$^4$ is —NR$^a$— or —NR$^a$S(=O)$_2$—; L is an optional linker; —NH—R$^3$ is the polypeptide; and v is 1, 2, 3, or 4.

In some embodiments, v is 1; and

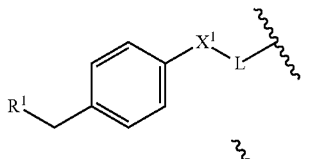

is:

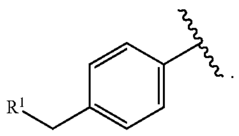

In some embodiments, v is 1; and

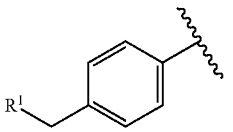

is:

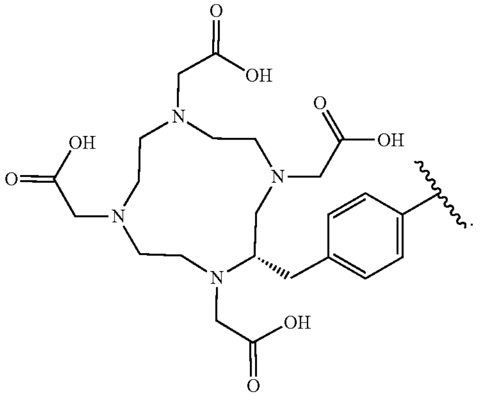

In some embodiments, v is 1; and

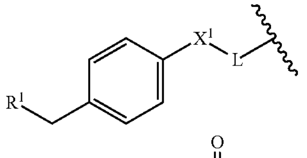

is:

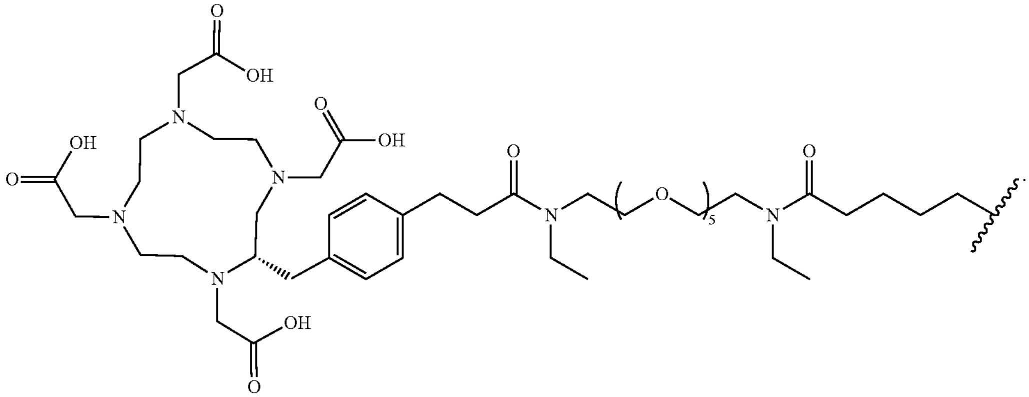

Disclosed herein, in some embodiments, are immunoconjugates prepared by conjugating the polypeptide (R$^3$) of any one of the embodiments disclosed herein to a chelating agent or a radionuclide complex thereof (R$^1$).

In some embodiments, the chelating agent or the radionuclide complex thereof comprises:

1,4,7,10-tetraazacyclododecane-1,4,7,10-tetraacetic acid (DOTA);

1,4,7,10-tetraazacyclododecane-1,4,7-triacetic acid (DO3A);

1,4,7,10-tetraazacyclododecane-1,7-diacetic acid (DO2A);

α,α',α",α'"-tetramethyl-1,4,7,10-tetraazacyclododecane-1,4,7,10-tetraacetic acid (DOTMA);

1,4,7,10-tetrakis(carbamoylmethyl)-1,4,7,10-tetraazacyclododecane (DOTAM);

1,4,7,10-tetraazacyclododecane-1,4,7,10-tetrapropionic acid (DOTPA);

2,2',2"-(10-(2-amino-2-oxoethyl)-1,4,7,10-tetraazacyclododecane-1,4,7-triyl)triacetic acid;

6,6'-(((pyridine-2,6-diylbis(methylene))bis((carboxymethyl)azanediyl))-bis(methylene))dipicolinic acid (H4pypa);

6,6',6",6'"-(((pyridine-2,6-diylbis(methylene))bis(azanetriyl))tetrakis(methylene))-tetrapicolinic acid (H4py4pa);

10-((6-carboxypyridin-2-yl)methyl)-1,4,7,10-tetra-azacyclododecane-1,4,7-triacetic acid (DO3Apic); or 3,6,9,12-tetrakis(carboxymethyl)-3,6,9,12-tetraazatetradecanedioic acid (TTHA).

In some embodiments, the chelating agent is selected from the list consisting of: DOTMA, DOTPA, DO3AM-acetic acid, DOTP, DOTMP, DOTA-4AMP, CB-TE2A, NOTA, NOTP, TETPA, TETA, PEPA, H4Octapa, H2Dedpa, DO2P, EDTA, DTPA-BMA, 3,2,3-LI(HOPO), 3,2-HOPO, Neunpa, Octapa, PyPa, Porphyrin, Deferoxamine, DFO*, and combinations thereof.

In some embodiments, the chelating agent is DOTA. In some embodiments, the chelating agent is DOTAGA. In some embodiments, the chelating agent is Py4Pa.

In some embodiments, the chelating agent comprises a moiety (R$^2$) that is capable of reacting with an amine (—NH$_2$) of the polypeptide and comprises a tetrafluorophenyl ester, pentafluorophenyl ester, dinitrophenyl ester, succinimide ester, sulfosuccinimide ester, or isothiocyanate.

In some embodiments, the chelating agent comprises a moiety ($R^2$) that is capable of reacting with an amine ($—NH_2$) of the polypeptide and comprises:

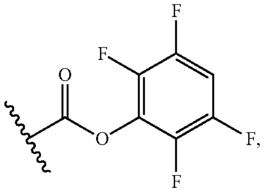

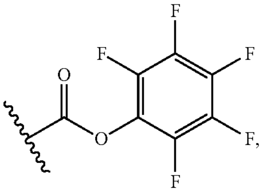

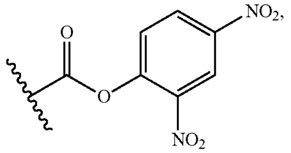

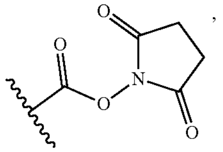

,

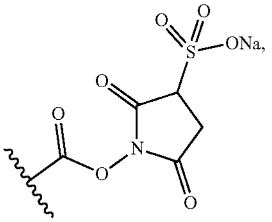

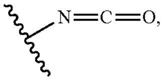

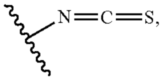

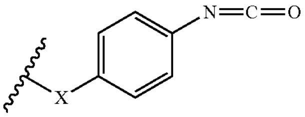

or

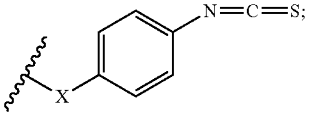

X is absent, —O—, —S—, —S(═O)—, $—S(O)_2—$, $—NR^a—$, —C(═O)—, $—NR^aC(O)—$, $—C(═O)NR^a—$, —C(═O)O—, —OC(═O)—, $—OC(═O)NR^a—$, $—NR^aC(═O)NR^a—$, $—NR^aC(═S)NR^a—$, $—NR^aC(═O)O—$; and each R is independently selected from hydrogen and $C_1$-$C_4$ alkyl.

In some embodiments, the chelating agent comprises a moiety ($R^2$) that is capable of reacting with a thiol (—SH) of the polypeptide $R^3$ and comprises a maleimide group, a haloacetamide group, a haloacetyl group, a haloacetate group, a pyrdinylthio group, a vinylcarbonyl group, an aziridinyl group, a disulfide group, an acetylene group, a hydroxysuccinimide group, or a thiol group.

In some embodiments, the chelating agent comprises a moiety ($R^2$) that is capable of reacting with a thiol (—SH) of the polypeptide $R^3$ and comprises:

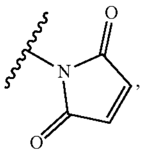

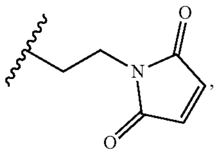

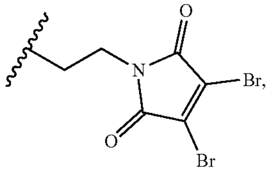

-continued

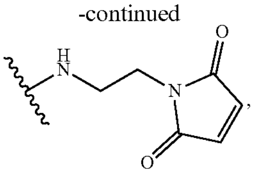

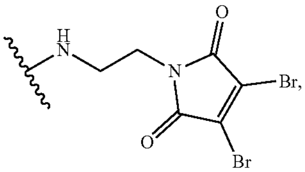

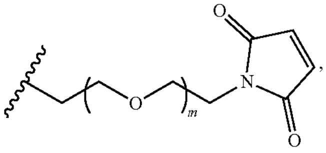

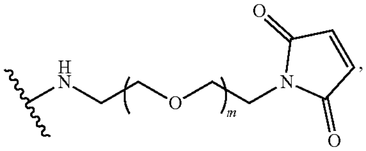

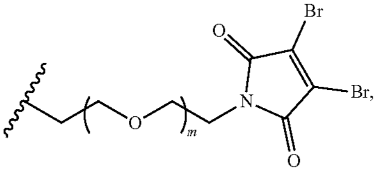

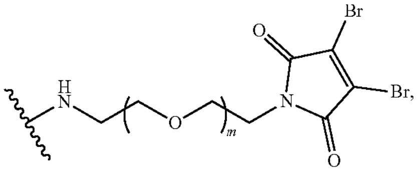

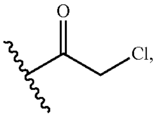

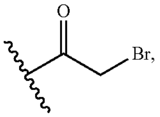

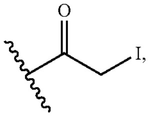

or

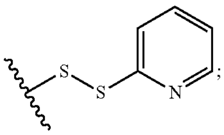

wherein m is 0, 1, 2, 3, 4, or 5.

In some embodiments, the immunoconjugate comprises a linker covalently linking the chelating agent or radionuclide complex thereof to the $R^2$ moiety.

In some embodiments, the linker is represented by:

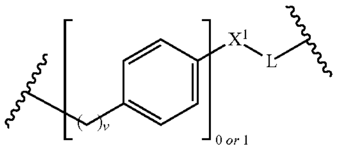

wherein:

$X^1$-L- is as defined in any one of the embodiments disclosed herein.

In some embodiments, the immunoconjugate is prepared by conjugating the polypeptide ($R^3$) of any one the embodiments disclosed herein to a chelating agent or a radionuclide complex thereof ($R^1$) represented by Formula (VIa) or a pharmaceutically acceptable salt thereof:

Formula (VIa)

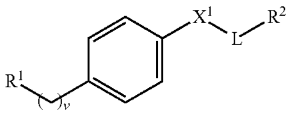

wherein:

$R^1$ is a chelating agent or a radionuclide complex thereof; and $X^1$-L- is as defined in any one of the embodiments disclosed herein.

In some embodiments, the immunoconjugate is prepared by conjugating the polypeptide ($R^3$) of any one of the embodiments disclosed herein to a chelating agent or a radionuclide complex thereof ($R^1$) represented by Formula (VIb) or a pharmaceutically acceptable salt thereof:

Formula (VIb)

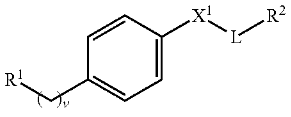

wherein:

$R^1$ is a chelating agent or a radionuclide complex thereof; and $X^1$-L- is as defined in any one of the embodiments disclosed herein.

In some embodiments, the immunoconjugate is prepared by conjugating the polypeptide ($R^3$) of any one of the embodiments disclosed herein to a chelating agent or a radionuclide complex thereof ($R^1$) represented by Formula (VIb) or a pharmaceutically acceptable salt thereof:

Formula (VIb)

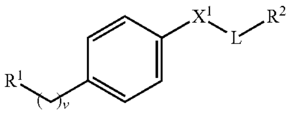

wherein:

$R^1$ is a chelating agent or a radionuclide complex thereof;

$X^1$-L- is as defined in any one of the embodiments disclosed herein; and $R^2$ is a moiety that is capable of reacting with an amine ($—NH_2$) of the polypeptide and comprises:

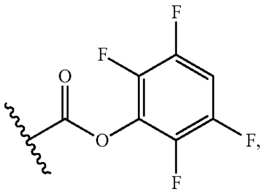

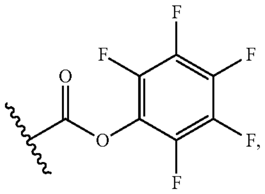

-continued

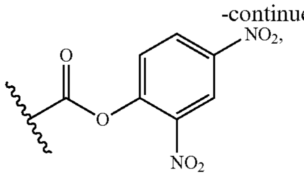

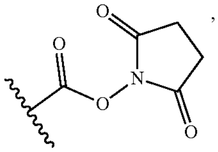

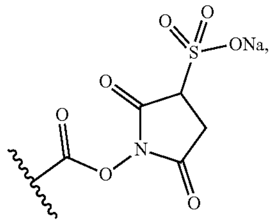

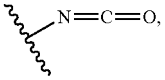

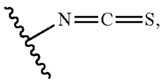

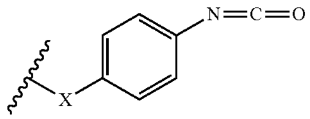

or

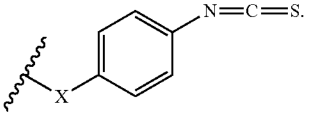

In some embodiments, $R^2$ is a moiety that is capable of reacting with an amine ($—NH_2$) of the polypeptide and comprises:

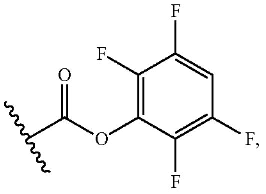

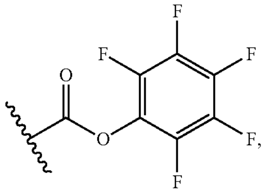

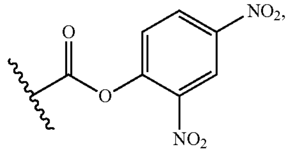

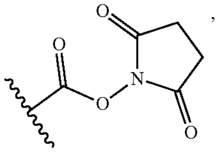

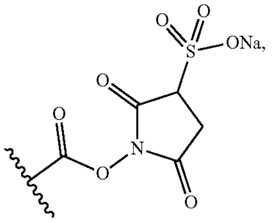

or

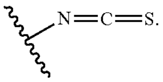

In some embodiments, $R^2$ is a moiety that is capable of reacting with an amine ($—NH_2$) of the polypeptide and comprises:

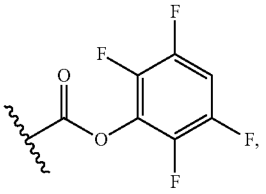

or

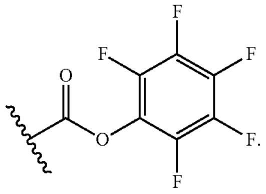

In some embodiments, $R^2$ is a moiety that is capable of reacting with an amine (—$NH_2$) of the polypeptide and comprises —SCN.

In some embodiments, the immunoconjugate is prepared by conjugating the polypeptide ($R^3$) of any one of the embodiments disclosed herein to a chelating agent or a radionuclide complex thereof ($R^1$) represented by Formula (VIb) or a pharmaceutically acceptable salt thereof:

Formula (VIb)

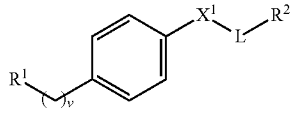

wherein:
v is 1;

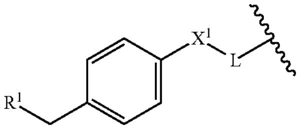
is:

Formula (VIb)

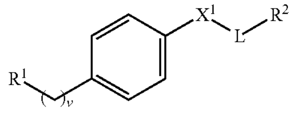

wherein:
v is 1;

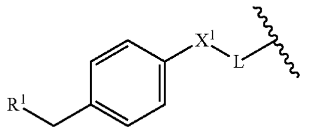
is:

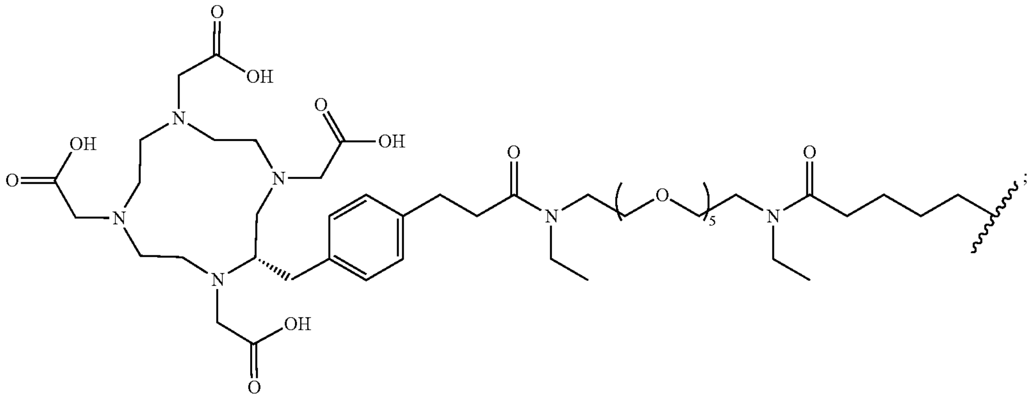
;

$R^2$ is a moiety that is capable of reacting with an amine (—$NH_2$) of the polypeptide and comprises:

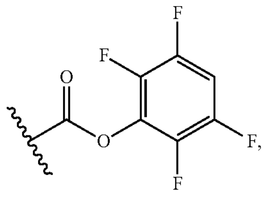
or
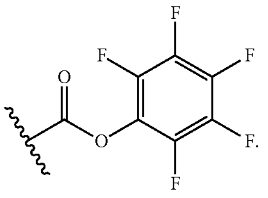

In some embodiments, the immunoconjugate is prepared by conjugating the polypeptide ($R^3$) of any one the embodiments disclosed herein to a chelating agent or a radionuclide complex thereof ($R^1$) represented by Formula (VIb) or a pharmaceutically acceptable salt thereof:

-continued

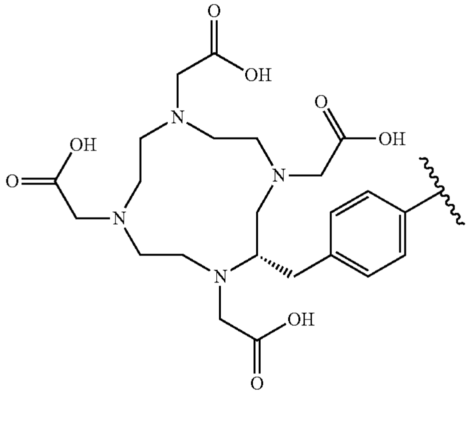
;

$R^2$ is a moiety that is capable of reacting with an amine (—$NH_2$) of the polypeptide and comprises:

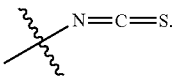

In some embodiments, the immunoconjugate is prepared by conjugating the polypeptide ($R^3$) of any one of the embodiments disclosed herein to TFP-Ad-PEG5-DOTAGA, p-SCN-Bn-DOTA, p-SCN-Ph-Et-Py4Pa, and TFP-Ad-PEG5-Ac-Py4Pa.

In some embodiments, the immunoconjugate is prepared by conjugating the polypeptide ($R^3$) of any one of the embodiments disclosed herein to TFP-Ad-PEG5-DOTAGA.

In some embodiments, the immunoconjugate is prepared by conjugating the polypeptide ($R^3$) of any one of the embodiments disclosed herein to p-SCN-Bn-DOTA.

In some embodiments, the immunoconjugate is prepared by conjugating the polypeptide ($R^3$) of any one of the embodiments disclosed herein to p-SCN-Ph-Et-Py4Pa.

In some embodiments, the immunoconjugate is prepared by conjugating the polypeptide ($R^3$) of any one of the embodiments disclosed herein to TFP-Ad-PEG5-Ac-Py4Pa.

In some embodiments, the chelating agent is coupled to the antigen binding region and/or the immunoglobulin heavy chain constant region by a linker.

In some embodiments, the radionuclide complex comprises a radionuclide. In some embodiments, the radionuclide is a diagnostic or a therapeutic radionuclide. In some embodiments, the radionuclide is an Auger electron-emitting radionuclide, an α-emitting radionuclide, a β-emitting radionuclide, or a γ-emitting radionuclide. In some embodiments, the radionuclide is an α-emitting radionuclide.

In some embodiments, the radionuclide is an Auger electron-emitting radionuclide that is 111-indium ($^{111}In$), 67-gallium ($^{67}Ga$), 68-gallium ($^{68}Ga$), 99m-technetium ($^{99m}Tc$), or 195m-platinum ($^{195m}Pt$); or the radionuclide is an α-emitting radionuclide that is 225-actinium ($^{225}Ac$), 213-bismuth ($^{213}Bi$), 223-Radium ($^{223}Ra$), or 212-lead ($^{212}Pb$); or the radionuclide is a β-emitting radionuclide that is 90-yttrium ($^{90}Y$), 177-lutetium ($^{177}Lu$), 186-rhenium ($^{186}Re$), 188-rhenium ($^{188}Re$), 64-copper ($^{64}Cu$), 67-copper ($^{67}Cu$), 153-samarium ($^{153}Sm$), 89-strontium ($^{89}Sr$), 198-gold ($^{198}Au$), 169-Erbium ($^{169}Er$), 165-dysprosium ($^{165}Dy$), 99m-technetium ($^{99m}Tc$), 89-zirconium ($^{89}Zr$), or 52-manganese ($^{52}Mn$); or the radionuclide is a γ-emitting radionuclide that is 60-cobalt ($^{60}Co$), 103-pallidum ($^{103}Pd$), 137-cesium ($^{137}Cs$), 169-ytterbium ($^{169}Yb$), 192-iridium ($^{192}Ir$, or 226-radium ($^{226}Ra$).

In some embodiments, the radionuclide is suitable for positron emission tomography (PET) analysis, single-photon emission computerized tomography (SPECT), or magnetic resonance imaging (MRI). In some embodiments, the radionuclide is 225-actinium ($^{225}Ac$).

In some embodiments, the immunoconjugate of any one of the embodiments disclosed herein further comprises a pharmaceutically acceptable excipient, carrier or diluent. In some embodiments, the immunoconjugate of any one of the embodiments disclosed is formulated for intravenous administration.

Disclosed herein, in some embodiments, are methods of targeting a radionuclide to a 5T4 expressing cancer or tumor cell of an individual, wherein the method comprises administering to the individual the immunoconjugate of any one of the embodiments disclosed herein.

Disclosed herein, in some embodiments, are methods of treating a cancer or tumor of an individual, wherein the method comprises administering to the individual the polypeptide or the immunoconjugate of any one of the embodiments disclosed herein.

Disclosed herein, in some embodiments, are methods of making the immunoconjugate of any one of the embodiments disclosed herein comprising complexing a radionuclide to the chelating agent coupled to the polypeptide.

Disclosed herein, in some embodiments, are host cells comprising a nucleic acid encoding the polypeptide of any one of the embodiments disclosed herein. Further disclosed herein, in some embodiments, are host cells comprising the nucleic acid. In some embodiments, the host cell comprises a eukaryotic cell. In some embodiments, the eukaryotic cell comprises a CHO cell. In some embodiments, the host cell comprises a prokaryotic cell.

Further disclosed herein, in some embodiments, are methods of making a polypeptide that binds 5T4 comprising culturing a host cell comprising a nucleic acid encoding the polypeptide of any one of the embodiments disclosed herein under conditions to sufficient to express and secret the polypeptide and recovering the polypeptide from the culture media.

Further disclosed herein, in some embodiments, are methods of making radioimmunoconjugates comprising complexing the immunoconjugates of any one of the embodiments disclosed herein to a radionuclide, thereby obtaining a radioimmunoconjugate.

DETAILED DESCRIPTION

Figure 1A:
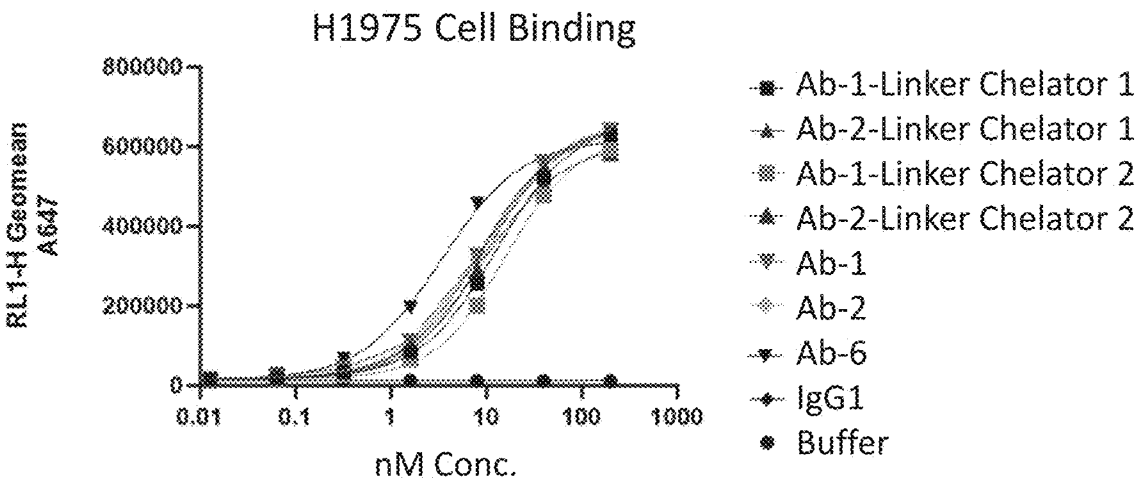
FIGS. 1A-1B show binding of 5T4 expressing NCI-H411975 cells by antibodies and conjugate antibodies of the present disclosure.

The present invention is described more fully hereinafter using illustrative, non-limiting embodiments, This invention may, however, be embodied in many different forms and should not be construed as to be limited to the embodiments set forth below. Rather, these embodiments are provided so that this disclosure is thorough and conveys the scope of the invention to those skilled in the art. In order that the present invention may be more readily understood, certain terms are defined below. Additional definitions may be found within the detailed description of the invention.

Polypeptides that Bind 5T4

Described and exemplified are polypeptides with binding regions that specifically bind to 5T4. These binding regions may be further incorporated into a polypeptide comprising an immunoglobulin hinge region, an immunoglobulin Fc region, or both (e.g., VHH-Fc). The VHH-Fcs of this disclosure may dimerize (through their respective Fc regions) to form a bivalent binding molecule. In some embodiments, the polypeptides bind to human 5T4. In some embodiments, the polypeptides bind to cynomolgus 5T4. In some embodiments, the 5T4 binding polypeptides comprise a heavy chain binding region, such as a VHH. In some embodiments, the 5T4 binding polypeptides do not comprise an immunoglobulin light chain.

Disclosed herein, in some embodiments, are polypeptides that bind 5T4, wherein the polypeptides comprise an immunoglobulin variable domain comprising: (i) a complementarity determining region 1 (CDR1) comprising the amino acid sequence of SEQ ID NO: 1; a complementarity determining region 2 (CDR2) comprising the amino acid sequence of SEQ ID NO: 2; and a complementarity determining region 3 (CDR3) comprising the amino acid sequence of SEQ ID NO: 3; (ii) a complementarity determining region 1 (CDR1) comprising the amino acid sequence of SEQ ID NO: 4; a complementarity determining region 2 (CDR2) comprising the amino acid sequence of SEQ ID NO: 5; and a complementarity determining region 3 (CDR3) comprising the amino acid sequence of SEQ ID NO: 6; (iii) a complementarity determining region 1 (CDR1) comprising the amino acid sequence of SEQ ID NO: 7; a complementarity determining region 2 (CDR2) comprising the amino acid sequence of SEQ ID NO: 8; and a complementarity determining region 3 (CDR3) comprising the amino acid sequence of SEQ ID NO: 9; or (iv) a complementarity determining region 1 (CDR1) comprising the amino acid sequence of SEQ ID NO: 10; a complementarity determining region 2 (CDR2) comprising the amino acid sequence of SEQ ID NO: 11; and a complementarity determining region 3 (CDR3) comprising the amino acid sequence of SEQ ID NO: 12. In some embodiments, the polypeptide comprises an immunoglobulin variable domain comprising a complementarity determining region 1 (CDR1) comprising the amino acid sequence of SEQ ID NO: 1; a complementarity determining region 2 (CDR2) comprising the amino acid sequence of SEQ ID NO: 2; and a complementarity determining region 3 (CDR3) comprising the amino acid sequence of SEQ ID NO: 3. In some embodiments, the polypeptide comprises an immunoglobulin variable domain comprising a complementarity determining region 1 (CDR1) comprising the amino acid sequence of SEQ ID NO: 4; a complementarity determining region 2 (CDR2) comprising the amino acid sequence of SEQ ID NO: 5; and a complementarity determining region 3 (CDR3) comprising the amino acid sequence of SEQ ID NO: 6. In some embodiments, the polypeptide comprises an immunoglobulin variable domain comprising a complementarity determining region 1 (CDR1) comprising the amino acid sequence of SEQ ID NO: 7; a complementarity determining region 2 (CDR2) comprising the amino acid sequence of SEQ ID NO: 8; and a complementarity determining region 3 (CDR3) comprising the amino acid sequence of SEQ ID NO: 9. In some embodiments, the polypeptide comprises an immunoglobulin variable domain comprising a complementarity determining region 1 (CDR1) comprising the amino acid sequence of SEQ ID NO: 10; a complementarity determining region 2 (CDR2) comprising the amino acid sequence of SEQ ID NO: 11; and a complementarity determining region 3 (CDR3) comprising the amino acid sequence of SEQ ID NO: 12.

In some embodiments, the immunoglobulin variable domain comprises at least 80%, 85%, 90%, 95%, 97%, 98%, 99%, or 100% sequence identity to SEQ ID NO: 25. In some embodiments, the immunoglobulin variable domain comprises at least 80% sequence identity to SEQ ID NO: 25. In some embodiments, the immunoglobulin variable domain comprises at least 85% sequence identity to SEQ ID NO: 25. In some embodiments, the immunoglobulin variable domain comprises at least 90% sequence identity to SEQ ID NO: 25. In some embodiments, the immunoglobulin variable domain comprises at least 95% sequence identity to SEQ ID NO: 25. In some embodiments, the immunoglobulin variable domain comprises at least 97% sequence identity to SEQ ID NO: 25. In some embodiments, the immunoglobulin variable domain comprises at least 98% sequence identity to SEQ ID NO: 25. In some embodiments, the immunoglobulin variable domain comprises at least 99% sequence identity to SEQ ID NO: 25. In some embodiments, the immunoglobulin variable domain comprises 100% sequence identity to SEQ ID NO: 25.

In some embodiments, the immunoglobulin variable domain comprises at least 80%, 85%, 90%, 95%, 97%, 98%, 99%, or 100% sequence identity to SEQ ID NO: 26. In some embodiments, the immunoglobulin variable domain comprises at least 80% sequence identity to SEQ ID NO: 26. In some embodiments, the immunoglobulin variable domain comprises at least 85% sequence identity to SEQ ID NO: 26. In some embodiments, the immunoglobulin variable domain comprises at least 90% sequence identity to SEQ ID NO: 26. In some embodiments, the immunoglobulin variable domain comprises at least 95% sequence identity to SEQ ID NO: 26. In some embodiments, the immunoglobulin variable domain comprises at least 97% sequence identity to SEQ ID NO: 26. In some embodiments, the immunoglobulin variable domain comprises at least 98% sequence identity to SEQ ID NO: 26. In some embodiments, the immunoglobulin variable domain comprises at least 99% sequence identity to SEQ ID NO: 26. In some embodiments, the immunoglobulin variable domain comprises 100% sequence identity to SEQ ID NO: 26.

Disclosed herein, in some embodiments, are polypeptides that bind 5T4, wherein the polypeptides comprise an immunoglobulin variable domain comprising: (i) a complementarity determining region 1 (CDR1) comprising the amino acid sequence of SEQ ID NO: 13; a complementarity determining region 2 (CDR2) comprising the amino acid sequence of SEQ ID NO: 14; and a complementarity determining region 3 (CDR3) comprising the amino acid sequence of SEQ ID NO: 15; (ii) a complementarity determining region 1 (CDR1) comprising the amino acid sequence of SEQ ID NO: 16; a complementarity determining region 2 (CDR2) comprising the amino acid sequence of SEQ ID NO: 17; and a complementarity determining region 3 (CDR3) comprising the amino acid sequence of SEQ ID NO: 18; (iii) a complementarity determining region 1 (CDR1) comprising the amino acid sequence of SEQ ID NO: 19; a complementarity determining region 2 (CDR2) comprising the amino acid sequence of SEQ ID NO: 20; and a complementarity determining region 3 (CDR3) comprising the amino acid sequence of SEQ ID NO: 212 or (iv) a complementarity determining region 1 (CDR1) comprising the amino acid sequence of SEQ ID NO: 22; a complementarity determining region 2 (CDR2) comprising the amino acid sequence of SEQ ID NO: 23; and a complementarity determining region 3 (CDR3) comprising the amino acid sequence of SEQ ID NO: 24. In some embodiments, the polypeptide comprises an immunoglobulin variable domain comprising a complementarity determining region 1 (CDR1) comprising the amino acid sequence of SEQ ID NO: 13; a complementarity determining region 2 (CDR2) comprising the amino acid sequence of SEQ ID NO: 14; and a complementarity determining region 3 (CDR3) comprising the amino acid sequence of SEQ ID NO: 15. In some embodiments, the polypeptide comprises an immunoglobulin variable domain comprising a complementarity determining region 1 (CDR1) comprising the amino acid sequence of SEQ ID NO: 16; a complementarity determining region 2 (CDR2) comprising the amino acid sequence of SEQ ID NO: 17; and a complementarity determining region 3 (CDR3) comprising the amino acid sequence of SEQ ID NO: 18. In some embodiments, the polypeptide comprises an immunoglobulin variable domain comprising a complementarity determining region 1 (CDR1) comprising the amino acid sequence of SEQ ID NO: 19; a complementarity determining region 2 (CDR2) comprising the amino acid sequence of SEQ ID NO: 20; and a complementarity determining region 3 (CDR3) comprising the amino acid sequence of SEQ ID NO: 21. In some embodiments, the polypeptide comprises an immunoglobulin variable domain comprising a complementarity determining region 1 (CDR1) comprising the amino acid sequence of SEQ ID NO: 22; a complementarity determining region 2 (CDR2) comprising the amino acid sequence of SEQ ID NO: 23; and a complementarity determining region 3 (CDR3) comprising the amino acid sequence of SEQ ID NO: 24.

In some embodiments, the immunoglobulin variable domain comprises at least 80%, 85%, 90%, 95%. 97%, 98%, 99%, or 100% sequence identity to SEQ ID NO: 27. In some embodiments, the immunoglobulin variable domain comprises at least 80% sequence identity to SEQ ID NO: 27. In some embodiments, the immunoglobulin variable domain comprises at least 85% sequence identity to SEQ ID NO: 27. In some embodiments, the immunoglobulin variable domain comprises at least 90% sequence identity to SEQ ID NO: 27. In some embodiments, the immunoglobulin variable domain comprises at least 95% sequence identity to SEQ ID NO: 27. In some embodiments, the immunoglobulin variable domain comprises at least 97% sequence identity to SEQ ID NO: 27. In some embodiments, the immunoglobulin variable domain comprises at least 98% sequence identity to SEQ ID NO: 27. In some embodiments, the immunoglobulin variable domain comprises at least 99% sequence identity to SEQ ID NO: 27. In some embodiments, the immunoglobulin variable domain comprises 100% sequence identity to SEQ ID NO: 27.

In some embodiments, the immunoglobulin variable domain comprises at least 80%, 85%, 90%, 95%, 97%, 98%, 99%, or 100% sequence identity to SEQ ID NO: 28. In some embodiments, the immunoglobulin variable domain comprises at least 80% sequence identity to SEQ ID NO: 28. In some embodiments, the immunoglobulin variable domain comprises at least 85% sequence identity to SEQ ID NO: 28. In some embodiments, the immunoglobulin variable domain comprises at least 90% sequence identity to SEQ ID NO: 28. In some embodiments, the immunoglobulin variable domain comprises at least 95% sequence identity to SEQ ID NO: 28. In some embodiments, the immunoglobulin variable domain comprises at least 97% sequence identity to SEQ ID NO: 28. In some embodiments, the immunoglobulin variable domain comprises at least 98% sequence identity to SEQ ID NO: 28. In some embodiments, the immunoglobulin variable domain comprises at least 99% sequence identity to SEQ ID NO: 28. In some embodiments, the immunoglobulin variable domain comprises 100% sequence identity to SEQ ID NO: 28.

In some embodiments, the immunoglobulin variable domain comprises at least 80%, 85%, 90%, 95%, 97%, 98%, 99%, or 100% sequence identity to SEQ ID NO: 29. In some embodiments, the immunoglobulin variable domain comprises at least 80% sequence identity to SEQ ID NO: 29. In some embodiments, the immunoglobulin variable domain comprises at least 85% sequence identity to SEQ ID NO: 29. In some embodiments, the immunoglobulin variable domain comprises at least 90% sequence identity to SEQ ID NO: 29. In some embodiments, the immunoglobulin variable domain comprises at least 95% sequence identity to SEQ ID NO: 29. In some embodiments, the immunoglobulin variable domain comprises at least 97% sequence identity to SEQ ID NO: 29. In some embodiments, the immunoglobulin variable domain comprises at least 98% sequence identity to SEQ ID NO: 29. In some embodiments, the immunoglobulin variable domain comprises at least 99% sequence identity to SEQ ID NO: 29. In some embodiments, the immunoglobulin variable domain comprises 100% sequence identity to SEQ ID NO: 29.

In some embodiments, the polypeptide of any one of the embodiments disclosed herein comprises an Fc domain and/or an immunoglobulin hinge region. In some embodiments, the Fc domain and/or hinge region comprises an amino acid sequence having at least about 80%, 85%, 90%, 95%, 97%, 98%, 99%, or 100% sequence identity to SEQ ID NO: 47. In some embodiments, the Fc domain is a human Fc domain. In some embodiments, the human Fc domain is an IgG1 Fc domain. In some embodiments, the human Fc domain is an IgG4 Fc domain. In some embodiments, the Fc domain comprises one or more amino acid residue alterations that reduce effector function of polypeptide. In some embodiments, the one or more amino acid residue alterations comprises L234A, L235E, G237A, A330S, and P331S. In some embodiments, the Fc domain comprises one or more amino acid residues that alter binding of the polypeptide to the neonatal Fe receptor (FcRn), thereby reducing the serum half-life of the polypeptide. In some embodiments, the one or more amino acid residues that alter binding of the polypeptide to the neonatal Fc receptor (FcRn) comprise H310A, H31 OD, 1H310E, 11310Q, H435A, H435Q, and combinations thereof, per EU numbering.

Disclosed herein, in some embodiments, are polypeptides comprising an immunoglobulin variable domain having at least 80%, 85%, 90%, 95%, 97%, 98%, 99%, or 100% sequence identity to any one of SEQ ID NOs: 25-29. In some embodiments, the polypeptide comprises an immunoglobulin variable domain having at least 80% sequence identity to SEQ ID NO: 25. In some embodiments, the polypeptide comprises an immunoglobulin variable domain having at least 85% sequence identity to SEQ ID NO: 25. In some embodiments, the polypeptide comprises an immunoglobulin variable domain having at least 90% sequence identity to SEQ ID NO: 25. In some embodiments, the polypeptide comprises an immunoglobulin variable domain having at least 95% sequence identity to SEQ ID NO: 25. In some embodiments, the polypeptide comprises an immunoglobulin variable domain having at least 97% sequence identity to SEQ ID NO: 25. In some embodiments, the polypeptide comprises an immunoglobulin variable domain having at least 98% sequence identity to SEQ ID NO: 25. In some embodiments, the polypeptide comprises an immunoglobulin variable domain having at least 99% sequence identity to SEQ ID NO: 25. In some embodiments, the polypeptide comprises an immunoglobulin variable domain having 100% sequence identity to SEQ ID NO: 25. In some embodiments, the polypeptide comprises an immunoglobulin variable domain having at least 80% sequence identity to SEQ ID NO: 26. In some embodiments, the polypeptide comprises an immunoglobulin variable domain having at least 85% sequence identity to SEQ ID NO: 26. In some embodiments, the polypeptide comprises an immunoglobulin variable domain having at least 90% sequence identity to SEQ ID NO: 26. In some embodiments, the polypeptide comprises an immunoglobulin variable domain having at least 95% sequence identity to SEQ ID NO: 26. In some embodiments, the polypeptide comprises an immunoglobulin variable domain having at least 97% sequence identity to SEQ ID NO: 26. In some embodiments, the polypeptide comprises an immunoglobulin variable domain having at least 98% sequence identity to SEQ ID NO: 26. In some embodiments, the polypeptide comprises an immunoglobulin variable domain having at least 99% sequence identity to SEQ ID NO: 26. In some embodiments, the polypeptide comprises an immunoglobulin variable domain having 100% sequence identity to SEQ ID NO: 26. In some embodiments, the polypeptide comprises an immunoglobulin variable domain having at least 80% sequence identity to SEQ ID NO: 27. In some embodiments, the polypeptide comprises an immunoglobulin variable domain having at least 85% sequence identity to SEQ ID NO: 27. In some embodiments, the polypeptide comprises an immunoglobulin variable domain having at least 90% sequence identity to SEQ ID NO: 27. In some embodiments, the polypeptide comprises an immunoglobulin variable domain having at least 95% sequence identity to SEQ ID NO: 27. In some embodiments, the polypeptide comprises an immunoglobulin variable domain having at least 97% sequence identity to SEQ ID NO: 27. In some embodiments, the polypeptide comprises an immunoglobulin variable domain having at least 98% sequence identity to SEQ ID NO: 27. In some embodiments, the polypeptide comprises an immunoglobulin variable domain having at least 99% sequence identity to SEQ ID NO: 27. In some embodiments, the polypeptide comprises an immunoglobulin variable domain having 100% sequence identity to SEQ ID NO: 27. In some embodiments, the polypeptide comprises an immunoglobulin variable domain having at least 80% sequence identity to SEQ ID NO: 28. In some embodiments, the polypeptide comprises an immunoglobulin variable domain having at least 85% sequence identity to SEQ ID NO: 28. In some embodiments, the polypeptide comprises an immunoglobulin variable domain having at least 90% sequence identity to SEQ ID NO: 28. In some embodiments, the polypeptide comprises an immunoglobulin variable domain having at least 95% sequence identity to SEQ ID NO: 28. In some embodiments, the polypeptide comprises an immunoglobulin variable domain having at least 97% sequence identity to SEQ ID NO: 28. In some embodiments, the polypeptide comprises an immunoglobulin variable domain having at least 98% sequence identity to SEQ ID NO: 28. In some embodiments, the polypeptide comprises an immunoglobulin variable domain having at least 99% sequence identity to SEQ ID NO: 28. In some embodiments, the polypeptide comprises an immunoglobulin variable domain having 100% sequence identity to SEQ ID NO: 28. In some embodiments, the polypeptide comprises an immunoglobulin variable domain having at least 80% sequence identity to SEQ ID NO: 29. In some embodiments, the polypeptide comprises an immunoglobulin variable domain having at least 85% sequence identity to SEQ ID NO: 29. In some embodiments, the polypeptide comprises an immunoglobulin variable domain having at least 90% sequence identity to SEQ ID NO: 29. In some embodiments, the polypeptide comprises an immunoglobulin variable domain having at least 95% sequence identity to SEQ ID NO: 29. In some embodiments, the polypeptide comprises an immunoglobulin variable domain having at least 97% sequence identity to SEQ ID NO: 29. In some embodiments, the polypeptide comprises an immunoglobulin variable domain having at least 98% sequence identity to SEQ ID NO: 29. In some embodiments, the polypeptide comprises an immunoglobulin variable domain having at least 99% sequence identity to SEQ ID NO: 29. In some embodiments, the polypeptide comprises an immunoglobulin variable domain having 100% sequence identity to SEQ ID NO: 29.

Disclosed herein, in some embodiments, are polypeptides comprising an amino acid sequence having at least 80%, 85%, 90%, 95%, 97%, 98%, 99%, or 100% sequence identity to any one of SEQ ID NOs: 30-34. In some embodiments, the polypeptide comprises an amino acid sequence having at least 80% sequence identity to SEQ ID NO: 30. In some embodiments, the polypeptide comprises an amino acid sequence having at least 85% sequence identity to SEQ ID NO: 30. In some embodiments, the polypeptide comprises an amino acid sequence having at least 90% sequence identity to SEQ ID NO: 30. In some embodiments, the polypeptide comprises an amino acid sequence having at least 95% sequence identity to SEQ ID NO: 30. In some embodiments, the polypeptide comprises an amino acid sequence having at least 97% sequence identity to SEQ ID NO: 30. In some embodiments, the polypeptide comprises an amino acid sequence having at least 98% sequence identity to SEQ ID NO: 30. In some embodiments, the polypeptide comprises an amino acid sequence having at least 99% sequence identity to SEQ ID NO: 30. In some embodiments, the polypeptide comprises an amino acid sequence having 100% sequence identity to SEQ ID NO: 30. In some embodiments, the polypeptide comprises an amino acid sequence having at least 80% sequence identity to SEQ ID NO: 31. In some embodiments, the polypeptide comprises an amino acid sequence having at least 85% sequence identity to SEQ ID NO: 31. In some embodiments, the polypeptide comprises an amino acid sequence having at least 90% sequence identity to SEQ ID NO: 31. In some embodiments, the polypeptide comprises an amino acid sequence having at least 95% sequence identity to SEQ ID NO: 31. In some embodiments, the polypeptide comprises an amino acid sequence having at least 97% sequence identity to SEQ ID NO: 31. In some embodiments, the polypeptide comprises an amino acid sequence having at least 98% sequence identity to SEQ ID NO: 31. In some embodiments, the polypeptide comprises an amino acid sequence having at least 99% sequence identity to SEQ ID NO: 31. In some embodiments, the polypeptide comprises an amino acid sequence having at 100% sequence identity to SEQ ID NO: 31. In some embodiments, the polypeptide comprises an amino acid sequence having at least 80% sequence identity to SEQ ID NO: 32. In some embodiments, the polypeptide comprises an amino acid sequence having at least 85% sequence identity to SEQ ID NO: 32. In some embodiments, the polypeptide comprises an amino acid sequence having at least 90% sequence identity to SEQ ID NO: 32. In some embodiments, the polypeptide comprises an amino acid sequence having at least 95% sequence identity to SEQ ID NO: 32. In some embodiments, the polypeptide comprises an amino acid sequence having at least 97% sequence identity to SEQ ID NO: 32. In some embodiments, the polypeptide comprises an amino acid sequence having at least 98% sequence identity to SEQ ID NO: 32. In some embodiments, the polypeptide comprises an amino acid sequence having at least 99% sequence identity to SEQ ID NO: 32. In some embodiments, the polypeptide comprises an amino acid sequence having 100% sequence identity to SEQ ID NO: 32. In some embodiments, the polypeptide comprises an amino acid sequence having at least 80% sequence identity to SEQ ID NO: 33. In some embodiments, the polypeptide comprises an amino acid sequence having at least 85% sequence identity to SEQ ID NO: 33. In some embodiments, the polypeptide comprises an amino acid sequence having at least 90% sequence identity to SEQ ID NO: 33. In some embodiments, the polypeptide comprises an amino acid sequence having at least 95% sequence identity to SEQ ID NO: 33. In some embodiments, the polypeptide comprises an amino acid sequence having at least 97% sequence identity to SEQ ID NO: 33. In some embodiments, the polypeptide comprises an amino acid sequence having at least 98% sequence identity to SEQ ID NO: 33. In some embodiments, the polypeptide comprises an amino acid sequence having at least 99% sequence identity to SEQ ID NO: 33. In some embodiments, the polypeptide comprises an amino acid sequence having 100% sequence identity to SEQ ID NO: 33. In some embodiments, the polypeptide comprises an amino acid sequence having at least 80% sequence identity to SEQ ID NO: 34. In some embodiments, the poly peptide comprises an amino acid sequence having at least 85% sequence identity to SEQ ID NO: 34. In some embodiments, the polypeptide comprises an amino acid sequence having at least 90% sequence identity to SEQ ID NO: 34. In some embodiments, the polypeptide comprises an amino acid sequence having at least 95% sequence identity to SEQ ID NO: 34. In some embodiments, the polypeptide comprises an amino acid sequence having at least 97% sequence identity to SEQ ID NO: 34. In some embodiments, the polypeptide comprises an amino acid sequence having at least 98% sequence identity to SEQ ID NO: 34. In some embodiments, the polypeptide comprises an amino acid sequence having at least 99% sequence identity to SEQ ID NO: 34. In some embodiments, the polypeptide comprises an amino acid sequence having 100% sequence identity to SEQ ID NO: 34.

In some embodiments, the polypeptide comprises an amino acid sequence having at least 80%, 85%, 90%, 95%, 97%, 98%, 99%, or 100% sequence identity to SEQ ID NO: 42. In some embodiments, the polypeptide comprises an amino acid sequence having at least 80%, 85%, 90%, 95%, 97%, 98%, 99%, or 100% sequence identity to SEQ ID NO: 43.

In some embodiments, the polypeptide of any one of the embodiments disclosed herein binds to a 5T4 protein with an equilibrium dissociation constant (KD) equal to or less than $100\times10^{-9}$M, $50\times10^{-9}$M, $25\times10^{-9}$ M, $15\times10^{-9}$ M, $10\times10^{-9}$ M, or $5\times10^{-9}$ M. In some embodiments, the polypeptide binds to a 5T4 protein with a KD equal to or less than $100\times10^{-9}$ M. In some embodiments, the polypeptide binds to a 5T4 protein with a KD equal to or less than $50\times10^{-9}$ M. In some embodiments, the polypeptide binds to a 5T4 protein with a KD equal to or less than $25\times10^{-9}$ M. In some embodiments, the polypeptide binds to a 5T4 protein with a KD equal to or less than $15\times10^{-9}$ M. In some embodiments, the polypeptide binds to a 5T4 protein with a KD equal to or less than $10\times10^{-9}$ M. In some embodiments, the polypeptide binds to a 5T4 protein with a KD equal to or less than $5\times10^{-9}$ M. In some embodiments, the 5T4 protein comprises the amino acid sequence of SEQ ID NO: 37.

In some embodiments, the polypeptide of any one of the embodiments disclosed herein is internalized by a cell expressing 5T4 (e.g., increased internalization relative to an H18 control). In some embodiments, the cell is a NCI-H1975 cell or a MDA-MB-231 cell. In some embodiments, the polypeptide is internalized by the cell expressing 5T4 is at least 2-fold greater than an H8 antibody, wherein the H8 antibody comprises: a heavy chain variable domain comprising SEQ ID NO: 39 and a light chain variable domain comprising SEQ ID NO: 40.

In some embodiments, the immunoglobulin variable domain of any one of the embodiments disclosed herein is an immunoglobulin heavy chain variable domain, optionally wherein the immunoglobulin heavy chain variable domain is a VHH.

Disclosed herein, in some embodiments, is a dimer comprising two of the polypeptides disclosed herein.

Disclosed herein, in some embodiments, are nucleic acids encoding a polypeptide of any one of the embodiments disclosed herein. Further disclosed herein, in some embodiments, are host cells comprising the nucleic acid. In some embodiments, the host cell comprises a eukaryotic cell. In some embodiments, the eukaryotic cell comprises a CHO cell. In some embodiments, the host cell comprises a prokaryotic cell.

Further disclosed herein, in some embodiments, are methods of making a polypeptide that binds 5T4 comprising culturing a host cell comprising a nucleic acid encoding the polypeptide of any one of the embodiments disclosed herein under conditions to sufficient to express and secret the polypeptide and recovering the polypeptide from the culture media.

Immunoconjugates

Disclosed herein, in some embodiments, are immunoconjugates comprising the polypeptide of any one of the embodiments disclosed herein conjugated to a chelating agent or a radionuclide complex thereof.

In some embodiments, the chelating agent or the radionuclide complex thereof comprises:

- 1,4,7,10-tetraazacyclododecane-1,4,7,10-tetraacetic acid (DOTA);
- 1,4,7,10-tetraazacyclododecane-1,4,7-triacetic acid (DO3A);

1,4,7,10-tetraazacyclododecane-1,7-diacetic acid (DO2A);

α,α',α",α'"-tetramethyl-1,4,7,10-tetraazacyclododecane-1,4,7,10-tetraacetic acid (DOTMA);

1,4,7,10-tetrakis(carbamoylmethyl)-1,4,7,10-tetraazacyclododecane (DOTAM);

1,4,7,10-tetraazacyclododecane-1,4,7,10-tetrapropionic acid (DOTPA);

2,2',2"-(10-(2-amino-2-oxoethyl)-1,4,7,10-tetraazacyclododecane-1,4,7-triyl)triacetic acid;

6,6'-(((pyridine-2,6-diylbis(methylene))bis((carboxymethyl)azanediyl))-bis(methylene))dipicolinic acid (H4pypa);

6,6',6",6'"-(((pyridine-2,6-diylbis(methylene))bis(azanetriyl))tetrakis(methylene))-tetrapicolinic acid (H4py4pa);

10-((6-carboxypyridin-2-yl)methyl)-1,4,7,10-tetra-azacyclododecane-1,4,7-triacetic acid (DO3Apic); or 3,6,9,12-tetrakis(carboxymethyl)-3,6,9,12-tetraazatetradecanedioic acid (TTHA).

In some embodiments, the immunoconjugate comprises a linker covalently linking the chelating agent or radionuclide complex thereof to the polypeptide.

In some embodiments, the immunoconjugate is represented by Formula (T) or a pharmaceutically acceptable salt thereof:

Formula (I)

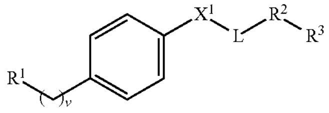

wherein:

$R^1$ is a chelating agent or a radionuclide complex thereof;

$X^1$ is absent, —O—, —S—, —S(═O)—, —S(═O)$_2$—, —NRa—, —C(═O)—, —NR$^a$C(═O)—, —C(═O)NR$^a$—, —($C_1$-$C_6$ alkylene)-$X^2$—, or —($C_4$-$C_{20}$polyethylene glycol)-$X^2$—;

$X^2$ is absent, —C(═O)—, —NR$^a$C(═O)—, —C═O)NR$^a$—, or —C(═O)$X^4$—;

each $R^a$ is independently selected from hydrogen and $C_1$-$C_4$ alkyl;

$X^4$ is —NR$^a$— or —NRaS(═O)$_2$—;

L is an optional linker;

$R^2$ is a moiety that is capable of reacting with an amine (—$NH_2$) or thiol (—SH) of the polypeptide;

$R^3$ is the polypeptide; and v is 1, 2, 3, or 4.

In some embodiments, $R^2$ is a moiety that is capable of reacting with an amine (—$NH_2$) of the polypeptide and comprises a tetrafluorophenyl ester, pentafluorophenyl ester, dinitrophenyl ester, succinimide ester, sulfosuccinimide ester, or isothiocyanate.

In some embodiments, $R^2$ is a moiety that is capable of reacting with an amine (—$NH_2$) of the polypeptide and —$R^2$-$R^3$ comprises:

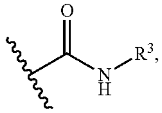
,
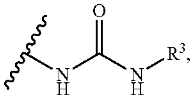
,
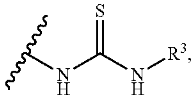
,

-continued

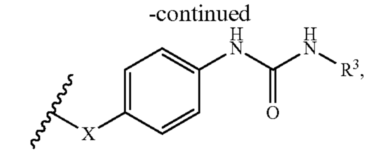
,

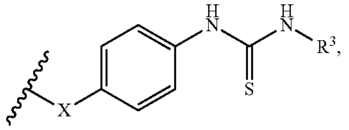
, or

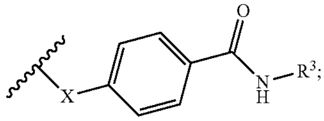
;

X is absent, —O—, —S—, —S(═O)—, —S(═O)$_2$—, —NR$^a$—, —C(═O)—, —NR$^a$C(═O)—, —C(═O)NR$^a$—, —C(═O)O—, —OC(═O)—, —OC(═O)NR$^a$—, —NR$^a$C(═O)NR$^a$—, —NR$^a$C(═S)NR$^a$—, —NR$^a$C(═O)O—;

each $R^a$ is independently selected from hydrogen and $C_1$-$C_4$ alkyl; and

—NH—$R^3$ is the polypeptide.

In some embodiments, the immunoconjugate is represented by any one of Formulas (II)-(V) or a pharmaceutically acceptable salt thereof:

Formula (II)

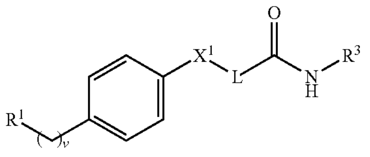

Formula (III)

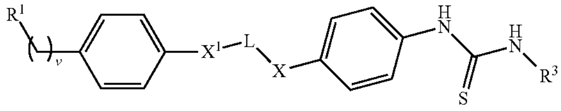

Formula (IV)

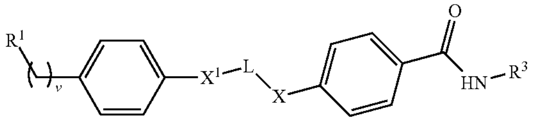

Formula (V)

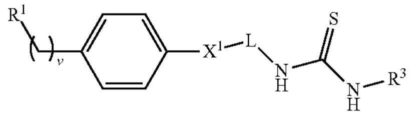

wherein:

$R^1$ is a chelating agent or a radionuclide complex thereof;

$X^1$ is absent, —O—, —S—, —S(═O)—, —S(═O)$_2$—, —NR$^a$—, —C(═O)—, —NR$^a$C(═O)—, —C(═O)NR$^a$—, —($C_1$-$C_6$alkylene)-$X^2$—, or —($C_4$-$C_{20}$polyethylene glycol)-$X^2$—;

$X^2$ is absent, —C(═O)—, —NR$^a$C(═O)—, —C(═O)NR$^a$—, or —C(═O)$X^4$—;

each $R^a$ is independently selected from hydrogen and $C_1$-$C_4$ alkyl;

$X^4$ is —NR$^a$— or —NR$^a$S(═O)$_2$—;

L is an optional linker;

—NH—$R^3$ is the polypeptide; and v is 1, 2, 3, or 4.

In some embodiments, $R^2$ is a moiety that is capable of reacting with a thiol (—SH) of a polypeptide $R^3$ and comprises a maleimide group, a haloacetamide group, a haloacetyl group, a haloacetate group, a pyrdinylthio group, a vinylcarbonyl group, an aziridinyl group, a disulfide group, an acetylene group, a hydroxysuccinimide group, or a thiol group.

In some embodiments, $R^2$ is a moiety that is capable of reacting with a thiol (—SH) of the polypeptide $R^3$ and —$R^2$-$R^3$ comprises:

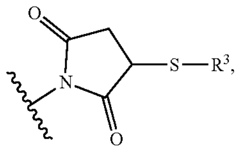

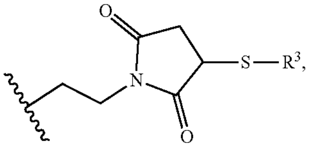

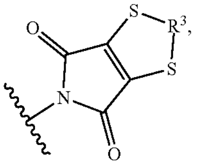

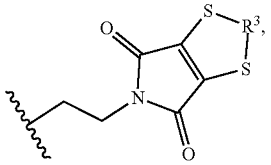

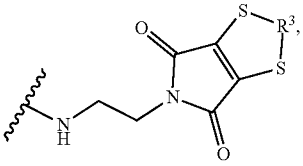

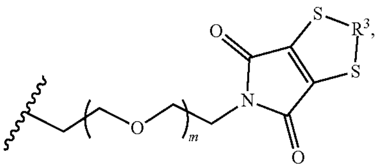

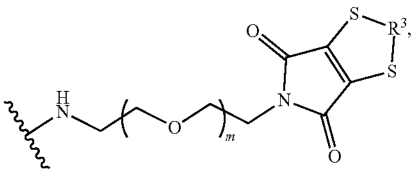

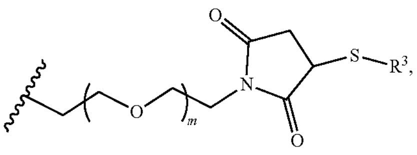

-continued

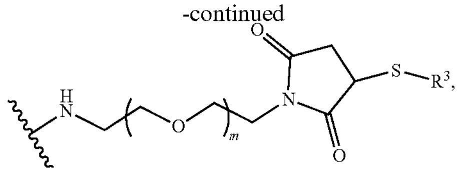

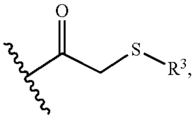

or

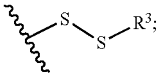

wherein m is 0, 1, 2, 3, 4, or 5.

In some embodiments, the chelating agent or radionuclide complex thereof comprises a structure represented by Formula (IIa) or Formula (IIb), or a pharmaceutically acceptable salt thereof:

Formula (IIa)

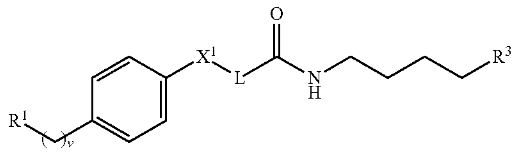

Formula (IIb)

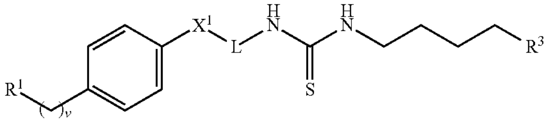

wherein:

—$NHCH_2CH_2CH$—$CH_2$— is the side chain of a lysine residue of the polypeptide $R^3$.

In some embodiments, the immunoconjugate is represented by any one of Formulas (VI)-(IXI) or a pharmaceutically acceptable salt thereof:

Formula (VI)

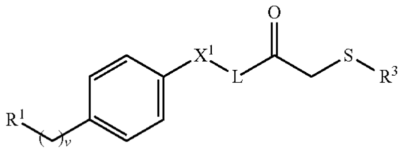

Formula (VII)

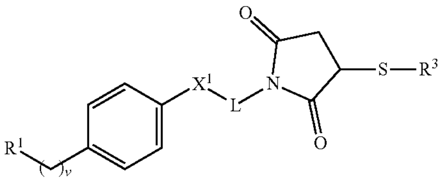

Formula (VIII)

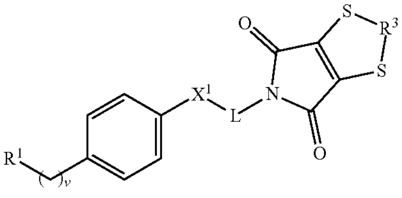

-continued

Formula (IX)

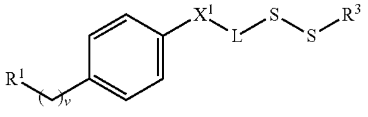

wherein:

$R^1$ is a chelating agent or a radionuclide complex thereof;

$X^1$ is absent, —O—, —S—, —S(=O)—, —S(=O)$_2$—, —NR$^a$—, —C(=O)—, —NR$^a$C(=O)—, —C(=O)NR$^a$—, —($C_1$-$C_6$alkylene)-$X^2$—, or —($C_4$-$C_{20}$polyethylene glycol)-$X^2$—;

$X^2$ is absent, —C(=O)—, —NRC(=O)—, —C(=O)NR$^a$—, or —C(=O)$X^4$—;

each $R^a$ is independently selected from hydrogen and $C_1$-$C_4$alkyl;

$X^4$ is —NR$^a$— or —NR$^a$S(=O)$_2$—;

L is an optional linker;

—S—$R^3$ is the polypeptide; and v is 1, 2, 3, or 4.

In some embodiments, $R^1$ is:

1,4,7,10-tetraazacyclododecane-1,4,7,10-tetraacetic acid (DOTA);

1,4,7,10-tetraazacyclododecane-1,4,7-triacetic acid (DO3A);

1,4,7,10-tetraazacyclododecane-1,7-diacetic acid (DO2A);

α,α',α",α'"-tetramethyl-1,4,7,10-tetraazacyclododecane-1,4,7,10-tetraacetic acid (DOTMA);

1,4,7,10-tetrakis(carbamoylmethyl)-1,4,7,10-tetraazacyclododecane (DOTAM);

1,4,7,10-tetraazacyclododecane-1,4,7,10-tetrapropionic acid (DOTPA);

2,2',2"-(10-(2-amino-2-oxoethyl)-1,4,7,10-tetraazacyclododecane-1,4,7-triyl)triacetic acid;

6,6'-(((pyridine-2,6-diylbis(methylene))bis((carboxytmethyl)azanediyl))-bis(methylene))dipicolinic acid ($H_4$pypa);

6,6',6",6'"-(((pyridine-2,6-diylbis(methylene))bis(azanetriyl))tetrakis(methylene))-tetrapicolinic acid ($H_4$py4pa);

10-((6-carboxypyridin-2-yl)methyl)-1,4,7,10-tetra-azacyclododecane-1,4,7-triacetic acid (DO3Apic); or 3,6,9,12-tetrakis(carboxymethyl)-3,6,9,12-tetraazatetradecanedioic acid (TTHA).

In some embodiments, $R^1$ is a chelating moiety or a radionuclide complex thereof, wherein the chelating moiety is:

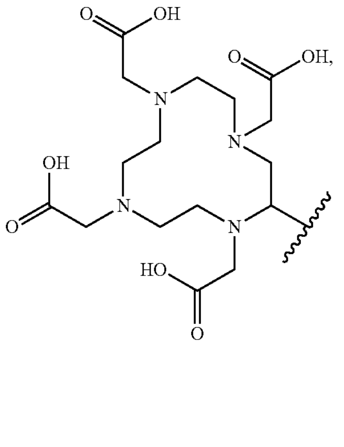

-continued

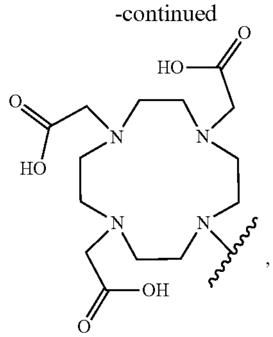

, or

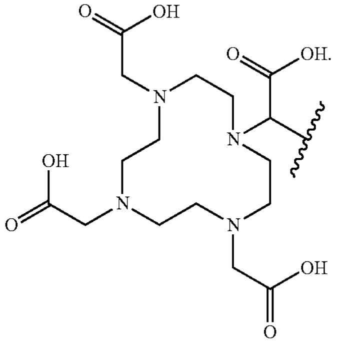

In some embodiments, $X^1$ is absent, —O—, —S—, —NR$^a$—, —C(=O)—, —NR$^a$C(=O)—, or —C(=O)NR$^a$—; or $X^1$ is —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2$—$X^2$—, —$CH_2CH_2$—$X^2$—, —$CH_2CH_2CH_2$—$X^2$—$CH_2CH_2CH_2CH_2$—$X^2$—, —$CH_2CH_2CH_2CH_2CH_2$—$X^2$—, or —$CH_2CH_2CH_2CH_2CH_2CH_2$—$X^2$—.

In some embodiments, $X^1$ is —$CH_2CH_2$— or —$CH_2CH_2$—$X^2$—;

$X^2$ is —C(=O)$X^4$—; and $X^4$ is —NH—, —N($CH_3$)—, or —N($CH_2CH_3$)—.

In some embodiments, $X^1$ is —$CH_2CH_2$—C(=O)N($CH_3$)— or —$CH_2CH_2$—C(=O)N($CH_2CH_3$)—.

In some embodiments,

L is absent, -$L^2$-$L^4$-, or -$L^1$-$L^2$-$L^3$-$L^4$-$L^5$:

$L^1$ is absent, unsubstituted or substituted $C_1$-$C_{20}$ alkylene, unsubstituted or substituted $C_1$-$C_{20}$ heteroalkylene, $C_4$-$C_{20}$ polyethylene glycol, unsubstituted or substituted $C_3$-$C_8$ cycloalkylene, unsubstituted or substituted monocyclic $C_3$-$C_8$heterocycloalkylene, unsubstituted or substituted phenylene, or unsubstituted or substituted monocyclic heteroarylene;

$L^2$ is absent, unsubstituted or substituted $C_1$-$C_{10}$alkylene, —C(=O)NR$^4$-(unsubstituted or substituted $C_1$-$C_{10}$alkylene)-, unsubstituted or substituted $C_1$-$C_{10}$alkylene, —NR$^4$C(=O)-(unsubstituted or substituted $C_1$-$C_{10}$alkylene)-, —C(=O)—($CH_2CH_2O$)$_m$—($CH_2$)$_p$—, —C(=O)NR$^4$—($CH_2CH_2O$)$_m$—($CH_2$)$_p$—, —NR$^4$C(=O)—($CH_2CH_2O$)$_m$—($CH_2$)$_p$—, or —($CH_2CH_2O$)$_m$—($CH_2$)$_p$—;

each $R^4$ is independently selected from hydrogen and $C_1$-$C_6$alkyl;

each in is independently 1, 2, 3, 4, 5, 6, 7, 8, 9, 10, 11, or 12;

each p is independently 1, or 2;

$L^3$ is absent, —C(═O)-(unsubstituted or substituted $C_1$-$C_{10}$alkylene)-, —C(═O)$NR^4$-(unsubstituted or substituted $C_1$-$C_{10}$alkylene)-, —$NR^4$C(═O)-(unsubstituted or substituted $C_1$-$C_{10}$alkylene)-, —C(═O)—$(CH_2CH_2O)_t$—$(CH_2)_u$—, —C(═O)$NR^4$—$(CH_2CH_2O)_t$—$(CH_2)_u$—, —$NR^4$C(═O)—$(CH_2CH_2O)_t$—$(CH_2)_u$—, or —$(CH_2CH_2O)$—$(CH_2)_u$—;

each t is independently 1, 2, 3, 4, 5, 6, 7, 8, 9, 10, 11, or 12;

each u is independently 1 or 2;

$L^4$ is absent, —C(═O)—$(CH_2)_n$—, —C(═O)$NR^4$—$(CH_2)_n$—, —$NR^4$C(═O)—$(CH_2)_n$—, —C(═O)—$(CH_2CH_2O)_n$—$(CH_2)_q$—, —C(═O)$NR^4$—$(CH_2CH_2O)_n$—$(CH_2)_q$—, —$NR^4$C(═O)—$(CH_2CH_2O)_n$—$(CH_2)_q$—, —$(CH_2CH_2O)_n$—$(CH_2)_q$—, —C(═O)—$(OCH_2CH_2)_n$—, or —$(OCH_2CH_2)_n$—;

each n is independently 1, 13, 4, 5, 6, 7, 8, 9, 10, 11, or 12;

each q is independently 0, 1, or 2;

wherein heteroalkylene is an alkylene where one carbon atom is replaced with —S(═O)(═NH)—, —S(═O)(═$NR^5$)—, —P(═O)OH—, —NHC(═N—CN)NH—, or —NHC(═N—$R^5$)NH—;

wherein when any one of -$L^1$-, -$L^2$-, -$L^3$-, -$L^4$-, and -$L^5$- is substituted then -$L^1$-, -$L^2$-, -$L^3$-, -$L^4$-, and -$L^5$- is substituted with 1, 2, 3, or 4 groups selected from halogen, —OH, —$OR^5$, —$CO_2H$, —$NHR^5$, —C(═O)$NHR^5$, —NHC(═O)$R^5$ and substituted $C_1$-$C_6$alkyl, wherein the substituted $C_1$-$C_6$alkyl is substituted with —OH, —$CO_2H$, —$NHR^5$, —C(═O)$NHR^5$, or —NHC(═O)$R^5$; and each $R^5$ is independently selected from $C_1$-$C_{10}$alkyl, $C_4$-$C_{30}$polyethvlene glycol, unsubstituted or substituted arylene, and unsubstituted or substituted heteroarylene.

In some embodiments, $L^1$ is unsubstituted or substituted $C_1$-$C_6$ alkylene, unsubstituted or substituted $C_1$-$C_{10}$ heteroalkylene, $C_4$-$C_{20}$ polyethylene glycol, unsubstituted or substituted cyclohexylene, or unsubstituted or substituted phenylene.

In some embodiments, $L^5$ is absent, —$NR^4$C(═O)—$(CH_2)_n$—, —C(═O)—$(CH_2CH_2O)_n$—$(CH_2)_q$—, —C(═O)$NR^4$—$(CH_2CH_2O)_n$—$(CH_2)_q$—, or —$NR^4$C(═O)—$(CH_2CH_2O)_n$—$(CH_2)_q$—; each q is independently 1, or 2.

In some embodiments, $L^1$ is absent, unsubstituted or substituted $C_1$-$C_6$alkylene, unsubstituted or substituted $C_1$-$C_{10}$heteroalkylene, $C_4$-$C_{20}$polyethylene glycol, unsubstituted or substituted cyclohexylene, or unsubstituted or substituted phenylene;

$L^2$ is absent, —C(═O)$NR^4$-(unsubstituted or substituted $C_1$-$C_{10}$alkylene)-, —$NR^4$C(═O)-(unsubstituted or substituted $C_1$-$C_{10}$alkylene)-, —C(═O)—$(CH_2CH_2O)_m$—$(CH_2)_p$—, —C(═O)$NR^4$—$(CH_2CH_2O)_m$—$(CH_2)_p$—, —$NR^4$C(═O)—$(CH_2CH_2O)_{m1}$—$(CH_2)_p$—, or —$(CH_2CH_2O)_m$—$(CH_2)_p$—;

each m is independently 1, 2, 3, 4, 5, 6, 7, 8, 9, 10, 11, or 12;

each p is independently 1 or 2;

$L^4$ is absent;

$L^5$ is —$NR^4$C(═O)—$(CH_2)_n$—, —C(═O)—$(CH_2CH_2O)_n$—$(CH_2)_q$—, —C(═O)$NR^4$—$(CH_2CH_2O)_n$—$(CH_2)_q$—, or —$NR^4$C(═O)—$(CH_2CH_2O)_n$—$(CH_2)_q$—;

each n is independently 1, 2, 3, 4, 5, 6, 7, 8, 9, 10, 11, or 12; and each q is independently 1 or 2.

In some embodiments, $L^1$ is unsubstituted or substituted $C_1$-$C_6$ alkylene, unsubstituted or substituted $C_1$-$C_{10}$heteroalkylene, $C_4$-$C_{20}$polyethylene glycol, unsubstituted or substituted cyclohexylene, or unsubstituted or substituted phenylene;

$L^2$ is absent, —C(═O)$NR^4$-(unsubstituted or substituted $C_1$-$C_{10}$alkylene)-, —$NR^4$C(═O)-(unsubstituted or substituted $C_1$-$C_{10}$alkylene)-, —C(═O)—$(CH_2CH_2O)_m$—$(CH_2)_p$—, —C(═O)$NR^4$—$(CH_2CH_2O)_m$—$(CH_2)_p$—, —$NR^4$C(═O)—$(CH_2CH_2O)_m$—$(CH_2)_p$— or —$(CH_2CH_2O)_m$—$(CH_2)_p$—;

each m is independently 1, 2, 3, 4, 5, or 6;

each p is independently 1 or 2;

$L^4$ is absent;

$L^5$ is absent, —$NR^4$C(═O)—$(CH_2)_n$—, —C(═O)—$(CH_2CH_2O)_n$—$(CH_2)_q$—, —C(═O)$NR^4$—$(CH_2CH_2O))_n$—$(C_2)_q$—, or —$NR^4$C(═O)—$(CH_2CH_2O)_n$—$(CH_2)_q$—;

each n is independently 1, 2, 3, 4, 5, or 6; and each q is independently 1 or 2.

In some embodiments, $L^1$ is unsubstituted or substituted $C_1$-$C_6$ alkylene, unsubstituted or substituted $C_1$-$C_{10}$ heteroalkylene, $C_4$-$C_{20}$ polyethylene glycol, unsubstituted or substituted cyclohexylene, or unsubstituted or substituted phenylene;

$L^2$ is absent;

$L^4$ is absent;

$L^5$ is absent, —$NR^4$C(═O)—$(CH_2)_n$—, —C(═O)—$(CH_2CH_2O)_n$—$(CH_2)_q$—, —C(═O)$NR^4$—$(CH_2CH_2O)_n$—$(CH_2)_q$—, or —$NR^4$C(═O)—$(CH_2CH_2O)_n$—$(CH_2)_q$—;

each n is independently 1, 2, 3, 4, 5, or 6; and each q is independently 1 or 2.

In some embodiments, the immunoconjugate is represented by Formula (II) or a pharmaceutically acceptable salt thereof:

Formula (II)

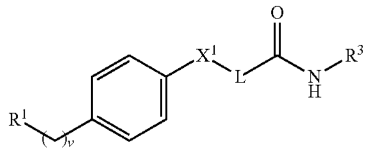

wherein:

$X^1$ is absent, —C(═O)NH—, —C(═O)N($CH_3$)—, —C(═O)N($CH_2CH_3$)—, —$CH_2$—C(═O)NH—, —$CH_2$—C(═O)N($CH_3$)—, —$CH_2$—C(═O)N($CH_2CH_3$)—, $CH_2CH_2$—C(═O)NH—, —$CH_2CH_2$—C(═O)N($CH_3$)— or —$CH_2CH_2$—C(═O)N($CH_2CH_3$)—;

L is -$L^2$-$L^4$-;

$L^2$ is unsubstituted or substituted $C_1$-$C_{10}$alkylene, —C(═O)$NR^4$-(unsubstituted or substituted $C_1$-$C_{10}$alkylene)-, unsubstituted or substituted $C_1$-$C_{10}$alkylene, —$NR^4$C(═O)-(unsubstituted or substituted $C_1$-$C_{10}$alkylene)-, —C(═O)—$(CH_2CH_2O)_m$—$(CH_2)_p$—, —C(═O)$NR^4$—$(CH_2CH_2O)_m$—$(CH_2)_p$—, —$NR^4$C(═O)—$(CH_2CH_2O)_m$—$(CH_2)_p$—, or —$(CH_2CH_2O)_m$—$(CH_2)_p$—;

each m is independently 1, 2, 3, 4, 5, 6, 7, 8, 9, 10, I1, or 12;

each p is independently 0, 1, or 2

$L^4$ is $-C(=O)-(CH_2)_n$, $-C(=O)NR^4-(CH_2)_n-$, $-NR^4C(=O)-(CH_2)_n-$, $-C(=O)-(CH_2CH_2O)_n-(CH_2)_q-$, $-C(=O)NR^4-(CH_2CH_2O)_n-(CH_2)_q-$, $-NR^4C(=O)-(CH_2CH_2O)_n-(CH_2)_q-$, $-(CH_2CH_2O)_n-(CH_2)_q-$, $-C(=O)-(OCH_2CH_2)_n-$, or $-(OCH_2CH_2)_n-$;

each n is independently 1, 2, 3, 4, 5, 6, 7, 8, 9, 10, 11, or 12; and each q is independently 0, 1, or 2.

In some embodiments, $X^1$ is $-C(=O)NH-$, $-C(=O)N(CH_3)-$, $-C(=O)N(CH_2CH_3)-$, $-CH_2-C(=O)NH-$, $-CH_2-C(=O)N(CH_3)-$, $-CH_2-C(=O)N(CH_2CH_3)-$, $CH_2CH_2-C(=O)NH-$, $-CH_2CH_2-C(=O)N(CH_3)-$ or $-CH_2CH_2-C(=O)N(CH_2CH_3)-$;

L is $-L^2-L^4-$;

$L^2$ is unsubstituted or substituted $C_1$-$C_{10}$alkylene, unsubstituted or substituted $C_1$-$C_{10}$alkylene, or $-(CH_2CH_2O)_m-(CH_2)_p-$;

each m is independently 1, 2, 3, 4, 5, or 6;

each p is 2;

$L^4$ is $-C(=O)NR^4-(CH_2)_n-$, $-NR^4C(=O)-(CH_2)_n-$, $-C(=O)NR^4-(CH_2CH_2O)_n-(CH_2)_q-$, or $-NR^4C(=O)-(CH_2CH_2O)_n-(CH_2)_q-$;

each n is independently 1, 2, 3, 4, 5, or 6; and each q is 2.

In some embodiments, $L^2$ is unsubstituted $C_1$-$C_{10}$alkylene, or $-(CH_2CH_2O)_m-(CH_2)_p-$; and $L^4$ is $-NR^4C(=O)-(CH_2)_n-$, or $-NR^4C(=O)-(CH_2CH_2O)_n-(CH_2)_q-$.

In some embodiments, $X^1$ is absent, $-CH_2-$, or $-CH_2CH_2-$;

L is $-L^2-L^4-$;

$L^2$ is $-C(=O)NR^4$-(unsubstituted or substituted $C_1$-$C_{10}$alkylene)-, $-NR^4C(=O)$-(unsubstituted or substituted $C_1$-$C_{10}$alkylene)-, $-C(=O)-(CH_2CH_2O)_m-(CH_2)_p-$, $-C(=O)NR^4-(CH_2CH_2O)_m-(CH_2)_p-$, or $-NR^4C(=O)-(CH_2CH_2O)_m-(CH_2)_p-$; and $L^4$ is $-C(=O)-(CH_2)_n-$, $-C(=O)NR^4-(CH_2)_n-$, $-NR^4C(=O)-(CH_2)_n-$, $-C(=O)-(CH_2CH_2O)_n-(CH_2)_q-$, $-C(=O)NR^4-(CH_2CH_2O)_n-(CH_2)_q-$, $-NR^4C(=O)-(CH_2CH_2O)_n-(CH_2)_q-$, $-(CH_2CH_2O)_n-(CH_2)_q-$, $-C(=O)-(OCH_2CH_2)_n-$, or $-(OCH_2CH_2)_n$.

In some embodiments, $L^2$ is $-C(=O)NR^4$-(unsubstituted or substituted $C_1$-$C_{10}$alkylene)-, or $-C(=O)NR^4-(C_2CH_2O)_m-(CH_2)_p-$; and $L^4$ is $-NR^4C(=O)-(CH_2)_n-$, or $-NR^4C(=O)-(CH_2CH_2O)_n-(CH_2)_q$.

In some embodiments, each $R^a$ is independently selected from $C_1$-$C_6$ alkyl; and each $R^4$ is independently selected from $C_1$-$C_6$ alkyl.

In some embodiments, $X^1$-L is:

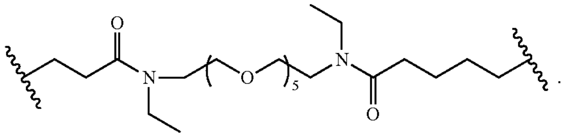

In some embodiments, v is 1; and

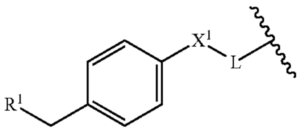

is:

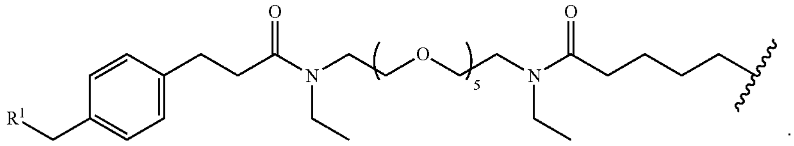

In some embodiments, the immunoconjugate is represented by Formula (V) or a pharmaceutically acceptable salt thereof:

Formula (V)

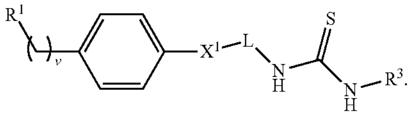

In some embodiments, v is 1; and

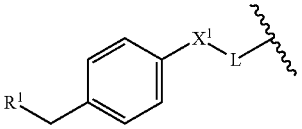

is:

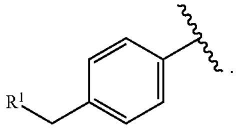

In some embodiments, v is 1; and

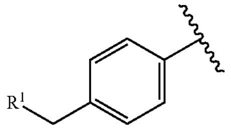

is:

-continued

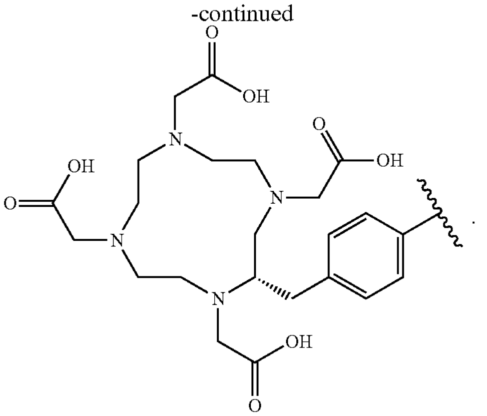

In some embodiments, v is 1; and

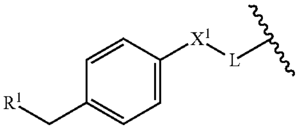

is:

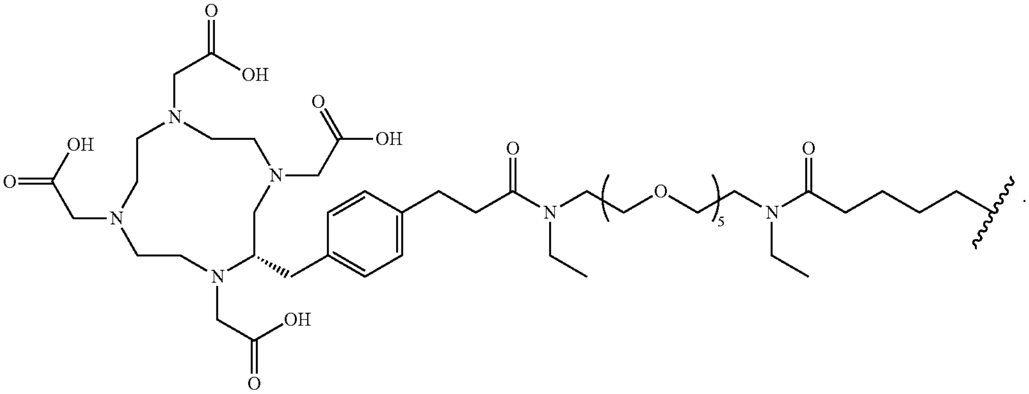

Disclosed herein, in some embodiments, are immunoconjugates prepared by conjugating the polypeptide ($R^3$) of any one of the embodiments disclosed herein to a chelating agent or a radionuclide complex thereof ($R^1$).

In some embodiments, the chelating agent or the radionuclide complex thereof comprises:

1,4,7,10-tetraazacyclododecane-1,4,7,10-tetraacetic acid (DOTA);

1,4,7,10-tetraazacyclododecane-1,4,7-triacetic acid (DO3A);

1,4,7,10-tetraazacyclododecane-1,7-diacetic acid (DO2A);

α,α',α",α'"-tetramethyl-1,4,7,10-tetraazacyclododecane-1,4,7,10-tetraacetic acid (DOTMA);

1,4,7,10-tetrakis(carbamoylmethyl)-1,4,7,10-tetraazacyclododecane (DOTAM);

1,4,7,10-tetraazacyclododecane-1,4,7,10-tetrapropionic acid (DOTPA);

2,2',2"-(10-(2-amino-2-oxoethyl)-1,4,7,10-tetraazacyclododecane-1,4,7-triyl)triacetic acid;

6,6'-(((pyridine-2,6-diylbis(methylene))bis((carboxymethyl)azanediyl))-bis(methylene))dipicolinic acid (H4pypa);

6,6',6",6'"-(((pyridine-2,6-diylbis(methylene))bis(azanetriyl))tetrakis(methylene))-tetrapicolinic acid (H4py4pa);

10-((6-carboxypyridin-2-yl)methyl)-1,4,7,10-tetra-azacyclododecane-1,4,7-triacetic acid (DO3Apic); or 3,6,9,12-tetrakis(carboxymethyl)-3,6,9,12-tetraazatetradecanedioic acid (TTHA).

In some embodiments, the chelating agent is selected from the list consisting of: DOTMA, DOTPA, DO3AM-acetic acid, DOTP, DOTMP, DOTA-4AMP, CB-TE2A, NOTA, NOTP, TETPA, TETA, PEPA, H4Octapa, H2Dedpa, DO2P, EDTA, DTPA-BMA, 3,2,3-LI(HOPO), 3,2-HOPO, Neunpa, Octapa, PyPa, Porphyrin, Deferoxamine, DFO*, and combinations thereof.

In some embodiments, the chelating agent is DOTA. In some embodiments, the chelating agent is DOTAGA. In some embodiments, the chelating agent is Py4Pa.

In some embodiments, the chelating agent comprises a moiety ($R^2$) that is capable of reacting with an amine (—$NH_2$) of the polypeptide and comprises a tetrafluorophenyl ester, pentafluorophenyl ester, dinitrophenyl ester, succinimide ester, sulfosuccinimide ester, or isothiocyanate.

In some embodiments, the chelating agent comprises a moiety ($R^2$) that is capable of reacting with an amine (—$NH_2$) of the polypeptide and comprises:

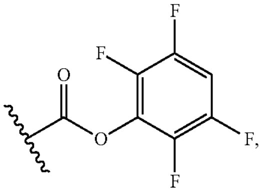

,

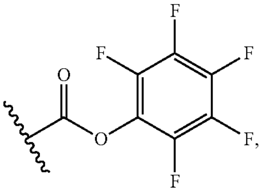

,

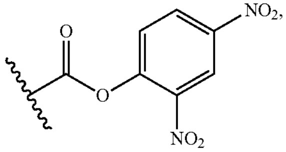

,

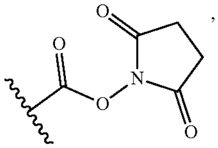

,

-continued

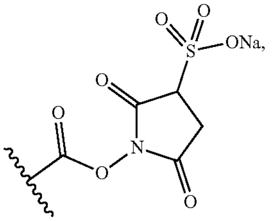

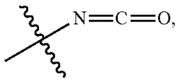

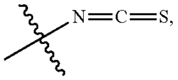

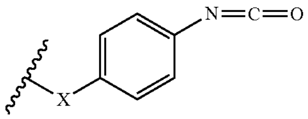

or

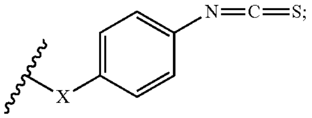

X is absent, —O—, —S—, —S(═O)—, —S(═O)$_2$—, —NR$^a$—, —C(═O)—, —NR$^a$C(═O)—, —C(═O)NR$^a$—, —C(═O)O—, —OC(═O)—, —OC(═O)NR$^a$—, —NR$^a$C(═O)NR$^a$—, —NR$^a$C(═S)NR$^a$—, —NR$^a$C(═O)O—; and each R$^a$ is independently selected from hydrogen and C$_1$-C$_4$ alkyl.

In some embodiments, the chelating agent comprises a moiety (R$^2$) that is capable of reacting with a thiol (—SH) of the polypeptide R$^3$ and comprises a maleimide group, a haloacetamide group, a haloacetyl group, a haloacetate group, a pyrdinylthio group, a vinylcarbonyl group, an aziridinyl group, a disulfide group, an acetylene group. a hydroxysuccinimide group or a thiol group.

In some embodiments, the chelating agent comprises a moiety (R$^2$) that is capable of reacting with a thiol (—SH) of the polypeptide R$^3$ and comprises:

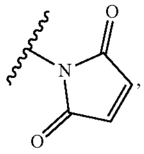

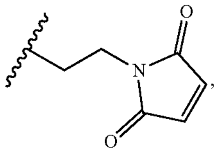

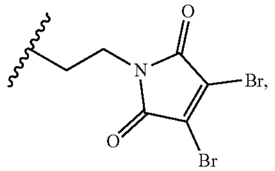

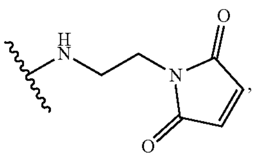

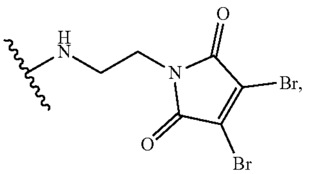

-continued

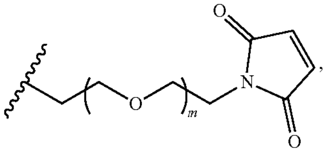

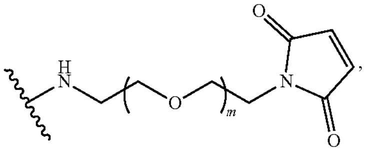

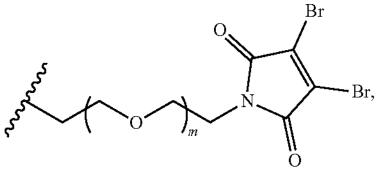

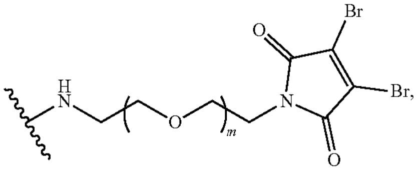

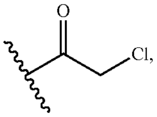

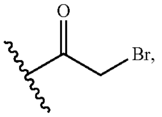

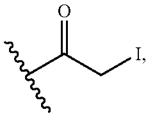

or

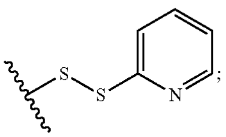

wherein m is 0, 1, 2, 3, 4, or 5.

In some embodiments, the immunoconjugate comprises a linker covalently linking the chelating agent or radionuclide complex thereof to the R$^2$ moiety.

In some embodiments, the linker is represented by:

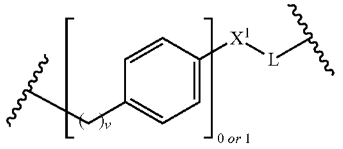

wherein:

X$^1$-L- is as defined in any one of the embodiments disclosed herein.

In some embodiments, the immunoconjugate is prepared by conjugating the polypeptide (R$^3$) of any one the embodiments disclosed herein to a chelating agent or a radionuclide complex thereof (R$^1$) represented by Formula (VIa) or a pharmaceutically acceptable salt thereof:

Formula (VIa)

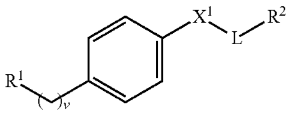

wherein:

$R^1$ is the chelating moiety or a radionuclide complex thereof; and $X^1$-L- is as defined in any one of the embodiments disclosed herein.

In some embodiments, the immunoconjugate is prepared by conjugating the polypeptide ($R^3$) of any one of the embodiments disclosed herein to a chelating agent or a radionuclide complex thereof ($R^1$) represented by Formula (VIb) or a pharmaceutically acceptable salt thereof:

Formula (VIb)

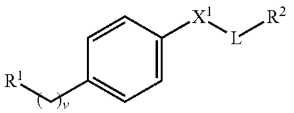

wherein:

$R^1$ is the chelating moiety or a radionuclide complex thereof:

$X^1$-L- is as defined in any one of the embodiments disclosed herein.

In some embodiments, the immunoconjugate is prepared by conjugating the polypeptide ($R^3$) of any one of the embodiments disclosed herein to a chelating agent or a radionuclide complex thereof ($R^1$) represented by Formula (VIb) or a pharmaceutically acceptable salt thereof:

Formula (VIb)

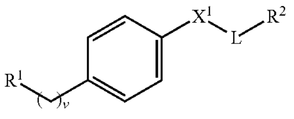

wherein:

$R^1$ is the chelating moiety or a radionuclide complex thereof;

$X^1$-L- is as defined in any one of the embodiments disclosed herein; and $R^2$ is a moiety that is capable of reacting with an amine (—$NH_2$) of the polypeptide and comprises:

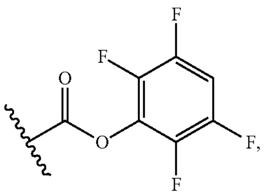

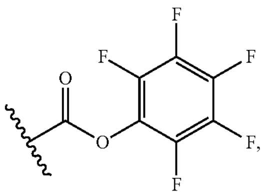

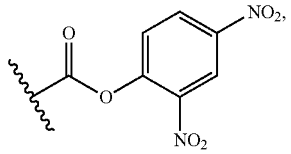

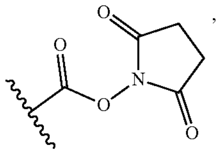

-continued

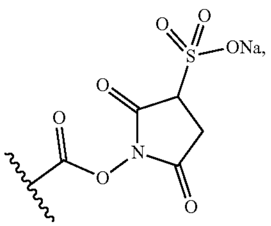

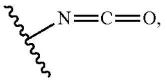

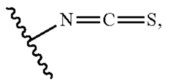

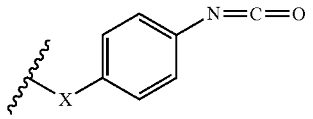

or

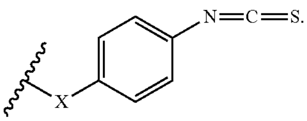

In some embodiments, $R^2$ is a moiety that is capable of reacting with an amine (—$NH_2$) of the polypeptide and comprises:

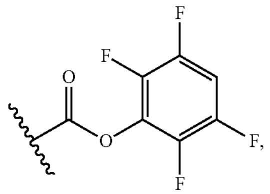

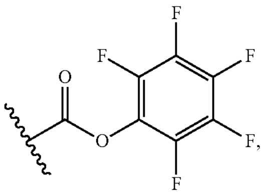

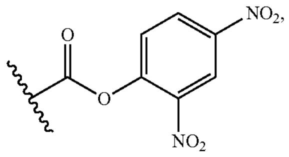

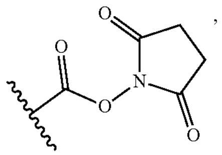

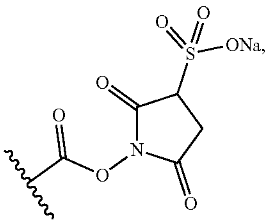

or

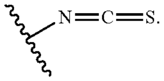

In some embodiments, $R^2$ is a moiety that is capable of reacting with an amine (—$NH_2$) of the polypeptide and comprises:

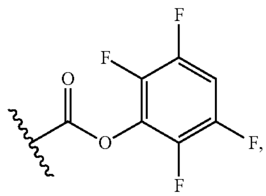

or

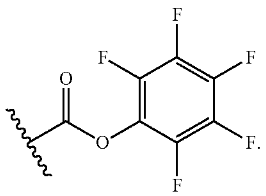

In some embodiments, $R^2$ is a moiety that is capable of reacting with an amine (—$NH_2$) of the polypeptide and comprises —SCN.

In some embodiments, the immunoconjugate is prepared by conjugating the polypeptide ($R^3$) of any one of the embodiments disclosed herein to a chelating agent or a radionuclide complex thereof ($R^1$) represented by Formula (VIb) or a pharmaceutically acceptable salt thereof:

Formula (VIb)

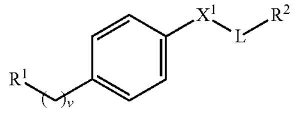

wherein:

v is 1:

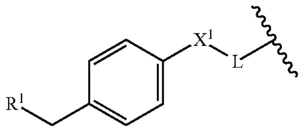

is:

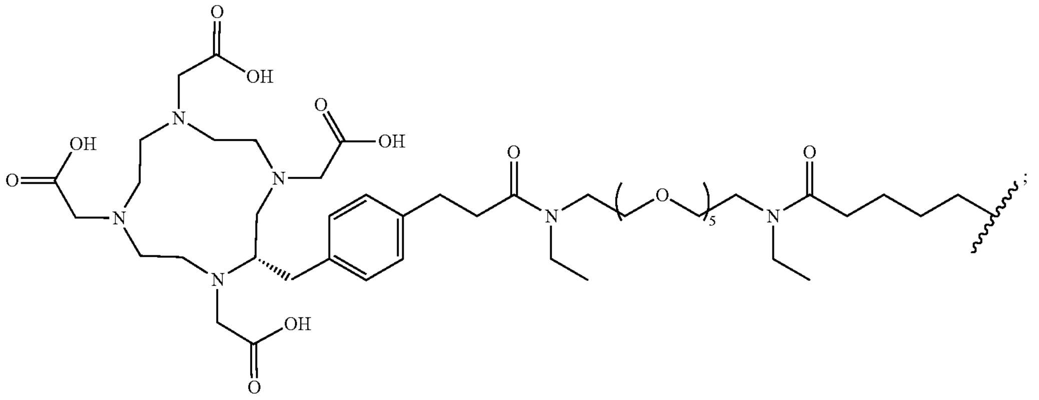

;

and $R^2$ is a moiety that is capable of reacting with an amine (—$NH_2$) of the polypeptide and comprises:

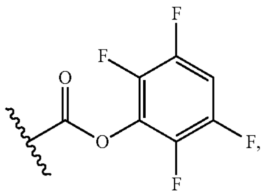

or

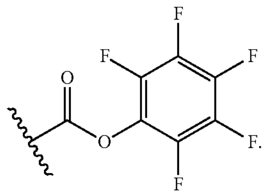

In some embodiments, the immunoconjugate is prepared by conjugating the polypeptide ($R^3$) of any one the embodiments disclosed herein to a chelating agent or a radionuclide complex thereof ($R^1$) represented by Formula (VIb) or a pharmaceutically acceptable salt thereof:

Formula (VIb)

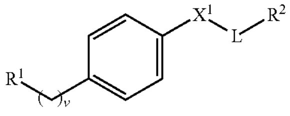

wherein:

v is 1;

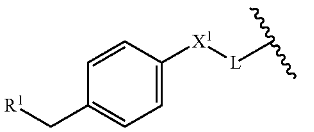

is:

-continued

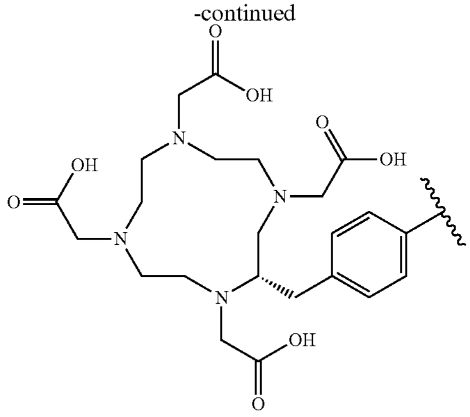

;

and $R^2$ is a moiety that is capable of reacting with an amine (—$NH_2$) of the polypeptide and comprises:

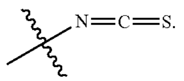 [SMILES: *N=C=S]

In some embodiments, the immunoconjugate is prepared by conjugating the polypeptide ($R^3$) of any one of the embodiments disclosed herein to TFP-Ad-PEG5-DOTAGA, p-SCN-Bn-DOTA, p-SCN-Ph-Et-Py4Pa, and TFP-Ad-PEG5-Ac-Py4Pa.

In some embodiments, the immunoconjugate is prepared by conjugating the polypeptide ($R^3$) of any one of the embodiments disclosed herein to TFP-Ad-PEG5-DOTAGA.

In some embodiments, the immunoconjugate is prepared by conjugating the polypeptide ($R^3$) of any one of the embodiments disclosed herein to p-SCN-Bn-DOTA.

In some embodiments, the immunoconjugate is prepared by conjugating the polypeptide ($R^3$) of any one of the embodiments disclosed herein to p-SCN-Ph-Et-Py4Pa.

In some embodiments, the immunoconjugate is prepared by conjugating the polypeptide ($R^3$) of any one of the embodiments disclosed herein to TFP-Ad-PEG5-Ac-Py4Pa.

In some embodiments, the chelating agent is coupled to the antigen binding region and/or the immunoglobulin heavy chain constant region by a linker.

Radionuclide

In some embodiments, the radionuclide complex comprises a radionuclide. In some embodiments, the radionuclide is a diagnostic or therapeutic radionuclide. In some embodiments, the radionuclide is an Auger electron -emitting radionuclide, α-emitting radionuclide, β-emitting radionuclide, or γ-emitting radionuclide. In some embodiments, the radionuclide is α-emitting radionuclide.

In some embodiments, the radionuclide is an Auger electron-emitting radionuclide that is 111-indium ($^{111}$In), 67-gallium ($^{67}$Ga), 68-gallium ($^{68}$Ga), 99m-technetium ($^{99m}$Tc), or 195m-platinum ($^{195m}$Pt); or the radionuclide is an u-emitting radionuclide that is 225-actinium ($^{225}$Ac), 213-bismuth ($^{213}$Bi), 223-Radium ($^{223}$Ra), or 212-lead ($^{212}$Pb); or the radionuclide is a β-emitting radionuclide that is 90-yttrium ($^{90}$Y), 177-lutetium ($^{177}$Lu), 186-rhenium ($^{186}$Re), 188-rhenium ($^{188}$Re), 64-copper ($^{64}$Cu), 67-copper ($^{67}$Cu), 153-samarium ($^{153}$Sm), 89-strontium ($^{89}$Sr), 198-gold ($^{198}$Au), 169-Erbium ($^{169}$Er), 165-dysprosium ($^{165}$Dy), 99m-technetium ($^{99m}$Tc), 89-zirconium ($^{89}$Zr), or 52-manganese ($^{52}$Mn); or the radionuclide is a γ-emitting radionuclide that is 60-cobalt ($^{60}$Co), 103-palladium ($^{103}$Pd), 137-cesium ($^{137}$Cs), 169-ytterbium ($^{169}$Yb), 192-iridium ($^{192}$Ir), or 226-radium ($^{226}$Ra).

In some embodiments, the radionuclide is suitable for positron emission tomography (PET) analysis, single-photon emission computerized tomography (SPECT), or magnetic resonance imaging (MRI).

In some embodiments, the radionuclide is 225-actinium ($^{225}$Ac).

In some embodiments, the immunoconjugate of any one of the preceding embodiments further comprises a pharmaceutically acceptable excipient, carrier or diluent.

In some embodiments, the immunoconjugate of any one of the preceding embodiments is formulated for intravenous administration.

Disclosed herein, in some embodiments, are methods of targeting a radionuclide to a 5T4 expressing cancer or tumor cell of an individual, wherein the method comprises administering to the individual the immunoconjugate of any one of the embodiments disclosed herein.

Disclosed herein, in some embodiments, are methods of treating a cancer or tumor of an individual, wherein the method comprises administering to the individual the polypeptide or the immunoconjugate of any one of the embodiments disclosed herein.

Disclosed herein, in some embodiments, are methods of making the immunoconjugate of any one of the preceding embodiments comprising complexing a radionuclide to the chelating agent coupled to the polypeptide.

Further disclosed herein, in some embodiments, are methods of making radioimmunoconjugates comprising complexing the immunoconjugates of any one of the preceding embodiments to a radionuclide, thereby obtaining a radioimmunoconjugate.

Certain Definitions

In this description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

The practice of the present invention will employ, unless otherwise indicated, techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. 1. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The skilled worker will recognize many methods and materials similar or equivalent to those described herein, which could be used in the practice of the present invention. Indeed, the present invention is in no way limited to the methods and materials described. For purposes of the present invention, some terms are defined below.

As used in the specification and the appended claims, the terms "a," "an" and "the" include both singular and the plural referents unless the context clearly dictates otherwise.

Throughout this specification, the term "including" is used to mean "including but not limited to." "Including" and "including but not limited to" are used interchangeably.

The term "about" as used herein refers to the usual error range for the respective value readily known to the skilled person in this technical field. Reference to "about" a value or parameter herein includes (and describes) embodiments that are directed to that value or parameter per se. The term "about" when used before a numerical designation, e.g., a numerical temperature, time, amount, or concentration, including a range, indicates approximations which may vary by ±10%.

The term “amino acid residue” or “amino acid” includes reference to an amino acid that is incorporated into a protein, polypeptide, and/or peptide. The term “polypeptide” includes any polymer of amino acids or amino acid residues. The term “polypeptide sequence” refers to a series of amino acids or amino acid residues which physically comprise a polypeptide and can be any length. A “protein” is a macromolecule comprising one or more polypeptides or polypeptide “chains.” A “peptide” is a small polypeptide of a size of 2 to 20 amino acid residues. The term “amino acid sequence” refers to a series of amino acids or amino acid residues which physically comprise a peptide or polypeptide depending on the length. Unless otherwise indicated, polypeptide and protein sequences disclosed herein are written from left to right representing their order from an amino terminus to a carboxy terminus.

The terms “amino acid,” “amino acid residue,” “amino acid sequence,” or polypeptide sequence include naturally occurring amino acids (including L and D isosteriomers) and, unless otherwise limited, also include known analogs of natural amino acids that can function in a similar manner as the common natural amino acids, such as selenocysteine, pyrrolysine, N-formylmethionine, gamma-carboxyglutamate, hydroxyprolinehypusine, pyroglutamic acid, and selenomethionine (see, e.g., Ho J et al., *ACS Synth Biol* 5: 163-71 (2016); Wang Y. Tsao M, *Chembiochem* 17: 2234-9 (2016)).

The terms “complementarity determining region,” and “CDR,” which are synonymous with “hypervariable region” or “HVR,” are known in the art to refer to non-contiguous sequences of amino acids within antibody variable regions, which confer antigen specificity and/or binding affinity. In general, there are three CDRs in each variable domain (CDR-H1, CDR-H2, CDR-H3) and three CDRs in each light chain variable region (CDR-L1, CDR-L2, CDR-L3). “Framework regions” and “FR” are known in the art to refer to the non-CDR portions of the VHH variable regions of the heavy and light chains. In general, there are four FRs in each full-length variable domain (FR—H1, FR—H2, FR—H3, and FR—H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), “Sequences of Proteins of Immunological Interest,” 5th Ed. Public Health Service, National Institutes of Health, Bethesda. MD (“Kabat” numbering scheme), Al-Lazikani et al., (1997) *JMB* 273,927-948 (“Chothia” numbering scheme); MacCallum et al., *J. Mol. Biol.* 262:732-745 (1996), “Antibody-antigen interactions: Contact analysis and binding site topography,” *J. Mol. Biol.* 262, 732-745.” (“Contact” numbering scheme); Lefranc M P et al., “IMGT unique numbering for immunoglobulin and T cell receptor variable domains and Ig superfamily V-like domains,” Dev Comp *Immunol,* 2003 January; 27(1):55-77 (“IMGT” numbering scheme); Honegger A and Plückthun A, “Yet another numbering scheme for immunoglobulin variable domains: an automatic modeling and analysis tool,” *J Mol Biol,* 2001 Jun. 8; 309(3):657-70, (“Aho” numbering scheme); and Whitelegg N R and Rees A R, “WAM: an improved algorithm for modelling antibodies on the WEB,” *Protein Eng.* 2000 December; 13(12):819-24 (“AbM” numbering scheme. In certain embodiments, the CDRs of the antibodies described herein can be defined by a method selected from Kabat, Chothia, IMGT, Aho, AbM, or combinations thereof.

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, “30a,” and deletions appearing in some antibodies. The two schemes place certain insertions and deletions (“indels”) at different positions, resulting in differential numbering. The Contact scheme is based on analysis of complex crystal structures and is similar in many respects to the Chothia numbering scheme.

The term “variable region” or “variable domain” refers to the domain of an antibody heavy or light chain that is involved in binding the antibody to antigen. The VHH variable domains of the heavy chain and light chain ($V_H$ and $V_L$, respectively) of a native antibody generally have similar structures, with each domain comprising four conserved framework regions (FRs) and three CDRs (See e.g., Kindt et al. Kuby *Immunology,* 6th ed., W.H. Freeman and Co., page 91(2007)). A single $V_H$ or $V_L$ domain may be sufficient to confer antigen-binding specificity. Furthermore, antibodies that bind aparticular antigen may be isolated using a $V_H$ or $V_L$ domain from an antibody that binds the antigen to screen a library of complementary $V_L$ or $V_H$ domains, respectively (See e.g., Portolano et al., *J. Immunol.* 150:880-887 (1993); Clarkson et al., *Nature* 352:624-628 (1991)).

The antigen binding regions of the antibodies described herein may be humanized. “Humanized” refers to an antigen binding region in which all or substantially all CDR amino acid residues are derived from non-human CDRs and all or substantially all FR amino acid residues are derived from human FRs. A humanized antibody optionally may include at least a portion of an antibody constant region derived from a human antibody.

The phrase “antigen binding region”, as used herein, refers to the region of a polypeptide responsible for specific binding to an antigen, such region one or more antigen binding domains comprising complementarity determining regions, variable regions and framework regions, which may be derived from, modeled on, or may mimic, antibodies or fragments thereof, as are known by the person of ordinary skill in the art. In one embodiment, the “antigen binding region” of an antigen binding arm contains one or two antigen binding domains. In some embodiments, the “antigen binding region” of an antigen binding arm consists of a single antigen binding domain, which antigen binding domain is preferably a VHH polypeptide.

As described herein an “epitope” refers to the binding determinant of an antibody or fragment described herein minimally necessary for specific binding of the antibody or fragment thereof to a target antigen. When the target antigen is a polypeptide the epitope will be a continuous or discontinuous epitope. A continuous epitope is formed by one region of the target antigen, while a discontinuous epitope may be formed from two or more separate regions. A discontinuous epitope, for example, may form when a target antigen adopts a tertiary structure that brings two amino acid sequences together and forms a three-dimensional structure bound by the antibody. When the target antigen is a polypeptide the epitope will generally be a plurality of amino acids linked into a polypeptide chain. A continuous epitope may comprise 5, 6, 7, 8, 9, 10, 11, 12, 13, 14, 15, 16, 17, 18, 19, or 20 contiguous amino acids. While an epitope may comprise a contiguous polymer of amino acids, not every amino acid of the polymer may be contacted by an amino acid residue of the antibody. Such non-contacted amino acids will still comprise part of the epitope as they may be important for the structure and linkage of the contacted amino acids. The skilled artisan may determine if any given antibody binds an epitope of a reference antibody, for example, by cross-blocking experiments with a reference antibody. In certain embodiments, described herein, are antibodies that bind the same epitope of the described antibodies. In certain embodiments, described herein, are antibodies that are competitively blocked by the described antibodies. In certain embodiments, described herein, are antibodies that compete for binding with the described antibodies.

The term "VHH polypeptide", or single variable domain on a heavy chain, as used herein encompasses natural and synthetic compositions and refers to a polypeptide constituting a VHH fragment as it is known in the art, i.e., a polypeptide that constitutes a single domain heavy chain only variable domain fragment, or a polypeptide that structurally and functionally resembles a VHH fragment, as such structure is further described below and has the ability to specifically bind antigen is described below, and as both are well known in the art. In preferred embodiments, the VHH polypeptides comprise a variable domain comprising three heavy chain CDRs. In some embodiments, the VHH polypeptide is derived from a camelid. In other embodiments, the VHH polypeptide is derived from a library. VHH polypeptides bind to antigens with specificity and high affinity. In a preferred embodiment, the VHH polypeptide is a single variable domain comprising the arrangement: FR1, CDR1, FR2, CDR2, FR3, CDR3, and FR4. VHH polypeptides may be obtained, for example, as the antigen binding fragments of heavy chain only antibodies generated in vivo (e.g., in camelids). VHH polypeptides may also be obtained from synthetic libraries, e.g., phage display libraries. For example, see McMahon et al., Nature Structural & Molecular Biology | VOL 25 | Mar. 2018 | 289-296 *Yeast surface display platform for rapid discovery of conformationally selective nanobodies; Moutel et al., eLife* 2016; 5:e16228 NaLi—H1*: A universal synthetic library of humanized nanobodies providing highly functional antibodies and intrabodies*. De Genst E. Saerens D, Muyldermans S, Conrath K. Antibody repertoire development in camelids. Dev Comp Immunol. 2006; 30(1-2):187-98. doi: 10.1016/j.dci.2005.06.010. PMID: 16051357. Vincke C, Gutierrez C, Wernery U, Devoogdt N, Hassanzadeh-Ghassabeh G, Muyldermans S. Generation of single domain antibody fragments derived from camelids and generation of manifold constructs. Methods Mol Biol. 2012; 907:145-76. doi: 10.1007/978-1-61779-604-7_8. PMID: 22907350. Arbabi Ghahroudi M, Desmyter A, Wyns L, Hamers R, Muyldermans S. Selection and identification of single domain antibody fragments from camel heavy-chain antibodies. FEBS Lett. 1997 Sep. 15; 414(3):521-6. doi: 10.1016/s0014-5793(97)01062-4. PMID: 9323027.

For VHH humanization, see, for example, Vincke C, Loris R, Saerens D, Martinez-Rodriguez S, Muyldermans S, Conrath K. General strategy to humanize a camelid single-domain antibody and identification of a universal humanized nanobody scaffold. J Biol Chem. 2009 Jan. 30; 284(5):3273-84. doi: 10.1074/jbc.M806889200. Epub 2008 Nov. 14. PMID: 19010777.

For VHH stability, see, for example, Kunz P, Flock T, Soler N, Zaiss M, Vincke C, Sterckx Y, Kastelic D, Muyldermans S, Hoheisel J D. Exploiting sequence and stability information for directing nanobody stability engineering. Biochim Biophys Acta Gen Subj. 2017 September; 1861(9): 2196-2205. doi: 10.1016/j.bbagen.2017.06.014. Epub 2017 Jun. 20. PMID: 28642127; PMCID: PMC5548252; Kunz P, Zinner K, Mücke N, Bartoschik T, Muyldermans S, Hoheisel J D. The structural basis of nanobody unfolding reversibility and thermoresistance. Sci Rep. 2018 May 21; 8(1):7934. doi: 10.1038/s41598-018-26338-z. PMID: 29784954; PMCID: PMC5962586.

An Fc domain generally encompasses and/or refers to a C-terminal region of an immunoglobulin heavy chain that contains at least a portion of the constant region, such as an immunoglobulin $CH_2$ and $CH_3$ domain. The term includes native sequence Fc regions and variant Fc regions. For example, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fe region or constant region is according to the EU numbering system, also called the EU index, as described in Kabat et al., Sequences of Proteins of Immunological Interest, 5th Ed. Public Health Service, National Institutes of Health, Bethesda, MD, 1991. In certain embodiments, the Fe region include IgG and sub-classes thereof (e.g., IgG1 and IgG4), IgM, IgE, IgA, and/or IgD heavy chain constant regions and/or heavy chain constant regions derived from IgG and sub-classes thereof (e.g., IgG1 and IgG4), IgM, IgE, IgA, and IgD.

In some embodiments, the Fc domain comprises an immunoglobulin (e.g., IgG1) $CH_2$ domain, and immunoglobulin $CH_3$ domain, or both of an immunoglobulin $CH_2$ and $CH_3$ domain. In certain embodiments, the Fc domain comprises an immunoglobulin CH-2 and $CH_3$ domain. The Fc domain is attached (e.g., linked or fused) to the VHH variable domain (e.g., VIIH). Generally, the antibodies described herein have the format variable domain—hinge—Fc domain, wherein the hinge sequence is included as part of the Fc domain sequence.

In some instances, the Fc region of an immunoglobulin is important for many important antibody functions (e.g. effector functions), such as antigen-dependent cellular cytotoxicity (ADCC), complement dependent cytotoxicity (CDC), and antibody-dependent cell-mediated phagocytosis (ADCP), result in killing of target cells, albeit by different mechanisms. Accordingly, in some embodiments, the polypeptides described herein comprise the variable domains of the invention combined with constant domains comprising different Fe regions, selected based on the biological activities of the antibody for the intended use. In certain instances, Human IgGs, for example, can be classified into four subclasses, IgG1, IgG2, IgG3, and IgG4, and each these of these comprises an Fe region having a unique profile for binding to one or more of Fcγ receptors (activating receptors FcγRI (CD64), FcγRIIA, FcγRIIC (CD32); FcγRIIIA and FcγRIIIB (CD16) and inhibiting receptor FcγRIIB), and for the first component of complement (C1q). Human IgG1 and IgG3 bind to all Fcγ receptors; IgG2 binds to $Fc\gamma RIIA_{H131}$, and with lower affinity to $Fc\gamma RIIA_{R131}$ $Fc\gamma RIIIA_{V158}$; IgG4 binds to FcγRI, FcγRIIA, FcγRIIB, FcγRIIC, and $Fc\gamma RIIIA_{V158}$; and the inhibitory receptor FcγRIIB has a lower affinity for IgG1, IgG2 and IgG3 than all other Fcγ receptors. Studies have shown that FcγRI does not bind to IgG2, and FcγRIIIB does not bind to IgG2 or IgG4. Id. In general, with regard to ADCC activity, human IgG1≥IgG3>>IgG4≥IgG2.

In some embodiments, the polypeptides of this disclosure comprise an Fc region that are variants that possess reduced effector functions, which make it a desirable candidate for applications in which certain effector functions (such as complement fixation and ADCC) are unnecessary or deleterious. Such antibodies can have decreased complement-dependent cytotoxicity (CDC), antibody -dependent cell cytotoxicity (ADCC), or antibody dependent cellular phagocytosis (ADCP). In some embodiments, the antibodies of this disclosure are variants that possess increased effector functions for applications in which increased immunogenicity would be beneficial. Such antibodies can have increased CDC, ADCC, or ADCP, or a combination thereof. Non-limiting examples of in vitro assays to assess ADCC activity of a molecule of interest is described in U.S. Pat. Nos. 5,500,362 and 5,821,337. Alternatively, non-radioactive assays methods may be employed (e.g., ACTI™ and CytoTox 96® non-radioactive cytotoxicity assays). Useful effector cells for such assays include peripheral blood mononuclear cells (PBMC), monocytes, macrophages, and Natural Killer (NK) cells.

An antibody that "binds" an antigen or epitope of interest is one that binds the antigen or epitope with sufficient affinity that is measurably different from a non -specific interaction. Specific binding can be measured, for example, by determining binding of a molecule compared to binding of a control molecule, which generally is a molecule of similar structure that does not have binding activity (e.g., an isotype control).

"Specific binding" refers to an antibody that is capable of binding antigen with sufficient affinity such that the antibody is useful as a diagnostic and/or therapeutic agent in targeting that antigen.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways using available computer software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and whereY is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "affinity" refers to the strength of the sum total of noncovalent interactions between a single binding site of a molecule (e.g., an antibody) and its binding partner (e.g., an antigen or epitope). Unless indicated otherwise, as used herein, "binding affinity" refers to intrinsic binding affinity which reflects a 1:1 interaction between members of a binding pair (e.g., antibody and antigen or epitope). The affinity of a molecule X for its partner Y can generally be represented by the dissociation constant ($K_D$). Affinity can be measured by common methods known in the art, including those described herein. Specific illustrative embodiments for measuring binding affinity are described herein.

A nucleic acid as disclosed herein includes one or more nucleic acid molecules. An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present at extrachromosomal location or at a chromosomal location that is different from its natural chromosomal location.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

As used herein, the terms "expressed," "expressing," or "expresses," and grammatical variants thereof, refer to translation of a polynucleotide or nucleic acid into a protein.

As used herein, the term "immunoconjugate" refers to a molecular complex comprising an at least one antigen binding region derived from an antibody (e.g., variable regions or complementarity determining regions) further coupled to at least one non-antibody derived molecule, such as a chelator or cytotoxic agent. Non-antibody derived molecules may for example be conjugated to one or more lysine or cysteine resides of the antigen binding region or to a constant region coupled (by peptide linkage or otherwise) to the antigen binding region. In some embodiments, the immunoconjugate further comprises a chelating agent (interchangeably, "chelator"). In one embodiment, an immunoconjugate comprises an antibody construct of this disclosure linked directly or indirectly to a cytotoxic agent or radioisotope. A "radionuclide" as used herein are a class of chemicals where the nucleus of an atom is unstable.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

EXAMPLES

Example 1. Antibody Production

Antibody plasmids were generated by cloning the VHH sequence, with a hinge and Fc portion (human IgG1 CH2-CH3) into a mammalian expression vector. In some instances, mutations were introduced into the Fc portion. To produce recombinant VHH-Fc and variants thereof, plasmid was transfected into HEK293.SUS cells (ATUM, or similar). After 3-5 days of secretion, the antibody-containing supernatant was cleared of cells by centrifugation and sterile filtration. Antibodies were purified using Mab Select™ SuRe™ PCC column (GE, Cat #: 11003495) and buffer exchanged into PBS, pH 7.0. Proteins were quantified using A280 or BCA. The purity of the antibodies were tested by SDS-PAGE, capillary electrophoresis, HPLC-SEC and LC-MS using standard protocols. Regarding VHH polypeptides, see, for example, McMahon et al., Nature Structural & Molecular Biology VOL 25 I March 2018 I289-296 *Yeast surface display platform for rapid discovery of conformationally selective nanobodies*; Moutel et al., eLife 2016; 5:e16228 NaLi—H1*: A universal synthetic library ofhumanized nanobodies providing highly functional antibodies and intrabodies*. De Genst E, Saerens D, Muyldermans S, Conrath K. Antibody repertoire development in camelids. Dev Comp Immunol. 2006; 30(1-2):187-98. doi: 10.1016/j.dci.2005.06.010. PMID: 16051357. Vincke C, Gutiérrez C, Wernery U, Devoogdt N, Hassanzadeh-Ghassabeh G, Muyldermans S. Generation of single domain antibody fragments derived from camelids and generation of manifold constructs. Methods Mol Biol. 2012:907:145-76. doi: 10.1007/978-1-61779-974-7_8. PMID: 22907350. Arbabi Ghahroudi M, Desmyter A, Wyns L, Hamers R, Muyldermans S. Selection and identification of single domain antibody fragments from camel heavy-chain antibodies. FEBS Lett. 1997 Sep. 15; 414(3):521-6. doi: 10.1016/s0014-5793(97)01062-4. PMID: 9323027.

For VH—H humanization, see, for example, Vincke C, Loris R, Saerens D, Martinez-Rodriguez S, Muyldermans S, Conrath K. General strategy to humanize a camelid single-domain antibody and identification of a universal humanized nano body scaffold. J Biol Chem. 2009 Jan. 30; 284(5): 3273-84, doi: 10.1074/jbc.M806889200. Epub 2008 Nov. 14. PMID: 19010777.

For the antibodies disclosed herein, humanization was performed by a contract research organization (CRO) (IPA) using an in silico design.

The CDRs were defined in the parental llama VHI and matched to closest human germline and therapeutic VHH sequences. The parental CDRs were grafted onto a selected human germline, adding human germline J region with highest similarity to parental germline V region. Homology models were used to determine best fit and design back mutations for structural deviations whilst maintaining conserved VHH residues. Humanness was assessed using OAS database. See, for example, Kovaltsuk A, Leem J, Kelm S, Snowden J, Deane CM, Krawczyk, K. Observed Antibody Space: A Resource for Data Mining Next-Generation Sequencing of Antibody Repertoires. J. Immunol. 2018 Oct. 15; 201(8): 2502-2509.

For VHH stability, see, for example, Kunz P, Flock T, Soler N, Zaiss M, Vincke C, Sterckx Y, Kastelic D, Muyldermans S, Hoheisel JD. Exploiting sequence and stability information for directing nanobody stability engineering. Biochim Biophys Acta Gen Subj. 2017 September; 1861(9): 2196-2205. doi: 10.1016/j.bbagen.2017.06.014. Epub 2017 Jun. 20. PMID: 28642127; PMCID: PMC5548252; Kunz P, Zinner K, Mücke N, Bartoschik T, Muyldernans S, Hoheisel J D. The structural basis of nano body unfolding reversibility and thermoresistance. Sci Rep. 2018 May 21; 8(1):7934. doi: 10.1038/s41598-018-26338-z. PMID: 29784954; PMCID: PMC5962586.

Example 2. Chelators

Antibodies were conjugated to linker chelator 1 or linker chelator 2. Linker chelator 1 is -p-SCN-Bn-DOTA which is available from Macrocyclics (Plano, TX). Linker chelator 2 has the following structure:

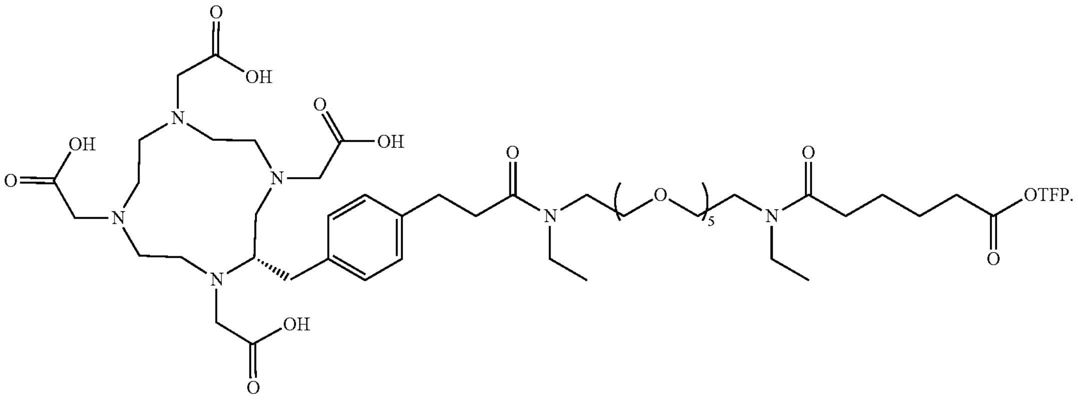

wherein TFP is tetrafluorophenyl. The TFP ester of linker chelator 2 couples to the antibody by reaction with an amine or thiol group of the antibody.

Example 3. Conjugation to Linker Chelators

VHH-Fcs were conjugated to linker chelator 1 or linker chelator 2. The VHH-Fc was buffer-exchanged into 0.1 M NaHCO—$_3$, pH 9 by Amicon® Centrifugal Device (regenerated cellulose), followed by sterile filtration with a Costar® Spin-X® Centrifuge Tube, 0.22 μm (Corning®, Cat #: 8160). The buffer-exchanged antibody was quantified by A280. An appropriate molar excess (5-10 eq) of chelator-linker (50 mM in DMSO) was added to the VHH-Fc (5 mg/mL final concentration) and the reaction was incubated at 25° C. overnight in the Thermomixer® at 550 rpm. After the reaction was complete, the sample was passed through a Zeba column (ThermoFisher®, Cat #: 87770) according to the manufacturer's protocol to remove unused chelator-linker and buffer-exchange into PBS (pH 7.4) (LifeTechnologies®, Cat #: 10010-023) using a Millipore® Ultrafree® Centrifugal Filter, (centrifuge for 4 min at 4000 g). To remove high molecular weight species (HMWS) and low molecular weight species (LMWS), VHH-Fcs were purified by SEC using an AKTA Pure™ FPLC system with a Cytiva® HiLoad™ 16/600 Superdex™ 200 pg column. TBS buffer (50 mM Tris, 150 mM NaCl, OmniTrace® Ultra™ water [VWR, Cat #: CAWX0003-2]), pH 7.6 was used for the SEC buffer. After SEC, the fractions containing intact VHH-Fcs were pooled together and concentrated using Amicon regenerated cellulose unit to 5-10 mg/ml. The concentrated sample was transferred to an Ultrafree®-MC GV Centrifugal Filter, 0.22 μm 0.5 mL (Millipore®, Cat #: UFC30GV0S) and spun at 3,000×g for 3 minutes. Protein content was quantified with a Lunatic® (Unchained Labs®) UV/vis A280.

Mass Spectronetry Analysis

Conjugates were analyzed by HPLC-Q-TOF-MS using an Agilent® AdvanceBio™ 6545XT LC/QTOF mass spectrometer with a mobile phase of 30% acetonitrile in Milli-Q® water with 0.2% formic acid and 0.1% trifluoroacetic acid (all solvents and acids LC-MS grade) using an isocratic elution with a constant flow rate of 0.5 mL/min. on an Agilent® AdvanceBio™ SEC column (I.D. 4.6 mm/Length: 150 mm/Particle size: 1.9 m/Pore size: 200 Å, Part #: PL1580-3201) combined with an Agilent® AdvanceBio™ SEC guard column (I.D. 4.6 mm/Length: 30 mm/Particle size: 1.9 μm/Pore size: 200 Å, Part #: PL1580-1201). De-convolution of raw data and CAR calculations were done with Agilent's® BioConfirm® software (Version 12.0) on Agilent's® MassHunter® workstation.

Example 4. Size-Exclusion Chromatography (SEC) Analysis—Purity

Purity analysis was performed for conjugates and non-conjugated VHH-Fcs using an Agilent® 1290 Infinity 11' HPLC equipped with a UV/VIS PDA detector and a Tosoh Bioscience® TSKgel® G3000SWXL (I.D. 7.8 mm/Length: 300 mm/Particle size: 5 μm/Pore size: 250 Å, Part #: 08541) column combined with a guard column (TSKgel® SWXL Guard Column I.D. 6.0 mm/Length: 40 mm/Particle size: 7 μm, Part #: 08543) using an isocratic elution with a mobile phase consisting of 78 mM $KHPO_4$, 122 mM $K_2HPO_4$, 250 mM KCl, 15% 2-propanol (HPLC-grade), pH- 7.0, 0.2 μm filtered, over 45 min at a constant flow rate of 0.5 mL/min. Purity was assed using 280 nm traces.

Example 5. Antibody Binding, Cell Internalization, and Characterization Data

Table 1 provides binding and internalization properties for antibodies of the present disclosure. Tables 2-6 provide characterization data for antibodies of the present disclosure. Table 5 provides data to show that Ab-5 VHH-Fc (SEQ ID NO: 34) binds with high affinity to human and cynomolgus 5T4 (Biacore® Affinity Characterization). Table 6 provides data to show that conjugation has no impact on binding affinity, as performed by bio-layer interferometry (BLI).

TABLE 1

Antibody Binding and Internalization Properties

| Antibody/ Antibody Conjugate | NCI-H1975 $EC_{50}$ (nM) | NCI-H1975 Internalization (AUC) | Biacore $K_D$ (nM) human/ cynomolgus 5T4 | hFcRn $K_D$ (nM) (wt = 0.84 nM) |
|---|---|---|---|---|
| Ab-1(SEQ ID NO: 30) | 8.20 | 19.61 | 20.2/28.7 | 38.55 |
| Ab-1(SEQ ID NO: 30)-linker chelator 1 | 12.70 | 17.02 | — | — |
| Ab-1(SEQ ID NO: 30)-linker chelator 2 | 15.53 | 19.64 | — | — |
| Ab-2(SEQ ID NO: 31) | 8.85 | 22.23 | 21/26.6 | 56.38 |
| Ab-2(SEQ ID NO: 31)-linker chelator 1 | 10.07 | 17.91 | — | — |
| Ab-2(SEQ ID NO: 31)-linker chelator 2 | 9.24 | 14.07 | — | — |
| Ab-3(SEQ ID NO: 32) | 2.45 | 14.64 | 2.2/1.67 | weak |
| Ab-3(SEQ ID NO: 32)-linker chelator 1 | 3.48 | 15.42 | — | — |
| Ab-3(SEQ ID NO: 32)-linker chelator 2 | 3.09 | 13.71 | — | — |

TABLE 1-continued

| Antibody Binding and Internalization Properties | | | | |
|---|---|---|---|---|
| Antibody/ Antibody Conjugate | NCI-H1975 $EC_{50}$ (nM) | NCI-H1975 Internalization (AUC) | Biacore $K_D$ (nM) human/ cynomolgus 5T4 | hFcRn $K_D$ (nM) (wt = 0.84 nM) |
| Ab-4(SEQ ID NO: 33) | 0.64 | 16.40 | 3.2/15.1 | 39.2 |
| Ab-4(SEQ ID NO: 33)-linker chelator 1 | 0.96 | 16.1 | — | — |
| Ab-4(SEQ ID NO: 33)-linker chelator 2 | 0.80 | 13.02 | — | — |
| Ab-5(SEQ ID NO: 34) | 0.49 | 5.33 | 1.1/1.23 | 49.75 |
| Ab-5(SEQ ID NO: 34)-linker chelator 1 | 0.81 | 5.33 | — | — |
| Ab-5(SEQ ID NO: 34)-linker chelator 2 | 0.76 | 3.09 | — | — |
| H8 | | 3.8 | | |
| Ab-6 | | 7.6 | | |

TABLE 2

| Antibody Characterization | | | | | |
|---|---|---|---|---|---|
| Antibody/ Antibody Conjugate | Polyreactivity Scores | AC-SINS score (dlambda Max) | Tm1 (° C.) (standard deviation) | Tonset (° C.) (standard deviation) | Tagg (° C.) (standard deviation) |
| Ab-1(SEQ ID NO: 30) | 8.85/10.40 | 10.64 | 58.5 (0.11) | 50.3 (0.6) | 66.3 (0.78) |
| Ab-1(SEQ ID NO: 30)-linker chelator 1 | 3.07/3.77 | 3.21 | 57.3 (0.48) | 49.5 (0.07) | 74.2 (0.42) |
| Ab-1(SEQ ID NO: 30)-linker chelator 2 | 2.71/3.10 | 4.70 | 55.5 (0.33) | 47.7 (0.43) | 61 (0.53) |
| Ab-2(SEQ ID NO: 31) | 9.9/10.6 | 8.66 | 58.1 (0.18) | 50.1 (0.13) | 61.7 (0.11) |
| Ab-2(SEQ ID NO: 31)-linker chelator 1 | 3.7/4.26 | 4.70 | 57.2 (0.04) | 49.7 (0.07) | 77 (0.37) |
| Ab-2(SEQ ID NO: 31)-linker chelator 2 | 3.63/4.10 | 3.21 | 54.8 (0.15) | 48.4 (2.45) | 71.1 (3.34) |
| Ab-3(SEQ ID NO: 32) | 2.02/2.8 | 6.68 | 58.7 (0.33) | 51.1 (0.7) | 72.5 (0.95) |
| Ab-3(SEQ ID NO: 32)-linker chelator 1 | 1.14/1.27 | 5.19 | 57 (0.17) | 49.5 (0.39) | 76.6 (0.7) |
| Ab-3(SEQ ID NO: 32)-linker chelator 2 | 1.14/1.26 | 4.70 | 55.6 (0.11) | 47.5 (0.67) | 71.9 (0.55) |
| Ab-4(SEQ ID NO: 33) | 1.98/2.79 | 6.68 | 59.2 (0.17) | 56.5 (0.12) | 76.3 (0.37) |
| Ab-4(SEQ ID NO: 33)-linker chelator 1 | 1.17/1.36 | 4.70 | 58.7 (0.16) | 56.4 (0.25) | 71.7 (0.18) |
| Ab-4(SEQ ID NO: 33)-linker chelator 2 | 1.26/1.43 | 4.70 | 57.3 (0.4) | 54.3 (0.11) | 77.2 (0.58) |
| Ab-5(SEQ ID NO: 34) | 1.74/2.31 | 5.19 | 63.2 (0.06) | 60.2 (0.11) | 76.2 (0.41) |
| Ab-5(SEQ ID NO: 34)-linker chelator 1 | 1.10/1.22 | 5.19 | 63.2 (0.26) | 60 (0.5) | 77.8 (0.67) |
| Ab-5(SEQ ID NO: 34)-linker chelator 2 | 1.04/1.16 | 4.70 | 62.2 (0.22) | 58.3 (0.31) | 76 (0.61) |

TABLE 3

| Antibody Characterization | | | | |
|---|---|---|---|---|
| Antibody | PDI (standard deviation) | Peak 1 Diameter (nm) (standard deviation) | HIC (RT, min) | pI (cIEF) |
| Ab-1(SEQ ID NO: 30) | 0.24 (0.03) | 8.19 (0.37) | 5.06 | 9.49 |
| Ab-1(SEQ ID NO: 30)-linker chelator 1 | 0.35 | 6.81 (1.8) | 5.15 | 5-9.2 |
| Ab-1(SEQ ID NO: 30)-linker chelator 2 | 0.21 | 8.64 (0.38) | 6.20 | 5-9.2 |
| Ab-2(SEQ ID NO: 31) | 0.17 (0.04) | 8.02 (0.95) | 4.19 | 9.48 |
| Ab-2(SEQ ID NO: 31)-linker chelator 1 | 0.24 | 7.99 (0.35) | 4.28 | 5-9.2 |
| Ab-2(SEQ ID NO: 31)-linker chelator 2 | 0.19 | 8.45 (1.1) | 5.14 | 5-9.5 |
| Ab-3(SEQ ID NO: 32) | 0.33 (0.01) | 7.21 (0.57) | 4.24 | 8.57 |
| Ab-3(SEQ ID NO: 32)-linker chelator 1 | 0.29 | 7.795 (0.035) | 4.46 | 5-8.6 |
| Ab-3(SEQ ID NO: 32)-linker chelator 2 | 0.26 | 8.4 (0) | 5.46 | 4.7-8.6 |
| Ab-4(SEQ ID NO: 33) | 0.39 (0.02) | 8.03 (0.69) | 3.85 | 8.55 |
| Ab-4(SEQ ID NO: 33)-linker chelator 1 | 0.39 | 7.16 (1.68) | 3.82 | 5-8.6 |
| Ab-4(SEQ ID NO: 33)-linker chelator 2 | 0.21 | 6.83 (2.23) | 4.87 | 4.7-8.6 |
| Ab-5(SEQ ID NO: 34) | 0.38 (0.05) | 8.03 (0.69) | 3.74 | 8.56 |
| Ab-5(SEQ ID NO: 34)-linker chelator 1 | 0.25 | 7.82 (0.64) | 3.80 | 5-8.6 |
| Ab-5(SEQ ID NO: 34)-linker chelator 2 | 0.18 | 8.66 (1.05) | 4.86 | 4.7-8.6 |

TABLE 4

| Antibody Characterization | | |
|---|---|---|
| Antibody | Immunogenicity (in silico) DRB1 score | Immunogenicity (T cell dep) |
| Ab-1(SEQ ID NO: 30) | 609.1 | — |
| Ab-2(SEQ ID NO: 31) | 683.0 | Moderate risk |
| Ab-3(SEQ ID NO: 32) | 203.1 | Low risk |
| Ab-4(SEQ ID NO: 33) | 124.5 | Low risk |
| Ab-5(SEQ ID NO: 34) | 93.1 | Low risk |

TABLE 5

| Antibody Characterization of Ab-5 VHH-Fc (SEQ ID NO: 34) | | | | |
|---|---|---|---|---|
| Target | ka (1/Ms) | kd (1/s) | $K_D$ (nM) | Rmax (RU) |
| Human 5T4 | $1.57 \times 10^{-5}$ | $1.64 \times 10^{-4}$ | 1.07 | 69.8 |
| Cynomolgus 5T4 | $3.10 \times 10^{-5}$ | $3.81 \times 10^{-4}$ | 1.23 | 65.5 |

TABLE 6

| Conjugate binding of Human 5T4 to Ab-5 VHH-Fc (SEQ ID NO: 34) and Ab-5 VHH (SEQ ID NO: 29) | | | | |
|---|---|---|---|---|
| Target | ka (1/Ms) | kd (1/s) | $K_D$ (nM) | $R^2$ |
| Ab-5 VHH-Fc (SEQ ID NO: 34) | $1.43 \times 10^{-5}$ | $3.17 \times 10^{-4}$ | 2.3 | 0.9987 |
| Ab-5 VHH (SEQ ID NO: 29) | $1.32 \times 10^{-5}$ | $3.41 \times 10^{-4}$ | 2.6 | 0.9964 |

Example 6. Binding Studies

Antibody Binding to 5T4 Expressing Cells

Figure 1B:
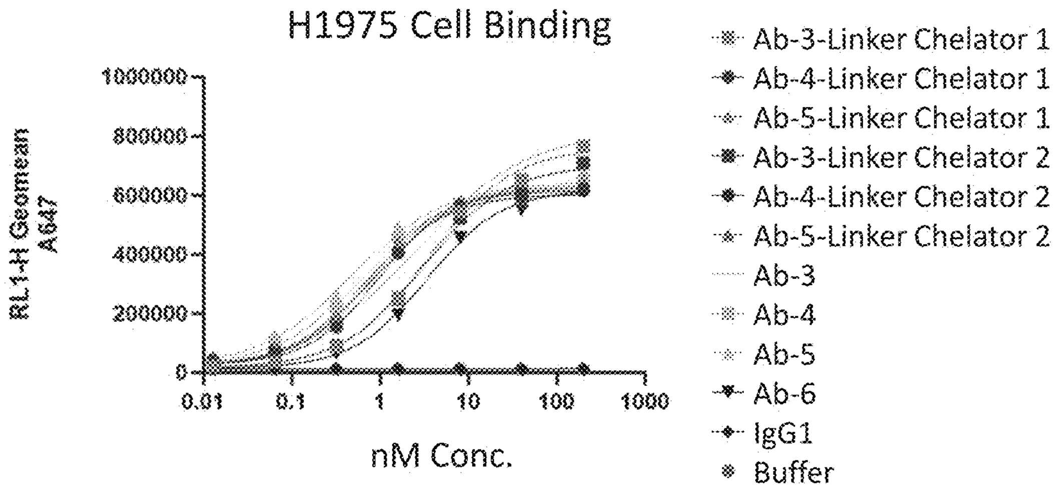
Figure 2A:
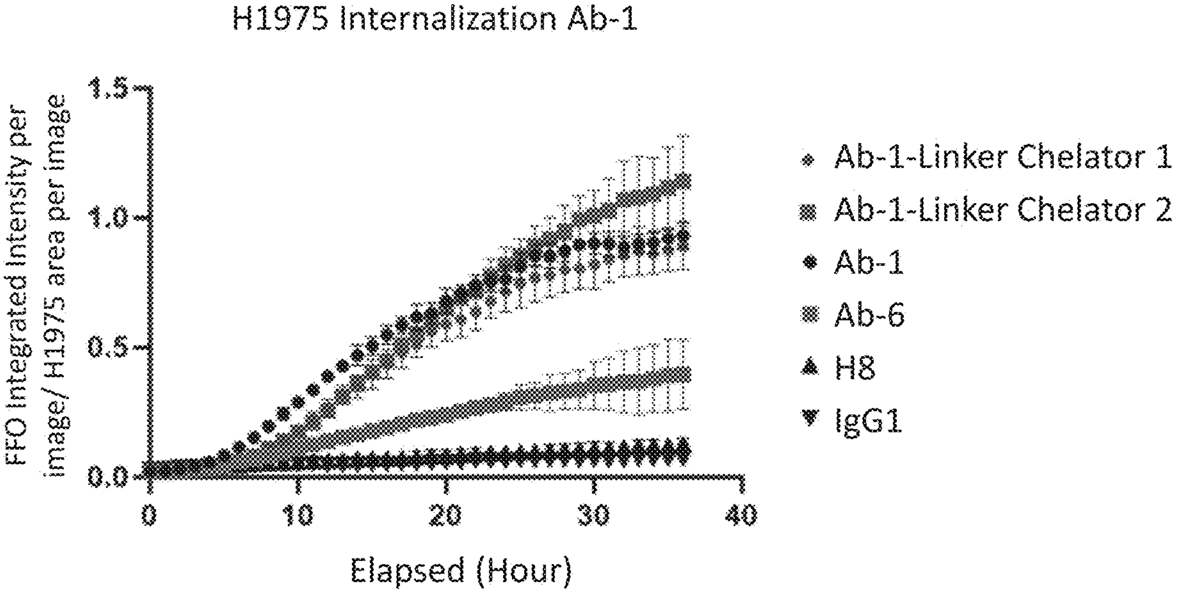
FIGS. 2A-2E show internalization of antibodies of the present disclosure by 5T4 expressing NCI-H1975 cells as a function of time.
Figure 2B:
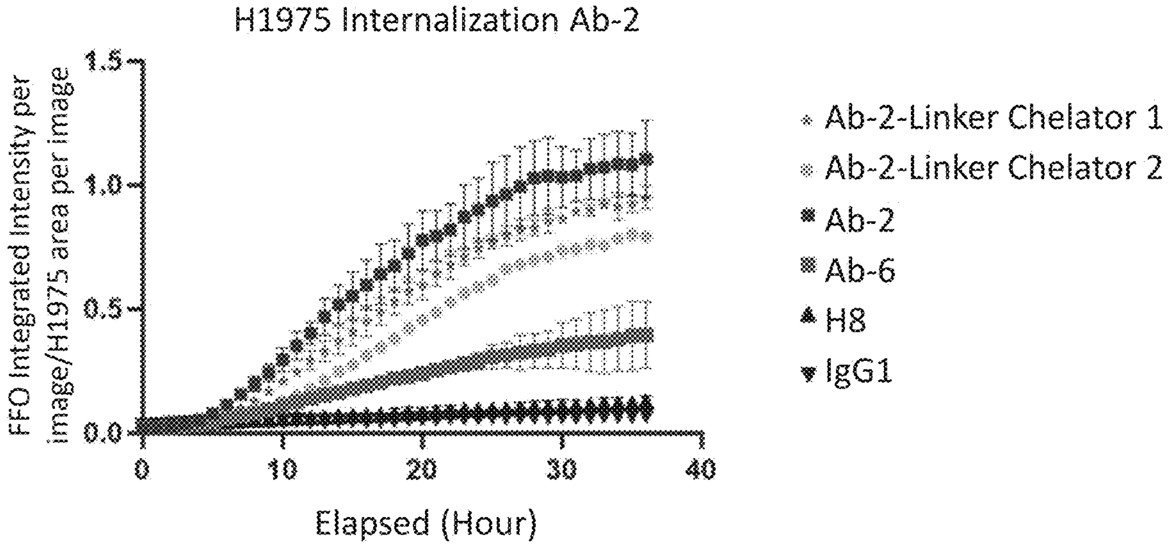
Figure 2C:
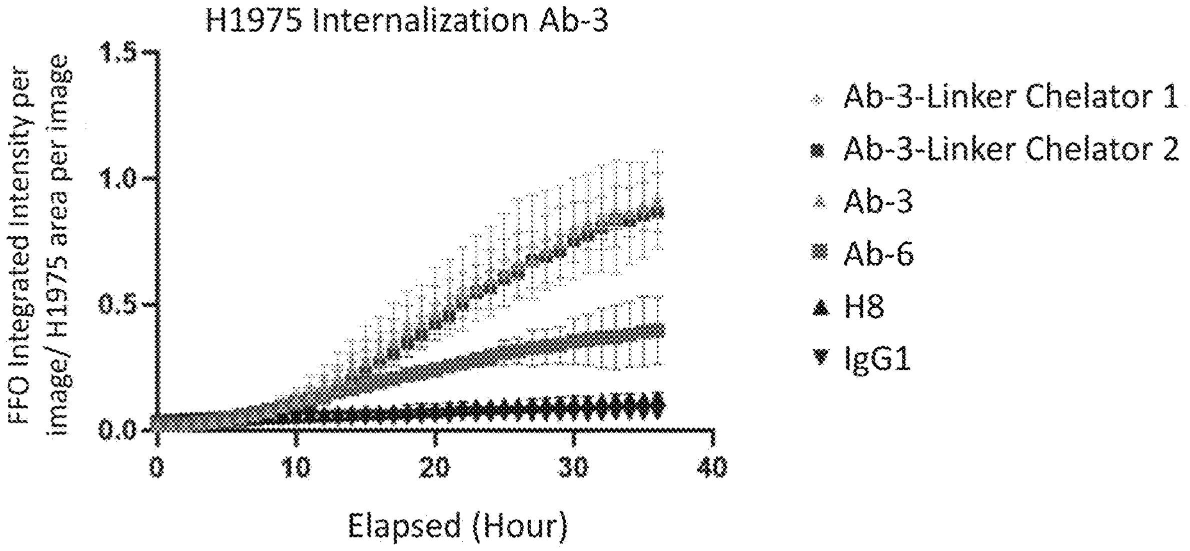
Figure 2D:
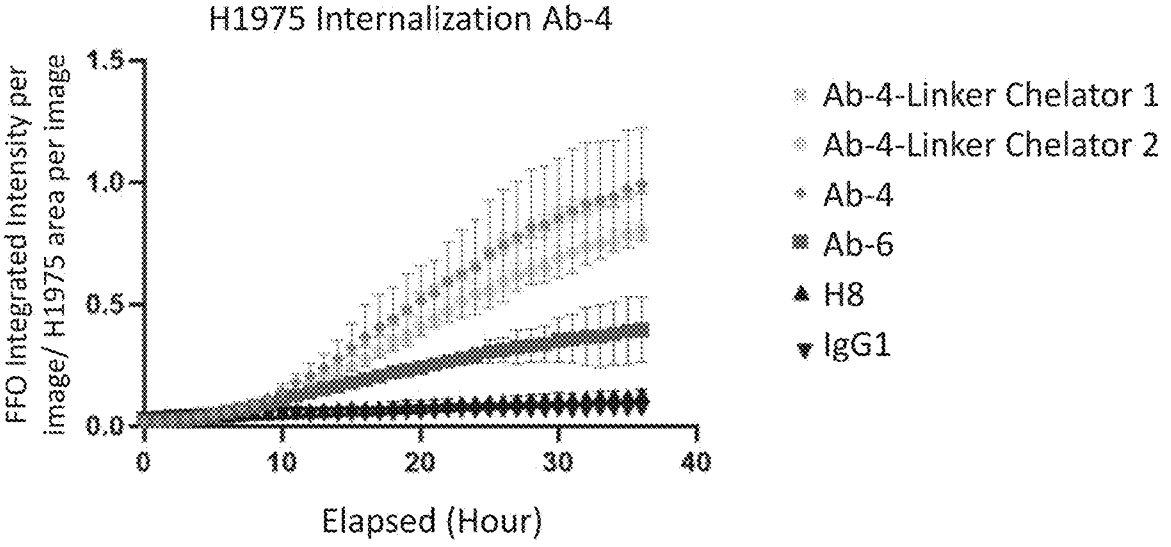
Figure 2E:
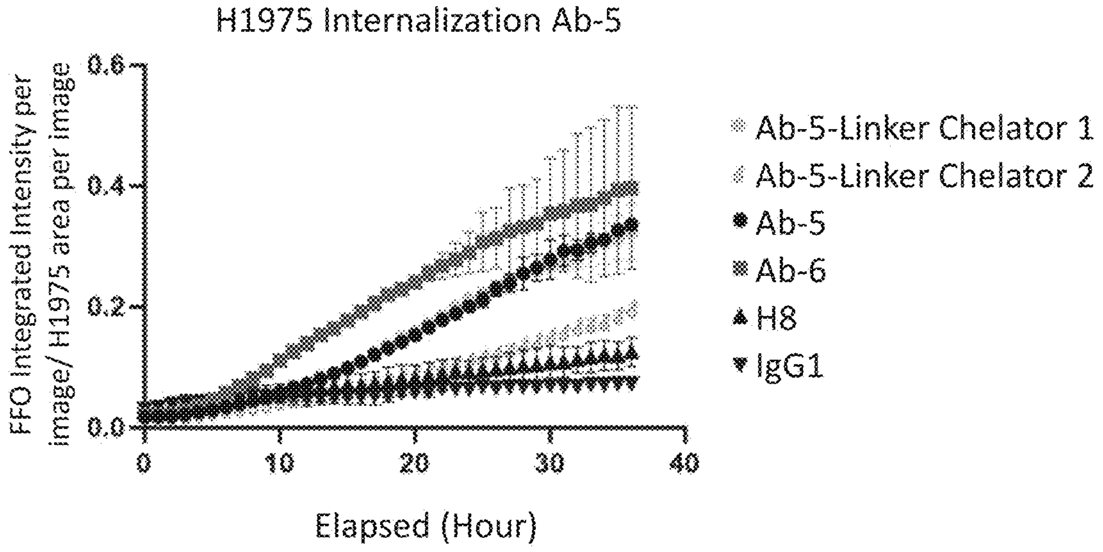
Figure 24A:
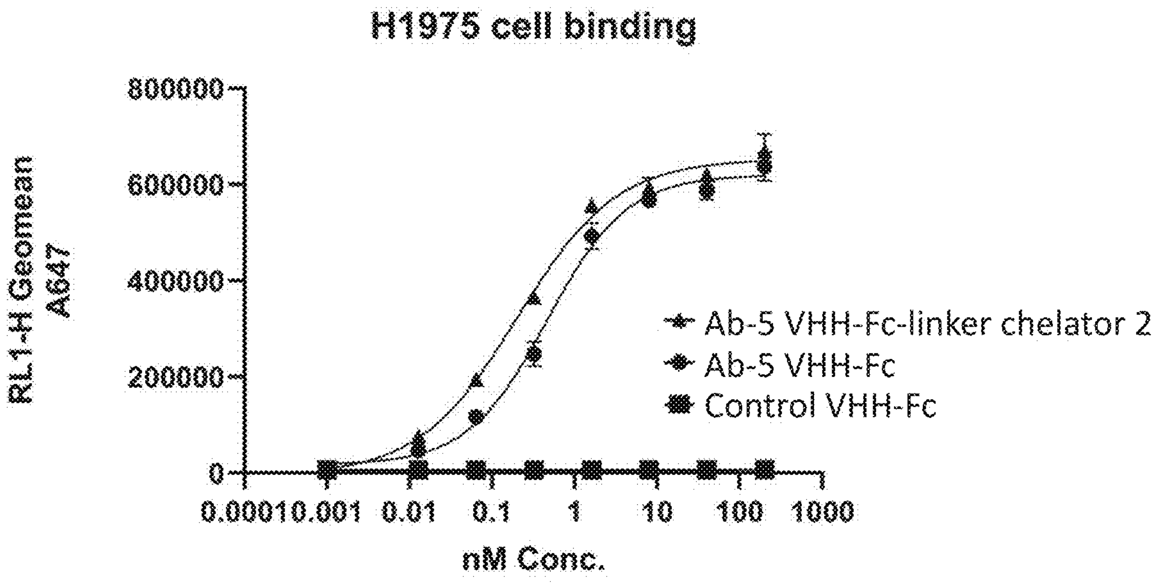
FIG. 24A illustrates binding curves for Ab-5 VHH-Fc and Ab-5 VHH-Fc-linker chelator 2 binding to NCI-H1975 cells, compared to control VHH-Fc (SEQ ID NO: 51).
Figure 24B:
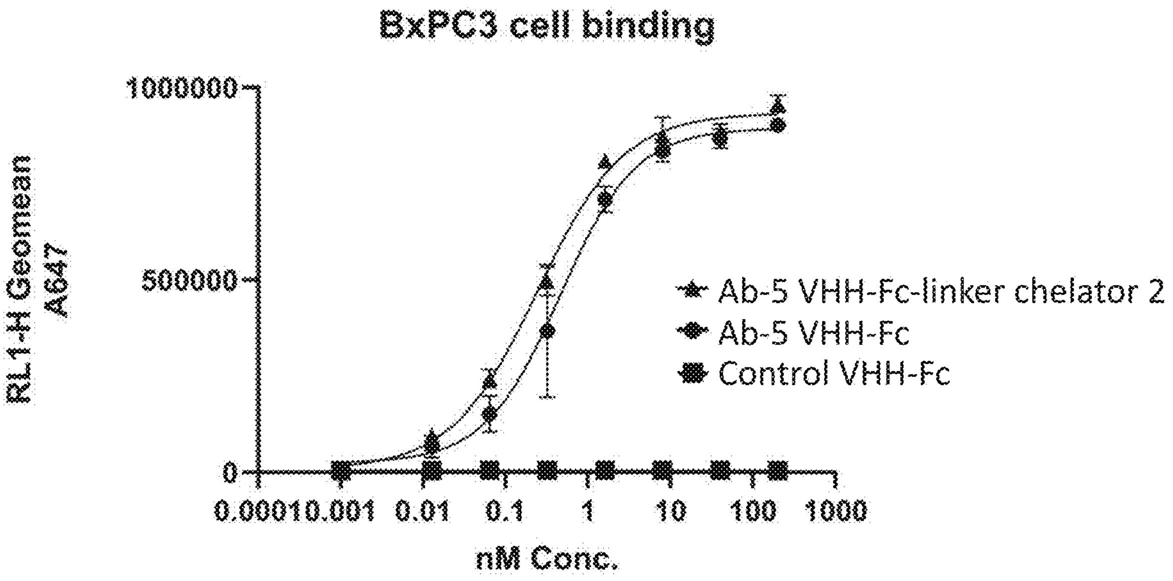
FIG. 24B illustrates binding curves for Ab-5 VHH-Fc and Ab-5 VHH-Fc-linker chelator 2 binding to Bx-PC-3 cells, compared to control VHH-Fc (SEQ ID NO: 51).
Figure 24C:
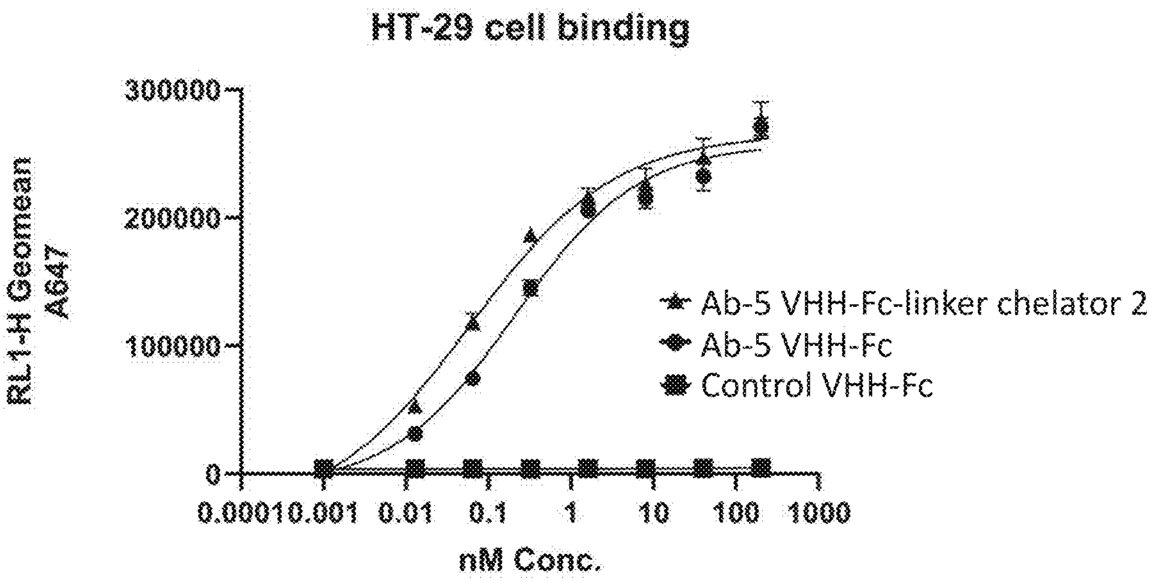
FIG. 24C illustrates binding curves for Ab-5 VHH-Fc and Ab-5 VHH-Fc-linker chelator 2 binding to HT-29 cells, compared to control VHH-Fc (SEQ ID NO: 51).

Antibodies were screened for binding to 5T4 expressing NCI-H1975 cells, BxPC-3 cells, and HT-29 cells. Antibodies were added to NCI-H1975 cells, BxPC-3 cells, and HT-29 cells at varying concentrations and incubated for 1 hour on ice. Cells were washed with 1% fetal bovine serum (FBS) in phosphate-buffered saline (PBS), centrifuged at 450 G for 4 minutes and incubated with 2 mg/mL AlexaFluor® 647 conjugated anti-human IgG (Jackson, Cat #109-605-098) or AlexaFluor® 647 conjugated anti-mouse IgG (Jackson, Cat #115-605-164) with 1:1000 DAPI (Biolegend®, Cat #422801) for 30 minutes on ice. Following two further washes, cells were resuspended, and analyzed by flow cytometry on the iQue® screener platform (Intellicyt®), and data was processed with Forecyt®, according to standard protocols. FIGS. 1A-1B show binding curves for antibody binding to NCI-H1975 cells. The data show that binding is specific to the target-positive cells (i.e., through binding comparison to negative controls). $EC_{50}$s for NCI-H1975 cell binding are provided in Table 1. FIG. 24A shows binding curves for Ab-5 VHH-Fc and Ab-5 VHH-Fc-linker chelator 2 binding to NCI-H1975 cells, compared to control VHH-Fc (SEQ ID NO: 51). Control VHH-Fc (SEQ ID NO: 51) targets viral protein rather than human protein and is a format matched control, with no evidence of binding to human cells. FIG. 24B shows binding curves for Ab-5 VHH-Fc and Ab-5 VHH-Fc-linker chelator 2 binding to Bx-PC-3 cells, compared to control VHH-Fc (SEQ ID NO: 51). FIG. 24C shows binding curves for Ab-5 VHH-Fc and Ab-5 VHH-Fc-linker chelator 2 binding to HT-29 cells, compared to control VHH-Fc (SEQ ID NO: 51).

Antibody Binding to 0.5T4

The KDs for antibody binding to h5T4 and c5T4 antigens were measured using surface-plasmon resonance assays using a BIACORE®-8000 instrument (BIAcore®, Inc., Piscataway, N.J.), e.g., using immobilized antigen CM5 chips at 25° C. and anti-human IgG capture. The KDs for human 5T4 (h5T4) and cynomolgus (c5T4) antigens as measured using surface-plasmon resonance (Biacore®) are provided in Table 1. Nanomolar affinities for h5T4 and c5T4 were demonstrated by surface-plasmon resonance measurements (see Table 1). Ab-3, Ab-4, and Ab-5 were found to have higher affinities for 5T4 compared to Ab-1 and Ab-2. KDs for binding to human 5T4 by Ab-4 and Ab-5 were also measured by surface-plasmon resonance at 25° C. and 37° C. (see Table 7) using a Biacore®1k instrument. Ab-5 was shown to have a higher affinity for 5T4 at both temperatures (see Table 7).

TABLE 7

| KDs for 5T4 Binding at 25° C. and 37° C. | | |
|---|---|---|
| Antibody | Temperature (° C.) | KD (nM) |
| Ab-4 | 25 | 9.1 |
| Ab-4 | 37 | 30 |
| Ab-5 | 25 | 2.5 |
| Ab-5 | 37 | 7.9 |

FcRn Affinity Determination

Antibody FcRn affinity can generally be used to predict the half-life of antibody serum clearance. (See, e.g., Datta-Mannan A et al. "FcRn affinity-pharmacokinetic relationship of five human IgG4 antibodies engineered for improved in vitro FcRn binding properties in cynomolgus monkeys." *Drug Metab Dispos.* 2012 August; 40(8):1545-55). Antibody FcRn binding affinities were determined using Octed RED 96e (Forebio). Briefly, 10 nM of biotinylated human FcRn (hFcRn) (Sino Biological®, Cat #: CT071-H27H-B) was captured with the SA biosensor. The hFcRN coated biosensor was dipped into the sample solutions in sodium phosphate buffer (100 mM Na2HPO4, 150 mM NaCl w/0.05% Tween-20, pH 6.0) with serial concentrations of tested antibodies and the association measured. The dissociation was measured by dipping the biosensors into sodium phosphate buffer without antibody. The $K_D$values were determined using Octet Data Analysis HT 11.0 software. 2:1 (Heterogeneous Ligand) binding model. $K_D$s for Ab-1 to Ab-5 binding to hFcRn are provided in Table 1.

Example 7. Internalization Assays

Antibodies were tested for internalization by 5T4 expressing NCI-H1975 (ATCC; CRL-5908), 5T4 expressing BxPC-3, and 5T4 expressing HT-29, using an Incucyte® cell internalization assay. VHH-Fcs were tested for internalization with target-expressing cells NCI-1H1975 (ATCC; CRL-5908) target-expressing BxPC-3, and target-expressing HT-29. VHHFcs were labelled with Fabfluor-pH orange (Sartorius®; 4812) according to the manufacturer's instructions. The Fabfluor-pH orange reagent has low or no fluorescence at pH>7 but fluoresces in acidic environments upon antibody internalization. Target-expressing cells were seeded 3,000 cells per well in a 96 well plate (Falcon®; 353072) and incubated overnight at 37° C. in 5% C02. Prior to the assay, VHH-Fcs and hu IgG1 isotype control were diluted to 50 nM in media containing 150 nM Fabfluor-pH orange reagent. VHH-Fc fluorophore complexes were incubated at 37° C. for 30 minutes. Equivalent volumes of VHH-Fc Fabfluor-pH orange complex was added to the target-expressing cells such that a 25 nM final concentration was obtained. Imaging was performed using Incucyte® SX5 (Sartorius®) with green/orange/NIR optical module at 20× magnification. The Incucyte® was housed within an incubator at 37° C. in 5% CO2. Images were obtained every hour for a 36-hour period using Incucyte® adherent Cell-by-Cell software module (Sartorius®). Internalization was quantified using Fabfluor-pH orange Integrated Intensity per image divided by target-expressing cell area per image. Area under curve (AUC) was calculated from the resulting graph.

Figure 3:
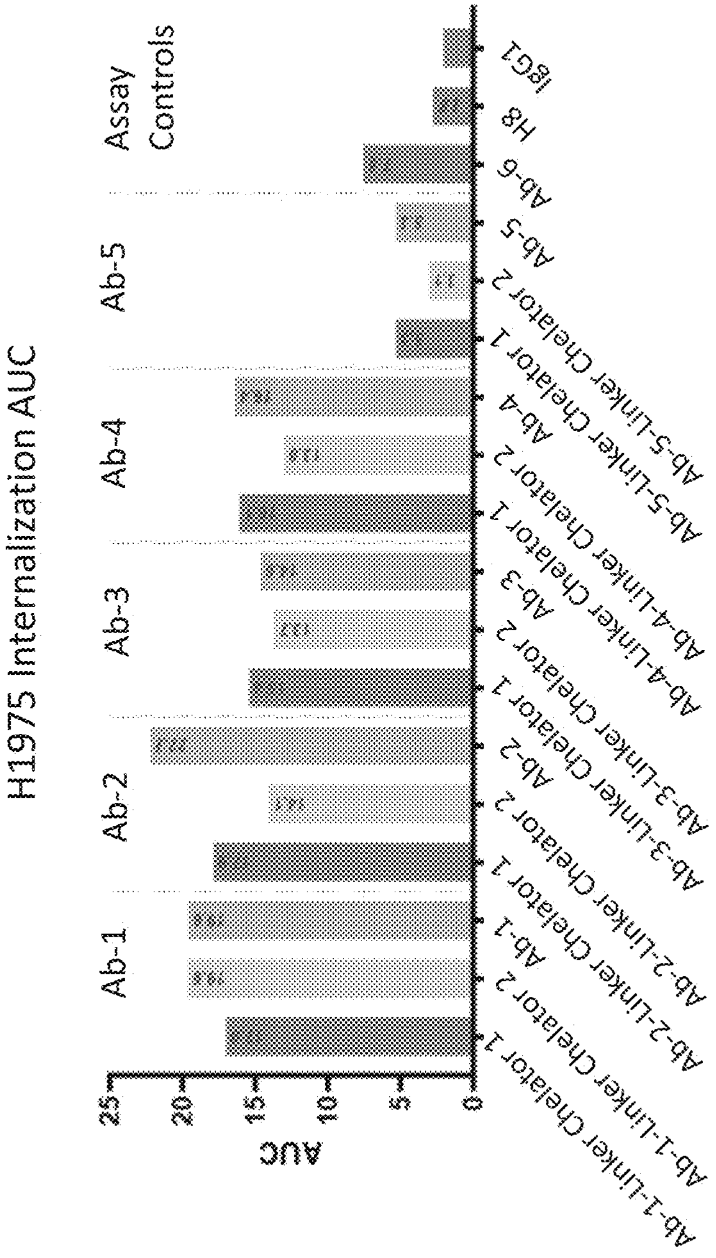
FIG. 3 shows internalization of antibodies of the present disclosure by 5T4 expressing NCI-H1975 cells.
Figure 25A:
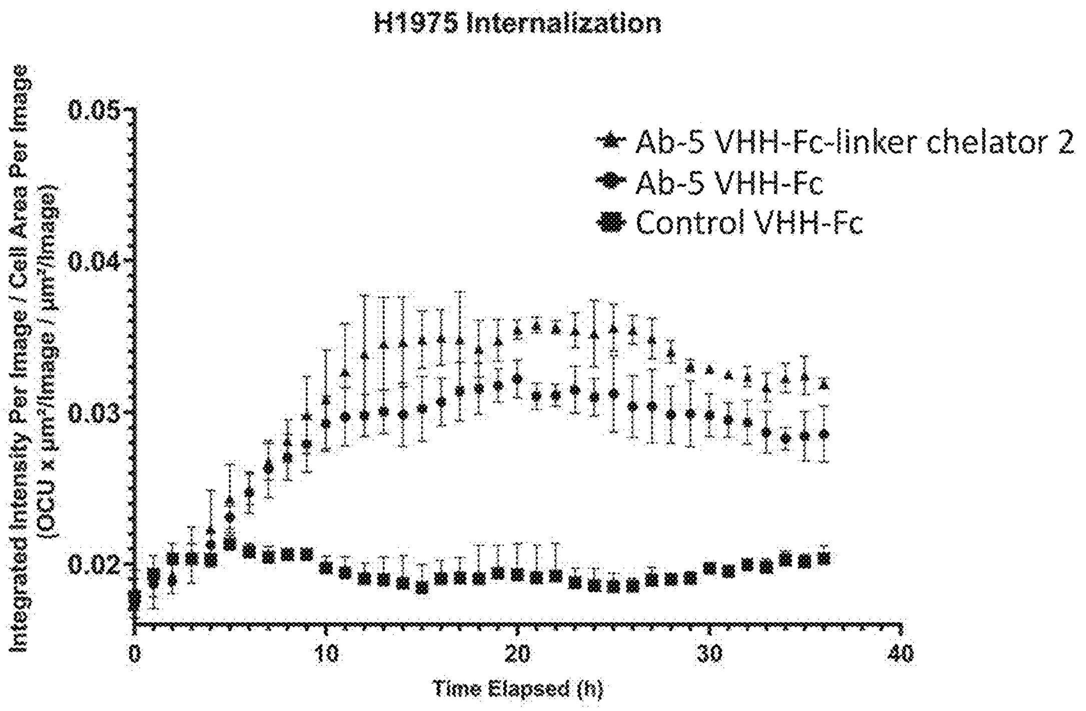
FIG. 25A illustrates NCT-H1975 cell internalization of Ab-5 VHH-Fc and Ab-5 VHH-Fc-linker chelator 2 compared to control VHH-Fc (SEQ ID NO: 51).
Figure 25B:
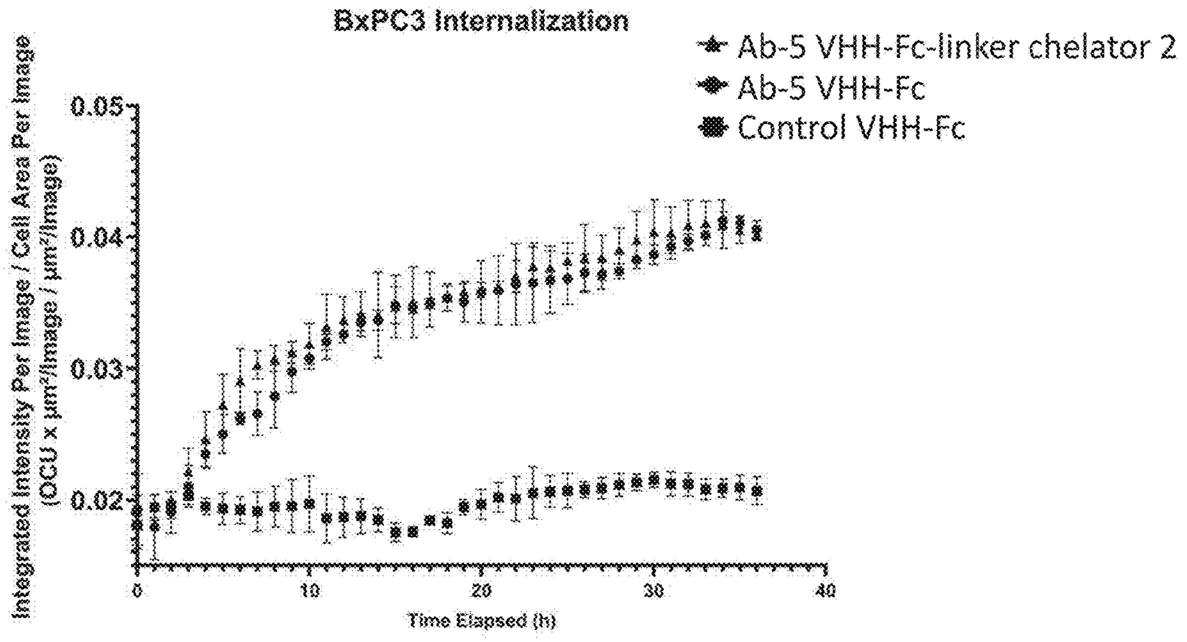
FIG. 25B illustrates BxPC-3 cell internalization of Ab-5 VHH-Fc and Ab-5 VHH-Fc-linker chelator 2 compared to control VHH-Fc (SEQ ID NO: 51).
Figure 25C:
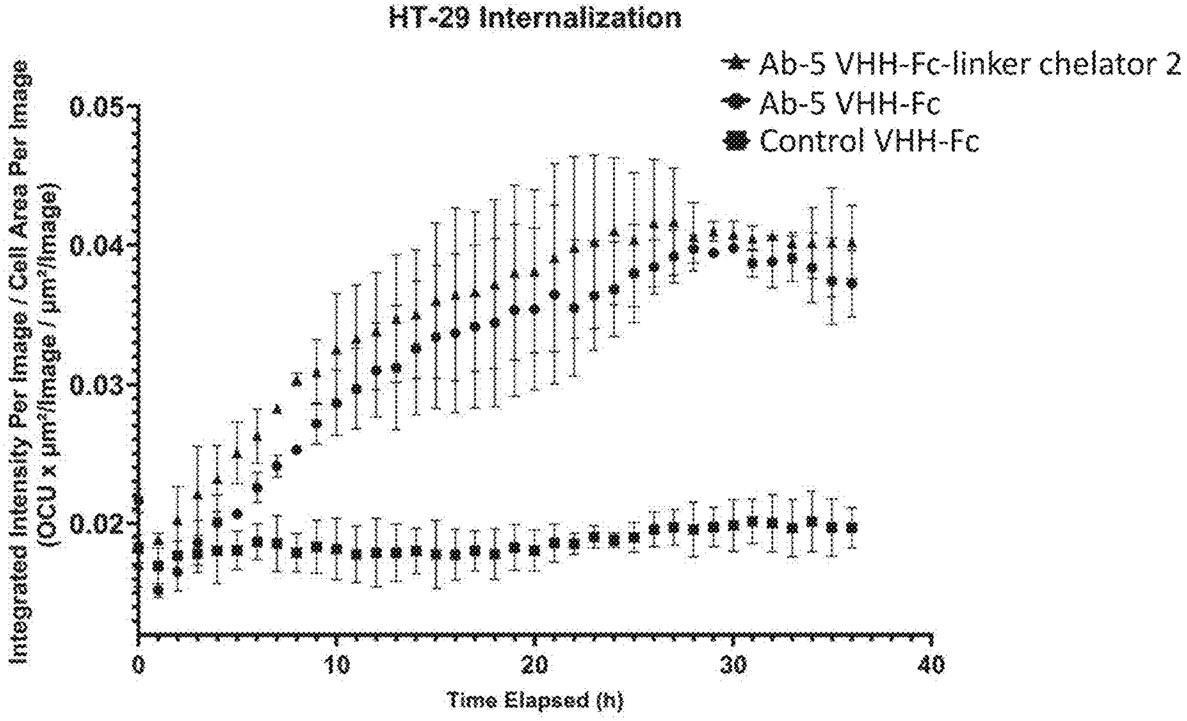
FIG. 25C illustrates HT-29 cell internalization of Ab-5 VHH-Fc and Ab-5 VHH-Fc-linker chelator 2 compared to control VHH-Fc (SEQ ID NO: 51).

FIGS. 2A-2E show NCI-H1975 cell internalization of Ab-1 to Ab-5 and control antibodies as monitored over 36 hours. FIG. 3 is a bar graph demonstrating NCI-H1975 cell internalization as measured using the Incucyte® cell internalization assay. Table 1 lists the corresponding NCI-H1975 cell internalization data (AUC values) of FIG. 3. As can be seen, Ab-5 is a lower internalizer as compared to Ab-1 to Ab-4, but similar to the Ab-6 control. Ab-6 includes the Fc region of SEQ ID NO: 47. Notably, control anti-5T4 (H8) antibody showed lower internalization compared to Ab-1 to Ab-5. FIGS. 25A-25C show Ab-5 VHH and Ab-5 VHH-Fc binding and internalization in NSCLC (NCI-H1975), pancreatic (BxPC-3), and colorectal cancer (HT-29) cell lines. FIG. 25A shows NCI-H1975 cell internalization of Ab-5 VHH-Fc and Ab-5 VHH compared to control VHH-Fc (SEQ ID NO: 51). FIG. 25B shows BxPC-3 cell internalization of Ab-5 VHH-Fc and Ab-5 VHH compared to control VHH-Fc (SEQ ID NO: 51). FIG. 25C shows HT-29 cell internalization of Ab-5 VHH-Fc and Ab-5 VHH compared to control antibody (H8). Table 8 provides an approximate copy number of 5T4 targets per NCI-H1975, BxPC-3, and HT-29 cells.

TABLE 8

| 5T4 expression in NSCLC, pancreatic, and colorectal cancer cell lines. | |
|---|---|
| Cell Line | 5T4 Copies/Cell (Ab-5 VHH-Fc) |
| NCI-H1975 (NSCLC) | About 34,000 |
| BxPC-3 (Pancreatic Cancer) | About 42,000 |
| HT-29 (Colorectal Cancer) | About 18,000 |

Example 8. Antibody Characterization Experiments

Antibody Self-Association Using AC-SINS

Antibody propensities for self-association was determined from affinity-capture self-interaction nanoparticle spectroscopy (AC-SINS) using gold nanoparticles (Au—NP) (Ted Pella®, Cat #: 15705) (PMID: 24492294, 30395473). Briefly, goat IgG and goat anti-human Fc IgG (1:4 mole ratio) were used to coat the Au—NP. Conjugated Au—NP was mixed with 5 μg of each antibody, in quadruplicates, in a 96-well plate. The wavelength scan was measured with Synergy Neo2® plate reader. The difference of maximum absorbance (Δλmax) was calculated by subtracting Emax of each reaction with that of PBS buffer. The data was analyzed with Linest function in Excel using second-order polynomial fitting. Control antibodies with known high AC-SINS scores (above the literature established cut-off of 11 for IgGs) were included in the assay. AC-SINS scores for Ab-1 to Ab-5 are provided in Table 2. AC-SINS scores for the control antibodies are provided in Table 9.

TABLE 9

| AC-SINS Scores for Control Antibodies | |
|---|---|
| Antibody | AC-SINS score (dlambda Max) |
| Infliximab high control | 21.04 |
| Trastuzumab low control | 4.70 |
| Mepolizumab low control | 0.74 |

Antibody Thermal Stabilities

Thermal stability was determined via dynamic scanning fluorimetry (DSF) on an UNCLE Instrument™ (Unchained-Labs®, Version 6.0.0.0 Firmware 1.23 I35). Protein samples were diluted to 1 mg/mL in PBS pH 7.4 (Thermo Scientific®, Cat #: 70011-069) and 9 uL was loaded into UNI miniature cuvettes (Unchained Labs R, Cat #: 201-1010) in triplicate. Filters for acquisition were uniquely determined by experiment ensuring sufficient signal to noise ratios. Acquisition was in a linear gradient of 0.3° C. per minute from 20-95° C., with a 0 second plate hold and a 60 second incubation. Each replicate and sample were independently processed and analyzed with UNCLE™ Analysis (Unchained Labs®, Version 6.0.0.0) (see Table 2).

Antibody Polydispersity

Antibody poly dispersity index (PDI) was assessed using dynamic light scattering (DLS). PDI is a representation of size distribution populations in a sample wherein a PDI of 0.0 represents a perfectly uniform sample with respect to particle size, and a PDI of 1.0 represents a highly polydisperse sample with multiple particle size populations. Dynamic light scanning (DLS) was examined on UNCLE™ (Unchained Labs®, Version 6.0.0.0 Firmware 1.23 I35). DLS data was acquired 20° C. and 95° C. At each temperature, 4 measurements were taken for 5 seconds each and were auto-attenuated, and data filter settings were 5%, 0.5 nM, 490 Da. Results were analyzed on UNCLE™ analysis (Unchained Labs®, Version 6.0.0.0) from triplicate samples were averaged and polydispersity index, peak 1 diameter, and peak 1 mass % were reported as mean with standard deviation. A polydispersity index (PDI) and peak 1 diameter was calculated for each of antibodies Ab-1 to Ab-5 (see Table 3).

Antibody Hydrophobicity

Relative surface hydrophobicity of the purified antibodies was assessed by analytical hydrophobic interaction chromatography (HIC). Conjugates and non-conjugated VHH-Fcs were analyzed using an Agilent® 1290 Infinity II™ HPLC equipped with a UV/VIS PDA detector with a mobile phase gradient of starting at 36% mobile phase A (Milli-Q® water with 2.5 M ammonium sulfate $(NH_4)_2SO_4$, 25 mM sodium phosphate at pH 7, 0.2 µm filtered) and 64% mobile phase B (Milli-Q® water with 25 mM sodium phosphate at pH 7, and 10% 2-propanol (LC-MS grade), 0.2 µm filtered) linearly changing to 100% mobile phase B over the next 15 min. and staying another 5 min. at 100% mobile phase B, at a constant flow rate of 0.5 mL/min on an Agilent® AdvanceBio® HIC column (I.D. 4.6 mm/Length: 100 mm/Particle size: 3.5 µm/Pore size: 450 Å, Part #: 685975-908). 280 nm traces were used for retention time comparisons. HIC retention times (RTs) for Ab-1 to Ab-5 are provided in Table 3. Trastuzumab as a low control showed a HIC RT of 3.724. Rituximab as a high control showed a HIC RT of 7.315. Ab-1 showed the highest retention time indicating higher hydrophobicity.

Polyreactivity Studies

Polyreactivity of antibodies against negatively charged biomolecules was determined by ELISA (As in Avery et al., "Establishing in vitro in vivo correlations to screen monoclonal antibodies for physicochemical properties related to favorable human pharmacokinetics." MAs. 2018 Febraury/March; 10(2):244-255). Briefly, an ELISA plate was coated with 5 Lg/mL of human insulin (SigmaAldrich®, Cat #: 19278) and 10 µg/mL of double stranded DNA (SigmaAldrich®, Cat #: D1626-250MG) overnight. The plate was blocked with ELISA buffer (PBS, 1 mM EDTA, 0.05% Tween-20, pH 7.4). 10 µg/mL of test antibody was loaded onto the plates in quadruplicates and incubated for 2 hours. Goat anti-human Fc (0.01 ug/ml) conjugated with horse radish peroxidase (HRP) was then added and the plate incubated for 1 hour. The signal was developed with TMB and A450 absorbance was measured with Synergy Neo2® plate reader. The signal was normalized with the signal of non-coated well for each antibody tested. Polyreactivity scores for Ab-1 to Ab-5 are provided in Table 2.

Isoelectric Point Determination

The isoelectric points (pIs) (or solution pH where the net charge of a protein is zero) for the antibodies were determined using capillary isoelectric focusing (cIEF)). VHH-Fc was diluted in DI water to 1 mg/ml concentration at 40 pl final volume. If sample concentration was lower than 5 mg/ml, 50 ug of VHH-Fc was buffer exchanged to DI water using Pierce Concentrator, PES, 30K MWCO, 0.5 ml (Thermo Fisher Scientific®, Cat #88502) prior to diluting the sample, to remove excess salt. The mix solution was prepared by combining following reagents. 1% methylcellulose solution (Protein Simple®, Cat #101876), 1% broad range pharmalyte 3-10 Cytiva®, Cat #17045601) 3% narrow range pharmalyte of choice (Cytiva®), 2 mM iminodiacetic acid (Sigma®, Cat #56781-50G) freshly prepared in water, 10 mM arginine (Signa®, cat #11009-25G-F) freshly prepared in water, 4 M Urea (Sigma., Cat #, U5378-100G) freshly prepared in water, pI markers of choice (Proten Simple®), top up with DI water to total volume of 160 µl per sample 160 µl of mix solution was added to each 1 mg/ml VHH-Fc sample. Empty control sample was prepared by mixing 40 µl of D1 water with 160 il of the mix solution. All samples including controls were vortexed and centrifuged for 10 min at 13,000 g. 160 µl of each sample was transferred to 96-well Maurice plates (Protein Simple®, Cat #046-021), and plate was centrifuged for 5 min at 1,000 g. The following reagents were added to the vials fluorescent calibration standard (Protein Simple®, Cat #046-025), DI water, and 0.5% methylcellulose solution (prepared by 1:1 dilution in DI water of 1% methylcellulose solution, Protein Simple®, Cat #101876). The cIEF cartridge (Protein Simple®, Cat # PS-MC02-C was prepared for experiment by adding 2. ml of catholyte (Protein Simple®, Cat #102728) and 2 ml of anolyte (Protein Simple®, Cat #102727). Injection conditions were applied: 1500 V for 1 min for Focus Period 1, and 3000 V for 5.5 min for focus period 2. Sample Load Duration was 55 seconds. Data was analyzed using Compass for iCE™ 4.0.0 Software. The pl of VHH-Fc was reported as the pI of the most abundant peak. The pIs of Ab-1 to Ab-5 are provided in Table 3.

In Silico Immunogenicity Assessment

Using Lonza's Epibase® in silico profiling platform, humanized antibodies were screened to identify the number and promiscuity of potential T-cell epitopes in the sequence in the global population, generating DRB1 scores (Table 4), and ranking of molecules for immunogenicity risk. The lower the score the more human-like, and lower the immunogenicity risk, for the antibody, based on DRB1 scores for 80 therapeutic antibodies.

In Vitro Immunogenicity

T-cell activation is an important part of the immune response to therapeutic proteins. In vitro T-cell assays allow an assessment of the capacity of a therapeutic protein to induce a T cell response in a human target population. Test products are added to human PBMC (peripheral blood mononuclear cells) and lymphocyte activation can be detected by vario us assays to determine the number of donors eliciting a significant T-cell response, and also the magnitude of the T-cell response over the test population in vitro. T-cell assays are often used during lead selection or lead optimization where test proteins can be ranked by their relative immunogenicity risk and enable the lowest risk candidates to be selected, An in vitro immunogenicity risk assessment for the antibodies disclosed herein was carried out using Lonza's in vitro DC:CD4 re-stimulation assay for the assessment of T-cell activation, using PBMC from 31 healthy human donors, qualified suitable for the assay, according to standard protocol. The DC:CD4 restimulation assay to determine CD4+ T-cell response induced by each antibody was assessed by IFNγ and IL-5 FluoroSpot. Analysis uses a non-parametric statistical test that compares each test condition and reference condition for each donor, and indicates if the difference is statistically significant, utilizing permutation resampling (DFR(eq)). See Table 4.

Example 9. Membrane Proteome Array—Specificity

Figure 23:
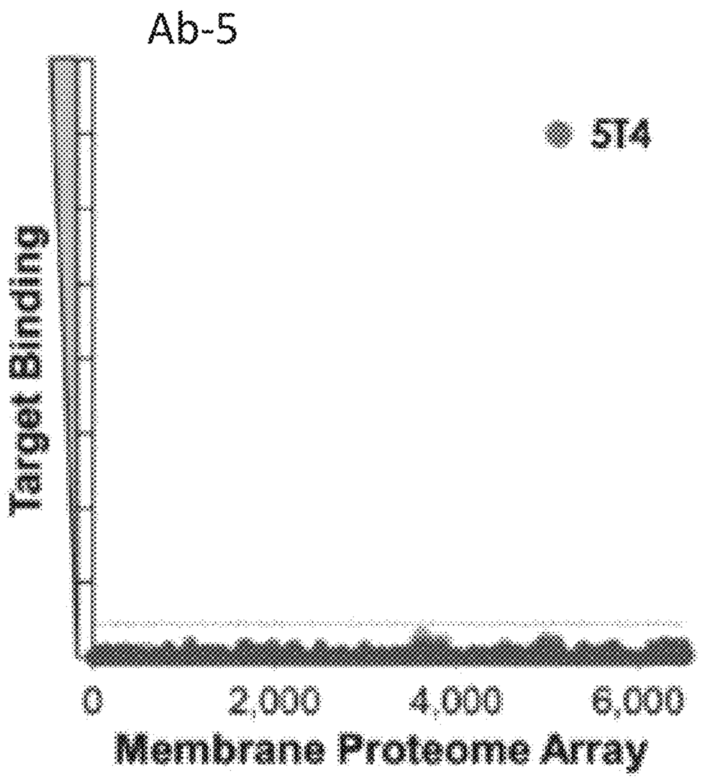
FIG. 23 illustrates specific binding of Ab-5 VHH-Fc to human 5T4 in a membrane proteome assay of human surface proteins.

Membrane Proteome Array (MPA) screening was conducted at Integral Molecular, Inc. The MPA is a protein library composed of 6,000 distinct human membrane protein clones, each overexpressed in live cells from expression plasmids. Each clone was individually transfected in separate wells of a 384-well plate followed by a 24 h incubation (Tucker et al., 2018). Cells expressing each individual MPA protein clone were arrayed in duplicate in a matrix format for high-throughput screening. Before screening on the MPA, the test ligand concentration for screening was determined on cells expressing positive (membrane-tethered Protein A) and negative (mock-transfected) binding controls, followed by detection by flow cytometry using a fluorescently-labeled secondary antibody. Each test ligand was added to the MPA at the predetermined concentration, and binding across the protein library was measured on an Intellicyt® iQue® using a fluorescently labeled secondary antibody. Each array plate contains both positive (Fc-binding) and negative (empty vector) controls to ensure plate-by-plate reproducibility. Test ligand interactions with any targets identified by MPA screening were confirmed in a second flow cytometry experiment using serial dilutions of the test antibody, and the target identity was re-verified by sequencing. FIG. 23 illustrates specific binding to 5T4 for Ab-5 VHH-Fc (SEQ ID NO: 34) in the MPA screen. Targets are screened in duplicate, and hits demonstrating binding signal >3 standard deviations above background in both wells were selected for downstream validation experiments. Non-specific fluorescence was determined to be any value below 3 standard deviations of the mean background value. Ab-1, Ab-2, Ab-3, Ab-4, and Ab-5 had no off-target hits, with only 5T4 validated as a true binding interaction. In addition to 5T4, Ab-6 had 1 off-target hit to HHIP (Q96QV1).

Example 10. Tissue Biodistribution of Radiolabeled Antibody Conjugates in Mice Following radiolabeling and in some cases purification, the radiochemical purity for all test articles used in vivo studies was >95%. Indium-111 ($^{111}$In) radioactivity was quantified by Single Photon Emission Computed Tomography (SPECT)/Computed Tomography (CT) imaging or gamma counting in blood and tissues. Actinium-225 ($^{225}$Ac) was quantified by gamma counting. The uptake or percentage injected dose (% ID) is defined as the tissue radioactivity (MBq) decay-corrected to the injection time, normalized to the activity injected. The activity concentration or percentage injected dose per gram of tissue (% ID/g) is the % ID normalized to the weight of the ex vivo gamma-counted tissue or the volume of the quantified tissue for in vivo SPECT/CT imaging data assuming a tissue density of 1 g/mL.

Plasma Elimination of Ab-5 VHH-Fc in Tg32 Mice

Figure 26:
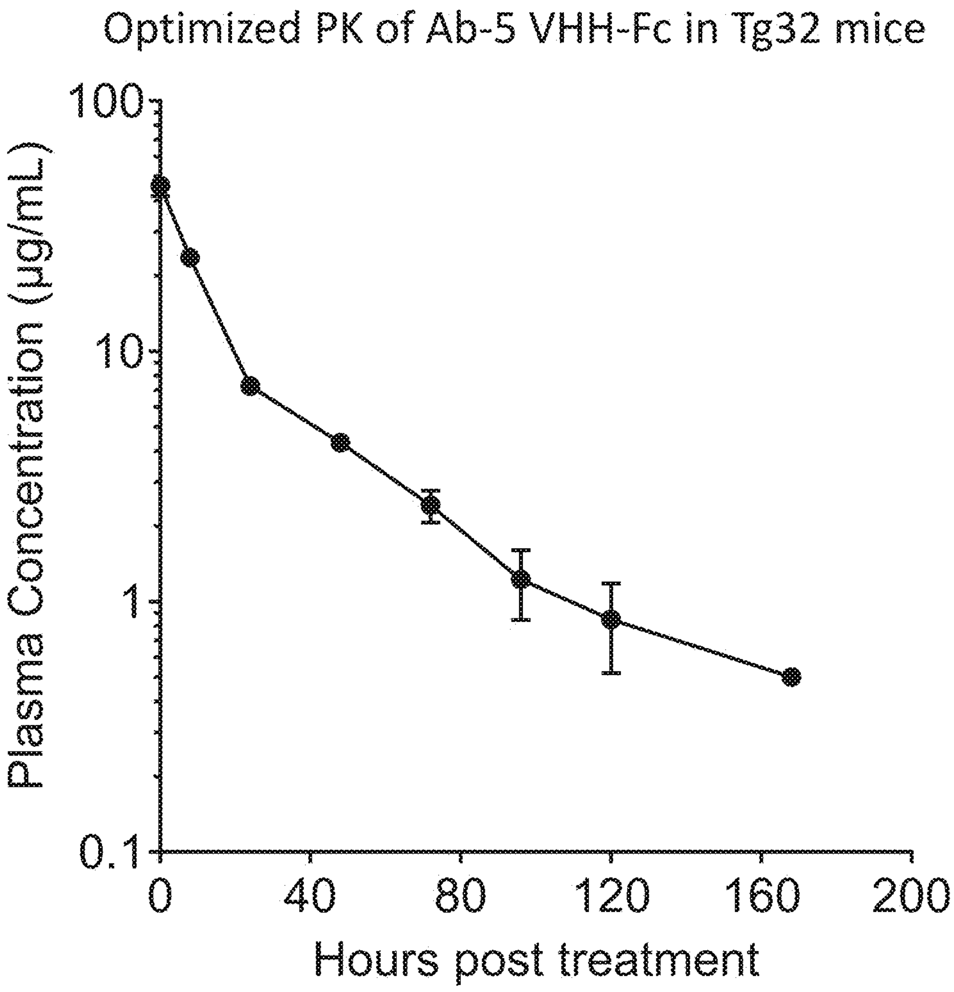
FIG. 26 illustrates plasma concentration (μg/mL) measured after single IV bolus 3 mg/kg dose of Ab-5 VHH-Fc administered in human FcRn transgenic (Tg32) mice.

Pharmacokinetic evaluation of Ab-5 VHH-Fc (unconjugated) was performed in Tg32 mice (N=4, naïve human neonatal Fc receptor (FcRn) transgenic mice). Plasma concentration (μg/mL) was measured after treatment with Ab-5 VHH-Fc, as provided in FIG. 26. Approximately 84% of the $C_0$ concentration cleared from the blood compartment within the first 24 hours post treatment, and showed a plasma elimination half-life$_{24\text{-}120\ h}$ of 30 hours.

Tissue Biodistribution of $^{111}$In-Radiolabeled Ab-6 Conjugated to Linker Chelator 1

Tissue biodistribution of $^{111}$In-radiolabeled prototype 5T4 binding conjugate (Ab-6-linker chelator 1 conjugate) was assessed in both naïve and tumor bearing mice. Naive CD-1 mice were administered $^{111}$In-Ab-6-linker chelator 1 (a human-specific 5T4 prototype) and a $^{111}$In radiolabeled mouse-specific 5T4 binding antibody conjugated to linker chelator 1 by single intravenous (IV) injection. Both the human-specific (Ab-6) and mouse-specific antibodies used were VHH-Fcs. Biodistribution was evaluated at day 1, 3 and 6 post-treatment. Mice (n=4 per group) were imaged using SPECT/CT and approximately 10 MBq $^{111}$In, a 1 mg/kg mass dose and a specific activity 0.5 MBq/μg. At the day 6 endpoint, tissues were collected (n=5 mice/group) to confirm biodistribution by gamma counting. Quantification of time course SPECT/CT images and ex vivo gamma counting of tissues (Day 6) showed $^{111}$In-Ab-6-linker chelator 1 had slower whole-body clearance consistent with increased non-target specific tissue retention when compared to the labeled mouse-specific 5T4 antibody. Higher $^{111}$In-Ab-6-linker chelator 1 exposure was observed in the kidneys as well as increased nuclear medicine signal in the spine, joints, and pelvic bone. For example, at the day 6 endpoint $^{111}$In-Ab-6-linker chelator 1 mean tissue activity was 23% ID/g in the knee joint followed by 14% ID/g in the kidney unlike the mouse binder with 6% ID/g in the kidney and 4% ID/g in the knee joint and by gamma counting.

For tumor biodistribution studies, human 5T4 expressing xenograft tumor models BxPC-3 (pancreatic cancer; 5T4 receptor density of approximately 42,000 epitopes/cell and NCI-H1975 (non-small cell lung cancer [NSCLC]); 5T4 receptor density of approximately 34,000 epitopes/cell) were implanted subcutaneously in NMRI nude or athymic nude mice. Established tumors were treated with a single IV dose of $^{111}$In-Ab-6-1inker chelator 1 (BxPC-3 and NCI-H1975: 10 MBq $^{111}$In, a 1 mg/kg mass dose, 0.5 MBq/μg specific activity, n=3-4 mice for day 1 to day 6 SPECT/CT and n=4 mice for gamma counting at the day 6 endpoint.

In both tumor models $^{111}$In-Ab-6-linker chelator 1 demonstrated a mean tumor targeting of 36% ID/g (Day 6, BxPC-3) and 16% ID/g (Day 6, NCI-H1975) by gamma counting. As in naïve CD1 mice, $^{111}$In-Ab-6-linker chelator 1 SPECT/CT imaging data in BxPC-3 xenograft model showed high kidney activity and a distinct nuclear medicine signal the spine region and joints as well as the lymph nodes. In the NCI-H1975 model, $^{111}$In-Ab-6-linker chelator 1 SPECT/CT imaging data also showed kidney activity and a clear nuclear medicine signal in the bone (knee joint, shoulder joint, and pelvic bone). At endpoint on day 6, other than the tumor, the highest $^{111}$In-mean activity was measured in the knee joint (20% ID/g), followed by the kidneys (14% ID/g). While demonstrating human 5T4 tumor targeting, Ab-6-linker chelator 1 had high non-specific normal tissue uptake.

Single Dose $^{111}$In Biodistribution of Humanized 5T4Binders (Ab-1, Ab-2, Ab-3, Ab-4, and Ab-5) Conjugated to Linker Chelator 1 in NCI-1-975 Tumor Bearing Mice NCI-H1975 tumor bearing athymic nude mice were administered $^{111}$In radiolabeled humanized 5T4 targeting conjugates (Ab-1-linker chelator 1, Ab-2-linker chelator 1, Ab-3-linker chelator 1, Ab-4-linker chelator 1 and Ab-5-linker chelator 1) by single IV injection and biodistribution was evaluated at day 1, 3 and 6 post-treatment. Mice (n=4 per group) were imaged using SPECT/CT and 6-10 MBq $^{111}$In, a 0.6-1 mg/kg mass dose and a specific activity 0.5 MBq/μg. At the day 6 endpoint, tissues were collected (n=5 mice/group) to confirm biodistribution by gamma counting.

Figure 4A:
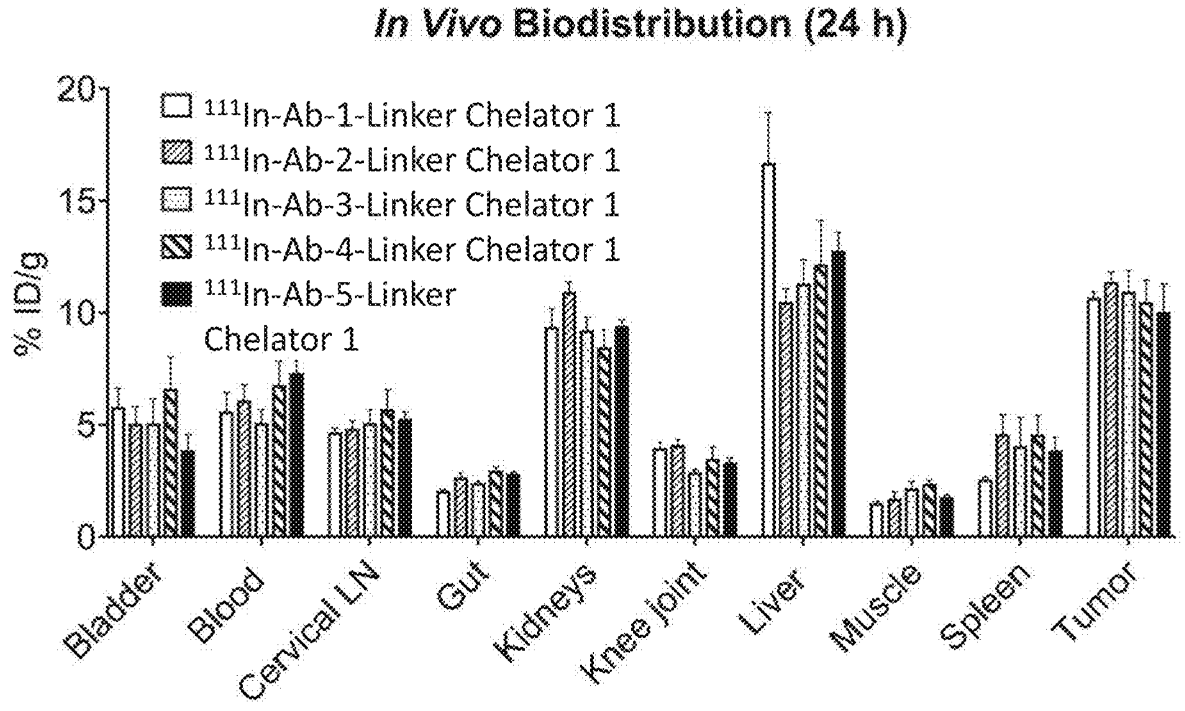
FIGS. 4A-4C show SPECT/CT in vivo tissue biodistribution after single IV dose administration of $^{111}In$ radiolabeled antibody conjugates in athymic nude mice bearing NCI-H1975 NSCLC xenografts at 24 hours (FIG. 4A), 72 hours (FIG. 4B), and 144 hours (FIG. 4C). SPECT/CT=single-photon emission computed tomography/computed tomography; NSCLC=non-small cell lung cancer; cervical LN=cervical lymph nodes; 6-10 megabecquerel (MBq), 0.6-1 mg/kg, 0.5 MBq/μg specificity, n=4/group, mean±SEM.
Figure 4B:
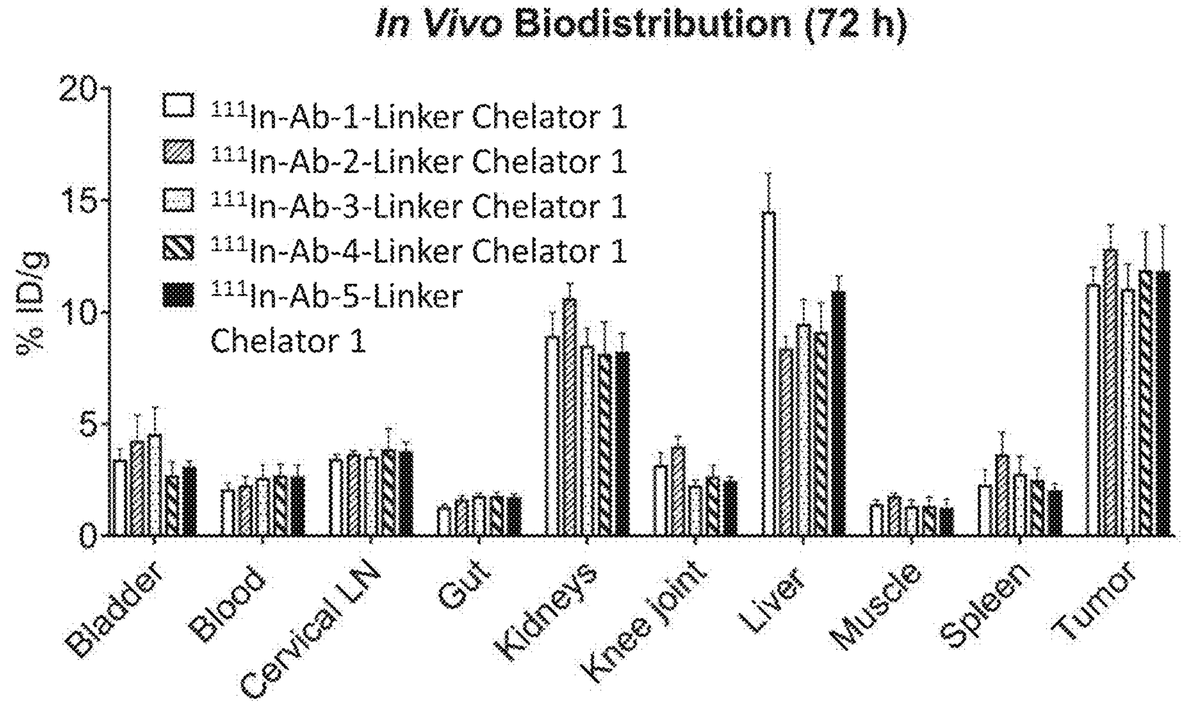
Figure 4C:
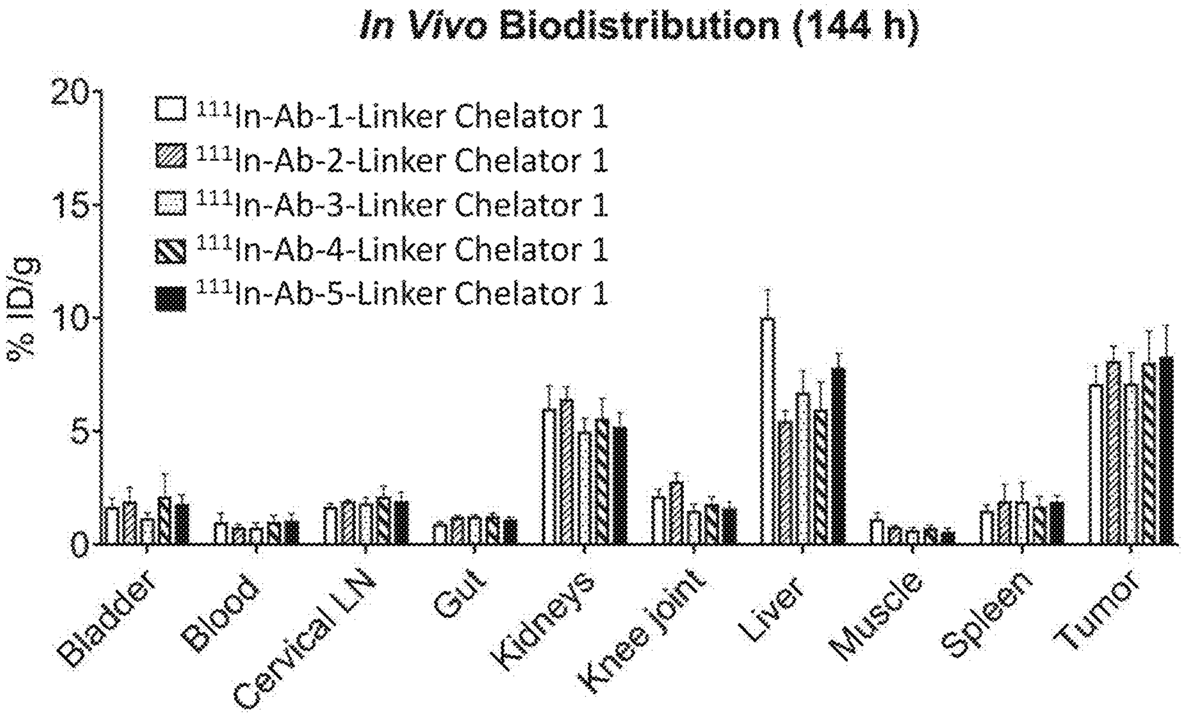
Figure 5:
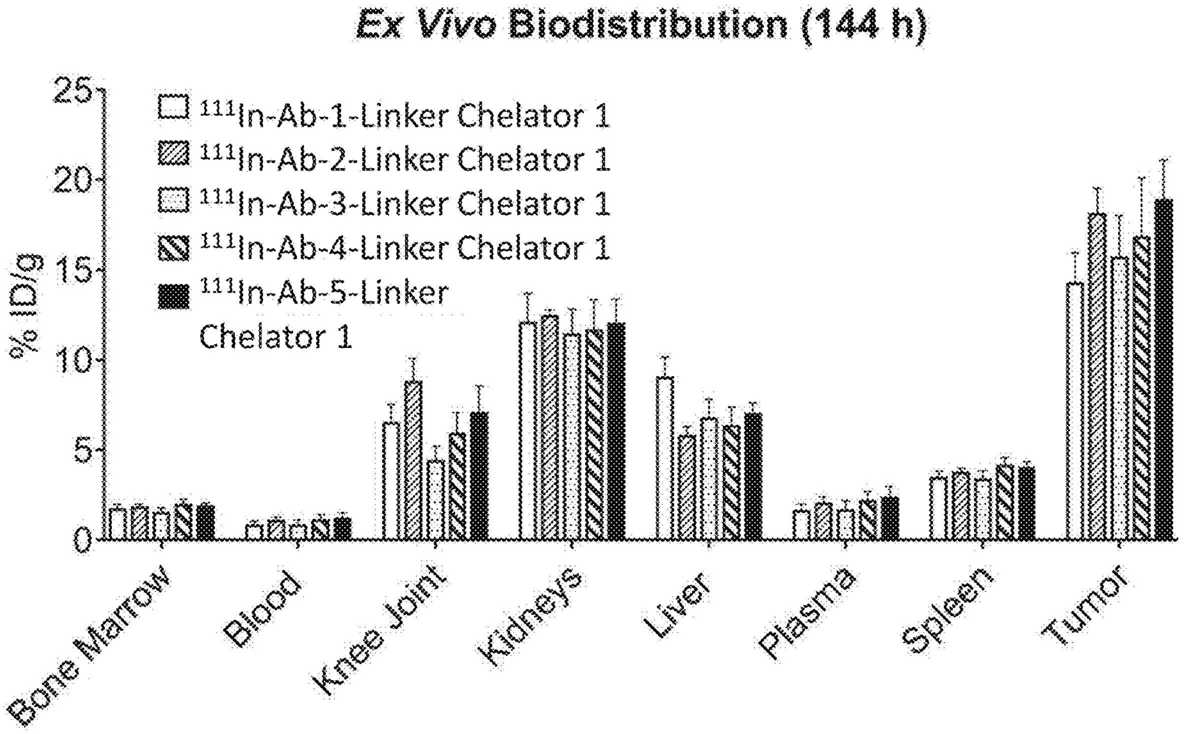
FIG. 5 shows ex vivo tissue biodistribution six days after single dose IV administration of $^{111}In$ radiolabeled antibody conjugates in athymic nude mice bearing NCI-H1975 xenografts. 6-10 MBq, 0.6-1 mg/kg, 0.5 MBq/μg specificity, n=5/group, mean±SEM.

All test articles showed comparable biodistribution patterns and tumor activity concentrations (FIGS. 4A-4C). Liver exposure was notably higher for $^{111}$In-Ab-1-linker chelator 1. At endpoint, the ex vivo tumor concentration was also comparable between conjugates with the mean ranging from 14% ID/g to 19% ID/g, with $^{111}$In-Ab-1-linker chelator 1 tumor activity at the lower end of the range (FIG. 5). Mean normal tissue concentrations were comparable between $^{111}$In-Ab-4-linker chelator 1 and $^{111}$In-Ab-5-linker chelator 1 at endpoint with 12% ID/g for both in the kidney and low concentration in the knee joint, 6% ID/g and 7% ID/g), respectively (FIG. 5). In comparison, the Day 6 biodistribution of $^{111}$In-Ab-6-linker chelator 1 in NCI-H1975 showed lower tumor uptake (16%) paired with higher concentration in the knee joint (20%). The 5 humanized 5T4 targeting conjugates had similar biodistribution properties and a preferred normal tissue biodistribution when compared to the prototype (Ab-6-linker chelator 1).

Single Dose 111-In Biodistribution of Humanized 5T4 Binders (Ab-4 and Ab-5) or Parental Binder (Ab-8) Conjugated to Linker Chelator 1 or Linker Chelator 2 in BxPC-3 Tumor Bearing Mice BxPC-3 tumor bearing NMRI nude mice were administered $^{111}$In radiolabeled humanized 5T4 targeting conjugates (Ab-4 and Ab-5 on two linkers linker chelator 1 and linker chelator 2) and parental conjugate ($^{111}$In-Ab-8-linker chelator 1) following a single IV injection and biodistribution was evaluated at day 1, 3 and 6 post-treatment. Parental binders Ab-7 and Ab-8 include the Fc region of SEQ ID NO: 47. Mice (n=4 per group) were imaged using SPECT/CT and 10 MBq $^{111}$In, a 1 mg/kg mass dose and a specific activity 0.5 MBq/μg. At the day 6 endpoint, tissues were collected (n=5 mice/group) to confirm biodistribution by gamma counting.

Figure 6A:
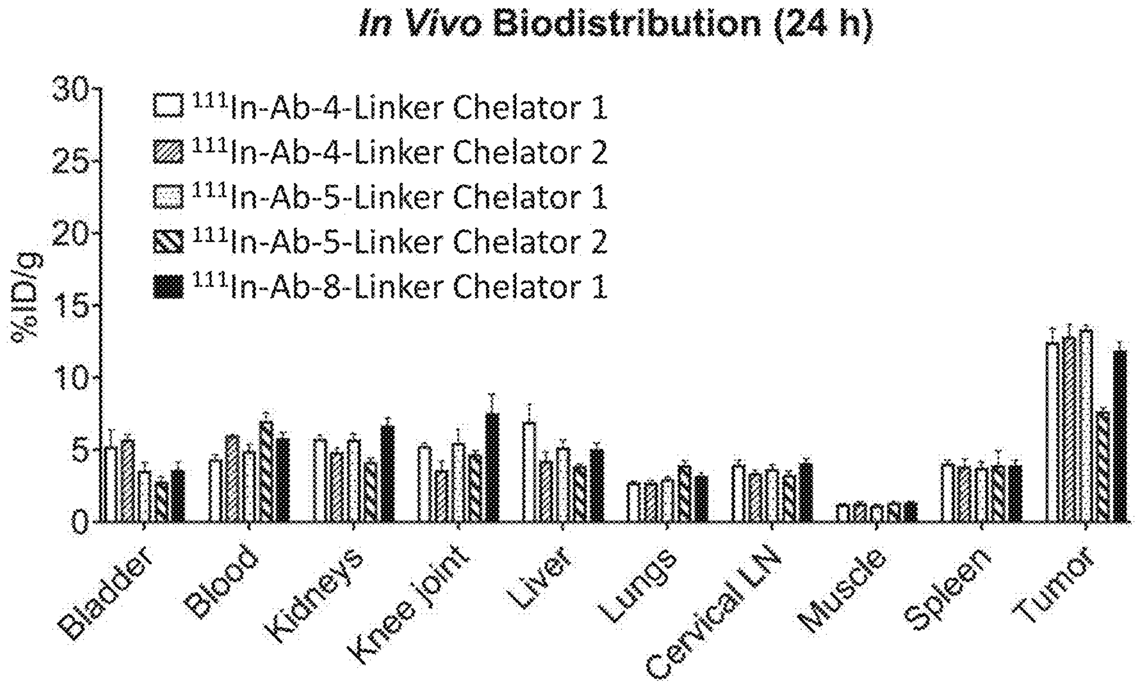
FIGS. 6A-6C show SPECT/CT in vivo tissue biodistribution after single dose IV administration of $^{111}In$ radiolabeled antibody conjugates in NMRI nude mice bearing BxPC-3 pancreatic cancer xenografts at 24 hours (FIG. 6A), 72 hours (FIG. 6B), and 144 hours (FIG. 6C). SPECT/CT=single-photon emission computed tomography/computed tomography; cervical LN=cervical lymph nodes; 10 MBq, 1 mg/kg, 0.5 MBq/mg specific activity, n=4/group, mean±SEM.
Figure 6B:
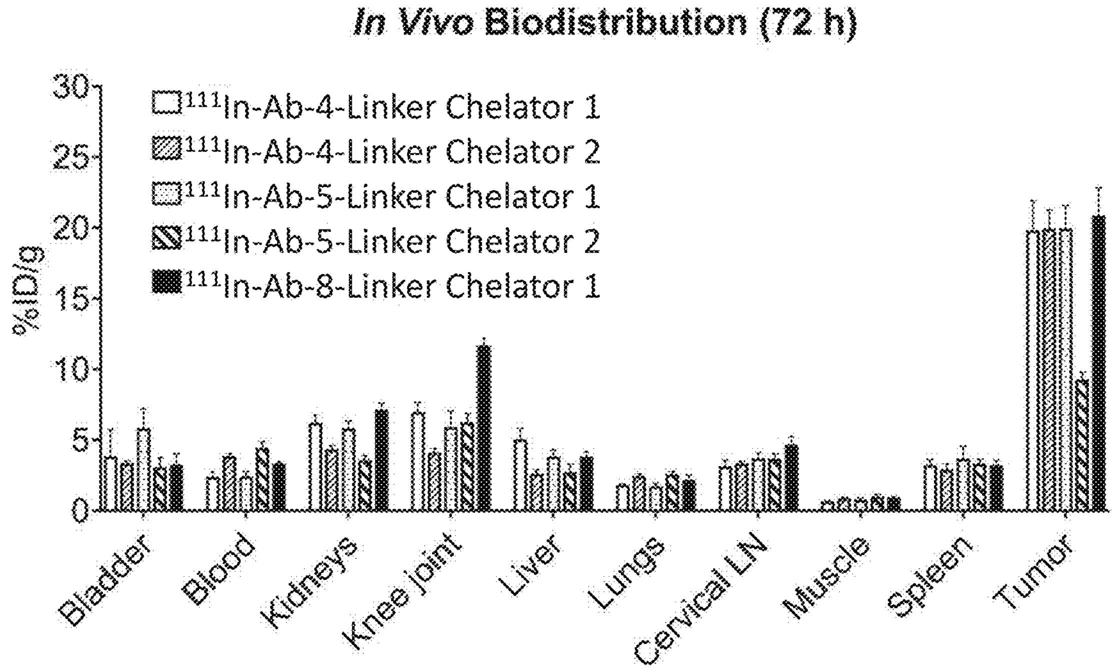
Figure 6C:
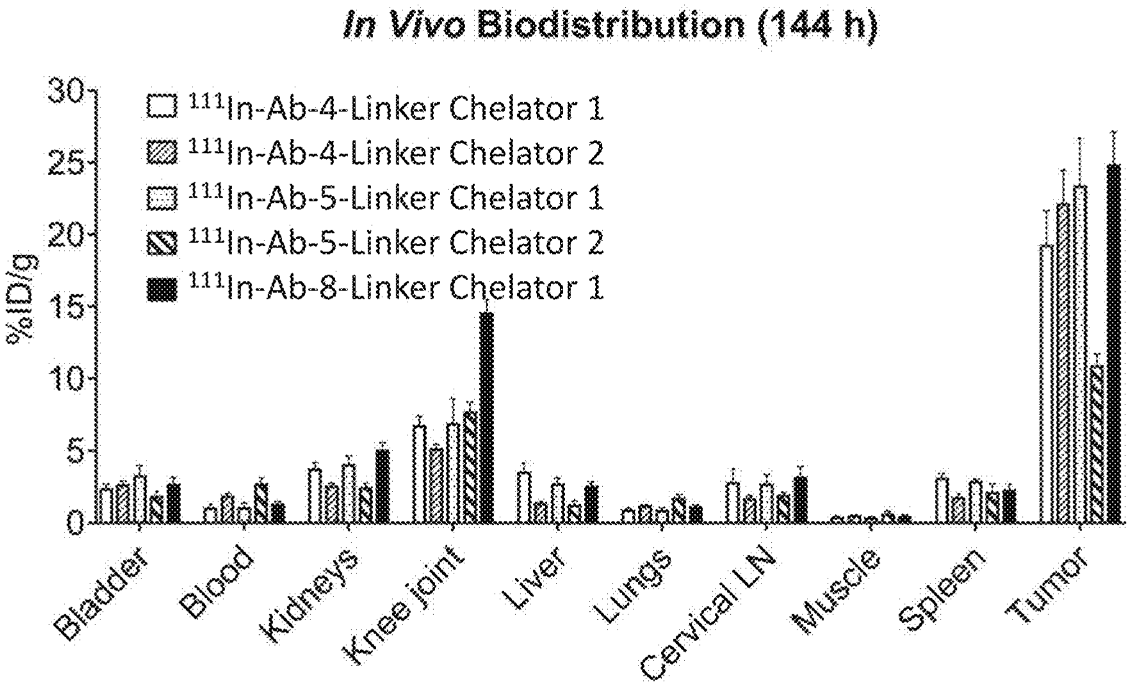
Figure 7:
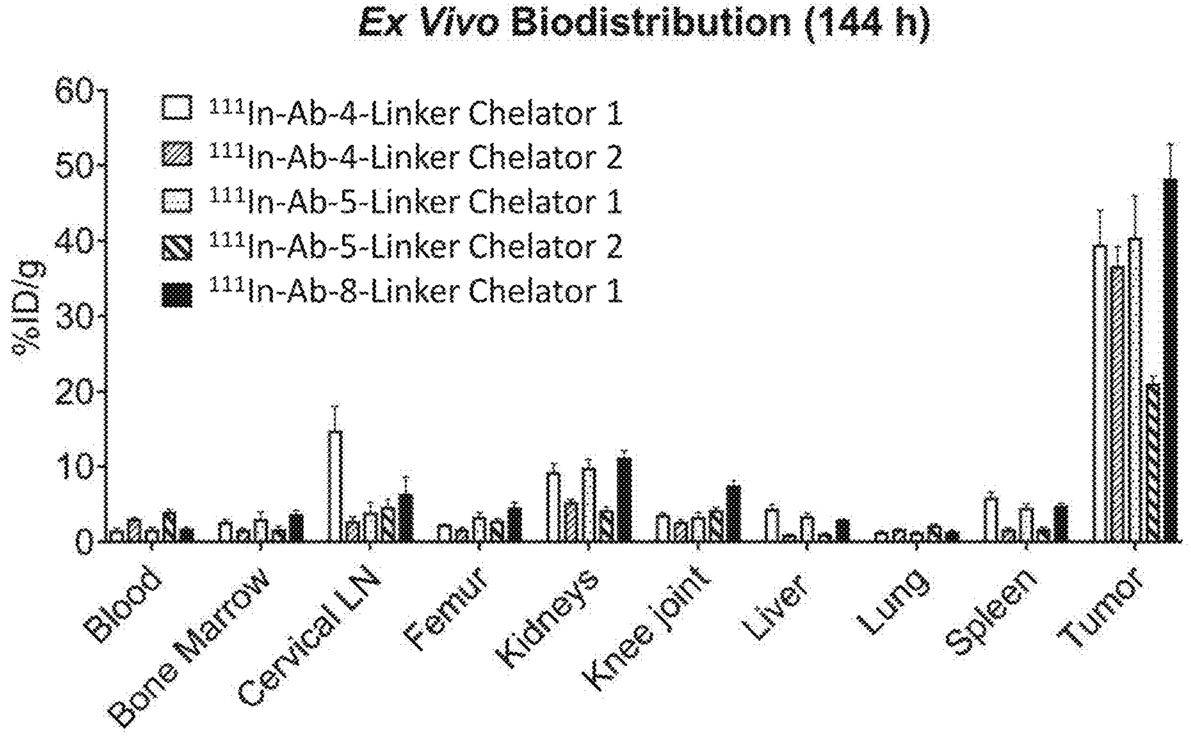
FIG. 7 shows ex vivo tissue biodistribution six days after single dose IV administration of $^{111}In$ radiolabeled antibody conjugates in NMRI nude mice bearing BxPC-3 pancreatic cancer xenografts. Cervical LN=cervical lymph nodes; 10 MBq, 1 mg/kg, 0.5 MBq/μg specific activity, n=5/group, mean±SEM.

All conjugates, apart from $^{111}$In-Ab-5-linker chelator 2 had an increase in vivo concentration in the tumor from Day 1 to 6, with tumor activity peaking on day 3 and being retained out to day 6 (FIGS. 6A-6C). Ab-4 and Ab-5 on the linker chelator 1 had generally consistent tumor and tissue biodistribution and exposure compared to the Ab-8 parental binder on the same linker, consistent with no impact of humanization. Ab-4 and Ab-5 on the linker chelator 2 linker showed lower normal tissue exposure including for the liver and kidney. The highest tumor to normal tissue differential was observed for $^{111}$In-Ab-4-linker chelator 2 with a tumor to kidney exposure ratio of 5 and a tumor to liver exposure ratio of 7. Similarly, at the terminal gamma counting endpoint $^{111}$In-Ab-4-linker chelator 2 had the highest tumor to normal tissue ratio with a tumor activity concentration of 37% ID/g and <5% ID/g for all normal tissues (FIG. 7).

Single Dose 225-Ac Biodistribution of Ab-4 and Ab-5 Conjugated to Linker Chelator 1 or Linker Chelator 2 in BxPC-3 Tumor Bearing Mice The distribution of $^{225}$Ac-Ab-4 and $^{225}$Ac-Ab-5 on linker chelator 1 and linker chelator 2 was evaluated in NMRI nude mice with xenografted BxPC-3 tumors (n=2-5 mice/group, 15 kBq $^{225}$Ac, 1 mg/kg mass dose, 0.5 kBq/μg specific activity). The activity concentrations of $^{225}$Ac in tumor, blood and normal organs were quantified by gamma counting tissues resected 3 days post injection. This method quantifies $^{221}$Fr and $^{213}$Bi in the $^{225}$Ac decay scheme, measured at least 6 hours after tissues were collected to allow for equilibration of $^{225}$Ac daughter ion decay. Gamma counts therefore reflect the amount of $^{225}$Ac that had accumulated in the tissues.

Figure 8:
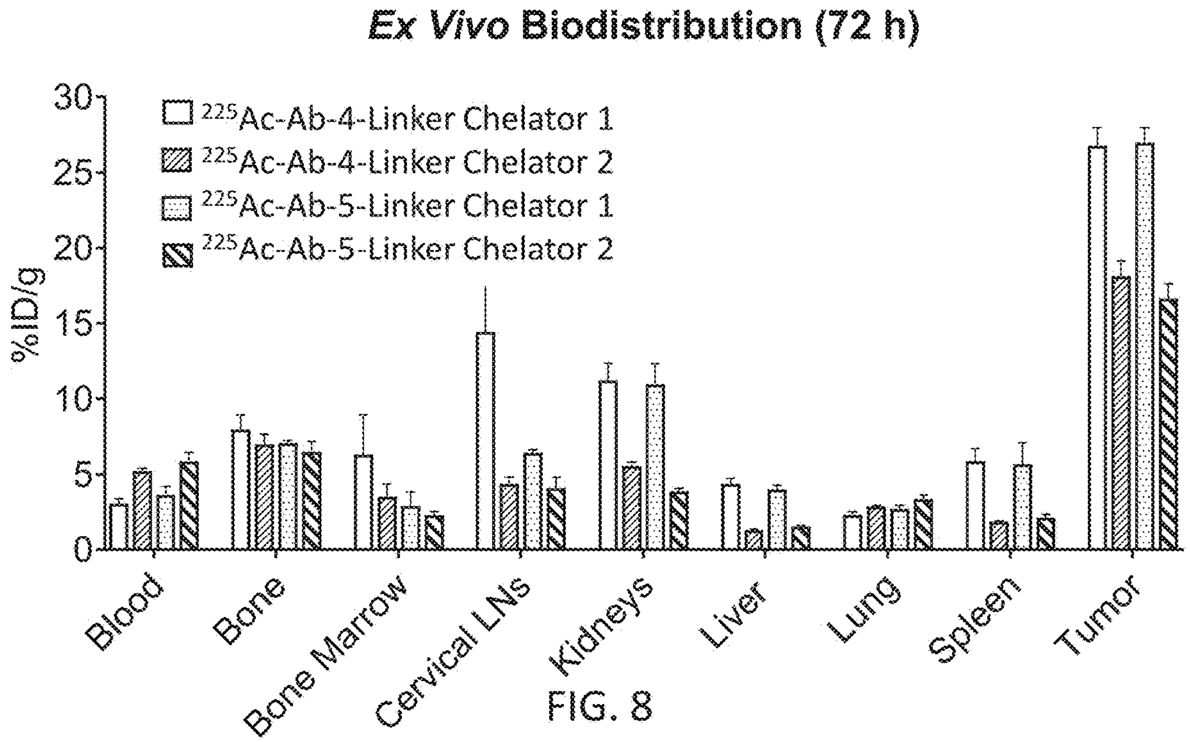
FIG. 8 shows ex vivo tissue biodistribution three days after single dose IV administration of $^{225}$Ac radiolabeled antibody conjugates in NMRI nude mice bearing BxPC-3 pancreatic cancer xenografts. Cervical LNs=cervical lymph nodes; 15 kilobecquerel (kBq), 1 mg/kg, 0.5 kBq/μg specific activity, n=2-5/group, mean±SEM.

The highest tumor activity concentration was observed for $^{225}$Ac-Ab-4-linker chelator 1 and $^{225}$Ac-Ab-5-linker chelator 1 with a mean concentration of 26% ID/g and 27% ID/g, respectively compared to $^{225}$Ac-Ab-4-linker chelator 2 and $^{225}$Ac-Ab-5-linker chelator 2 with 18% ID/g and 16% ID/g, respectively (FIG. 8). As observed in the prior study, both Ab-4 and Ab-5 on linker chelator 2 showed lower kidney, liver and spleen activity and the somewhat higher blood activity did not translate to differences in bone marrow activity compared to the linker chelator 1 linker. For example, Ab-4 and Ab-5 activity in the liver was reduced to ~1% ID/g with linker chelator 2 from 4% ID/g with linker chelator 1. Kidney activity concentration was similarly reduced from ~10% ID/g for linker chelator 1 to 5% ID/g for linker chelator 2. Improved tumor to liver, lung and spleen ratios were observed for the linker chelator 2 linker despite lower tumor activity.

Figure 27:
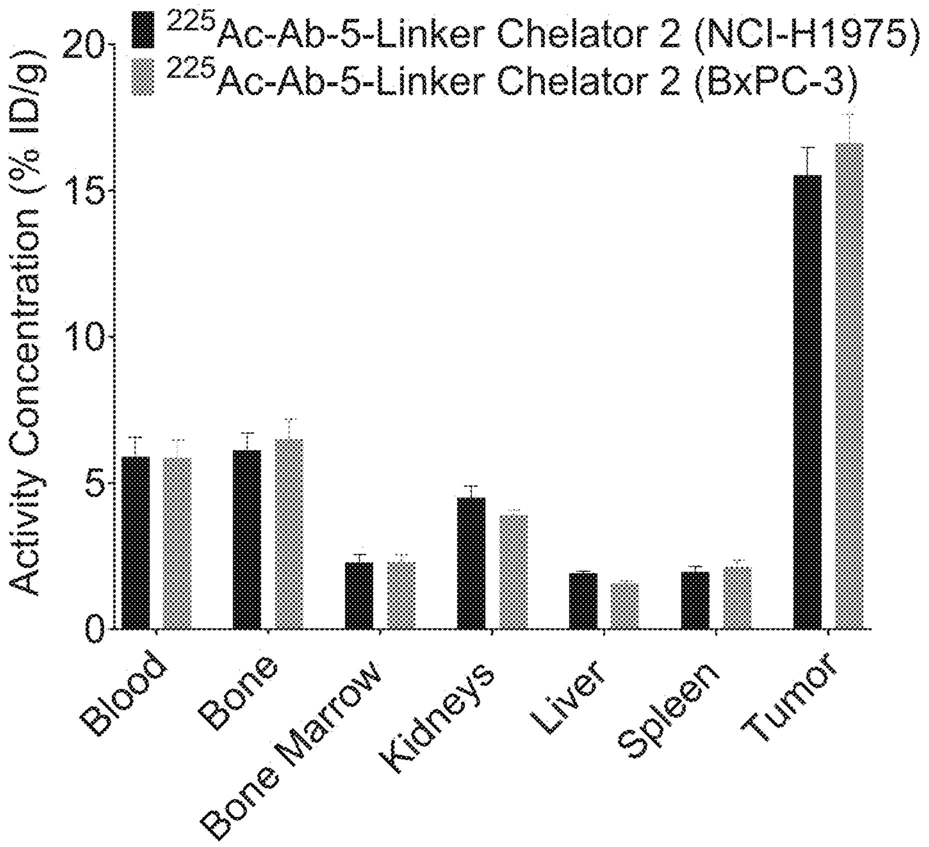
FIG. 27 illustrates mean ex vivo biodistribution (% ID/g) at 72 h following a single IV administration of $^{225}$Ac-Ab-5-linker chelator 2 in nude mice with xenografted BxPC-3 tumors or xenografted NCI-H1975 tumors (15 kBq, 30 kg; n=5/group).

Single Dose 225-Ac Biodistribution of 1Ab-5 Conjugated to Linker Chelator 2 in BxPC-3 or NCI-H1975 Tumor Bearing Mice The distribution of $^{225}$Ac-Ab-5 on linker chelator 2 was evaluated in athymic nude mice with xenografted NCI-H1975 tumors following a single IV administration (n=5 mice/group, 15 kBq $^{225}$Ac, 1.5 mg/kg mass dose, 0.5 kBq/μg specific activity). The activity concentrations of $^{225}$Ac in tumor, blood and normal organs were quantified by gamma counting tissues resected 3 days post injection. Data for the BxPC-3 study shown in FIG. 9 for $^{225}$Ac-Ab-5 on linker chelator 2 was plotted alongside the NCI-H1975 results. FIG. 27 shows comparable ex vivo biodistribution (% ID/g) in tumor, blood, and normal organs for $^{225}$Ac-Ab-5 conjugated to linker chelator 2 in nude mice with xenografted BxPC-3 tumors or xenografted NCI-H1975 tumors.

$^{111}$in Biodistribution of Humanized 5T4 Antibodies (Ab-4 and Ab-5) Conjugated with Linker Chelator 1 or Linker Chelator 2 in NCJ-H1975 Tumor Bearing Mice NCI-H1975 xenografted athymic nude mice were treated with a single IV dose of $^{111}$In-Ab-4 and $^{111}$In-Ab-5 on two linkers (linker chelator 1 and linker chelator 2), or the parental binder Ab-8 on linker chelator 1 (n=5 mice/group, 3 MBq $^{111}$In, 0.3 mg/kg, 0.5 MBq/μg specific activity). The biodistribution was determined by gamma counting of blood and tissues 3 days hours post-injection.

Figure 9:
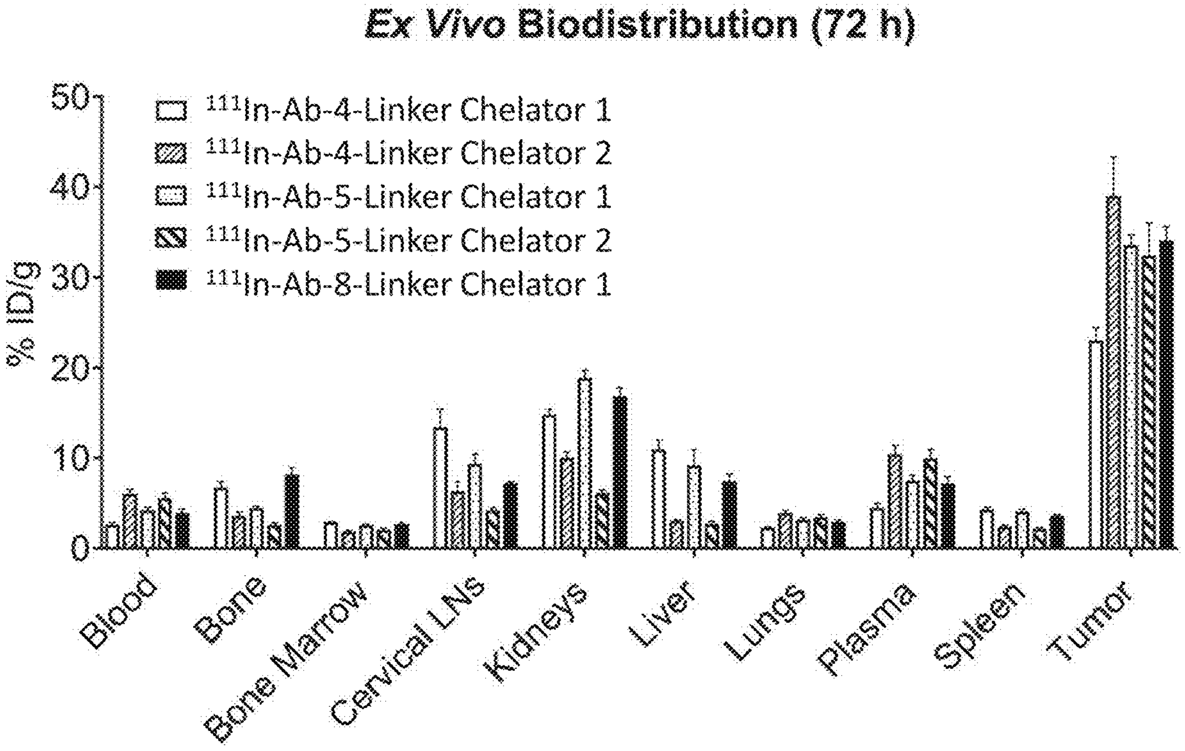
FIG. 9 shows ex vivo tissue biodistribution three days after single dose IV administration of $^{111}$In radiolabeled antibody conjugates in athymic nude mice bearing NCI-H1975 NSCLC xenografts. NSCLC=non-small cell lung cancer; cervical LNs=cervical lymph nodes; 3 MBq, 0.3 mg/kg, 0.5 MBq/μg specific activity, n=5/group, mean±SEM.
Figure 29:
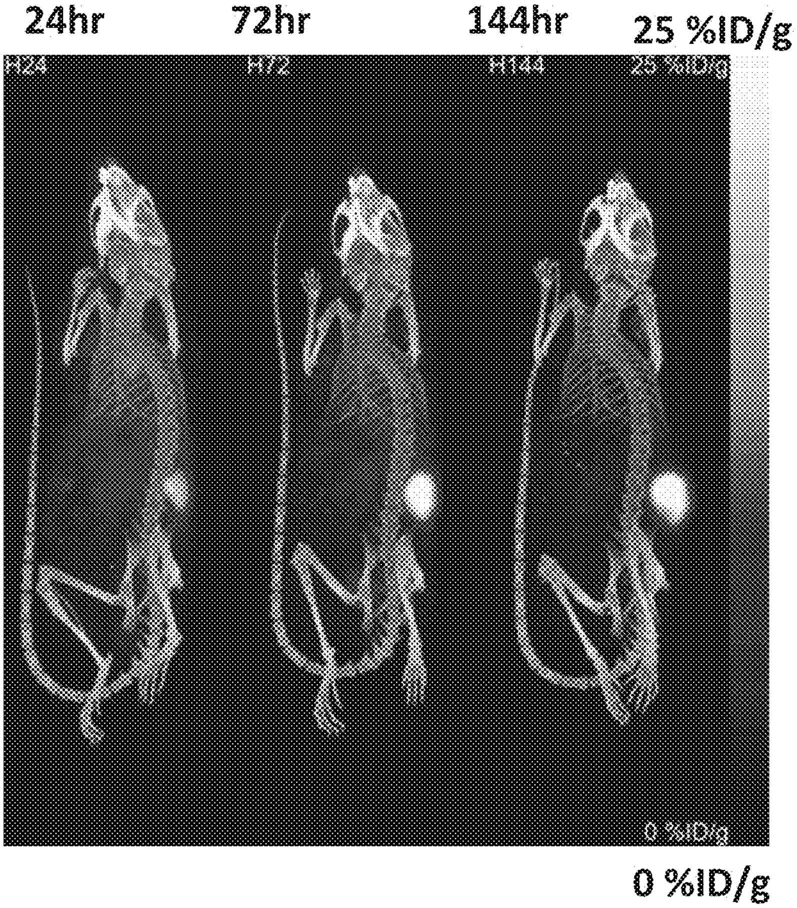
FIG. 29 shows time course SPECT/CT maximum intensity projections in a representative NCI-1975 tumor bearing mouse following a single administration of $^{111}$In-Ab-5-linker chelator 2.

Despite relatively low NCI-H1975 5T4 copy number, up to 39% ID/g concentration in tumors was observed Day 3 post dosing (FIG. 9). Of note, $^{111}$In-Ab-4-linker chelator 1 (23% ID/g) had the lowest tumor activity. There was no impact to tumor uptake observed for the humanized 5T4 conjugates (Ab-4, Ab-5) compared to Ab-8 aside from the lower tumor uptake for Ab-4-linker chelator 1. Both $^{111}$In-Ab-4-linker chelator 2 and $^{111}$Ab-5-linker chelator 2 retained high tumor activity (39% ID/g and 32% ID/g, respectively), paired with low activity concentration in the kidneys (10% ID/g and 6% ID/g), liver (3% ID/g for both) and cervical lymph node (6% ID/g and 4% ID/g respectively) at Day 3 post dosing (FIG. 9) compared to Ab-4-linker chelator 1, Ab-5-linker chelator 1, and Ab-8-linker chelator 1, which all had higher kidney (~17% ID/g), liver (~9% ID/g), and cervical lymph node (~10% ID/g) activity (FIG. 9). Of note, despite both Ab-4 and Ab-5 on linker chelator 2 showing higher blood activity, this did not result in higher bone marrow activity, consistent with previous data. Retained tumor activity with linker chelator 2 corresponded to higher tumor to tissue ratios for bone, bone marrow, cervical lymph node, kidney, liver, and spleen. FIG. 29 shows $^{111}$In-Ab-5-linker chelator 2 tissue biodistribution in the NCI-H1975 (24 h-144 h, representative mouse SPECT/CT images; left) from athymic nude mice given a single administration of $^{111}$In-Ab-5-linker chelator 2 (10 MBq $^{111}$In, 1 mg/kg, 0.5 MBq/μg specific activity).

Figure 28:
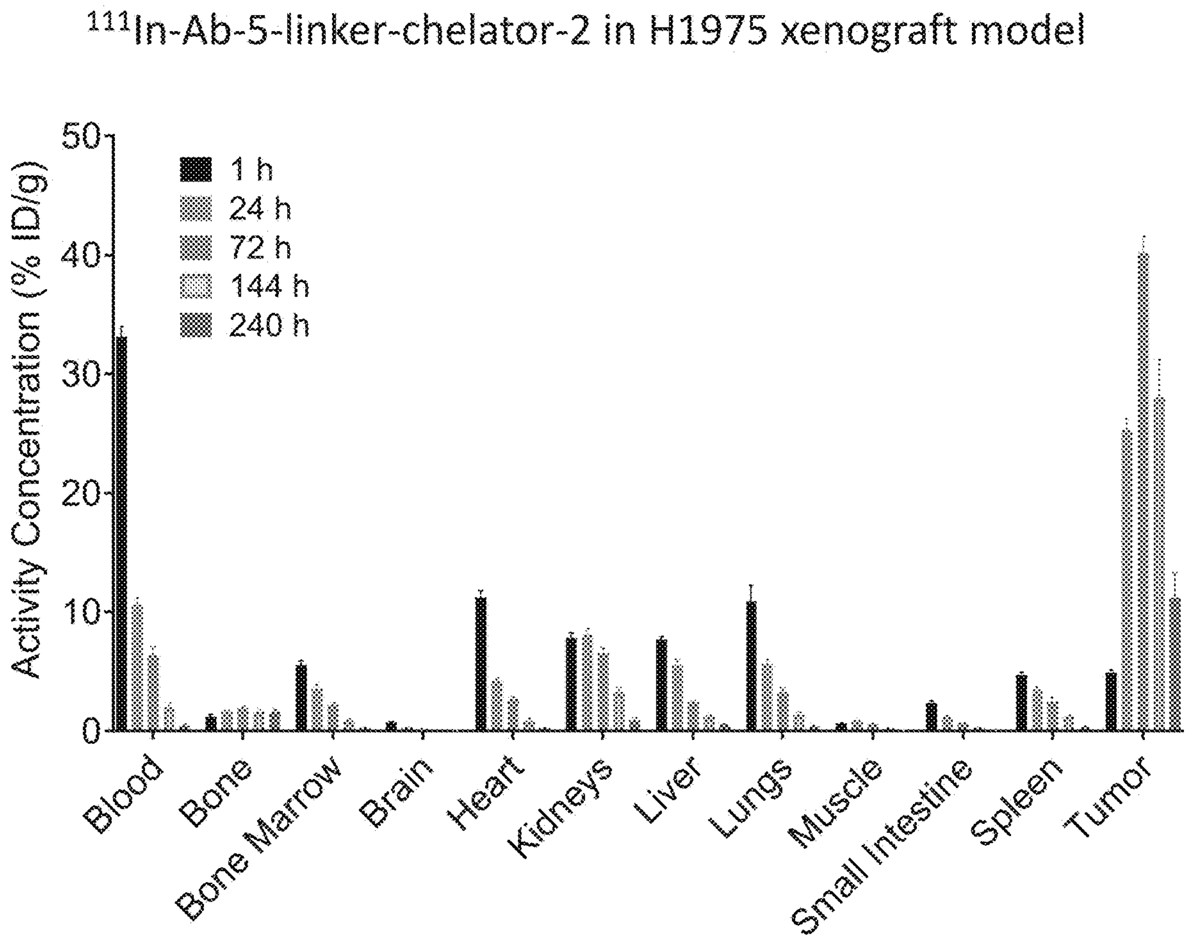
FIG. 28 illustrates ex vivo biodistribution (% ID/g) of $^{111}$In-Ab-5-linker chelator 2 in athymic nude mice with xenografted NCI-H1975 tumors at 1, 24, 72, 144, and 240 hours post-injection following a single IV administration (3 MBq, 6 μg; n=5-6 mice/timepoint).

$^{111}$in Biodistribution of Humanized 5T4 Antibody Ab-5 Conjugated with Linker Chelator 2 in NCI-H1975 Tumor Bearing Mice NCI-H1975 xenografted athymic nude mice received a single IV administration of $^{111}$In-Ab-5 on linker chelator 2 (n=5-6 mice/timepoint, 3 MBq $^{111}$In, 6 μg, 0.5 MBq/μg specific activity). The biodistribution was determined by gamma counting of tumor tissue, blood and normal tissues at 1, 24, 72, 144, and 240 hours post-injection. FIG. 28 shows the mean tissues activity concentration (% ID/g) with peak tumor accumulation of approximately 40% ID/g at 72 h. Table 10 provides $^{111}$In-Ab-5 conjugated to linker chelator 2 exposure comparisons in blood, bone marrow (BM), kidney, liver, spleen and tumor, as measured by AUC (% ID/g.h)±S.E.M., and relative ratios of tumor exposure to normal tissues. Overall, targeting of radioisotopes using Ab-5 on linker chelator 2 showed high tumor retention with a rapid clearance from non-tumor tissues resulting in favorable tumor to organ exposure ratios.

FIG. 28 shows tissue concentrations (% ID/g) at 1, 24, 72, 144, and 240 hours post-injection (bars left to right) of $^{111}$—In-Ab-5 conjugated to linker chelator 2. $^{111}$In-Ab-5 showed high tumor (maximum around 40% ID/g) to normal tissue exposure at 1 hour to 10 days post-treatment, with distinct uptake in tumor and clearance from normal tissues (6-fold tumor:kidney exposure ratio and 11-fold tumor:liver exposure ratio, as shown in Table 10 below).

TABLE 10

Tissue exposure comparisons and tumor:normal tissue exposure ratios for $^{111}$-In-Ab-5 conjugated to linker chelator 2.

| AUC (% ID/g · h) ± S.E.M. | | | | | |
|---|---|---|---|---|---|
| Blood | BM | Kidney | Liver | Spleen | Tumor |
| 1321 ± 106 | 402 ± 39 | 1087 ± 86 | 560 ± 36 | 445 ± 43 | 6254 ± 540 |

| Tumor:Organ Exposure Ratio | | | | |
|---|---|---|---|---|
| Tumor:Blood | Tumor:BM | Tumor:Kidney | Tumor:Liver | Tumor:Spleen |
| 5 | 16 | 6 | 11 | 14 |

Within-mouse dosimetry for $^{225}$Ac-Ab-5 conjugated to linker chelator 2 estimates an approximately 3× higher dose to tumor tissue than to the kidney, and an approximately 10× higher dose to tumor tissue compared to the liver. The estimated within-mouse $^{225}$Ac-Ab-5 conjugated to linker chelator 2 equivalent dose to the tumor is approximately 4Gy-RBF5/kBq in the NCI-H1975 xenograft model.

$^{111}$in Biodistribution of Humanized 5T4 Antibody Ab-5 Conjugated with Linker Chelator 2 in HT-29 Tumor Bearing NURI Nude Mice Tumor biodistribution was evaluated in mice xenografted with the human 5T4 expressing HT-29 colorectal cancer cell line (at a 5T4 receptor density of approximately 20,000 epitopes/cell) implanted subcutaneously in female NMRI nude mice. Mice with established tumors (n=5/group) were administered either $^{111}$In-Ab-5-linker-chelator-2 or $^{111}$In-irrelevant control (3 MBq, 6 μg protein, and 0.5 MBq/μg specific activity) by a single IV injection. The irrelevant control is a bioconjugate with an irrelevant VHH Fc which binds viral protein, contains the same engineered Fc, and is conjugated to the same linker-chelator. Es vivo biodistribution was evaluated by gamma counting of resected tissues at 72 h post-treatment (FIG. 30).

Figure 30:
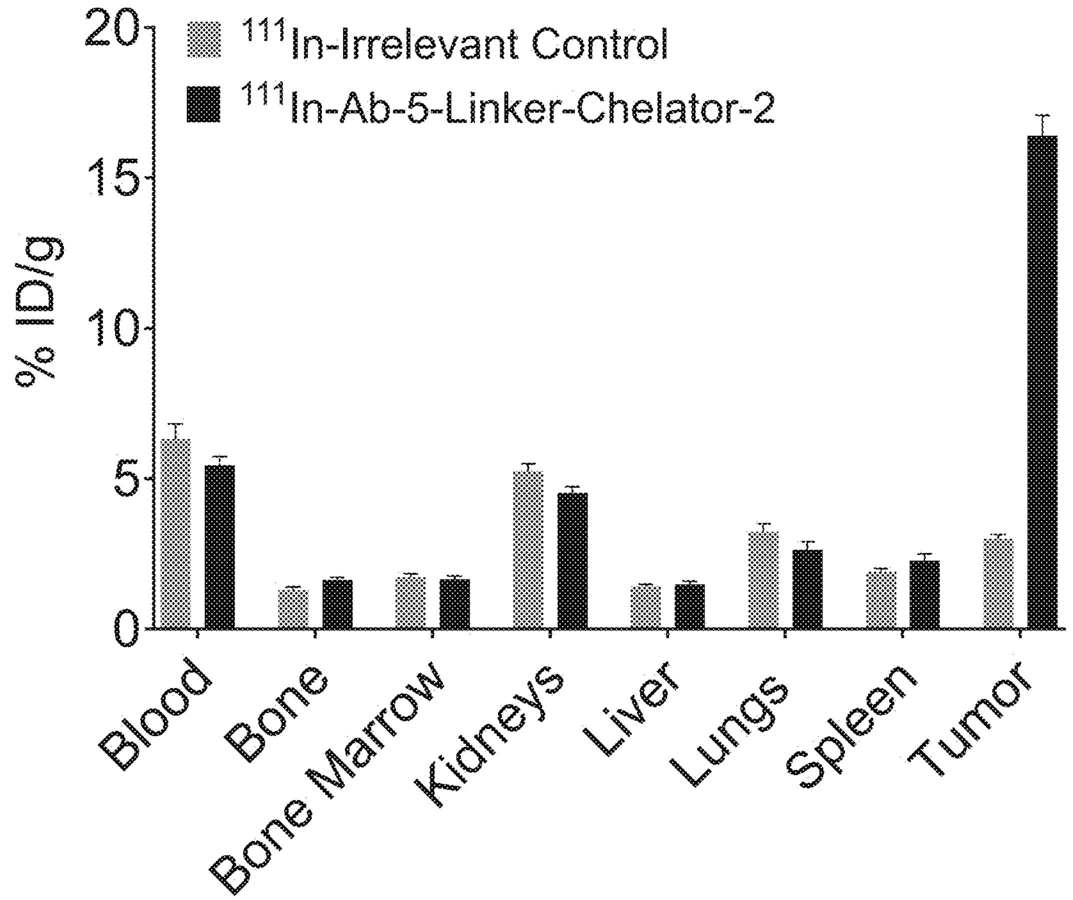
FIG. 30 illustrates ex vivo tissue biodistribution (% ID/g) of $^{111}$In-Ab-5-linker chelator 2 compared to ex vivo tissue biodistribution (% ID/g) of $^{111}$In-irrelevant control at 72 hours after a single I.V. bolus administration in HT-29 xenografted NMRI nude mice.

$^{111}$In-Ab-5-linker-chelator-2 showed a consistent normal tissue distribution previously observed in the NCI-H1975 (FIG. 28) model while $^{111}$In-irrelevant control is taken up by the tumor due to enhanced permeability and retention rather than 5T4 binding (FIG. 30). At the 72 h timepoint, $^{111}$In-Ab-5-linker-chelator-2 had the highest activity concentration in the tumor (16.40±0.69% ID/g) compared to low non-specific uptake of the $^{111}$In-irrelevant control (2.99±0.15% ID/g) (FIG. 30). Activity concentration for $^{111}$In-Ab-5-linker-chelator-2 was <6% ID/g in blood, bone, bone marrow, kidneys, liver, lungs and spleen (FIG. 30). The $^{111}$In-irrelevant control had generally comparable activity concentrations in the blood and normal tissues (FIG. 30).

$^{111}$in Biodistribution of Humanized 5T4 Antibody Ab-5 Conjugated with Linker Chelator 2 in HNSCC PDX Tumor Bearing NMRI Nude Mice Tumor biodistribution was assessed in the head and neck squamous cell carcinoma (HNSCC) patient derived xenograft tumor (PDX) model CTG-1140 that was confirmed to express 5T4. The PDX was implanted subcutaneously in female athymic nude mice. Mice with established tumors (n=5/group) were administered either $^{111}$In-Ab-5-linker-chelator-2 or the $^{111}$In-irrelevant control, as described herein (3 MBq, 6 μg protein, and 0.5 MBq/μg specific activity) by a single IV injection. Ex vivo biodistribution was evaluated by gamma counting of resected tissues at 72 h post-treatment endpoint (FIG. 31).

Figure 31:
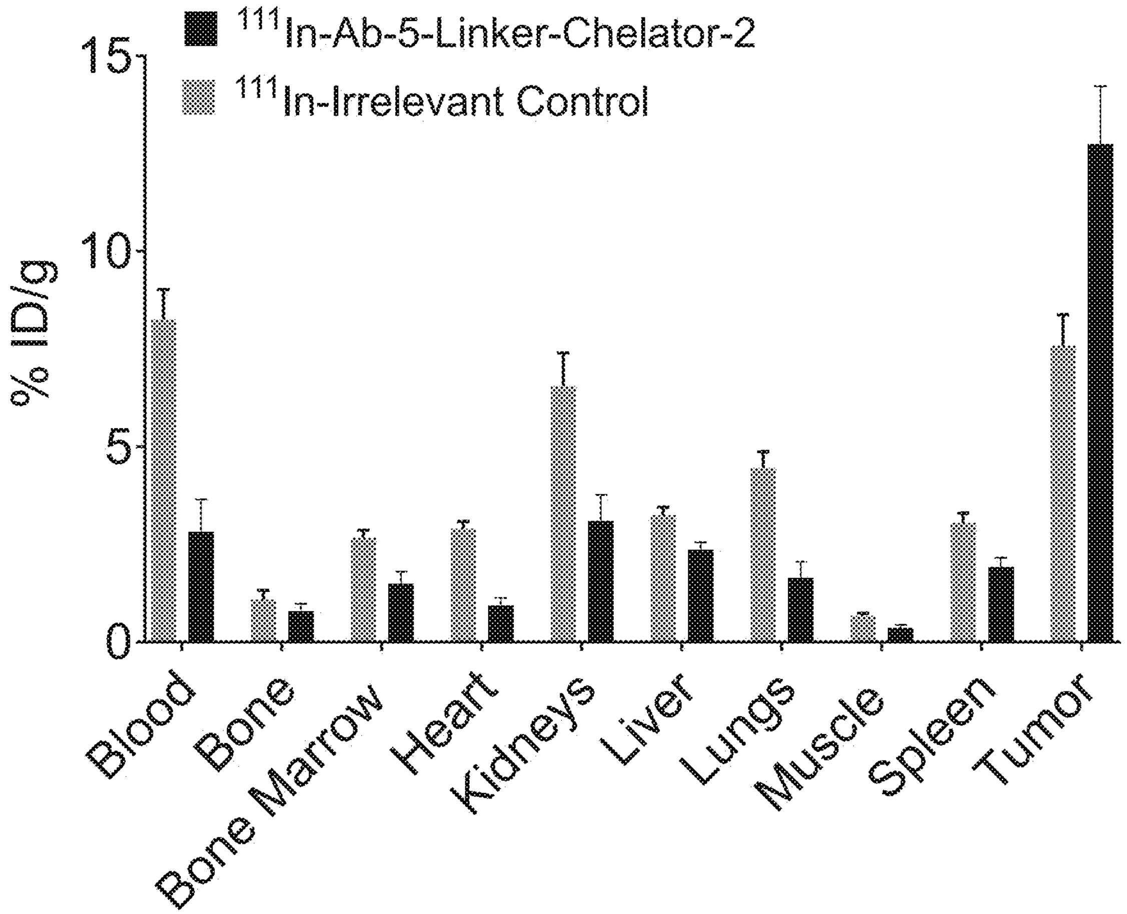
FIG. 31 illustrates ex vivo tissue biodistribution (% ID/g) of $^{111}$In-Ab-5-linker chelator 2 compared to ex vivo tissue biodistribution (% ID/g) of $^{111}$In-irrelevant control at 72 hours after a single I.V. bolus administration in HNSCC PDX tumor bearing athymic nude mice.

$^{111}$In-Ab-5-linker-chelator-2 showed a consistent normal tissue distribution as in cell line derived xenograft models (FIG. 31). At the 72 h timepoint, $^{111}$In-Ab-5-linker-chelator-2 had the highest activity concentration in the tumor (12.74±1.49% ID/g) while the $^{111}$In-irrelevant control had the highest activity concentration in the blood (8.26±0.76% ID/g) then the tumor (7.59±0.79% ID/g) (FIG. 31). Activity concentration for $^{111}$In-Ab-5-linker-chelator-2 was below ≤3% ID/g in blood, bone, bone marrow, heart, kidneys, liver, lungs, muscle and spleen vs ≤8% ID/g for the $^{111}$In-irrelevant control (FIG. 31).

Figure 10:
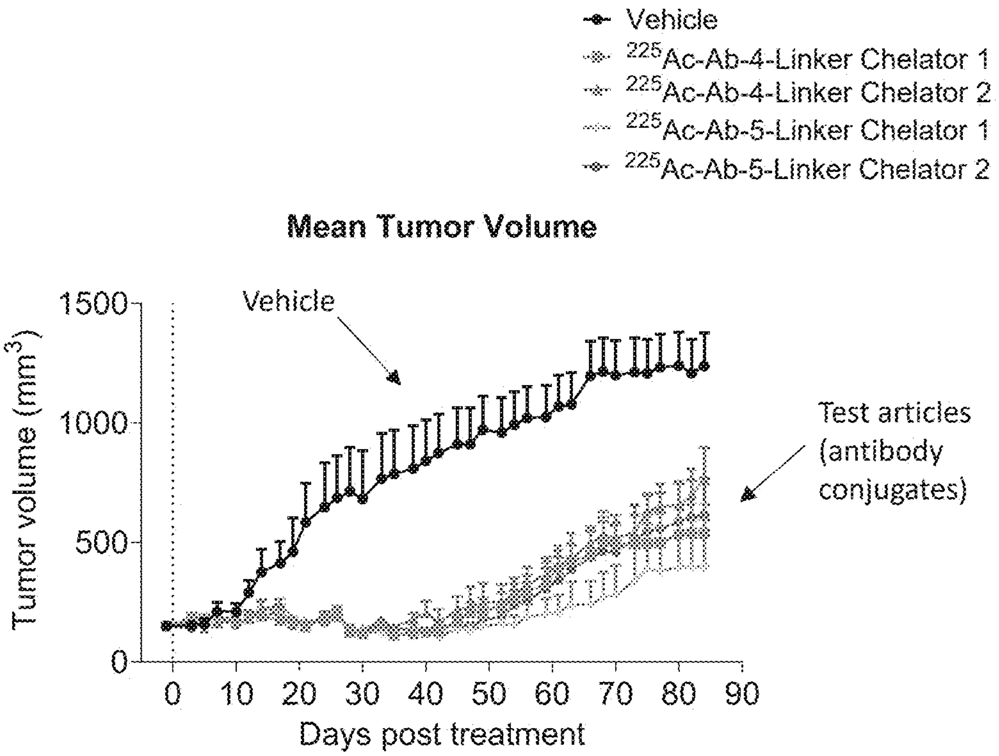
FIG. 10 shows suppression of BxPC-3 pancreatic cancer xenograft tumor growth in NMRI nude mice following a single 12kBq administration of $^{225}$Ac radiolabeled antibody conjugates ($^{225}$Ac-Ab-4-Linker Chelator 1, $^{225}$Ac-Ab-4-Linker Chelator 2, $^{225}$Ac-Ab-5-Linker Chelator 1, and $^{225}$Ac-Ab-5-Linker Chelator 2) compared to vehicle.
Figure 11:
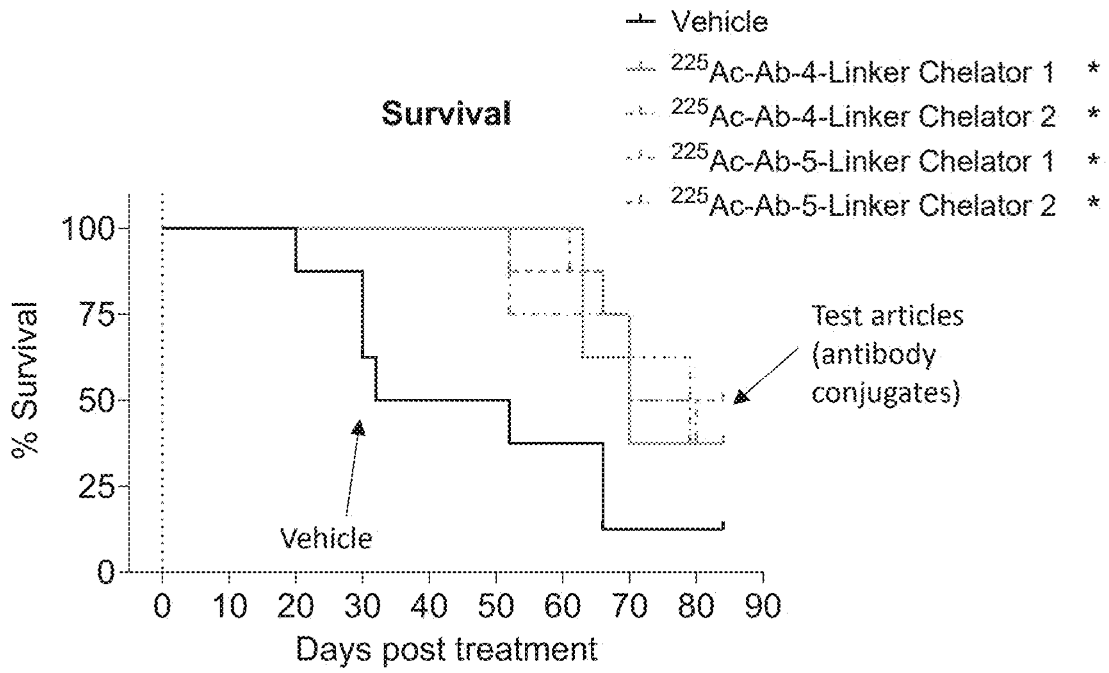
FIG. 11 shows a Kaplan-Meier survival curve with log-rank test comparing treatment groups to vehicle control (*p<0.05). Median survival of 42 days in vehicle control, and 70, 77, 79.5, 74.5 days in the 12kBq $^{225}$Ac-Ab-4-Linker Chelator 1, Ab-4-Linker Chelator 2, Ab-5-Linker Chelator 1, and Ab-5-Linker Chelator 2 groups, respectively.
Figure 12A:
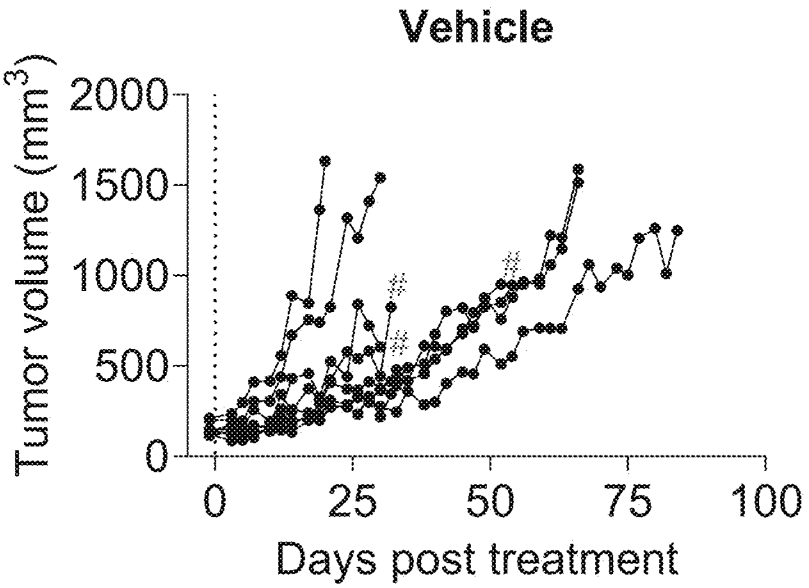
FIGS. 12A-12E show individual mouse tumor volume vs. time in BxPC-3 tumor-bearing NMR1 nude mice treated with vehicle and $^{225}$Ac radiolabeled antibodies. Tumor ulcerations are denoted with a #.
Figure 12B:
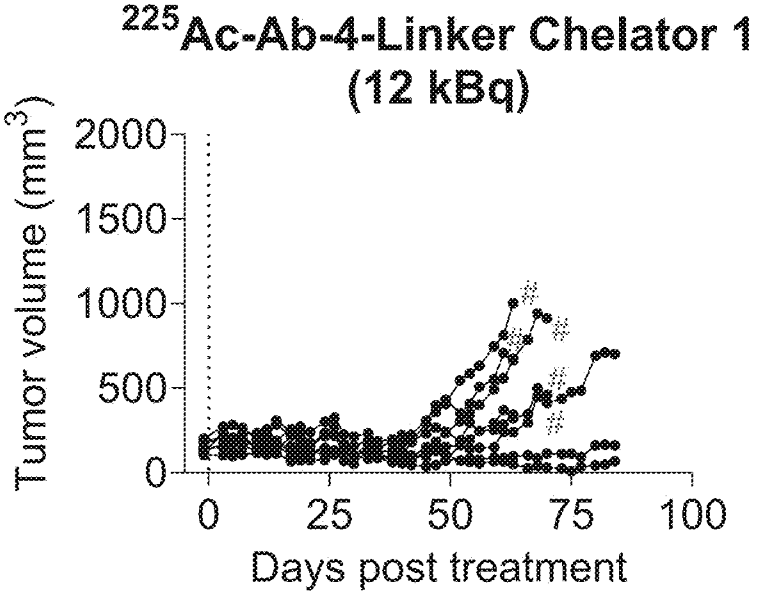
Figure 12C:
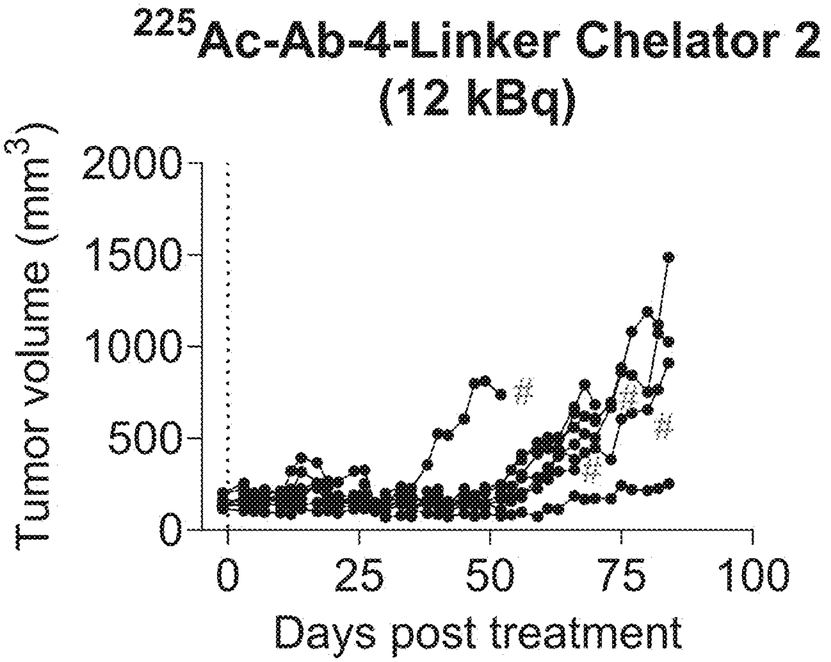
Figure 12D:
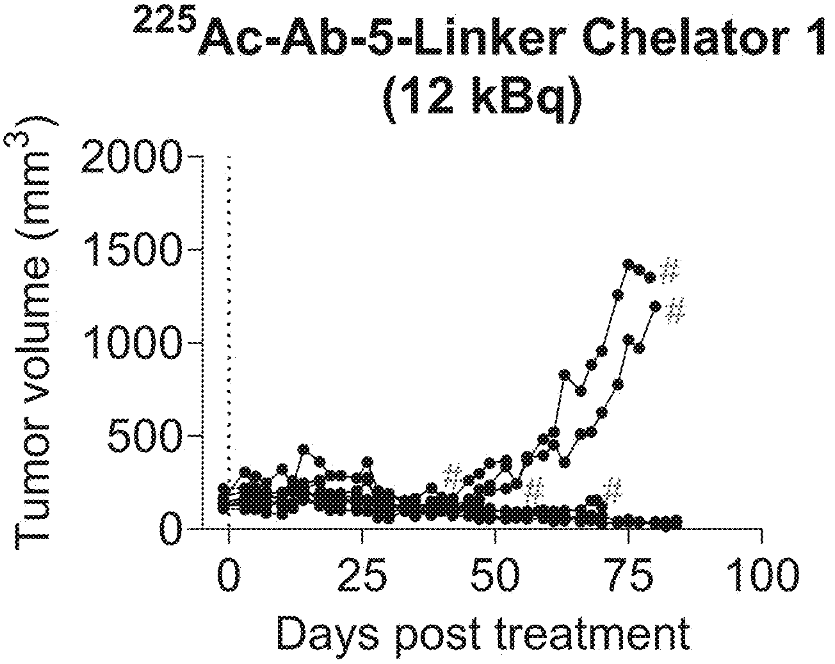
Figure 12E:
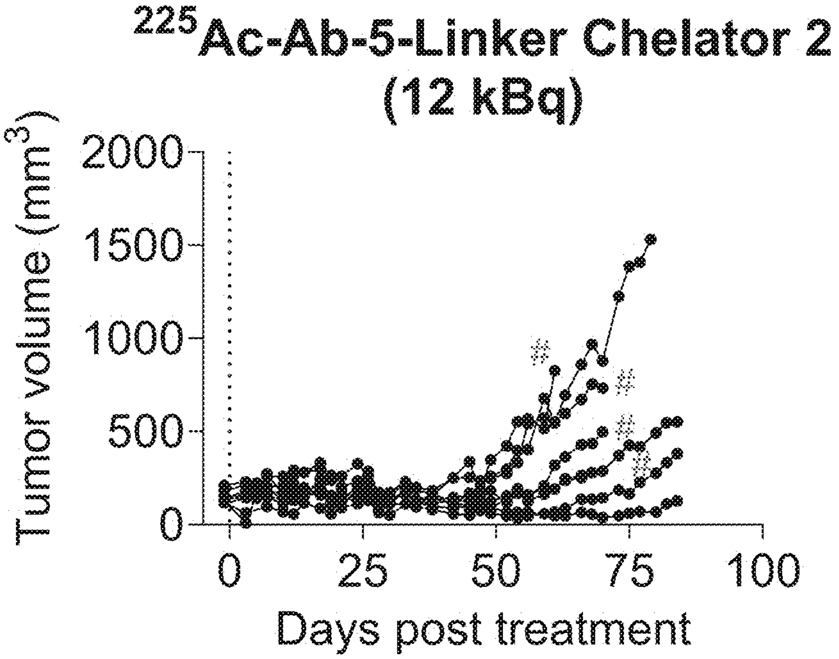

Example 11. Single-Dose Efficacy of $^{225}$Ac Radiolabeled Antibodies in BxPC-3 and NCI-H1975 Tumor-Bearing Mice Anti-tumor activity and extension of survival with 225Ac radiolabeled antibodies were evaluated in NMRI nude mice (N=8/group) with xenografted pancreatic BxPC-3 tumors. Animals were administered a single IV dose of vehicle or 225Ac radiolabeled antibody conjugates (12kBq 225Ac, ~1 mg/kg, 0.5 kBq/ug specific activity) on day 0. Body weight and tumor size were measured at specific time points throughout the study. Results for BxPC-3 tumor growth suppression with $^{225}$Ac-radiolabeled antibody conjugates are demonstrated in FIG. 10, which shows suppression of tumor growth in tumor bearing mice that received $^{225}$Ac-radiolabeled antibody conjugates, as compared to vehicle. Comparable and sustained tumor growth suppression was observed for all antibody conjugates in the first four weeks, compared to vehicle. Results for percent survival of the treated mice over time is shown in FIG. 11. Mice treated with the $^{225}$Ac-radiolabeled antibodies demonstrated significantly (*$p<0.05$) increased survival compared with vehicle treated mice. These data show increased survival in NMRI nude mice bearing BxPC-3 pancreatic cancer xenografts following a single 12 kBq administration of $^{225}$Ac radiolabeled antibody conjugates compared to vehicle. FIGS. 12A-12E show individual group tumor volume vs. time in BxPC-3 tumor-bearing mice treated with vehicle (FIG. 12A), Ab-4-linker chelator 1 (FIG. 12B), Ab-4-linker chelator 2 (FIG. 12C), Ab-5-linker chelator 1 (FIG. 12D), and Ab-5-linker chelator 2 (FIG. 12E).

Anti-tumor activity and extension of survival with $^{225}$Ac radiolabeled antibodies were evaluated in athymic nude mice with xenografted NSCLC NCI-H1975 tumors (n=9-10 per group). The NCI-H1975 cell line harbors an EGFR mutation preclinically implicated in higher radioresistance. Animals were administered a single intravenous (I.V.) dose of vehicle, non-radiolabeled Ab-5-Linker Chelator 2, or $^{225}$Ac radiolabeled Ab-5-Linker Chelator 2 on day 0. Body weight and tumor size were measured at specific time points throughout the study. Individual mice were dosed with 32 μg for the non-radiolabeled Ab-5-linker chelator 2 group, 20 μg for the $^{225}$Ac-Ab-5-linker chelator 2 (12kBq) group, 27 μg for the $^{225}$Ac-Ab-5-linker chelator 2 (16kBq) group, and 32 μg for the $^{225}$Ac-Ab-5-linker chelator 2 (20kBq) group for a specific activity of 0.6 kBq/μg.

Figure 19A:
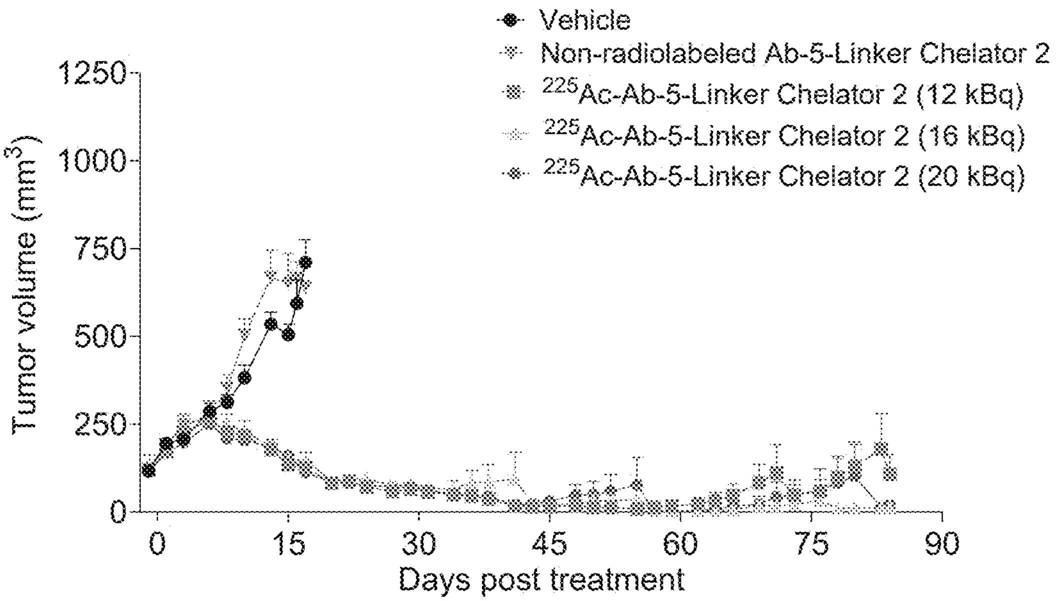
FIG. 19A illustrates mean tumor growth in NSCLC NCI-H1975 tumor bearing athymic nude mice treated with a single intravenous administration of vehicle, non-radiolabeled Ab-5-linker chelator 2 (32.5 μg) or $^{225}$Ac radiolabeled Ab-5-linker chelator 2 at 12 kBq (20 μg), 16 kBq (27 μg) and 20 kBq (32.5 μg).
Figure 19B:
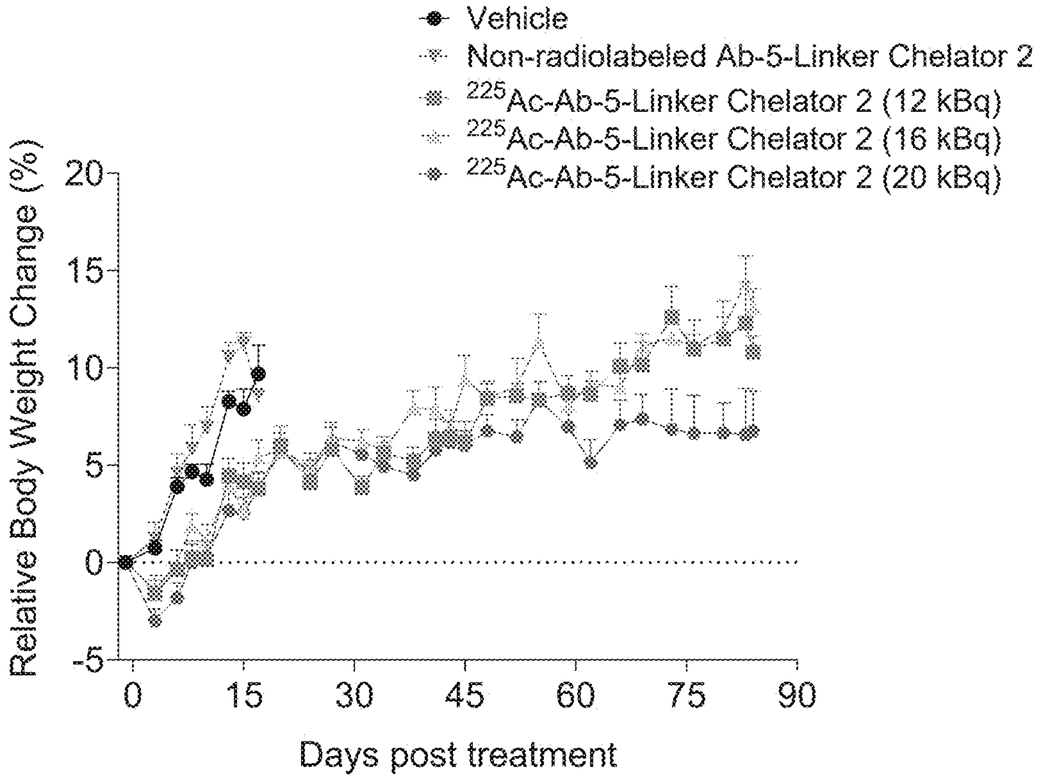
FIG. 19B illustrates mean body weight change in NCI-H1975 tumor bearing athymic nude mice treated with varying administered activities of $^{225}$Ac radiolabeled Ab-5-linker chelator 2, as described in FIG. 19A.
Figure 20A:
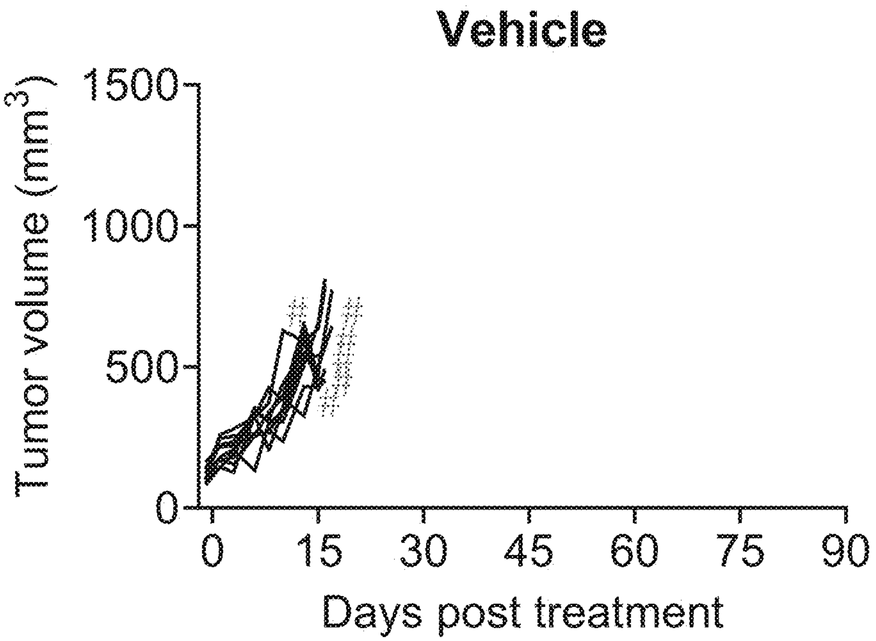
FIGS. 20A-20E illustrate NCI-H1975 efficacy study individual mouse tumor volumes for vehicle (FIG. 20A), non-radiolabeled Ab-5-linker chelator 2 (FIG. 20B), 12kBq $^{225}$Ac-Ab5-linker chelator 2 (FIG. 20C), 16kBq$^{225}$Ac-Ab-5-linker chelator 2 (FIG. 20D), or 20 kBq $^{225}$Ac-Ab-5-linker chelator 2 (FIG. 20E). Tumor ulcerations are denoted with a #.
Figure 20B:
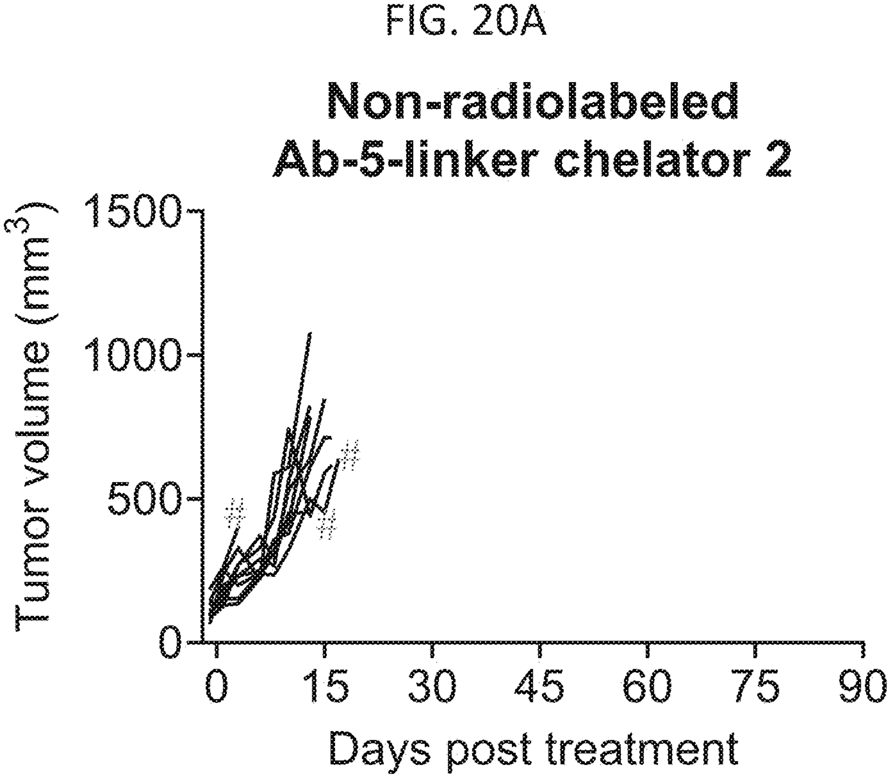
Figure 20C:
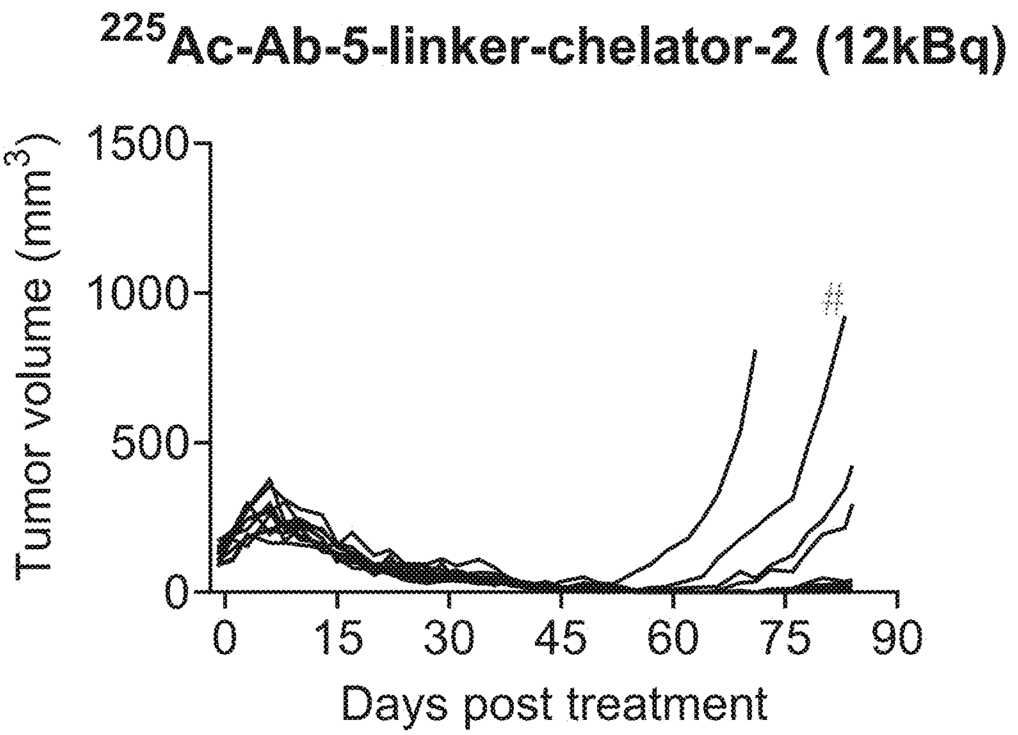
Figure 20D:
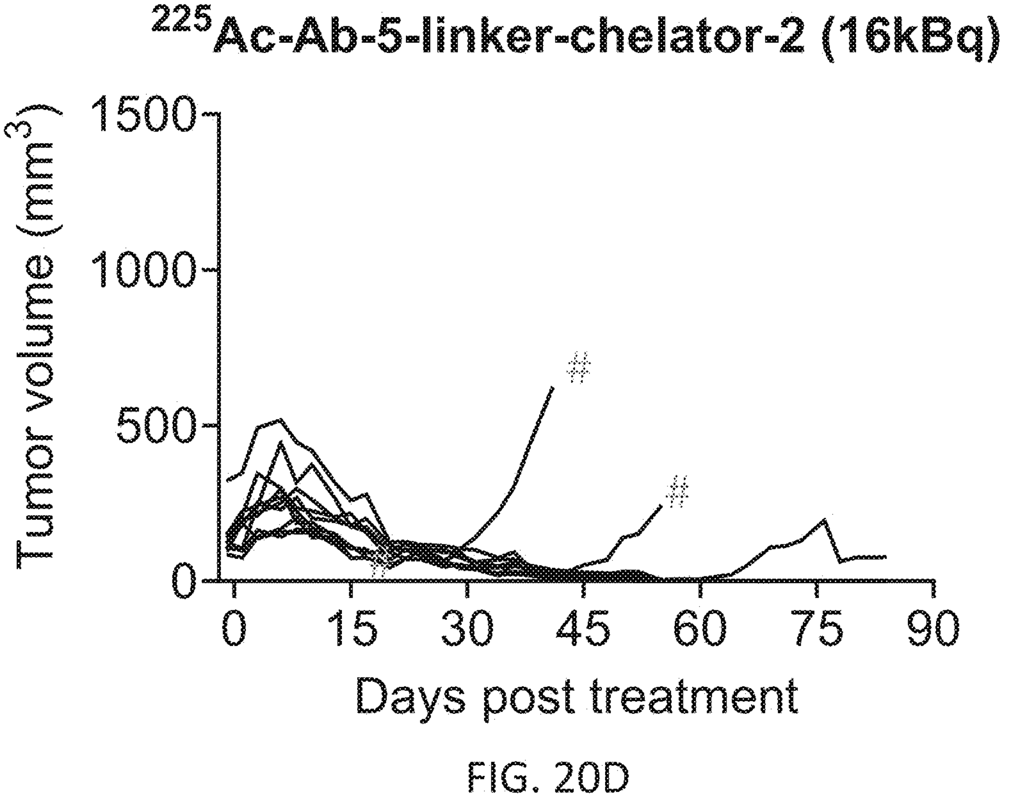
Figure 20E:
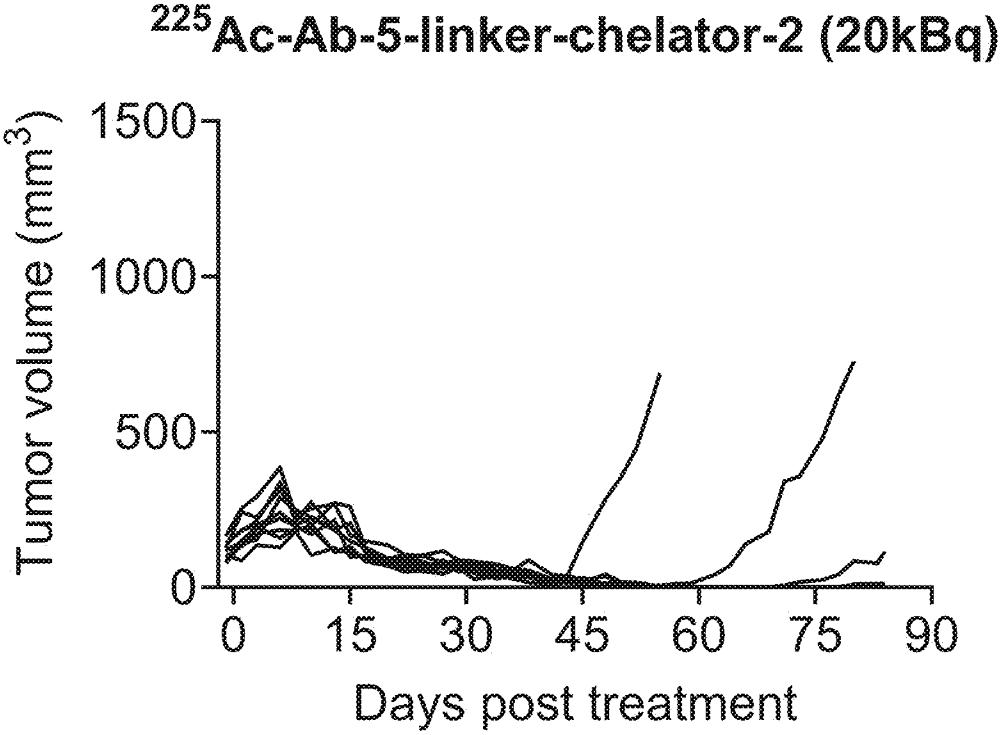

The treatment in the NCI-H1975 efficacy study was generally well tolerated in all groups based on measuring animal bodyweight, as shown in FIG. 19B. By day 16 all mice in the vehicle and non-radiolabeled Ab-5-linker chelator 2 group were euthanized due to rapid tumor outgrowth, while $^{225}$Ac-Ab-5-liner chelator 2 showed tumor suppression, as illustrated in FIG. 19A. Tumor regression was observed in all $^{225}$Ac-Ab-5-linker chelator 2 treated groups with sustained suppression of regrowth in most animals through to the study endpoint (day 84), as shown in FIGS. 20A-E.

Figure 21:
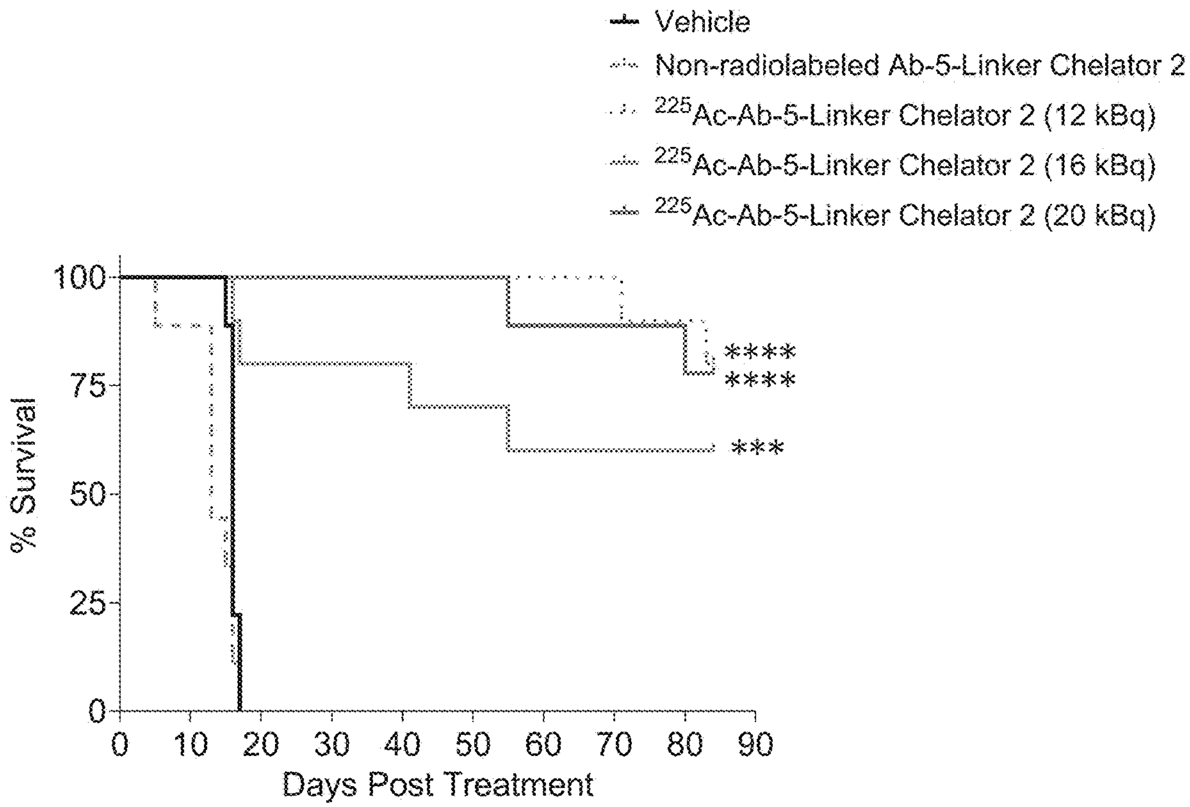
FIG. 21 illustrates a Kaplan-Meier survival curve for the NCI-H1975 efficacy study with log-rank test comparing treatment groups to vehicle control. Median survival of 16 days in the vehicle group, 13 days in the non -radiolabeled Ab-5-linker chelator 2 group, and undefined in the 12 kBq, 16 kBq and 20 kBq $^{225}$Ac-Ab-5-linker chelator 2 group. At study endpoint 8/10 (80%), 6/10 (60%), and 7/9 (78%) animals survived in the 12 kBq, 16 kBq and 20 kBq $^{225}$Ac-Ab-5-linker chelator 2 groups, respectively.

A survival assay was performed in mice with xenografted NSCLC NCI-H1975 tumors treated with a single IV. dose of vehicle, non-radiolabeled Ab5-linker chelator 2, $^{225}$Ac-Ab5-linker chelator 2 (12kBq), $^{225}$Ac-Ab5-linker chelator 2 (16kBq), and $^{225}$Ac-Ab5-linker chelator 2 (20kBq), as described herein. FIG. 21 illustrates a Kaplan-Meier overall survival (with log-rank test comparing treatment groups to vehicle control). These data provide a short median survival of 16 days in the vehicle group and 13 days in the non-radiolabeled Ab-5-linker chelator 2 treatment group, indicating no benefit of non-radiolabeled treatment. However, median survival was extended and undefined in all $^{225}$Ac-Ab-5-linker chelator 2 treatment groups. At study endpoint, the mice remaining on study were 8/10 in the 12 kBq group, 6/10 in the 16 kBq group and 7/9 in the 20 kBq -Ab-5-linker chelator 2 group. At Day 84, $^{225}$Ac/Ab test article treated mice at all activity levels showed sustained tumor regression or suppression of regrowth with mean tumor volumes as follows: 108 $mm^3$, 13 $mm^3$ and 18 $mm^3$ for the 12 kBq, 16 kBq and 20 kBq $^{225}$Ac -Ab-5-linker chelator 2 treatment groups, respectively.

FIGS. 20A-20E provide tumor volumes for individual mice with xenografted NSCLC NCI-H1975 tumors from Day 0 to endpoint post-treatment, treated with a single dose of vehicle (FIG. 20A), non-radiolabeled Ab-5-linker chelator 2 (FIG. 20B), $^{225}$Ac-Ab-5-linker chelator 2 (12kBq) (FIG. 20C), $^{225}$Ac-Ab-5-linker chelator 2 (16kBq) (FIG. 20D), or $^{225}$Ac-Ab-5-linker chelator 2 (20 kBq) (FIG. 20E) (# indicates animals excluded due to tumor ulceration).

Figure 22A:
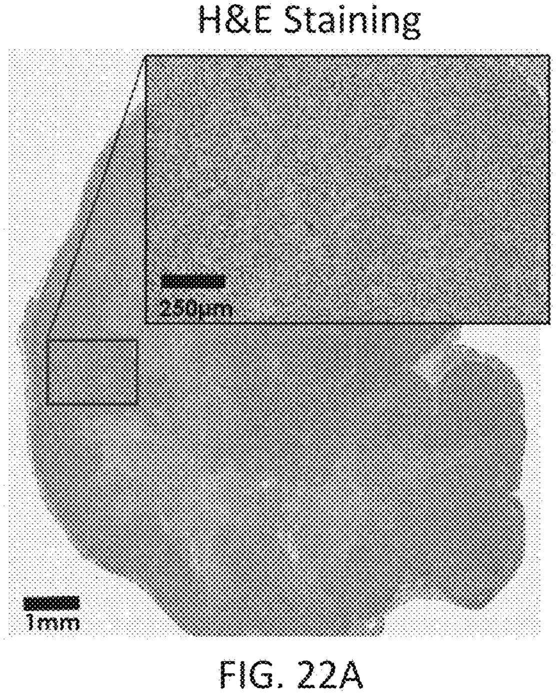
FIG. 22A shows a representative image of a hematoxylin and eosin (H&E) stained NCT-H1975 tumor section from a mouse treated with non-radiolabeled Ab-5-linker chelator 2.
Figure 22B:
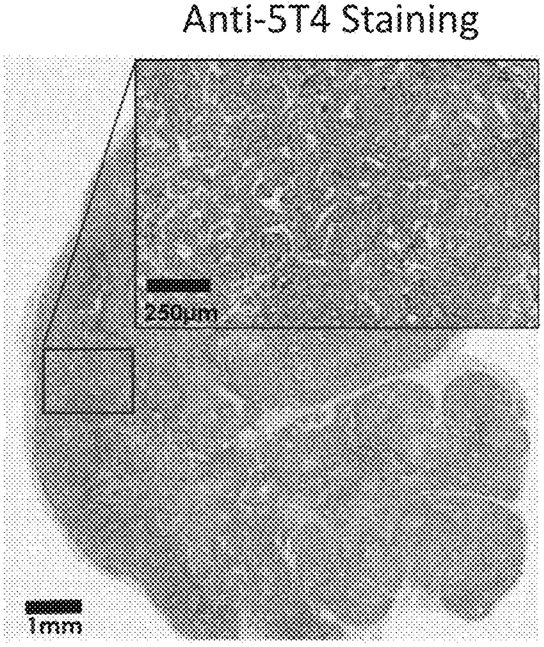
FIG. 22B shows a representative image of a 5T4 stained NCI-H1975 tumor section (using anti-5T4 antibody Abcam EPR5529) from a mouse treated with non-radiolabeled Ab-5-linker chelator 2.
Figure 22C:
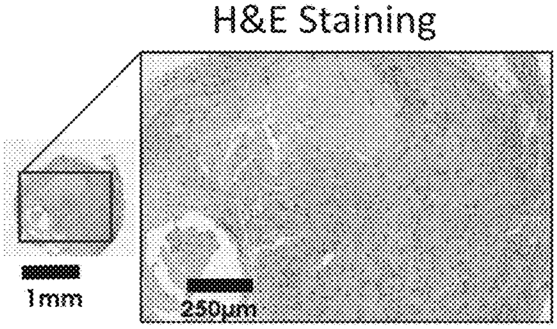
FIG. 22C shows a representative image of an H&E stained NCI-H1975 tumor section from a mouse treated with $^{225}$Ac-Ab-5-linker chelator 2 (20 kBq).
Figure 22D:
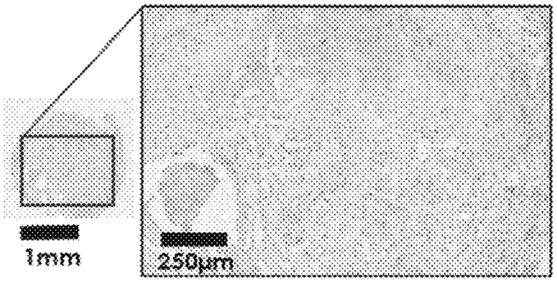
FIG. 22D shows a representative image of a 5T4 stained NCI-H1975 tumor section from a mouse treated with $^{225}$Ac-Ab-5-linker chelator 2 (20 kBq).

Histological analysis was performed on NSCLC NCI-H1975 tumor sections after a single IV. dose of $^{225}$Ac-Ab-5-linker chelator 2 (20 kBq) or non-radiolabeled Ab-5-linker chelator 2. Representative H&E stained NCI-H1975 tumor sections are shown for non-radiolabeled Ab-5-linker chelator 2 (FIG. 22A) and 20 kBq $^{225}$Ac-Ab-5-linker chelator 2 (FIG. 22C). Representative 5T4-stained NCI-H1975 tumor sections stained with anti-5T4 antibody (Abcam EPR5529) are shown for non-radiolabeled Ab-5-linker chelator 2 (FIG. 22B) and 20 kBq $^{225}$Ac-Ab-5-linker chelator 2 (FIG. 22D). The images demonstrate that treatment with $^{225}$Ac-Ab-5-linker chelator 2 (20 kBq) but not non-radiolabeled Ab-5-linker chelator 2 resulted in complete regression of NSCLC pathology following a single I.V. dose in some animals.

Figure 13:
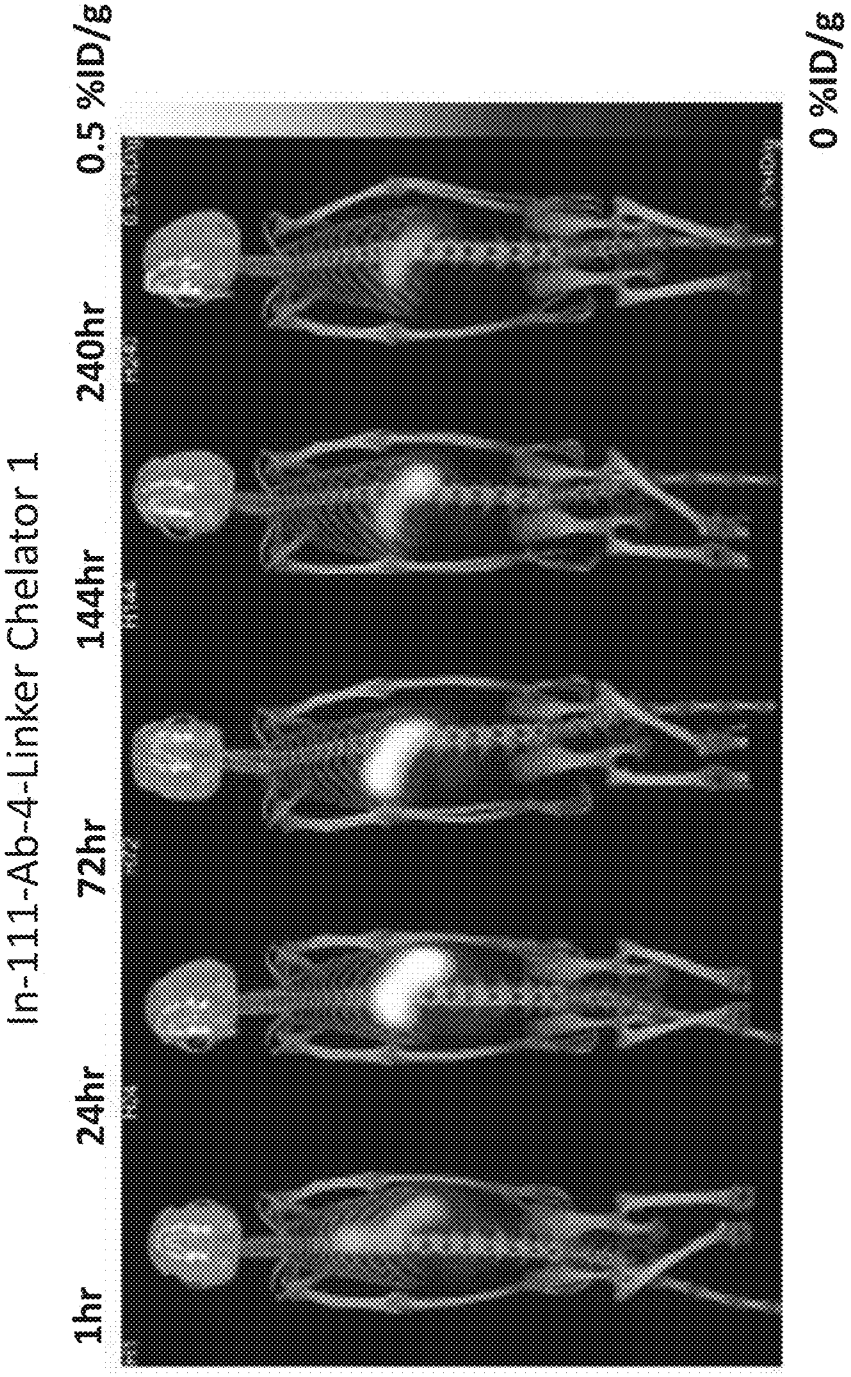
FIG. 13 shows time course SPECT/CT maximum intensity projections in a representative naïve cynomolgus monkey following a single administration of $^{111}$In radiolabeled Ab-4-linker chelator 1.
Figure 14:
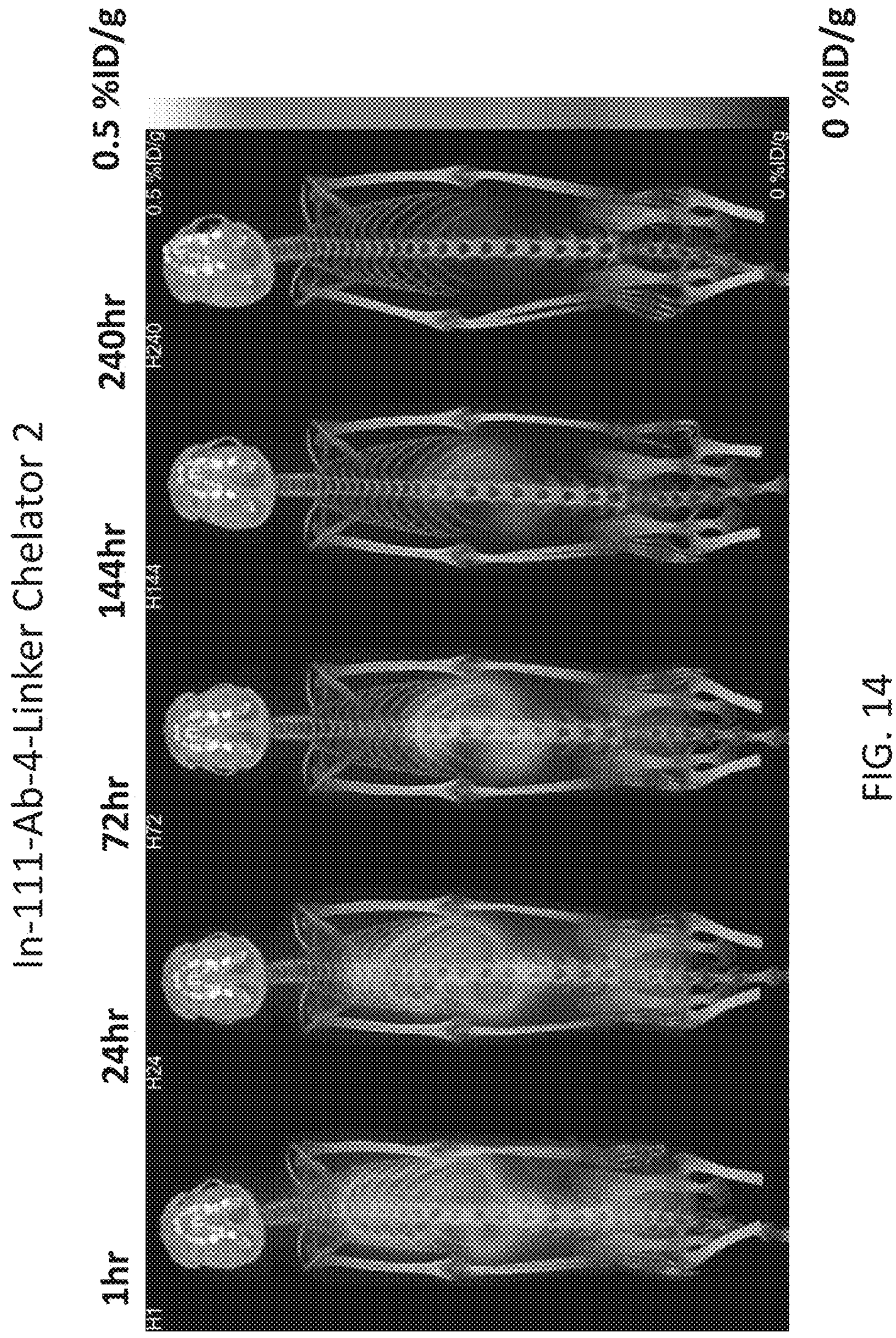
FIG. 14 shows time course SPECT/CT maximum intensity projections in a representative naïve cynomolgus monkey following a single administration of $^{111}$In radiolabeled Ab-4-linker chelator 2.
Figure 15:
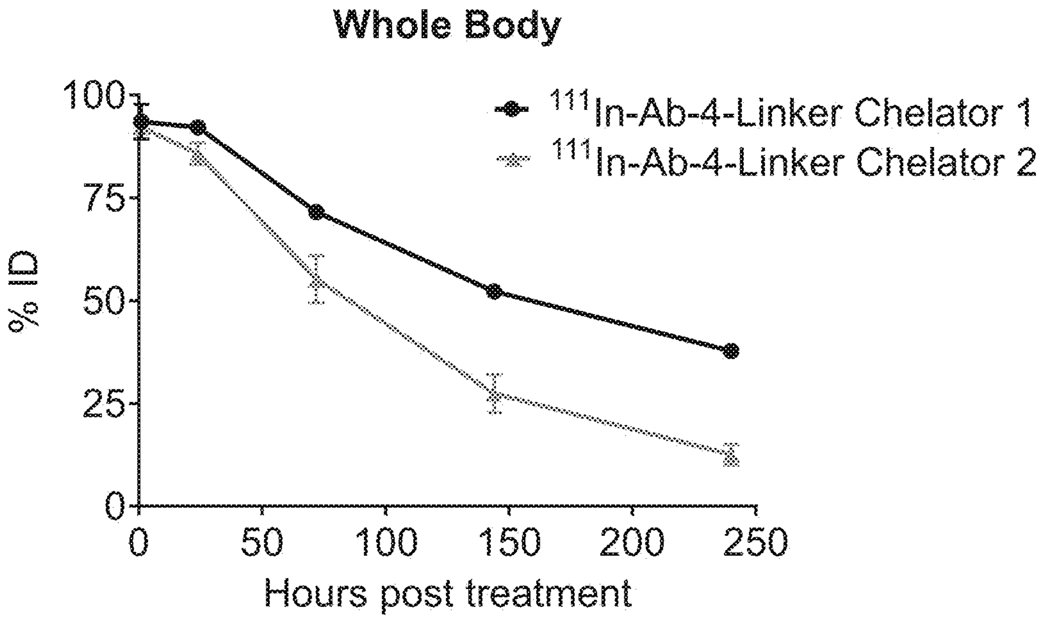
FIG. 15 shows whole body clearance in naïve cynomolgus monkeys (N=1/sex) following a single administration of $^{111}$In radiolabeled Ab-4-linker chelator 1 and $^{111}$In radiolabeled Ab-4-linker chelator 2 as measured by SPECT/CT imaging.
Figure 16:
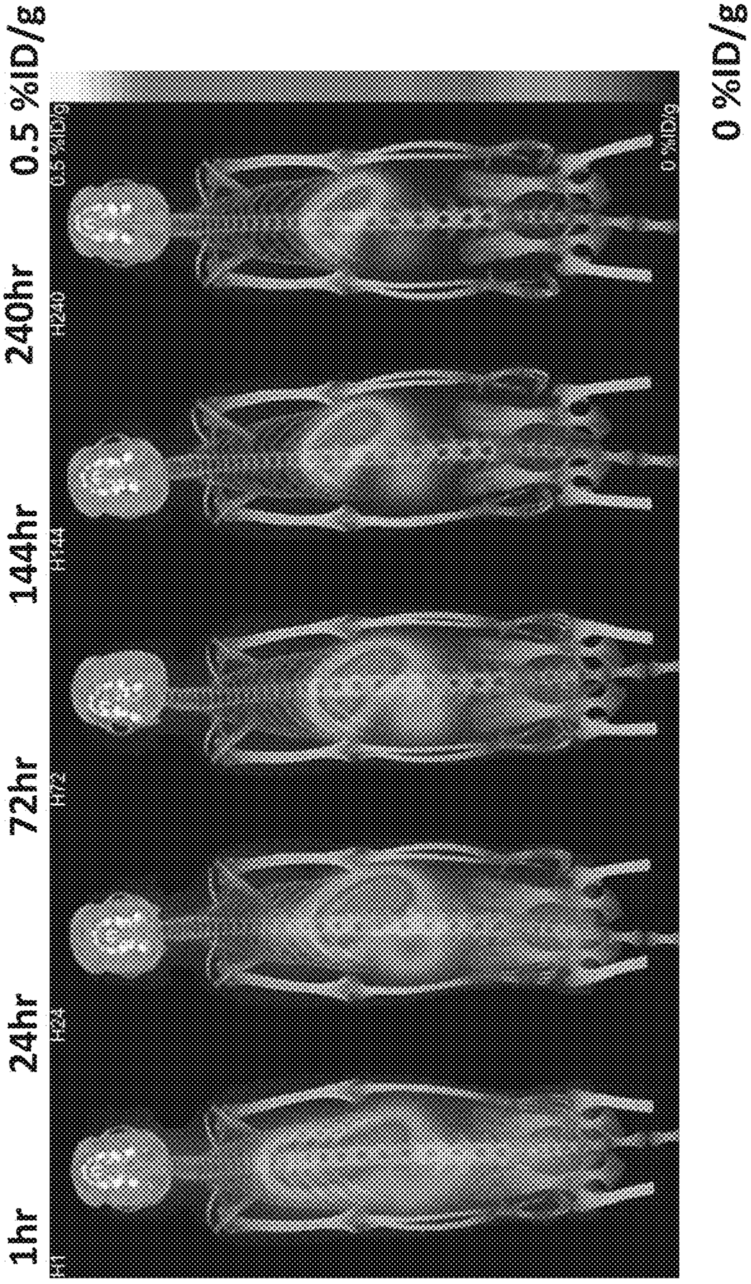
FIG. 16 shows time course SPECT/CT maximum intensity projections in a representative naïve cynomolgus monkey following a single administration of $^{111}$In radiolabeled Ab-5-linker chelator 1.
Figure 17:
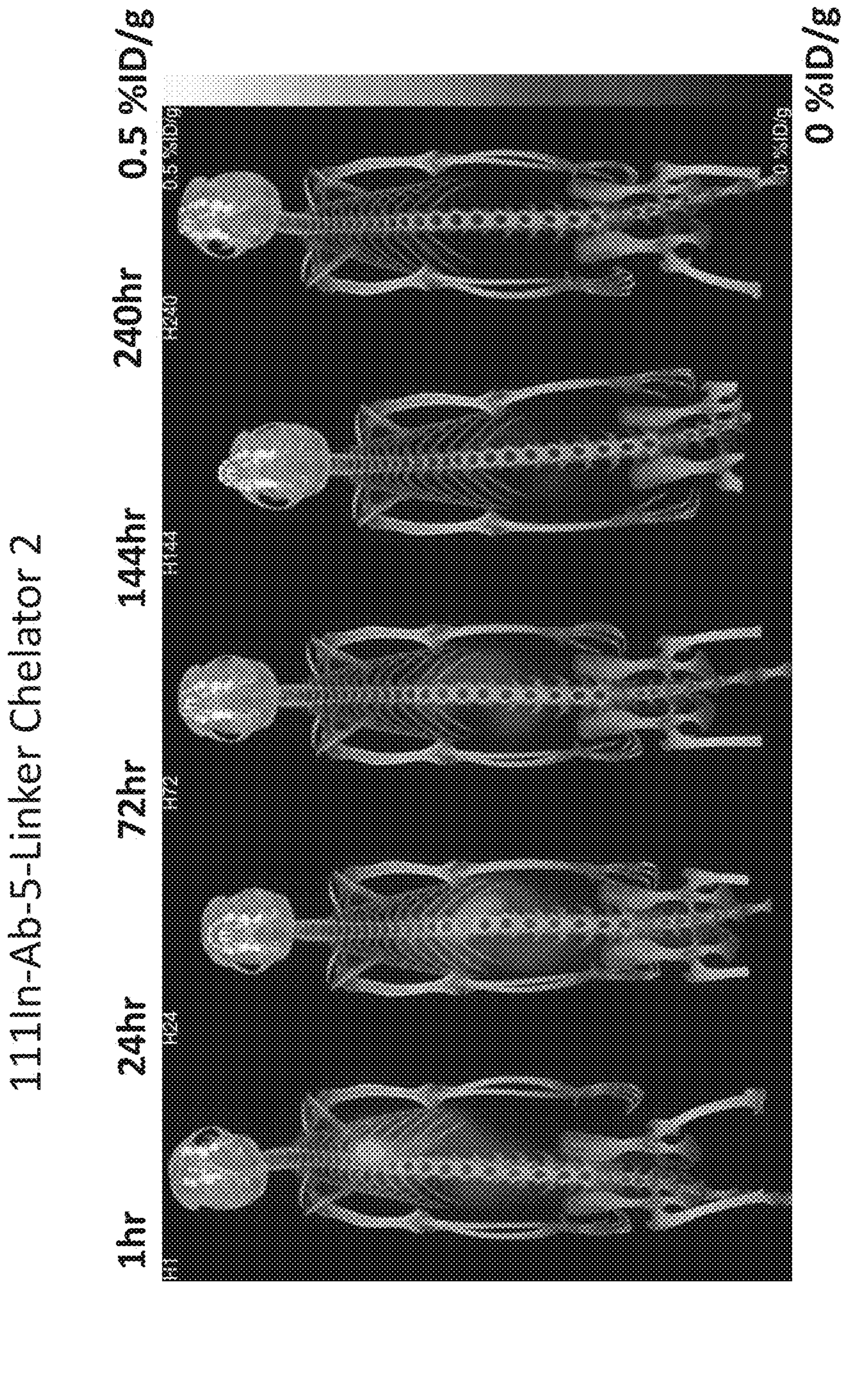
FIG. 17 shows time course SPECT/CT maximum intensity projections in a representative naïve cynomolgus monkey following a single administration of $^{111}$In radiolabeled Ab-5-linker chelator 2.
Figure 18:
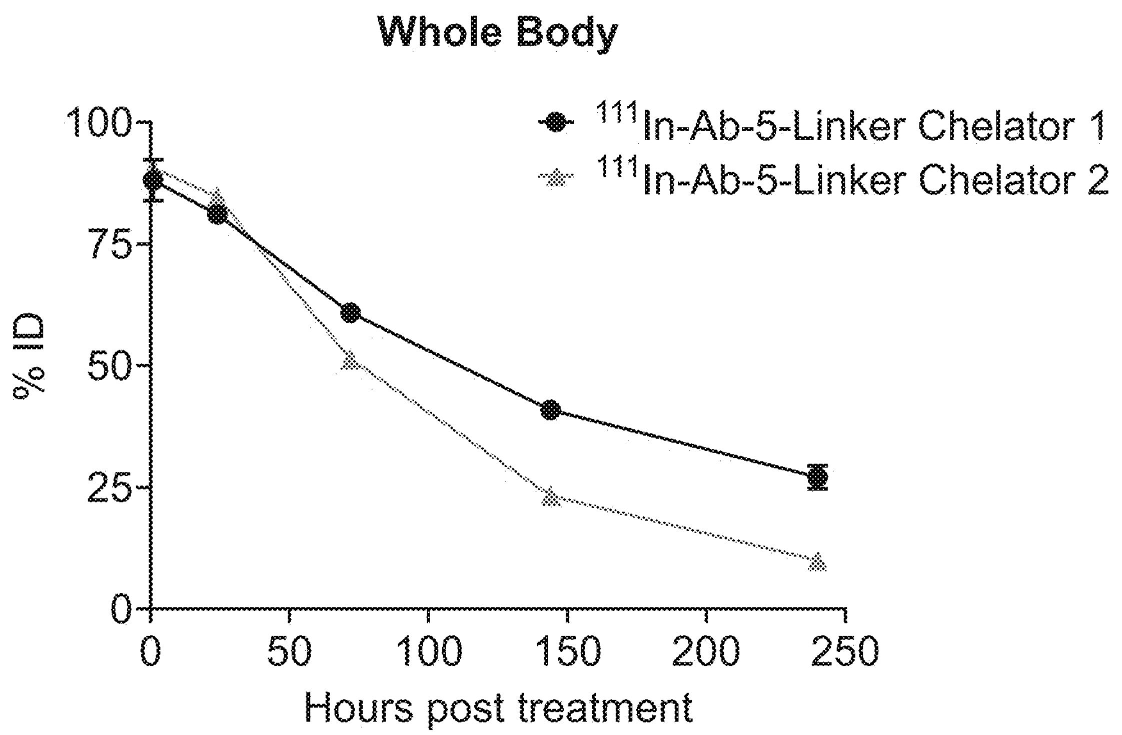
FIG. 18 shows whole body clearance in naïve non-human primate (N=1/sex) of $^{111}$In radiolabeled Ab-5-linker chelator 1 and $^{111}$In radiolabeled Ab-5-linker chelator 2 as measured by SPECT/CT imaging.

Example 12: Biodistribution and Pharmacokinetics of $^{111}$In Radiolabeled Antibodies in Naive Cynomolgus Monkeys Naïve cynomolgus monkeys were dosed with $^{111}$In radiolabeled anti-5T4 conjugate (1 male, 1 female per test article) and underwent SPECT/CTimaging at 1 h, 24 h, 72 h, 144 h and 240 h post-injection, followed by blood draws for gamma counting analysis. $^{111}$In radiolabeled Ab-4-linker chelator 1, Ab-4-linker chelator 2, Ab-5-linker chelator 1, and Ab-5-linker chelator 2 were assessed for biodistribution and clearance. FIGS. 13-14 show representative imaging results for biodistribution of $^{111}$In radiolabeled Ab-4-linker chelator 1 (FIG. 13) and Ab-4-linker chelator 2 (FIG. 14). FIG. 15 shows image-derived whole body clearance of $^{111}$In radiolabeled Ab-4-linker chelator 1 and $^{111}$In radiolabeled Ab-4-linker chelator 2. FIGS. 16-17 show representative imaging results for biodistribution of $^{111}$In radiolabeled Ab-5-linker chelator 1 (FIG. 16) and $^{111}$In radiolabeled Ab-5-linker chelator 2 (FIG. 17). FIG. 18 shows whole-body clearance of $^{111}$In radiolabeled Ab-5-linker chelator 1 and $^{111}$In radiolabeled Ab-5-linker chelator 2. The data show biodistribution to excretory organs, faster whole-body and liver clearance with linker chelator 2 compared to linker chelator 1, and no apparent 5T4 expression and binding in normal tissues.

Figure 32:
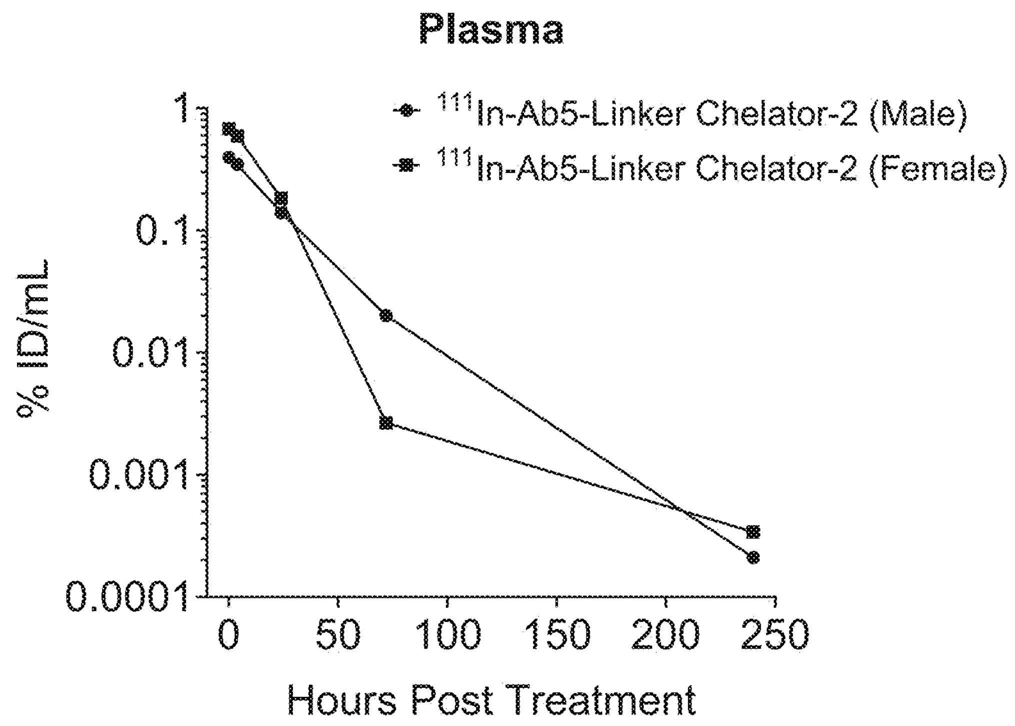
FIG. 32 illustrates plasma concentrations across time post treatment in a naïve male Cynomolgus monkey and a naïve female Cynomolgus monkey after a single I.V. bolus administration of $^{111}$In-Ab-5-linker chelator 2.

As Ab5 binds both human and cynomolgus monkey 5T4 with high affinity, but not mouse 5T4, pharmacokinetics were evaluated in cynomolgus monkeys, which are a pharmacologically relevant species. Naive male and female cynomolgus monkeys (n=1/sex) were administered $^{111}$In-Ab5-Linker Chelator-2 by single IV injection (male: 203.83 MBq, female: 116.15 MBq In-111, 0.3 mg/kg protein, and 0.1 MBq/μg specific activity). Similar to findings in human FcRn transgenic mice (FIG. 26), $^{111}$In-Ab5-Linker Chelator-2 cleared rapidly from the blood compartment with approximately 76% of the injected activity cleared in the first 24 hours and an elimination half-life in plasma of 26 h (FIG. 32).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

SEQUENCES

| SEQ ID NO: | Sequence | CDR Definition | Annotation |
|---|---|---|---|
| 1 | GYAVG | Kabat | CDR1 (Ab-1, Ab-2) |
| 2 | ALSRTGGSYYADSVKG | Kabat | CDR2 (Ab 1, Ab-2) |
| 3 | RSVASIHNNRYYTDVYDYTY | Kabat | CDR3 (Ab-1, Ab-2) |
| 4 | GRTFAGYA | IMGT | CDR1 (Ab-1, Ab-2) |
| 5 | LSRTGGS | IMGT | CDR2 (Ab-1, Ab-2) |
| 6 | ATRSVASIHNNRYYTDVYDYTY | IMGT | CDR3 (Ab-1, Ab-2) |
| 7 | GRTFAGYAVG | AbM | CDR1 (Ab-1, Ab-2) |
| 8 | ALSRTGGSY | AbM | CDR2 (Ab-1, Ab-2) |
| 9 | RSVASIHNNRYYTDVYDYTY | AbM | CDR3 (Ab-1, Ab-2) |
| 10 | GRTFAGY | Chothia | CDR1 (Ab-1, Ab-2) |
| 11 | SRTGG | Chothia | CDR2 (Ab-1, Ab-2) |
| 12 | RSVASIHNNRYYTDVYDYTY | Chothia | CDR3 (Ab-1, Ab-2) |
| 13 | SYAMS | Kabat | CDR1 (Ab-3, Ab-4, Ab-5) |
| 14 | SITTAGGSTRYADSVKG | Kabat | CDR2 (Ab-3, Ab-4, Ab-5) |
| 15 | ELGPRRLGMDY | Kabat | CDR3 (Ab-3, Ab-4, Ab-5) |
| 16 | GFTFSSYA | IMGT | CDR1 (Ab-3, Ab-4, Ab-5) |
| 17 | ITTAGGST | IMGT | CDR2 (Ab-3, Ab-4, Ab-5) |
| 18 | NAELGPRRLGMDY | IMGT | CDR3 (Ab 3, Ab-4, Ab-5) |

-continued

SEQUENCES

| SEQ ID NO: | Sequence | CDR Definition | Annotation |
|---|---|---|---|
| 19 | GFTFSSYAMS | AbM | CDR1 (Ab-3, Ab-4, Ab-5) |
| 20 | SITTAGGSTR | AbM | CDR2 (Ab-3, Ab-4, Ab-5) |
| 21 | ELGPRRLGMDY | AbM | CDR3 (Ab-3, Ab-4, Ab-5) |
| 22 | GFTFSSY | Chothia | CDR1 (Ab-3, Ab-4, Ab-5) |
| 23 | TTAGGS | Chothia | CDR2 (Ab-3, Ab-4, Ab-5) |
| 24 | ELGPRRLGMDY | Chothia | CDR3 (Ab-3, Ab-4, Ab-5) |
| 25 | QVQLVESGGGLVKPGGSLRLSCAASGRTFAGYAVGWF RQAPGKEREFVAALSRTGGSYYADSVKGRFTISRDNA KNSLYLQMNSLRAEDTAVYYCATRSVASIHNNRYYTD VYDYTYWGQGTLVTVSS | N/A | Ab-1 VHH |
| 26 | QVQLVESGGGLVKPGGSLRLSCAASGRTFAGYAVGWF RQAPGKEREFVSALSRTGGSYYADSVKGRFTISRDNA KNSLYLQMNSLKAEDTAVYYCATRSVASIHNNRYYTD VYDYTYWGQGTQVTVSS | N/A | Ab-2 VHH |
| 27 | EVQLVESGGGLVQPGGSLRLSCAASGFTFSSYAMSWY RQAPGKGLELVASITTAGGSTRYADSVKGRFTISRDN AKNTLYLQMNSLRAEDTAVYYCNAELGPRRLGMDYWG QGTLVTVSS | N/A | Ab-3 VHH |
| 28 | EVQLVESGGGLVQPGGSLRLSCAASGFTFSSYAMSWV RQAPGKEREWVASITTAGGSTRYADSVKGRFTISRDN AKNTLYLQMNSLRAEDTAVYYCNAELGPRRLGMDYWG QGTLVTVSS | N/A | Ab-4 VHH |
| 29 | EVQLVESGGGLVQPGGSLRLSCAASGFTFSSYAMSWY RQAPGKERELVASITTAGGSTRYADSVKGRFTISRDN AKNTLYLQMNSLRAEDTAVYYCNAELGPRRLGMDYWG QGTLVTVSS | N/A | Ab-5 VHH |
| 30 | QVQLVESGGGLVKPGGSLRLSCAASGRTFAGYAVGWF RQAPGKEREFVAALSRTGGSYYADSVKGRFTISRDNA KNSLYLQMNSLRAEDTAVYYCATRSVASIHNNRYYTD VYDYTYWGQGTLVTVSSEPKSSDKTHTCPPCPAPEAE GAPSVFLFPPKPKDTLMISRTPEVTCVVVDVSHEDPE VKFNWYVDGVEVHNAKTKPREEQYNSTYRVVSVLTVL HQDWLNGKEYKCKVSNKALPSSIEKTISKAKGQPREP QVYTLPPSREEMTKNQVSLTCLVKGFYPSDIAVEWES NGQPENNYKTTPPVLDSDGSFFLYSKLTVDKSRWQQG NVFSCSVMHEALHNQYTQKSLSLSPG | N/A | Ab-1 VHH-Fc |
| 31 | QVQLVESGGGLVKPGGSLRLSCAASGRTFAGYAVGWF RQAPGKEREFVSALSRTGGSYYADSVKGRFTISRDNA KNSLYLQMNSLKAEDTAVYYCATRSVASIHNNRYYTD VYDYTYWGQGTQVTVSSEPKSSDKTHTCPPCPAPEAE GAPSVFLFPPKPKDTLMISRTPEVTCVVVDVSHEDPE VKFNWYVDGVEVHNAKTKPREEQYNSTYRVVSVLTVL HQDWLNGKEYKCKVSNKALPSSIEKTISKAKGQPREP QVYTLPPSREEMTKNQVSLTCLVKGFYPSDIAVEWES NGQPENNYKTTPPVLDSDGSFFLYSKLTVDKSRWQQG NVFSCSVMHEALHNQYTQKSLSLSPG | N/A | Ab-2 VHH-Fc |
| 32 | EVQLVESGGGLVQPGGSLRLSCAASGFTFSSYAMSWY RQAPGKGLELVASITTAGGSTRYADSVKGRFTISRDN AKNTLYLQMNSLRAEDTAVYYCNAELGPRRLGMDYWG | N/A | Ab-3 VHH-Fc |

-continued

SEQUENCES

| SEQ ID NO: | Sequence | CDR Definition | Annotation |
|---|---|---|---|
| | QGTLVTVSSEPKSSDKTHTCPPCPAPEAEGAPSVFLF PPKPKDTLMISRTPEVTCVVVDVSHEDPEVKFNWYVD GVEVHNAKTKPREEQYNSTYRVVSVLTVLHQDWLNGK EYKCKVSNKALPSSIEKTISKAKGQPREPQVYTLPPS REEMTKNQVSLTCLVKGFYPSDIAVEWESNGQPENNY KTTPPVLDSDGSFFLYSKLTVDKSRWQQGNVFSCSVM HEALHNQYTQKSLSLSPG | | |
| 33 | EVQLVESGGGLVQPGGSLRLSCAASGFTFSSYAMSWV RQAPGKEREWVASITTAGGSTRYADSVKGRFTISRDN AKNTLYLQMNSLRAEDTAVYYCNAELGPRRLGMDYWG QGTLVTVSSEPKSSDKTHTCPPCPAPEAEGAPSVFLF PPKPKDTLMISRTPEVTCVVVDVSHEDPEVKFNWYVD GVEVHNAKTKPREEQYNSTYRVVSVLTVLHQDWLNGK EYKCKVSNKALPSSIEKTISKAKGQPREPQVYTLPPS REEMTKNQVSLTCLVKGFYPSDIAVEWESNGQPENNY KTTPPVLDSDGSFFLYSKLTVDKSRWQQGNVFSCSVM HEALHNQYTQKSLSLSPG | N/A | Ab-4 VHH-Fc |
| 34 | EVQLVESGGGLVQPGGSLRLSCAASGFTFSSYAMSWY RQAPGKERELVASITTAGGSTRYADSVKGRFTISRDN AKNTLYLQMNSLRAEDTAVYYCNAELGPRRLGMDYWG QGTLVTVSSEPKSSDKTHTCPPCPAPEAEGAPSVFLF PPKPKDTLMISRTPEVTCVVVDVSHEDPEVKFNWYVD GVEVHNAKTKPREEQYNSTYRVVSVLTVLHQDWLNGK EYKCKVSNKALPSSIEKTISKAKGQPREPQVYTLPPS REEMTKNQVSLTCLVKGFYPSDIAVEWESNGQPENNY KTTPPVLDSDGSFFLYSKLTVDKSRWQQGNVFSCSVM HEALHNQYTQKSLSLSPG | N/A | Ab-5 VHH-Fc |
| 37 | MPGGCSRGPAAGDGRLRLARLALVLLGWVSSSSPTSS ASSFSSSAPFLASAVSAQPPLPDQCPALCECSEAART VKCVNRNLTEVPTDLPAYVRNLFLTGNQLAVLPAGAF ARRPPLAELAALNLSGSRLDEVRAGAFEHLPSLRQLD LSHNPLADLSPFAFSGSNASVSAPSPLVELILNHIVP PEDERQNRSFEGMVVAALLAGRALQGLRRLELASNHF LYLPRDVLAQLPSLRHLDLSNNSLVSLTYVSFRNLTH LESLHLEDNALKVLHNGTLAELQGLPHIRVFLDNNPW VCDCHMADMVTWLKETEVVQGKDRLTCAYPEKMRNRV LLELNSADLDCDPILPPSLQTS | N/A | 5T4 protein |
| 39 | SIVMTQTPTFLLVSAGDRVTITCKASQSVSNDVAWYQ QKPGQSPTLLISYTSSRYAGVPDRFIGSGYGTDFTFT ISTLQAEDLAVYFCQQDYNSPPTFGGGTKLEIK | N/A | H8 VL (Ab-9) |
| 40 | EVQLQQSGPDLVKPGASVKISCKASGYSFTGYYMHWV KQSHGKSLEWIGRINPNNGVTLYNQKFKDKAILTVDK SSTTAYMELRSLTSEDSAVYYCARSTMITNYVMDYWG QVTSVTVSS | N/A | H8 VH (Ab-9) |
| 41 | QVQLVQSGGGLVQAGDSLTLSCAVSERPFGTYAMGWF RQAPGRERDLVAAVSRNGGASQYGDSVKGRFSISRDN IKNTMYLQMNSLKPEDTAVYYCAARSAAYSRSSEVYT GKDEYYYWGQGTQVTVKP | N/A | Ab-6 |
| 42 | QVQLVESGGGLVQAGGSLRLSCLASGRTFAGYAVGWF RQAPGKEREFVAALSRTGGSYYADSVKGRFTISRDNA ERTMNLQMNSLKPEDTAVYYCATRSVASIHNNRYYTD VYDYTYWGQGTQVTVSS | N/A | Ab-7 |
| 43 | QVQLVESGGGLVQPGGSLRLSCAASGFTFSSYAMSWY RQAPGEERELVASITTAGGSTRYADSVKGRFTISRDN AKNTVYLQMNSLKPEDTAVYYCNAELGPRRLGMDYWG EGTLVTVSA | N/A | Ab-8 |
| 45 | EPKSCDKTHTCPPCP | N/A | IgG1-hinge |
| 46 | EPKSSDKTHTCPPCP | N/A | C220S |
| 47 | EPKSSDKTHTCPPCPAPEAEGAPSVFLFPPKPKDTLM ISRTPEVTCVVVDVSHEDPEVKFNWYVDGVEVHNAKT KPREEQYNSTYRVVSVLTVLHQDWLNGKEYKCKVSNK ALPSSIEKTISKAKGQPREPQVYTLPPSREEMTKNQV SLTCLVKGFYPSDIAVEWESNGQPENNYKTTPPVLDS | N/A | Fc (435Q, AEASS, C220S) |

-continued

| SEQ ID NO: | Sequence | CDR Definition | Annotation |
|---|---|---|---|
| | DGSFFLYSKLTVDKSRWQQGNVFSCSVMHEALHNQYT QKSLSLSPG | | |
| 48 | APELLGGPSVFLFPPKPKDTLMISRTPEVTCVVVDVS HEDPEVKFNWYVDGVEVHNAKTKPREEQYNSTYRVVS VLTVLHQDWLNGKEYKCKVSNKALPAPIEKTISKAKG QPREPQVYTLPPSREEMTKNQVSLTCLVKGFYPSDIA VEWESNGQPENNYKTTPPVLDSDGSFFLYSKLTVDKS RWQQGNVFSCSVMHEALHNHYTQKSLSLSPG | N/A | Wild-Type Fc |
| 49 | MPGGCSRGPAAGDGRLRLARLALVLLGWVSSSSSTSS ASSSSSSAPFLASAASAQPPLPDQCPALCECSEAART VKCVNRNLTEVPTDLPLYVRNLFLTGNQLAVLPAGAF ARRPPLAELAALNLSGSRLDEVRGGAFEHLPSLRQLD LSHNPLAYLSPFAFSGSNASISAPSPLVELILNHIVP PDDKRQNRSFEGMVAAALVAGRALQGLHLLELASNHF LYLPRDVLAQLPSLRYLDLSNNSLVSLTYVSFRNLTH LESLHLEDNALKVLHNGTLAELQGLPHVRVFLDNNPW VCDCHMADMVTWLKQTGVVQGKDRLTCAFPEKMRNRV LLELNSADLDCDPILPPSLQTSYVFLGIVLALIGAIF LLVLYLNRKGIKKWMHNIRDACRDHMEGYHYRYEINA DPRLTNLSSNSDV | N/A | c5T4 |
| 50 | MPGGCSRGPAAGDGRLRLARLALVLLGWVSSSSPTSS ASSESSSAPFLASAVSAQPPLPDQCPALCECSEAART VKCVNRNLTEVPTDLPAYVRNLFLTGNQLAVLPAGAF ARRPPLAELAALNLSGSRLDEVRAGAFEHLPSLRQLD LSHNPLADLSPFAFSGSNASVSAPSPLVELILNHIVP PEDERQNRSFEGMVVAALLAGRALQGLRRLELASNHF LYLPRDVLAQLPSLRHLDLSNNSLVSLTYVSFRNLTH LESLHLEDNALKVLHNGTLAELQGLPHIRVFLDNNPW VCDCHMADMVTWLKETEVVQGKDRLTCAYPEKMRNRV LLELNSADLDCDPILPPSLATS | | Human 5T4 (h5T4) |
| 51 | DVQLQASGGGFVQPGDSLSLSCAASGGTFSSYSIGWF RQGPGKEREFVATISSSDSPWYGEPAKGRFTVARVNA KNTAYLHLNRIKPEDTATYYCAAGSVQHMANENEYVY WGQGTQVTVSS | | 2KD1 VHH anti-VP6 (Control VHH) |

SEQUENCE LISTING

```
Sequence total quantity: 51
SEQ ID NO: 1            moltype = AA  length = 5
FEATURE                 Location/Qualifiers
source                  1..5
                        mol_type = protein
                        organism = synthetic construct
SEQUENCE: 1
GYAVG                                                             5

SEQ ID NO: 2            moltype = AA  length = 16
FEATURE                 Location/Qualifiers
source                  1..16
                        mol_type = protein
                        organism = synthetic construct
SEQUENCE: 2
ALSRTGGSYY ADSVKG                                                 16

SEQ ID NO: 3            moltype = AA  length = 20
FEATURE                 Location/Qualifiers
source                  1..20
                        mol_type = protein
                        organism = synthetic construct
SEQUENCE: 3
RSVASIHNNR YYTDVYDYTY                                             20

SEQ ID NO: 4            moltype = AA  length = 8
FEATURE                 Location/Qualifiers
source                  1..8
                        mol_type = protein
```

```
                       organism = synthetic construct
SEQUENCE: 4
GRTFAGYA                                                                8

SEQ ID NO: 5           moltype = AA  length = 7
FEATURE                Location/Qualifiers
source                 1..7
                       mol_type = protein
                       organism = synthetic construct
SEQUENCE: 5
LSRTGGS                                                                 7

SEQ ID NO: 6           moltype = AA  length = 22
FEATURE                Location/Qualifiers
source                 1..22
                       mol_type = protein
                       organism = synthetic construct
SEQUENCE: 6
ATRSVASIHN NRYYTDVYDY TY                                                22

SEQ ID NO: 7           moltype = AA  length = 10
FEATURE                Location/Qualifiers
source                 1..10
                       mol_type = protein
                       organism = synthetic construct
SEQUENCE: 7
GRTFAGYAVG                                                              10

SEQ ID NO: 8           moltype = AA  length = 9
FEATURE                Location/Qualifiers
source                 1..9
                       mol_type = protein
                       organism = synthetic construct
SEQUENCE: 8
ALSRTGGSY                                                               9

SEQ ID NO: 9           moltype = AA  length = 20
FEATURE                Location/Qualifiers
source                 1..20
                       mol_type = protein
                       organism = synthetic construct
SEQUENCE: 9
RSVASIHNNR YYTDVYDYTY                                                   20

SEQ ID NO: 10          moltype = AA  length = 7
FEATURE                Location/Qualifiers
source                 1..7
                       mol_type = protein
                       organism = synthetic construct
SEQUENCE: 10
GRTFAGY                                                                 7

SEQ ID NO: 11          moltype = AA  length = 5
FEATURE                Location/Qualifiers
source                 1..5
                       mol_type = protein
                       organism = synthetic construct
SEQUENCE: 11
SRTGG                                                                   5

SEQ ID NO: 12          moltype = AA  length = 20
FEATURE                Location/Qualifiers
source                 1..20
                       mol_type = protein
                       organism = synthetic construct
SEQUENCE: 12
RSVASIHNNR YYTDVYDYTY                                                   20

SEQ ID NO: 13          moltype = AA  length = 5
FEATURE                Location/Qualifiers
source                 1..5
                       mol_type = protein
                       organism = synthetic construct
SEQUENCE: 13
SYAMS                                                                   5

SEQ ID NO: 14          moltype = AA  length = 17
FEATURE                Location/Qualifiers
source                 1..17
```

-continued

```
                        mol_type = protein
                        organism = synthetic construct
SEQUENCE: 14
SITTAGGSTR YADSVKG                                                  17

SEQ ID NO: 15           moltype = AA  length = 11
FEATURE                 Location/Qualifiers
source                  1..11
                        mol_type = protein
                        organism = synthetic construct
SEQUENCE: 15
ELGPRRLGMD Y                                                        11

SEQ ID NO: 16           moltype = AA  length = 8
FEATURE                 Location/Qualifiers
source                  1..8
                        mol_type = protein
                        organism = synthetic construct
SEQUENCE: 16
GFTFSSYA                                                            8

SEQ ID NO: 17           moltype = AA  length = 8
FEATURE                 Location/Qualifiers
source                  1..8
                        mol_type = protein
                        organism = synthetic construct
SEQUENCE: 17
ITTAGGST                                                            8

SEQ ID NO: 18           moltype = AA  length = 13
FEATURE                 Location/Qualifiers
source                  1..13
                        mol_type = protein
                        organism = synthetic construct
SEQUENCE: 18
NAELGPRRLG MDY                                                      13

SEQ ID NO: 19           moltype = AA  length = 10
FEATURE                 Location/Qualifiers
source                  1..10
                        mol_type = protein
                        organism = synthetic construct
SEQUENCE: 19
GFTFSSYAMS                                                          10

SEQ ID NO: 20           moltype = AA  length = 10
FEATURE                 Location/Qualifiers
source                  1..10
                        mol_type = protein
                        organism = synthetic construct
SEQUENCE: 20
SITTAGGSTR                                                          10

SEQ ID NO: 21           moltype = AA  length = 11
FEATURE                 Location/Qualifiers
source                  1..11
                        mol_type = protein
                        organism = synthetic construct
SEQUENCE: 21
ELGPRRLGMD Y                                                        11

SEQ ID NO: 22           moltype = AA  length = 7
FEATURE                 Location/Qualifiers
source                  1..7
                        mol_type = protein
                        organism = synthetic construct
SEQUENCE: 22
GFTFSSY                                                             7

SEQ ID NO: 23           moltype = AA  length = 6
FEATURE                 Location/Qualifiers
source                  1..6
                        mol_type = protein
                        organism = synthetic construct
SEQUENCE: 23
TTAGGS                                                              6

SEQ ID NO: 24           moltype = AA  length = 11
FEATURE                 Location/Qualifiers
```

-continued

```
source                  1..11
                        mol_type = protein
                        organism = synthetic construct
SEQUENCE: 24
ELGPRRLGMD Y                                                     11

SEQ ID NO: 25           moltype = AA  length = 128
FEATURE                 Location/Qualifiers
source                  1..128
                        mol_type = protein
                        organism = synthetic construct
SEQUENCE: 25
QVQLVESGGG LVKPGGSLRL SCAASGRTFA GYAVGWFRQA PGKEREFVAA LSRTGGSYYA  60
DSVKGRFTIS RDNAKNSLYL QMNSLRAEDT AVYYCATRSV ASIHNNRYYT DVYDYTYWGQ  120
GTLVTVSS                                                         128

SEQ ID NO: 26           moltype = AA  length = 128
FEATURE                 Location/Qualifiers
source                  1..128
                        mol_type = protein
                        organism = synthetic construct
SEQUENCE: 26
QVQLVESGGG LVKPGGSLRL SCAASGRTFA GYAVGWFRQA PGKEREFVSA LSRTGGSYYA  60
DSVKGRFTIS RDNAKNSLYL QMNSLKAEDT AVYYCATRSV ASIHNNRYYT DVYDYTYWGQ  120
GTQVTVSS                                                         128

SEQ ID NO: 27           moltype = AA  length = 120
FEATURE                 Location/Qualifiers
source                  1..120
                        mol_type = protein
                        organism = synthetic construct
SEQUENCE: 27
EVQLVESGGG LVQPGGSLRL SCAASGFTFS SYAMSWYRQA PGKGLELVAS ITTAGGSTRY  60
ADSVKGRFTI SRDNAKNTLY LQMNSLRAED TAVYYCNAEL GPRRLGMDYW GQGTLVTVSS  120

SEQ ID NO: 28           moltype = AA  length = 120
FEATURE                 Location/Qualifiers
source                  1..120
                        mol_type = protein
                        organism = synthetic construct
SEQUENCE: 28
EVQLVESGGG LVQPGGSLRL SCAASGFTFS SYAMSWVRQA PGKEREWVAS ITTAGGSTRY  60
ADSVKGRFTI SRDNAKNTLY LQMNSLRAED TAVYYCNAEL GPRRLGMDYW GQGTLVTVSS  120

SEQ ID NO: 29           moltype = AA  length = 120
FEATURE                 Location/Qualifiers
source                  1..120
                        mol_type = protein
                        organism = synthetic construct
SEQUENCE: 29
EVQLVESGGG LVQPGGSLRL SCAASGFTFS SYAMSWYRQA PGKERELVAS ITTAGGSTRY  60
ADSVKGRFTI SRDNAKNTLY LQMNSLRAED TAVYYCNAEL GPRRLGMDYW GQGTLVTVSS  120

SEQ ID NO: 30           moltype = AA  length = 359
FEATURE                 Location/Qualifiers
source                  1..359
                        mol_type = protein
                        organism = synthetic construct
SEQUENCE: 30
QVQLVESGGG LVKPGGSLRL SCAASGRTFA GYAVGWFRQA PGKEREFVAA LSRTGGSYYA  60
DSVKGRFTIS RDNAKNSLYL QMNSLRAEDT AVYYCATRSV ASIHNNRYYT DVYDYTYWGQ  120
GTLVTVSSEP KSSDKTHTCP PCPAPEAEGA PSVFLFPPKP KDTLMISRTP EVTCVVVDVS  180
HEDPEVKFNW YVDGVEVHNA KTKPREEQYN STYRVVSVLT VLHQDWLNGK EYKCKVSNKA  240
LPSSIEKTIS KAKGQPREPQ VYTLPPSREE MTKNQVSLTC LVKGFYPSDI AVEWESNGQP  300
ENNYKTTPPV LDSDGSFFLY SKLTVDKSRW QQGNVFSCSV MHEALHNQYT QKSLSLSPG   359

SEQ ID NO: 31           moltype = AA  length = 359
FEATURE                 Location/Qualifiers
source                  1..359
                        mol_type = protein
                        organism = synthetic construct
SEQUENCE: 31
QVQLVESGGG LVKPGGSLRL SCAASGRTFA GYAVGWFRQA PGKEREFVSA LSRTGGSYYA  60
DSVKGRFTIS RDNAKNSLYL QMNSLKAEDT AVYYCATRSV ASIHNNRYYT DVYDYTYWGQ  120
GTQVTVSSEP KSSDKTHTCP PCPAPEAEGA PSVFLFPPKP KDTLMISRTP EVTCVVVDVS  180
HEDPEVKFNW YVDGVEVHNA KTKPREEQYN STYRVVSVLT VLHQDWLNGK EYKCKVSNKA  240
LPSSIEKTIS KAKGQPREPQ VYTLPPSREE MTKNQVSLTC LVKGFYPSDI AVEWESNGQP  300
ENNYKTTPPV LDSDGSFFLY SKLTVDKSRW QQGNVFSCSV MHEALHNQYT QKSLSLSPG   359
```

```
SEQ ID NO: 32          moltype = AA  length = 351
FEATURE                Location/Qualifiers
source                 1..351
                       mol_type = protein
                       organism = synthetic construct
SEQUENCE: 32
EVQLVESGGG LVQPGGSLRL SCAASGFTFS SYAMSWYRQA PGKGLELVAS ITTAGGSTRY  60
ADSVKGRFTI SRDNAKNTLY LQMNSLRAED TAVYYCNAEL GPRRLGMDYW GQGTLVTVSS  120
EPKSSDKTHT CPPCPAPEAE GAPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPSSIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNQ YTQKSLSLSP G           351

SEQ ID NO: 33          moltype = AA  length = 351
FEATURE                Location/Qualifiers
source                 1..351
                       mol_type = protein
                       organism = synthetic construct
SEQUENCE: 33
EVQLVESGGG LVQPGGSLRL SCAASGFTFS SYAMSWVRQA PGKEREWVAS ITTAGGSTRY  60
ADSVKGRFTI SRDNAKNTLY LQMNSLRAED TAVYYCNAEL GPRRLGMDYW GQGTLVTVSS  120
EPKSSDKTHT CPPCPAPEAE GAPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPSSIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNQ YTQKSLSLSP G           351

SEQ ID NO: 34          moltype = AA  length = 351
FEATURE                Location/Qualifiers
source                 1..351
                       mol_type = protein
                       organism = synthetic construct
SEQUENCE: 34
EVQLVESGGG LVQPGGSLRL SCAASGFTFS SYAMSWYRQA PGKERELVAS ITTAGGSTRY  60
ADSVKGRFTI SRDNAKNTLY LQMNSLRAED TAVYYCNAEL GPRRLGMDYW GQGTLVTVSS  120
EPKSSDKTHT CPPCPAPEAE GAPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPSSIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNQ YTQKSLSLSP G           351

SEQ ID NO: 35          moltype =   length =
SEQUENCE: 35
000

SEQ ID NO: 36          moltype =   length =
SEQUENCE: 36
000

SEQ ID NO: 37          moltype = AA  length = 355
FEATURE                Location/Qualifiers
source                 1..355
                       mol_type = protein
                       note = 5T4 protein sequence
                       organism = unidentified
SEQUENCE: 37
MPGGCSRGPA AGDGRLRLAR LALVLLGWVS SSSPTSSASS FSSSAPFLAS AVSAQPPLPD  60
QCPALCECSE AARTVKCVNR NLTEVPTDLP AYVRNLFLTG NQLAVLPAGA FARRPPLAEL  120
AALNLSGSRL DEVRAGAFEH LPSLRQLDLS HNPLADLSPF AFSGSNASVS APSPLVELIL  180
NHIVPPEDER QNRSFEGMVV AALLAGRALQ GLRRLELASN HFLYLPRDVL AQLPSLRHLD  240
LSNNSLVSLT YVSFRNLTHL ESLHLEDNAL KVLHNGTLAE LQGLPHIRVF LDNNPWVCDC  300
HMADMVTWLK ETEVVQGKDR LTCAYPEKMR NRVLLELNSA DLDCDPILPP SLQTS       355

SEQ ID NO: 38          moltype =   length =
SEQUENCE: 38
000

SEQ ID NO: 39          moltype = AA  length = 107
FEATURE                Location/Qualifiers
source                 1..107
                       mol_type = protein
                       organism = synthetic construct
SEQUENCE: 39
SIVMTQTPTF LLVSAGDRVT ITCKASQSVS NDVAWYQQKP GQSPTLLISY TSSRYAGVPD  60
RFIGSGYGTD FTFTISTLQA EDLAVYFCQQ DYNSPPTFGG GTKLEIK                107

SEQ ID NO: 40          moltype = AA  length = 120
FEATURE                Location/Qualifiers
source                 1..120
                       mol_type = protein
                       organism = synthetic construct
```

-continued

```
SEQUENCE: 40
EVQLQQSGPD LVKPGASVKI SCKASGYSFT GYYMHWVKQS HGKSLEWIGR INPNNGVTLY  60
NQKFKDKAIL TVDKSSTTAY MELRSLTSED SAVYYCARST MITNYVMDYW GQVTSVTVSS  120

SEQ ID NO: 41          moltype = AA  length = 129
FEATURE                Location/Qualifiers
source                 1..129
                       mol_type = protein
                       organism = synthetic construct
SEQUENCE: 41
QVQLVQSGGG LVQAGDSLTL SCAVSERPFG TYAMGWFRQA PGRERDLVAA VSRNGGASQY  60
GDSVKGRFSI SRDNIKNTMY LQMNSLKPED TAVYYCAARS AAYSRSSEVY TGKDEYYYWG  120
QGTQVTVKP                                                          129

SEQ ID NO: 42          moltype = AA  length = 128
FEATURE                Location/Qualifiers
source                 1..128
                       mol_type = protein
                       organism = synthetic construct
SEQUENCE: 42
QVQLVESGGG LVQAGGSLRL SCLASGRTFA GYAVGWFRQA PGKEREFVAA LSRTGGSYYA  60
DSVKGRFTIS RDNAERTMNL QMNSLKPEDT AVYYCATRSV ASIHNNRYYT DVYDYTYWGQ  120
GTQVTVSS                                                           128

SEQ ID NO: 43          moltype = AA  length = 120
FEATURE                Location/Qualifiers
source                 1..120
                       mol_type = protein
                       organism = synthetic construct
SEQUENCE: 43
QVQLVESGGG LVQPGGSLRL SCAASGFTFS SYAMSWYRQA PGEERELVAS ITTAGGSTRY  60
ADSVKGRFTI SRDNAKNTVY LQMNSLKPED TAVYYCNAEL GPRRLGMDYW GEGTLVTVSA  120

SEQ ID NO: 44          moltype =   length =
SEQUENCE: 44
000

SEQ ID NO: 45          moltype = AA  length = 15
FEATURE                Location/Qualifiers
source                 1..15
                       mol_type = protein
                       organism = Homo sapiens
SEQUENCE: 45
EPKSCDKTHT CPPCP                                                   15

SEQ ID NO: 46          moltype = AA  length = 15
FEATURE                Location/Qualifiers
source                 1..15
                       mol_type = protein
                       organism = synthetic construct
SEQUENCE: 46
EPKSSDKTHT CPPCP                                                   15

SEQ ID NO: 47          moltype = AA  length = 231
FEATURE                Location/Qualifiers
source                 1..231
                       mol_type = protein
                       organism = synthetic construct
SEQUENCE: 47
EPKSSDKTHT CPPCPAPEAE GAPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPSSIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNQ YTQKSLSLSP G            231
```

-continued

```
SEQ ID NO: 48          moltype = AA  length = 216
FEATURE                Location/Qualifiers
source                 1..216
                       mol_type = protein
                       organism = Homo sapiens
SEQUENCE: 48
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSREEMTK NQVSLTCLVK GFYPSDIAVE WESNGQPENN YKTTPPVLDS DGSFFLYSKL  180
TVDKSRWQQG NVFSCSVMHE ALHNHYTQKS LSLSPG                           216

SEQ ID NO: 49          moltype = AA  length = 420
FEATURE                Location/Qualifiers
source                 1..420
                       mol_type = protein
                       organism = Macaca fascicularis
SEQUENCE: 49
MPGGCSRGPA AGDGRLRLAR LALVLLGWVS SSSSTSSASS SSSSAPFLAS AASAQPPLPD  60
QCPALCECSE AARTVKCVNR NLTEVPTDLP LYVRNLFLTG NQLAVLPAGA FARRPPLAEL  120
AALNLSGSRL DEVRGGAFEH LPSLRQLDLS HNPLAYLSPF AFSGSNASIS APSPLVELIL  180
NHIVPPDDKR QNRSFEGMVA AALVAGRALQ GLHLLELASN HFLYLPRDVL AQLPSLRYLD  240
LSNNSLVSLT YVSFRNLTHL ESLHLEDNAL KVLHNGTLAE LQGLPHVRVF LDNNPWVCDC  300
HMADMVTWLK QTGVVQGKDR LTCAFPEKMR NRVLLELNSA DLDCDPILPP SLQTSYVFLG  360
IVLALIGAIF LLVLYLNRKG IKKWMHNIRD ACRDHMEGYH YRYEINADPR LTNLSSNSDV  420

SEQ ID NO: 50          moltype = AA  length = 355
FEATURE                Location/Qualifiers
source                 1..355
                       mol_type = protein
                       organism = Homo sapiens
SEQUENCE: 50
MPGGCSRGPA AGDGRLRLAR LALVLLGWVS SSSPTSSASS FSSSAPFLAS AVSAQPPLPD  60
QCPALCECSE AARTVKCVNR NLTEVPTDLP AYVRNLFLTG NQLAVLPAGA FARRPPLAEL  120
AALNLSGSRL DEVRAGAFEH LPSLRQLDLS HNPLADLSPF AFSGSNASVS APSPLVELIL  180
NHIVPPEDER QNRSFEGMVV AALLAGRALQ GLRRLELASN HFLYLPRDVL AQLPSLRHLD  240
LSNNSLVSLT YVSFRNLTHL ESLHLEDNAL KVLHNGTLAE LQGLPHIRVF LDNNPWVCDC  300
HMADMVTWLK ETEVVQGKDR LTCAYPEKMR NRVLLELNSA DLDCDPILPP SLQTS       355

SEQ ID NO: 51          moltype = AA  length = 122
FEATURE                Location/Qualifiers
source                 1..122
                       mol_type = protein
                       organism = synthetic construct
SEQUENCE: 51
DVQLQASGGG FVQPGDSLSL SCAASGGTFS SYSIGWFRQG PGKEREFVAT ISSSDSPWYG  60
EPAKGRFTVA RVNAKNTAYL HLNRLKPEDT ATYYCAAGSV QHMANENEYV YWGQGTQVTV  120
SS                                                                122
```

What is claimed is:

1. A polypeptide that binds 5T4, wherein the polypeptide comprises an immunoglobulin variable domain comprising:

(i) a complementarity determining region 1 (CDR1) comprising the amino acid sequence of SEQ ID NO: 13; a complementarity determining region 2 (CDR2) comprising the amino acid sequence of SEQ ID NO: 14; and a complementarity determining region 3 (CDR3) comprising the amino acid sequence of SEQ ID NO: 15;

(ii) a complementarity determining region 1 (CDR1) comprising the amino acid sequence of SEQ ID NO: 16; a complementarity determining region 2 (CDR2) comprising the amino acid sequence of SEQ ID NO: 17; and a complementarity determining region 3 (CDR3) comprising the amino acid sequence of SEQ ID NO: 18;

(iii) a complementarity determining region 1 (CDR1) comprising the amino acid sequence of SEQ ID NO: 19; a complementarity determining region 2 (CDR2) comprising the amino acid sequence of SEQ ID NO: 20; and a complementarity determining region 3 (CDR3) comprising the amino acid sequence of SEQ ID NO: 21; or (iv) a complementarity determining region 1 (CDR1) comprising the amino acid sequence of SEQ ID NO: 22; a complementarity determining region 2 (CDR2) comprising the amino acid sequence of SEQ ID NO: 23; and a complementarity determining region 3 (CDR3) comprising the amino acid sequence of SEQ ID NO: 24.

2. The polypeptide of claim 1, wherein the immunoglobulin variable domain comprises at least 80% sequence identity to SEQ ID NOs: 27-29.

3. The polypeptide of claim 1, wherein the immunoglobulin variable domain comprises the sequence of any one of SEQ ID NOs: 27-29.

4. The polypeptide of claim 1, wherein the polypeptide comprises an Fc domain and/or an immunoglobulin hinge region.

5. The polypeptide of claim 4, wherein the Fc domain and/or the immunoglobulin hinge region comprises an amino acid sequence having at least about 80% sequence identity to SEQ ID NO: 47.

6. The polypeptide of claim 4, wherein the Fc domain and/or the immunoglobulin hinge region comprises an amino acid sequence set forth in SEQ ID NO: 47.

7. The polypeptide of claim 4, wherein the Fc domain is an IgG1 Fc domain.

8. The polypeptide of claim 4, wherein the Fc domain comprises one or more amino acid residue alterations that reduce effector function of the polypeptide and/or one or more amino acid residue alterations that alter binding of the polypeptide to a neonatal Fe receptor (FcRn), thereby reducing the serum half-life of the polypeptide.

9. The polypeptide of claim 8, wherein the one or more amino acid residue alterations that reduce effector function comprises L234A, L235E, G237A, A330S, and P331S per EU numbering.

10. The polypeptide of claim 8, wherein the one or more amino acid residues that alter binding of the polypeptide to the neonatal Fc receptor (FcRn) comprise H310A, H310D, H310E, H310Q, H435A, H435Q, and combinations thereof, per EU numbering.

11. The polypeptide of claim 8, wherein the one or more amino acid residues that alter binding of the polypeptide to the neonatal Fe receptor (FcRn) comprise H310A.

12. A method of making a polypeptide that binds 5T4, comprising culturing, in a culture medium, a host cell comprising a nucleic acid or a plurality of nucleic acids encoding the polypeptide of claim 1 under conditions sufficient to express and secrete the polypeptide and recovering the polypeptide from the host cell or the culture medium thereof.

13. The polypeptide of claim 8, wherein the one or more amino acid residues that alter binding of the polypeptide to the neonatal Fe receptor (FcRn) comprise H435Q.

14. The polypeptide of claim 1, wherein the immunoglobulin variable domain is an immunoglobulin heavy chain variable domain, and wherein the immunoglobulin heavy chain variable domain is a VHH.

15. A dimer comprising two polypeptides according to claim 1.

16. An immunoconjugate comprising the polypeptide of claim 1 conjugated to a chelating agent or a radionuclide complex thereof.

17. The immunoconjugate of claim 16, wherein the immunoconjugate comprises Formula (II) or a pharmaceutically acceptable salt thereof:

Formula (II)

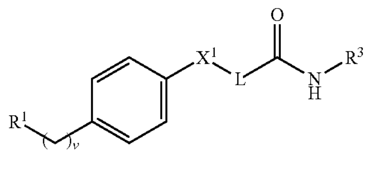

wherein, $R^1$ is a chelating agent or a radionuclide complex thereof;

$X^1$ is absent, —O—, —S—, —S(═O)—, —S(═O)$_2$—, —NR$^a$—, —C(═O)—, —NR$^a$C(═O)—, —C(═O)NR$^a$—, —($C_1$-$C_6$alkylene)-$X^2$—, or —($C_4$-$C_{20}$polyethylene glycol)-$X^2$—;

$X^2$ is absent, —C(═O)—, —NR$^a$C(═O)—, —C(═O)NR$^a$—, or —C(═O)$X^4$—;

each $R^a$ is independently selected from hydrogen and $C_1$-$C_4$ alkyl;

$X^4$ is —NR$^a$— or —NR$^a$S(═O)$_2$—;

L is an optional linker;

—NH—$R^3$ is the polypeptide; and v is 1, 2, 3, or 4.

18. The immunoconjugate of claim 17, wherein:

v is 1; and

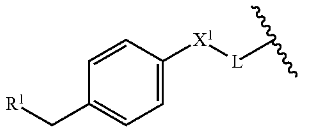

is:

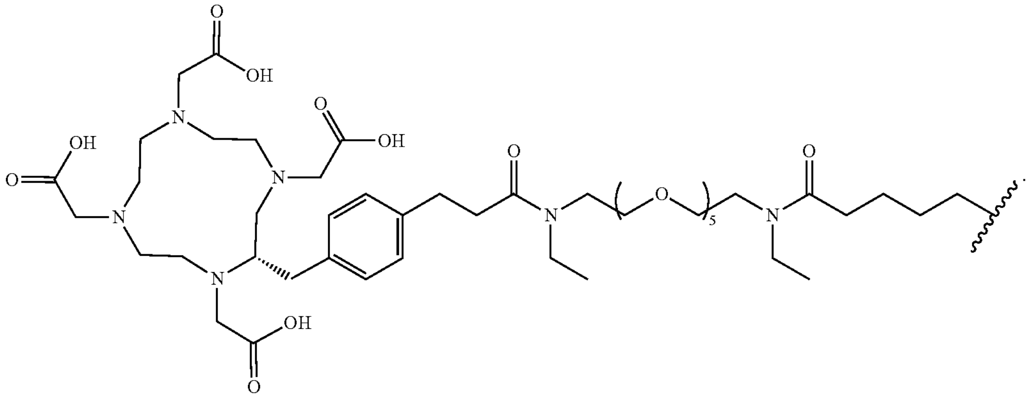

19. A nucleic acid encoding the polypeptide of claim 1.

20. A host cell comprising the nucleic acid of claim 19.

21. The immunoconjugate of claim 17, prepared by conjugating the polypeptide ($R^3$) of claim 1 to the following compound:

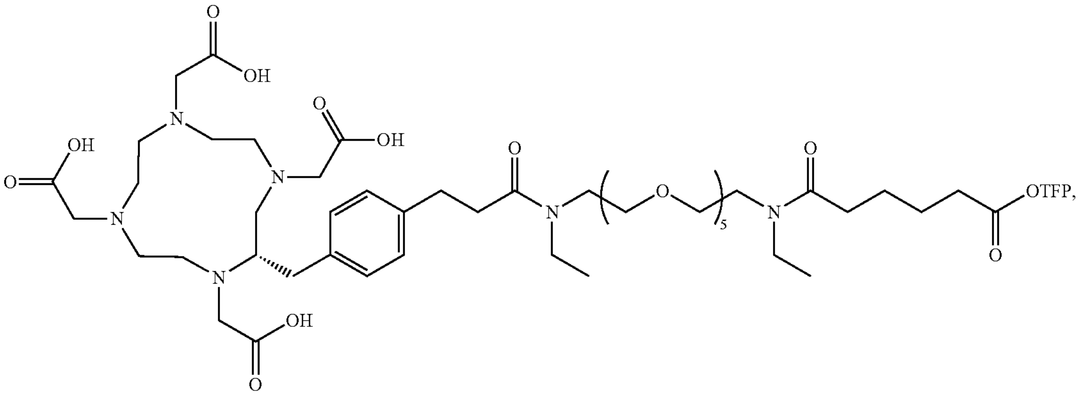
wherein TFP is tetrafluorophenyl.
22. The immunoconjugate of claim 17, wherein:
v is 1;
$R^1$ is
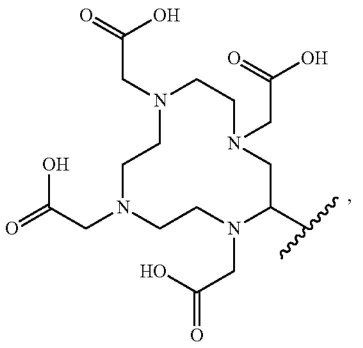 [SMILES: *C1CN(CC(=O)O)CCN(CC(=O)O)CCN(CC(=O)O)CCN1CC(=O)O]
and
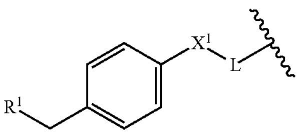
is:
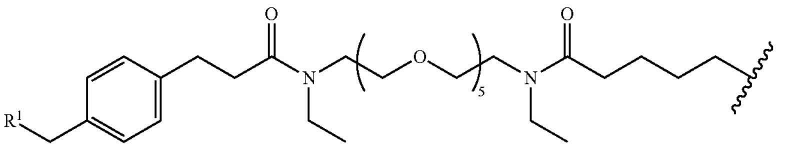
23. The immunoconjugate of claim 17, prepared by conjugating the polypeptide ($R^3$) of claim 1 to a compound of Formula (VIb):
Formula (VIb)
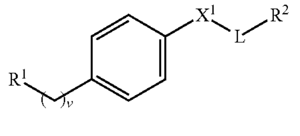
wherein:
v is 1;
$R^1$ is
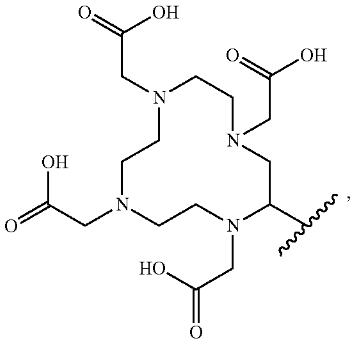 [SMILES: *C1CN(CC(=O)O)CCN(CC(=O)O)CCN(CC(=O)O)CCN1CC(=O)O]

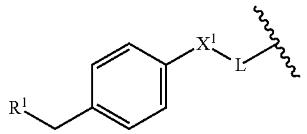

is:

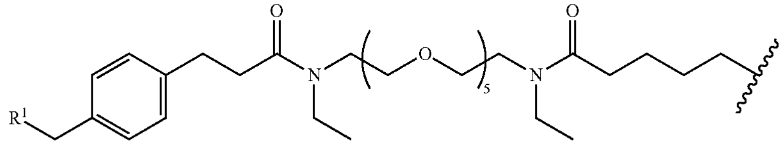

;

and $R^2$ is

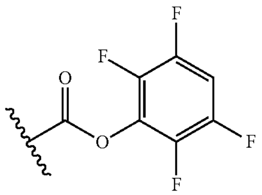

or

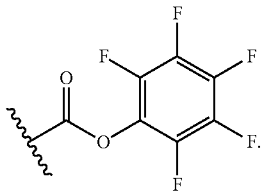

24. The immunoconjugate of claim 16, wherein the chelating agent is coupled to the g polypeptide by a linker.

25. The immunoconjugate of claim 16, wherein the chelating agent further comprises a radionuclide.

26. The immunoconjugate of claim 25, wherein the radionuclide is a diagnostic or a therapeutic radionuclide.

27. The immunoconjugate of claim 25, wherein the radionuclide is an Auger electron-emitting radionuclide, an α-emitting radionuclide, a β-emitting radionuclide, or a γ-emitting radionuclide.

28. The immunoconjugate of claim 25, wherein the radionuclide is an α-emitting radionuclide.

29. The immunoconjugate of claim 25, wherein the radionuclide is 225-actinium ($^{225}Ac$).

30. The immunoconjugate of claim 25, wherein the radionuclide is 111-indium ($^{111}In$).

31. A method of targeting a radionuclide to a 5T4 expressing cancer or tumor cell of an individual, the method comprising administering to the individual the immunoconjugate of claim 16.

32. A method of treating a cancer or tumor of an individual, the method comprising administering to the individual an effective amount of the polypeptide of claim 1 or the immunoconjugate of claim 16, thereby treating the cancer or the tumor of the individual.

33. A method of imaging a cancer or tumor of an individual, the method comprising administering to the individual an effective amount of the immunoconjugate of claim 16, thereby targeting the radionuclide to a 5T4-expressing cancer or tumor cell of the individual, and imaging the 5T4-expressing cancer or tumor cell of the individual.

34. The method of claim 32, wherein the cancer or tumor of the individual expresses 5T4.

35. The method of claim 32, wherein the cancer or tumor of the individual is a colorectal cancer or tumor, a cervical cancer or tumor, a pancreatic cancer or tumor, a non-small cell lung (NSCLC) cancer or tumor, or a head and neck squamous cell cancer or tumor.

36. A method of making the immunoconjugate of claim 16, comprising complexing a radionuclide to the chelating agent.

* * * * *